United States Patent
Gurijala et al.

(10) Patent No.: US 10,772,971 B2
(45) Date of Patent: Sep. 15, 2020

(54) METHODS OF PRODUCING DRUG-CARRYING POLYMER SCAFFOLDS AND PROTEIN-POLYMER-DRUG CONJUGATES

(71) Applicant: Mersana Therapeutics, Inc., Cambridge, MA (US)

(72) Inventors: Venu Reddy Gurijala, Lancaster, MA (US); Satyanarayan Reddy Bollu, Plainville, MA (US); Jacques Leblanc, Millbury, MA (US); Timothy B. Lowinger, Carlisle, MA (US); Dennis McGillicuddy, Reading, MA (US); Mao Yin, Needham, MA (US); Aleksandr V. Yurkovetskiy, Littleton, MA (US)

(73) Assignee: Mersana Therpeutics, Inc., Cambridge, MA (US)

( * ) Notice: Subject to any disclaimer, the term of this patent is extended or adjusted under 35 U.S.C. 154(b) by 76 days.

(21) Appl. No.: 16/015,623

(22) Filed: Jun. 22, 2018

(65) Prior Publication Data
US 2018/0369405 A1    Dec. 27, 2018

Related U.S. Application Data

(60) Provisional application No. 62/623,275, filed on Jan. 29, 2018, provisional application No. 62/545,296, filed on Aug. 14, 2017, provisional application No. 62/523,378, filed on Jun. 22, 2017.

(51) Int. Cl.
| | |
|---|---|
| *A61K 47/68* | (2017.01) |
| *A61K 38/08* | (2019.01) |
| *A61K 47/64* | (2017.01) |
| *A61K 47/59* | (2017.01) |

(52) U.S. Cl.
CPC .......... *A61K 47/6835* (2017.08); *A61K 38/08* (2013.01); *A61K 47/59* (2017.08); *A61K 47/64* (2017.08); *A61K 47/6803* (2017.08); *A61K 47/6849* (2017.08); *A61K 47/6851* (2017.08); *A61K 47/6883* (2017.08)

(58) Field of Classification Search
CPC ................ A61K 47/6835; A61K 47/59; A61K 47/6803; A61K 47/6883; A61K 47/6849; A61K 47/6851; A61K 47/64; A61K 38/08
See application file for complete search history.

(56) References Cited

U.S. PATENT DOCUMENTS

| | | |
|---|---|---|
| 5,811,510 A | 9/1998 | Papisov |
| 5,863,990 A | 1/1999 | Papisov |
| 5,958,398 A | 9/1999 | Papisov |
| 7,790,150 B2 | 9/2010 | Papisov et al. |
| 8,101,164 B2 | 1/2012 | Papisov et al. |
| 8,247,427 B2 | 8/2012 | Papisov et al. |
| 8,399,512 B2 | 3/2013 | Akullian et al. |
| 8,491,880 B2 | 7/2013 | Rolke et al. |
| 8,546,419 B2 | 10/2013 | Papisov et al. |
| 8,685,383 B2 | 4/2014 | Yurkovetskiy et al. |
| 8,808,679 B2 | 8/2014 | Yurkovetskiy et al. |
| 8,815,226 B2 | 8/2014 | Yurkovetskiy et al. |
| 8,821,850 B2 | 9/2014 | Yurkovetskiy et al. |
| 9,144,615 B2 | 9/2015 | Yurkovetskiy et al. |
| 9,254,339 B2 | 2/2016 | Yurkovetskiy et al. |
| 9,555,112 B2 | 1/2017 | Yurkovetskiy et al. |
| 9,738,720 B2 | 8/2017 | Yurkovetskiy et al. |
| 9,770,519 B2 | 9/2017 | Yurkovetskiy et al. |
| 9,849,191 B2 | 12/2017 | Yurkovetskiy et al. |
| 9,943,609 B2 | 4/2018 | Yurkovetskiy et al. |
| 2011/0059010 A1 | 3/2011 | Papisov et al. |
| 2012/0004255 A1 | 1/2012 | Papisov et al. |
| 2012/0289535 A1 | 11/2012 | Papisov et al. |
| 2013/0158046 A1 | 6/2013 | Akullian et al. |
| 2014/0004074 A1 | 1/2014 | Rolke et al. |
| 2015/0104407 A1 | 4/2015 | Yurkovetskiy et al. |
| 2017/0266311 A1 | 9/2017 | Bergstrom et al. |
| 2017/0313778 A1 | 11/2017 | Bodyak et al. |
| 2017/0348424 A1 | 12/2017 | Yurkovetskiy et al. |
| 2018/0140716 A1 | 5/2018 | Yurkovetskiy et al. |
| 2018/0243428 A1 | 8/2018 | Yurkovetskiy et al. |

FOREIGN PATENT DOCUMENTS

| | | |
|---|---|---|
| WO | WO 2014/160360 A1 | 10/2014 |
| WO | WO 2017/160754 A1 | 9/2017 |

OTHER PUBLICATIONS

Greene, T.W., et al.; Greene's Protective Groups in Organic Synthesis, 2007, p. 696-926.*
Thermo Scientific; Tech Tip #62: Ion exchange chromatography, 2007, p. 1-2.*

* cited by examiner

*Primary Examiner* — Robert S Jones
(74) *Attorney, Agent, or Firm* — Cooley LLP; Heidi A. Erlacher; Xixi Sun

(57) ABSTRACT

The disclosure provides methods of synthesis of polymeric scaffolds, e.g., those useful for conjugating with a protein based recognition-molecule (PBRM) to form PBRM-polymer-drug conjugates, and PBRM-polymer-drug conjugates thereof. The methods according to the disclosure allow for large-scale preparation of polymeric scaffolds having a high purity. In some embodiments, the methods according to the disclosure also allow for the preparation of scaffolds and conjugates thereof in better yield than previously used methods for preparing same. Also disclosed are methods of purifying polymeric scaffolds.

41 Claims, No Drawings

METHODS OF PRODUCING DRUG-CARRYING POLYMER SCAFFOLDS AND PROTEIN-POLYMER-DRUG CONJUGATES

RELATED APPLICATIONS

This application claims priority to, and the benefit of, U.S. Provisional Application Nos. 62/523,378, filed Jun. 22, 2017, 62/545,296, filed Aug. 14, 2017, and 62/623,275, filed Jan. 29, 2018, under 35 U.S.C. § 119(e). The content of these applications are hereby incorporated by reference in their entirety.

BACKGROUND

Traditionally, pharmaceuticals have primarily consisted of small molecules that are dispensed orally (as solid dosage forms and liquids) or as injectables. Over the past three decades, formulations (i.e., compositions that control the route and/or rate of drug delivery and allow delivery of the therapeutic agent at the site where it is needed) have become increasingly common and complex. Nevertheless, many questions and challenges regarding the development of new treatments as well as the mechanisms with which to administer them remain to be addressed. For example, many drugs exhibit limited or otherwise reduced potencies and therapeutic effects because they are either generally subject to partial degradation before they reach a desired target in the body, or accumulate in tissues other than the target, or both.

One objective in the field of drug delivery systems, therefore, is to deliver medications intact to specifically targeted areas of the body through a system that can stabilize the drug and control the in vivo transfer of the therapeutic agent utilizing either physiological or chemical mechanisms, or both.

Antibody-drug conjugates have been developed as target-specific therapeutic agents. Antibodies against various cancer cell-surface antigens have been conjugated with different cytotoxic agents that inhibit various essential cellular targets such as microtubules (maytansinoids, auristatins, taxanes: U.S. Pat. Nos. 5,208,020; 5,416,064; 6,333,410; 6,441,163; 6,340,701; 6,372,738; 6,436,931; 6,596,757; and 7,276,497); DNA (calicheamicin, doxorubicin, CC-1065 analogs; U.S. Pat. Nos. 5,475,092; 5,585,499; 5,846,545; 6,534,660; 6,756,397; and 6,630,579). Antibody conjugates with some of these cytotoxic drugs are actively being investigated in the clinic for cancer therapy (Ricart, A. D., and Tolcher, A. W., 2007, *Nature Clinical Practice*, 4, 245-255; Krop et al., 2010, *J. Clin. Oncol.*, 28, 2698-2704). However, existing antibody-drug conjugates have exhibited a few limitations. A major limitation is their inability to deliver a sufficient concentration of drug to the target site because of the limited number of targeted antigens and the relatively moderate cytotoxicity of cancer drugs like methotrexate, daunorubicin, maytansinoids, taxanes, and vincristine. One approach to achieving significant cytotoxicity is by linkage of a large number of drug molecules either directly or indirectly to the antibody. However such heavily modified antibodies often display impaired binding to the target antigen and fast in vivo clearance from the blood stream. In view of the foregoing, there is a need to develop improved antibody-drug conjugates and methods of preparing them.

SUMMARY

This disclosure is, at least in part, based on discovery of improved methods of preparing drug-carrying polymer scaffolds.

The present disclosure relates to methods of preparing and/or purifying a polymeric scaffold, which is useful to conjugate with a protein based recognition-molecule (PBRM). The present disclosure also relates to methods of preparing and/or purifying such conjugates comprising a polymeric scaffold and a PBRM. Further, the present disclosure relates to protein-polymer-drug conjugates (e.g., PBRM-polymer-drug conjugates) that are of substantially high purity and can be prepared by avoiding cumbersome steps with reduced time and costs.

In one aspect, the disclosure relates to a method of making a polymeric scaffold of Formula (A):

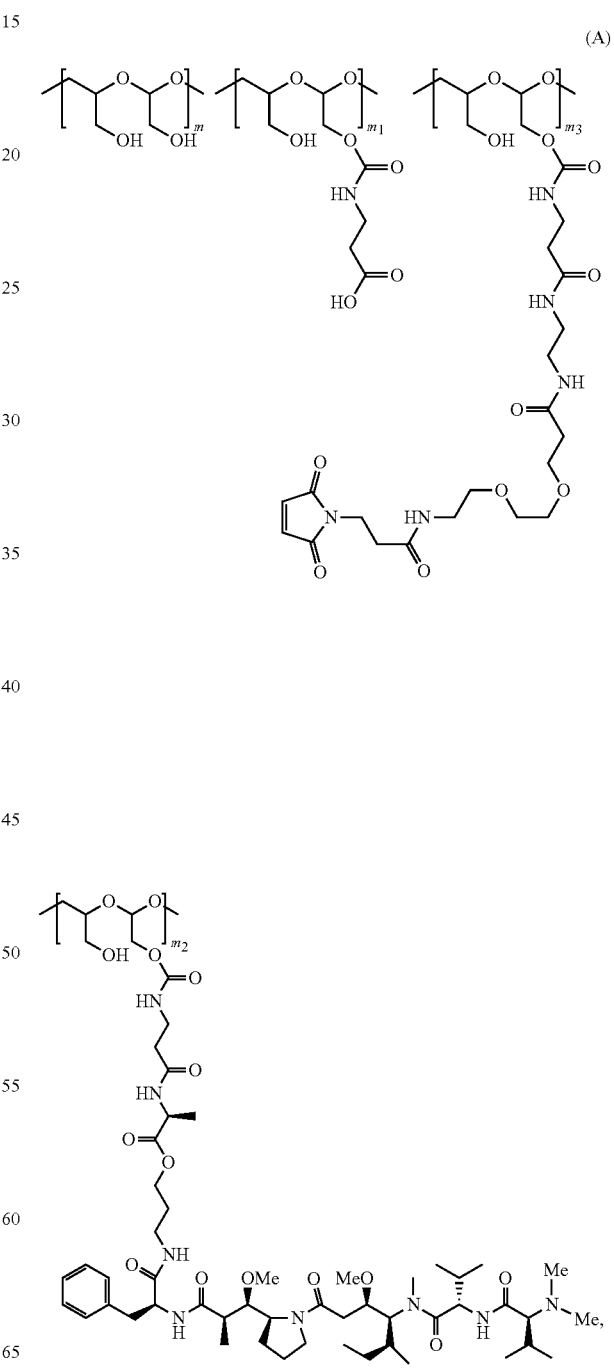

or a salt thereof, the method comprising one or more steps selected from:
(1) reacting

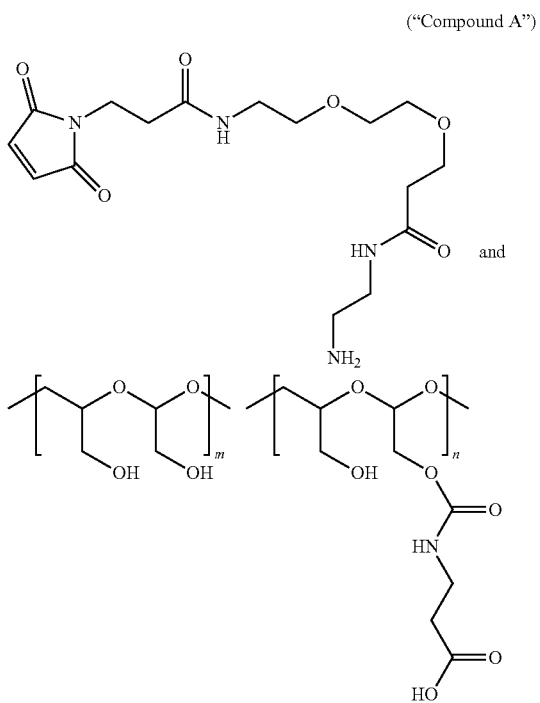

("Compound A")

under conditions to form a first reaction mixture; and
(2) adding

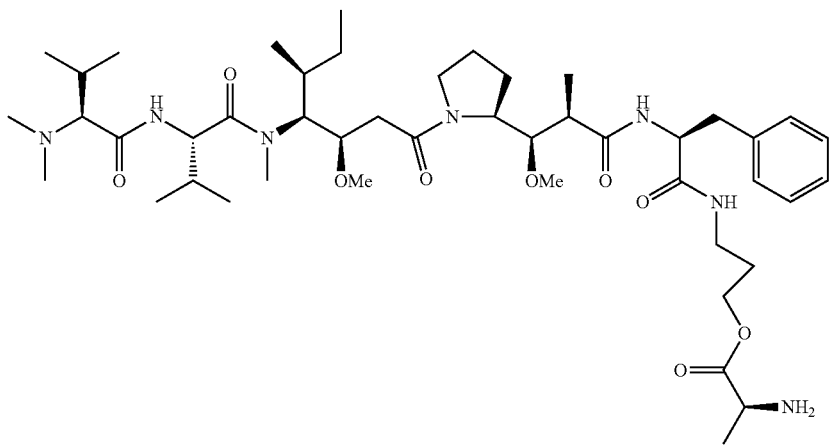

("Compound C")

or a salt thereof to the first reaction mixture to form a second reaction mixture comprising the scaffold of Formula (A) or the salt thereof;
wherein:
Compound B or the scaffold of Formula (A) comprises poly(l-hydroxymethylethylene hydroxymethyl-formal) (PHF) having a molecular weight ranging from about 5 kDa to about 10 kDa;
m is an integer from about 20 to about 75,
n is an integer from about 7 to about 40, and the ratio between m and n is about 2:1 to about 3:1,
$m_1$ is an integer from about 5 to about 35,
$m_2$ is an integer from about 3 to about 10,
$m_3$ is an integer from about 1 to about 5, and
the sum of m, $m_1$, $m_2$ and $m_3$ ranges from about 40 to about 75.

In some embodiments, the PHF has a molecular weight ranging from about 6 kDa to about 8 kDa.

In some embodiments, the PHF has a molecular weight ranging from about 6 kDa to about 7 kDa.

In some embodiments, Compound B has a molecular weight ranging from about 6 kDa to about 13 kDa, and n is about 26-34% of the sum of m and n. In some embodiments, Compound B has a molecular weight ranging from about 7 kDa to about 12 kDa, and n is about 28-32% of the sum of m and n. In some embodiments, Compound B has a molecular weight ranging from about 10 kDa to about 12 kDa.

In some embodiments, the method further comprises isolating the scaffold of Formula (A) or the salt thereof. In some embodiments, the scaffold of Formula (A) or the salt thereof is isolated with a reverse phase HPLC separation. In some embodiments, the reverse phase HPLC separation is performed with a mobile phase comprising sodium acetate buffer and acetonitrile. In some embodiments, prior to the reverse phase HPLC separation, the second reaction mixture is subject to one or more filtrations, one or more tangential flow filtrations, one or more diafiltration, one or more ultrafiltration, one or more nanofiltrations, or combinations thereof. In some embodiments, prior to the reverse phase HPLC separation, the second reaction mixture is subject to one or more non-adsorptive chromatography separations. In some embodiments, after to the reverse phase HPLC separation, the second reaction mixture is subject to one or more filtrations, one or more tangential flow filtrations, one or more diafiltration, one or more ultrafiltration, one or more nanofiltrations or combinations thereof. In some embodiments, after to the reverse phase HPLC separation, the second reaction mixture is subject to one or more non-adsorptive chromatography separations.

In some embodiments, the scaffold of Formula (A) has a molecular weight ranging from about 4 kDa to about 18 kDa, from about 5 kDa to about 17 kDa, from about 6 kDa to about 16 kDa, or from about 7 kDa to about 14.5 kDa.

In some embodiments, the scaffold of Formula (A) has a molecular weight ranging from about 7 kDa to about 14.5 kDa.

In some embodiments, $m_2$ is about 5% to about 13%, about 6% to about 12%, about 7% to about 11%, or about 7.5% to about 10.5% of the sum of m, $m_1$, $m_2$ and $m_3$.

In some embodiments, $m_2$ is about 8% to about 10% of the sum of m, $m_1$, $m_2$ and $m_3$.

In some embodiments, $m_3$ is about 2% to about 4% of the sum of m, $m_1$, $m_2$ and $m_3$.

In some embodiments, at least 80% of Compound A is consumed before Compound C or a salt thereof is added to the first reaction mixture.

In some embodiments, the first reaction mixture is not isolated before Compound C or a salt thereof is added.

In some embodiments, the reaction of Compound A and Compound B is performed in the presence of an activating reagent for a carboxylic acid and a coupling agent under a first temperature.

In some embodiments, the reaction of the first reaction mixture and Compound C or a salt thereof is performed in the presence of an activating reagent for a carboxylic acid and a coupling agent under a second temperature.

In some embodiments, the activating reagent is N-hydroxysuccinimide (NHS). In some embodiments, the coupling reagent is ethyl(dimethylaminopropyl) carbodiimide hydrochloride (EDC.HCl). In some embodiments, the first temperature is between about 0° C. and about 15° C. In some embodiments, the second temperature is between about 5° C. and about 15° C.

In some embodiments, the method further comprises providing Compound A by deprotecting a protected form of Compound A. In some embodiments, the protected form of Compound A is

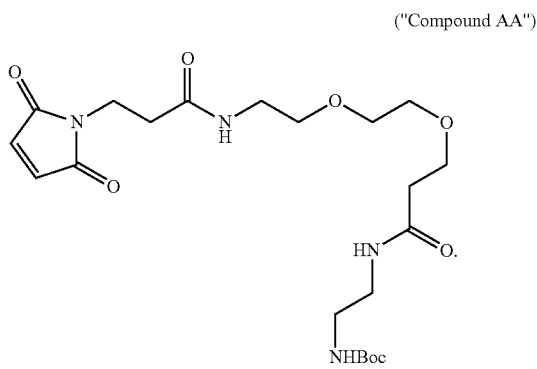 [SMILES: CC(C)(C)OC(=O)NCCNC(=O)CCOCCOCCNC(=O)CCN1C(=O)C=CC1=O]

("Compound AA")

In some embodiments, the method further comprises providing Compound AA by reacting 2,5-dioxopyrrolidin-1-yl 3-(2-(2-(3-(2,5-dioxo-2,5-dihydro-1H-pyrrol-1-yl)propanamido)ethoxy)ethoxy)propanoate with tert-butyl (2-aminoethyl)carbamate at a temperature between about 0° C. and about 25° C.

In some embodiments, the method further comprises providing Compound B by reacting PHF with methyl 3-isocyanatopropanoate to form a methyl ester of Compound B and converting the methyl ester to Compound B.

In some embodiments, the PHF has a molecular weight ranging from about 5 kDa to about 10 kDa. In some embodiments, the PHF has a molecular weight ranging from about 6 kDa to about 8 kDa.

In some embodiments, the PHF has a molecular weight ranging from about 6 kDa to about 7 kDa.

In some embodiments, the method further comprises purifying Compound B such that Compound B thus purified has a molecular weight ranging from about 6 kDa to about 13 kDa, and n is about 26-34% of the sum of m and n. In some embodiments, Compound B thus purified has a molecular weight ranging from about 7 kDa to about 12 kDa, and n is about 29-33% of the sum of m and n. In some embodiments, Compound B thus purified has a molecular weight ranging from about 10 kDa to about 12 kDa.

In some embodiments, Compound B is purified with a weak anion exchange chromatography separation. In some embodiments, the weak anion exchange column separation is performed with a mobile phase comprising a sodium phosphate buffer. In some embodiments, prior to the weak anion exchange chromatography separation, compound B is purified with one or more filtrations, one or more tangential flow filtrations, one or more diafiltration, one or more ultrafiltration, one or more nanofiltrations, or combinations thereof. In some embodiments, prior to the weak anion exchange chromatography separation, compound B is purified with one or more non-adsorptive chromatography separations.

In some embodiments, the method further comprises providing Compound C or a salt thereof by deprotecting a protected form of Compound C. In some embodiments, the protected form of Compound C is ("Compound CC")

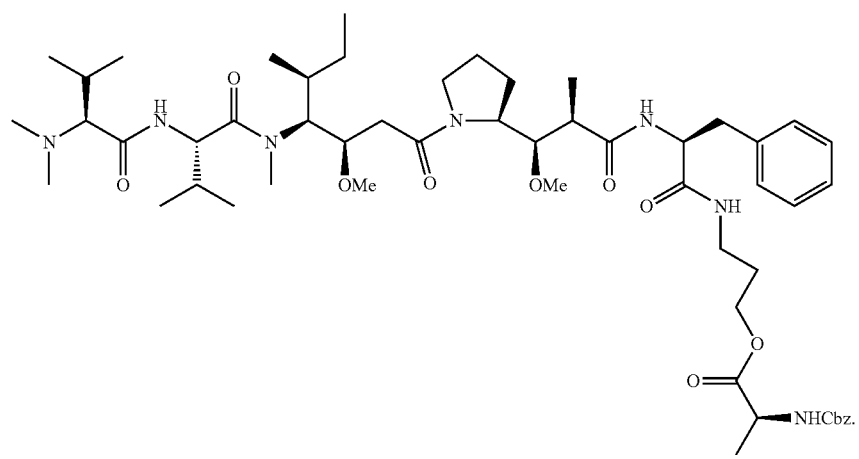

In some embodiments, the salt of Compound C is a trifluoroacetate salt.

In some embodiments, at least one of the non-adsorptive chromatography separations is performed with a column comprising cross-liked dextran. In some embodiments, at least one of the non-adsorptive chromatography separations is performed with a Sephadex column. In some embodiments, at least one of the non-adsorptive chromatography separations is performed with a Sephadex G-25 column.

In some embodiments, at least one of the tangential flow filtrations is performed with a membrane having a molecular weight cutoff between about 650 Da and 1000 Da. In some embodiments, the membrane has a molecular weight cutoff at about 650 Da. In some embodiments, at least one of the filtrations is performed with a membrane having a molecular weight cutoff between about 50 kDa and 100 kDa to obtain a permeate that contains the scaffold of Formula (A) or the salt thereof.

In some embodiments, at least one of the nanofiltrations is performed with a membranes of molecular weight cut off between 1000 Da to 4000 Da. In some embodiments, the membrane has a molecular weight cutoff at about 3500 Da.

In some embodiments, the scaffold of Formula (A) or the salt thereof thus produced has a purity of at least 75%, 80%, 85%, 90%, about 95%, about 98%, or about 99%. In some embodiments, the scaffold of Formula (A) or the salt thereof thus produced has a purity of at least 75%. In some embodiments, the scaffold of Formula (A) or the salt thereof thus produced has a purity of at least 80%. In some embodiments, the scaffold of Formula (A) or the salt thereof thus produced has a purity of at least 85%. In some embodiments, the scaffold of Formula (A) or the salt thereof thus produced has a purity of at least 90%. In some embodiments, the scaffold of Formula (A) or the salt thereof thus produced has a purity of at least 95%, In some embodiments, the scaffold of Formula (A) or the salt thereof thus produced has a purity of at least 98%. In some embodiments, the scaffold of Formula (A) or the salt thereof thus produced has a purity of at least 99%.

In some embodiments, the scaffold of Formula (A) or salt thereof is produced at a large scale. In some embodiments, at least 100 g of the scaffold of Formula (A) or salt thereof is produced in a single batch. In some embodiments, at least 200 g, 500 g, 1 kg, 1.5 kg, 2 kg, or 2.5 kg of the scaffold of Formula (A) or salt thereof is produced in a single batch. In some embodiments, at least 200 g of the scaffold of Formula (A) or salt thereof is produced in a single batch. In some embodiments, at least 500 g of the scaffold of Formula (A) or salt thereof is produced in a single batch. In some embodiments, at least 1 kg of the scaffold of Formula (A) or salt thereof is produced in a single batch. In some embodiments, at least 1.5 kg of the scaffold of Formula (A) or salt thereof is produced in a single batch. In some embodiments, at least 2 kg of the scaffold of Formula (A) or salt thereof is produced in a single batch. In some embodiments, at least 2.5 kg of the scaffold of Formula (A) or salt thereof is produced in a single batch.

In another aspect, the disclosure relates to a method of making a PBRM-polymer-drug conjugate, the method comprising:

(1) providing a polymeric scaffold of Formula (A) or a salt thereof and a reduced PBRM;

(2) adding the reduced PBRM to the polymeric scaffold of Formula (A) or the salt thereof to form a third reaction mixture comprising a PBRM-polymer-drug conjugate of Formula (B):

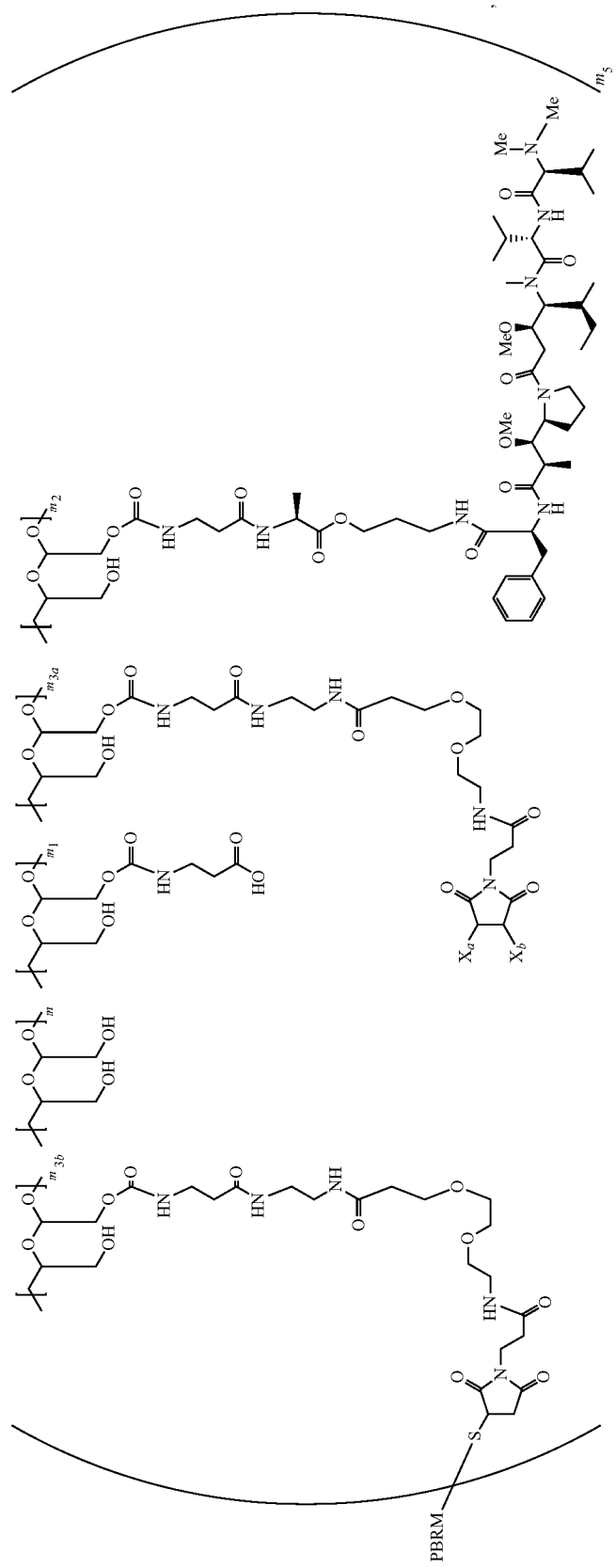

wherein:

one of $X_a$ and $X_b$ is H and the other is a water-soluble maleimido blocking moiety, or $X_a$ and $X_b$, together with the carbon atoms to which they are attached form a carbon-carbon double bond;

the PHF has a molecular weight ranging from about 5 kDa to about 10 kDa;

m is an integer from 20 to 75, $m_1$ is an integer from about 5 to about 35, $m_2$ is an integer from about 3 to about 10, $m_{3a}$ is an integer from 0 to about 4, $m_{3b}$ is an integer from 1 to about 5, the sum of m, $m_1$, $m_2$, $m_{3a}$, and $m_{3b}$ ranges from about 40 to about 75, and $m_5$ is an integer from 2 to about 4.

In some embodiments, the polymeric scaffold of Formula (A) or the salt thereof is prepared by performing a method of the disclosure.

In some embodiments, the reduced PBRM is prepared by reacting a PBRM with a reducing agent. In some embodiments, the PBRM is reacted with the reducing agent at a molar ratio ranging from about 1:2 to about 1:4 and, optionally, at a molar ratio of about 1:2.4, about 1:2.5, about 1:3.0, or about 1:3.5.

In some embodiments, one or more disulfide bonds of the PBRM are reduced by the reducing agent to one or more thiol groups.

In some embodiments, the reducing agent is tris(2-carboxyethyl)phosphine (TCEP) or a salt thereof. In some embodiments, the reducing agent is tris(2-carboxyethyl) phosphine (TCEP) hydrochloride.

In some embodiments, the polymeric scaffold of Formula (A) or the salt thereof is reacted with the reduced PBRM at a weight ratio ranging from about 0.5:1 to about 1.2:1. In some embodiments, the polymeric scaffold of Formula (A) or the salt thereof is reacted with the reduced PBRM at a weight ratio of about 0.7:1 to about 0.95:1.

In some embodiments, the reaction of the polymeric scaffold of Formula (A) or the salt thereof with the reduced PBRM is terminated by adding a maleimido blocking compound. In some embodiments, the maleimido blocking compound is selected from the group consisting of cysteine, N-acetyl cysteine, cysteine methyl ester, N-methyl cysteine, 2-mercaptoethanol, 3-mercaptopropanoic acid, 2-mercaptoacetic acid, mercaptomethanol, benzyl thiol, and salts thereof. In some embodiments, the maleimido blocking compound is cysteine.

In some embodiments, the method further comprises comprising isolating the PBRM-polymer-drug conjugate of Formula (B) from the third reaction mixture. In some embodiments, the PBRM-polymer-drug conjugate of Formula (B) is isolated with a chromatography separation. In some embodiments, the PBRM-polymer-drug conjugate of Formula (B) is isolated with an ion exchange chromatography separation.

In some embodiments, the PBRM-polymer-drug conjugate of Formula (B) is isolated with a strong cation exchange (SCX) chromatography separation. In some embodiments, the strong cation exchange chromatography separation is performed with a mobile phase comprising sodium acetate, sodium chloride, or a combination thereof. In some embodiments, the mobile phase has a pH value ranging from about 5 to about 7. In some embodiments, the mobile phase has a pH value ranging from about 5.5 to about 6.5. In some embodiments, the mobile phase has a pH value of about 5.8 to about 5.9.

In some embodiments, the strong cation exchange chromatography separation removes one or more acidic fractions, as determined by analytical HPLC WCX chromatography, with high AF HPA to PBRM ratio from the third reaction mixture. In some embodiments, the strong cation exchange chromatography separation removes one or more basic fractions, as determined by analytical HPLC WCX chromatography, with low AF HPA to PBRM ratio from the third reaction mixture. In some embodiments, the strong cation exchange chromatography separation removes one or more aggregated species from the third reaction mixture. In some embodiments, the strong cation exchange chromatography separation removes unreacted PBRM species from the third reaction mixture.

In some embodiments, one or more main fractions eluting between the acidic (e.g., early eluting) and basic (e.g., late eluting) fractions, as determined by analytical HPLC WCX chromatography, with the desired AF HPA to PBRM ratio are collected during the strong cation exchange chromatography separation, thereby providing the PBRM-polymer-drug conjugate of Formula (B) thus purified.

In some embodiments, the PBRM-polymer-drug conjugate of Formula (B) thus produced comprises auristatin F hydroxylpropylamide (AF HPA) and PBRM at a ratio ranging from about 20:1 to about 6:1. In some embodiments, the ratio between AF HPA and PBRM is about 20:1, about 19:1, about 18:1, about 17:1, about 16:1, about 15:1, about 14:1, about 13:1, about 12:1, about 11:1, about 10:1, about 9:1, about 8:1, about 7:1, or about 6:1. In some embodiments, the ratio between AF HPA and PBRM is about 10:1 to about 15:1. In some embodiments, the ratio between AF HPA and PBRM is about 10:1 to about 12:1. In some embodiments, the ratio between AF HPA and PBRM is about 12:1 to about 15:1. In some embodiments, the PBRM-polymer-drug conjugate of Formula (B) thus produced comprises AF HPA and PHF at a ratio ranging from about 6:1 to about 2:1. In some embodiments, the ratio between AF HPA and PHF is about 6:1, about 5:1, about 4:1, about 3:1, or about 2:1. In some embodiments, the ratio between AF HPA and PHF is about 4:1.

In some embodiments, the PBRM-polymer-drug conjugate of Formula (B) thus produced comprises PHF and PBRM at a ratio ranging from about 6:1 to about 2:1. In some embodiments, the ratio between PHF and PBRM is about 6:1, about 5:1, about 4:1, about 3:1, or about 2:1. In some embodiments, the ratio between PHF and PBRM is about 4:1. In some embodiments, the ratio between PHF and PBRM is about 3:1.

In some embodiments, the PBRM-polymer-drug conjugate of Formula (B) thus produced has a purity of at least about 75%, about 80%, about 85%, about 90%, about 95%, about 98%, or about 99%. In some embodiments, the PBRM-polymer-drug conjugate of Formula (B) thus produced has a purity of at least about 80%. In some embodiments, the PBRM-polymer-drug conjugate of Formula (B) thus produced has a purity of at least about 85%. In some embodiments, the PBRM-polymer-drug conjugate of Formula (B) thus produced has a purity of at least about 90%. In some embodiments, the PBRM-polymer-drug conjugate of Formula (B) thus produced has a purity of at least about 95%. In some embodiments, the PBRM-polymer-drug conjugate of Formula (B) thus produced has a purity of at least about 98%. In some embodiments, the PBRM-polymer-drug conjugate of Formula (B) thus produced has a purity of at least about 99%.

In some embodiments, the PBRM-polymer-drug conjugate of Formula (B) is produced at a large scale. In some embodiments, at least 200 g, 500 g, 1 kg, 1.5 kg, 2 kg, or 2.5 kg of the PBRM-polymer-drug conjugate of Formula (B) is produced in a single batch. In some embodiments, at least 200 g of the PBRM-polymer-drug conjugate of Formula (B) is produced in a single batch. In some embodiments, at least 500 g of the PBRM-polymer-drug conjugate of Formula (B) is produced in a single batch. In some embodiments, at least 1 kg of the PBRM-polymer-drug conjugate of Formula (B) is produced in a single batch. In some embodiments, at least 1.5 kg of the PBRM-polymer-drug conjugate of Formula (B) is produced in a single batch. In some embodiments, at least 2 kg of the PBRM-polymer-drug conjugate of Formula (B) is produced in a single batch. In some embodiments, at least 2.5 kg of the PBRM-polymer-drug conjugate of Formula (B) is produced in a single batch.

In yet another aspect, the disclosure relates to a polymeric scaffold of Formula (A) or a salt thereof prepared by a method of the disclosure.

In yet another aspect, the disclosure relates to a PBRM-polymer-drug conjugate of Formula (B) prepared by a method of the disclosure.

In yet another aspect, the disclosure relates to a method of making a pharmaceutical composition comprising PBRM-polymer-drug conjugate, the method comprising:

(1) providing a PBRM-polymer-drug conjugate of Formula (B); and (2) adding one or more pharmaceutically acceptable excipients to the PBRM-polymer-drug conjugate of Formula (B) to form the pharmaceutical composition.

In some embodiments, the PBRM-polymer-drug conjugate of Formula (B) is prepared by performing a method of the disclosure.

In yet another aspect, the disclosure relates to a pharmaceutical composition comprising a PBRM-polymer-drug conjugate of Formula (B) prepared a method of the disclosure.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

One of the advantages of the methods described herein is improvement in the yield and purity of the drug-carrying polymeric scaffolds and conjugates thereof without cumbersome purification steps. For example, the reaction product from Compounds A and B does not need to be worked up before Compound C or a salt thereof is added. Another advantage is that the methods of producing the drug-carrying polymeric scaffolds are readily scalable to produce a single batch of at least 100 g. Yet another advantage is that the protein-polymer-drug conjugates (e.g., PBRM-polymer-drug conjugates) or the drug-carrying polymeric scaffolds made by the methods described herein are substantively free of endotoxins and are substantively homogeneous. Other features and advantages of the methods, scaffolds and conjugates described herein will be apparent from the following detailed description and claims.

DETAILED DESCRIPTION

The present disclosure provides novel synthetic methods for making the drug-carrying polymeric scaffolds and PBRM conjugates thereof.

The present disclosure also provides drug-carrying polymeric scaffolds and conjugates thereof that are produced by the synthetic methods described herein.

The present disclosure also provides methods of preparing and/or purifying a polymeric scaffold, which is useful to conjugate with a protein based recognition-molecule (PBRM).

The present disclosure also provides methods of preparing and/or purifying such conjugates comprising a polymeric scaffold and a PBRM.

Further, the present disclosure also provides protein-polymer-drug conjugates (e.g., PBRM-polymer-drug conjugates) that are of substantially high purity and can be prepared by avoiding cumbersome steps with reduced time and costs.

Definitions/Terminology

Certain compounds of the present disclosure and definitions of specific functional groups are also described in more detail herein. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups.

The use of the articles "a", "an", and "the" in both the following description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. For example, a polymeric scaffold of a certain formula includes all the monomer units shown in the formula and may also include additional monomer units not shown in the formula. Additionally whenever "comprising" or another open-ended term is used in an embodiment, it is to be understood that the same embodiment can be more narrowly claimed using the intermediate term "consisting essentially of" or the closed term "consisting of."

The term "about", "approximately", or "approximate", when used in connection with a numerical value, means that a collection or range of values is included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the expressions "x being an integer between 1 and 6" and "x being an integer of 1 to 6" both mean "x being 1, 2, 3, 4, 5, or 6", i.e., the terms "between X and Y" and "range from X to Y, are inclusive of X and Y and the integers there between.

All methods described herein can be performed in any suitable order unless otherwise indicated herein or otherwise clearly contradicted by context. The use of any and all examples, or exemplary language (e.g., "such as") provided herein, is intended merely to better illustrate the invention and is not to be construed as a limitation on the scope of the claims unless explicitly otherwise claimed. No language in the specification is to be construed as indicating that any non-claimed element is essential to what is claimed.

"Antibody" refers to a full-length antibody or functional fragment of an antibody comprising an immunoglobulin. By a "functional fragment" it is meant a sufficient portion of the immunoglobulin or antibody is provided that the moiety effectively binds or complexes with the cell surface molecule for its target cell population, e.g., human oncofetal antigen.

As used herein, a human oncofetal antigen includes, e.g., tumor associated proteins such as alpha fetoprotein, carcinoembryonic antigen, prostate specific antigen, and oncofetal antigen protein (also known as immature laminin receptor protein, and which has been associated with, e.g., bowel and renal carcinomas).

An immunoglobulin may be purified, generated recombinantly, generated synthetically, or combinations thereof, using techniques known to those of skill in the art. While immunoglobulins within or derived from IgG antibodies are particularly well-suited for use in this disclosure, immunoglobulins from any of the classes or subclasses may be selected, e.g., IgG, IgA, IgM, IgD and IgE. Suitably, the immunoglobulin is of the class IgG including but not limited to IgG subclasses (IgG1, 2, 3 and 4) or class IgM which is able to specifically bind to a specific epitope on an antigen. Antibodies can be intact immunoglobulins derived from natural sources or from recombinant sources and can be immunoreactive portions of intact immunoglobulins. Antibodies may exist in a variety of forms including, for example, polyclonal antibodies, monoclonal antibodies, camelized single domain antibodies, intracellular antibodies ("intrabodies"), recombinant antibodies, anti-idiotypic antibodies, domain antibodies, linear antibody, multispecific antibody, antibody fragments, such as, Fv, Fab, F(ab)$_2$, F(ab)$_3$, Fab', Fab'-SH, F(ab')2, single chain variable fragment antibodies (scFv), tandem/bis-scFv, Fc, pFc', scFvFc (or scFv-Fc), disulfide Fv (dsfv), bispecific antibodies (bc-scFv) such as BiTE antibodies; camelid antibodies, resurfaced antibodies, humanized antibodies, fully human antibodies, single-domain antibody (sdAb, also known as NANOBODY®), chimeric antibodies, chimeric antibodies comprising at least one human constant region, dual-affinity antibodies such as, dual-affinity retargeting proteins (DART™), divalent (or bivalent) single-chain variable fragments (di-scFvs, bi-scFvs) including but not limited to minibodies, diabodies, triabodies or tribodies, tetrabodies, and the like, and multivalent antibodies. "Antibody fragment" refers to at least a portion of the variable region of the immunoglobulin molecule that binds to its target, i.e., the antigen-binding region. As used herein, the term "antibody" refers to both the full-length antibody and antibody fragments unless otherwise specified.

"Protein based recognition-molecule" or "PBRM" refers to a molecule that recognizes and binds to a cell surface marker or receptor such as, a transmembrane protein, surface immobilized protein, or protoglycan. Examples of PBRMs include but are not limited to, antibodies (e.g., Trastuzumab, Cetuximab, Rituximab, Bevacizumab, Epratuzumab, Veltuzumab, Labetuzumab, B7-H4, B7-H3, CA125, CD33, CXCR2, EGFR, FGFR1, FGFR2, FGFR3, FGFR4, HER2, NaPi2b, c-Met, NOTCH1, NOTCH2, NOTCH3, NOTCH4, PD-L1, c-Kit, MUC1 and anti-5T4) or peptides (LHRH receptor targeting peptides, EC-1 peptide), lipocalins, such as, for example, anticalins, proteins such as, for example, interferons, lymphokines, growth factors, colony stimulating factors, and the like, peptides or peptide mimics, and the like. The protein based recognition molecule, in addition to targeting the modified polymer conjugate to a specific cell, tissue or location, may also have certain therapeutic effect such as antiproliferative (cytostatic and/or cytotoxic) activity against a target cell or pathway. The protein based recognition molecule comprises or may be engineered to comprise at least one chemically reactive group such as, —COOH, primary amine, secondary amine —NHR, —SH, or a chemically reactive amino acid moiety or side chains such as, for example, tyrosine, histidine, cysteine, or lysine. In one embodiment, a PBRM may be a ligand (LG) or targeting moiety which specifically binds or complexes with a cell surface molecule, such as a cell surface receptor or antigen, for a given target cell population. Following specific binding or complexing of the ligand with its receptor, the cell is permissive for uptake of the ligand or ligand-drug-conjugate, which is then internalized into the cell. As used herein, a ligand that "specifically binds or complexes with" or "targets" a cell surface molecule preferentially associates with a cell surface molecule via intermolecular forces. For example, the ligand can preferentially associate with the cell surface molecule with a Kd of less than about 50 nM, less than about 5 nM, or less than 500 pM. Techniques for measuring binding affinity of a ligand to a cell surface molecule are well-known; for example, one suitable technique, is termed surface plasmon resonance (SPR). In one embodiment, the ligand is used for targeting and has no detectable therapeutic effect as separate from the drug which it delivers. In another embodiment, the ligand functions both as a targeting moiety and as a therapeutic or immunomodulatory agent (e.g., to enhance the activity of the active drug or prodrug).

"Biocompatible" as used herein is intended to describe compounds that exert minimal destructive or host response effects while in contact with body fluids or living cells or tissues. Thus a biocompatible group, as used herein, refers to an aliphatic, cycloalkyl, heteroaliphatic, heterocycloalkyl, aryl, or heteroaryl moiety, which falls within the definition of the term biocompatible, as defined above and herein. The term "Biocompatibility" as used herein, is also taken to mean that the compounds exhibit minimal interactions with recognition proteins, e.g., naturally occurring antibodies, cell proteins, cells and other components of biological systems, unless such interactions are specifically desirable. Thus, substances and functional groups specifically intended to cause the above minimal interactions, e.g., drugs and prodrugs, are considered to be biocompatible. Preferably (with exception of compounds intended to be cytotoxic, such as, e.g., antineoplastic agents), compounds are "biocompatible" if their addition to normal cells in vitro, at concentrations similar to the intended systemic in vivo concentrations, results in less than or equal to 1% cell death during the time equivalent to the half-life of the compound in vivo (e.g., the period of time required for 50% of the compound administered in vivo to be eliminated/cleared), and their administration in vivo induces minimal and medically acceptable inflammation, foreign body reaction, immunotoxicity, chemical toxicity and/or other such adverse effects. In the above sentence, the term "normal cells" refers to cells that are not intended to be destroyed or otherwise significantly affected by the compound being tested.

"Biodegradable": As used herein, "biodegradable" polymers are polymers that are susceptible to biological processing in vivo. As used herein, "biodegradable" compounds or moieties are those that, when taken up by cells, can be broken down by the lysosomal or other chemical machinery or by hydrolysis into components that the cells can either reuse or dispose of without significant toxic effect on the cells. The term "biocleavable" as used herein has the same meaning of "biodegradable". The degradation fragments preferably induce little or no organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis of the biodegradable protein-polymer-drug conjugates (e.g., PBRM-polymer-drug conjugates) or their components (e.g., the biodegradable polymeric carrier and the linkers between the carrier and the antibody or the drug molecule) described herein, for example, include exposure of the biodegradable conjugates to water at a temperature and a pH of lysosomal intracellular compartment. Biodegradation of some protein-polymer-drug conjugates (e.g., PBRM-polymer-drug conjugates) or their components (e.g., the biodegradable polymeric carrier and the linkers between the carrier and the antibody or the drug molecule), can also be enhanced extracellularly, e.g., in low pH regions of the animal body, e.g., an inflamed area, in the close vicinity of activated macrophages or other cells releasing degradation facilitating factors. In certain preferred embodiments, the effective size of the polymer carrier at pH-7.5 does not detectably change over 1 to 7 days, and remains within 50% of the original polymer size for at least several weeks. At pH-5, on the other hand, the polymer carrier preferably detectably degrades over 1 to 5 days, and is completely transformed into low molecular weight fragments within a two-week to several-month time frame. Polymer integrity in such tests can be measured, for example, by size exclusion HPLC. Although faster degradation may be in some cases preferable, in general it may be more desirable that the polymer degrades in cells with the rate that does not exceed the rate of metabolization or excretion of polymer fragments by the cells. In preferred embodiments, the polymers and polymer biodegradation byproducts are biocompatible.

"Bioavailability": The term "bioavailability" refers to the systemic availability (i.e., blood/plasma levels) of a given amount of drug or compound administered to a subject. Bioavailability is an absolute term that indicates measurement of both the time (rate) and total amount (extent) of drug or compound that reaches the general circulation from an administered dosage form.

"Hydrophilic": The term "hydrophilic" as it relates to substituents, e.g., on the polymer monomeric units or on a maleimido blocking moiety to render them hydrophilic or water soluble, does not essentially differ from the common meaning of this term in the art, and denotes chemical moieties which contain ionizable, polar, or polarizable atoms, or which otherwise may be solvated by water molecules. Thus a hydrophilic group, as used herein, refers to an aliphatic, cycloalkyl, heteroaliphatic, heterocycloalkyl, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters and polythioesters. In certain embodiments, hydrophilic substituents comprise a carboxyl group (COOH), an aldehyde group (CHO), a ketone group ($COC_{1-4}$ alkyl), a methylol ($CH_2OH$) or a glycol (for example, $CHOH$—$CH_2OH$ or $CH$—$(CH_2OH)_2$), $NH_2$, F, cyano, $SO_3H$, POSH, and the like.

The term "hydrophilic" as it relates to the polymers of the disclosure generally does not differ from usage of this term in the art, and denotes polymers comprising hydrophilic functional groups as defined above. In a preferred embodiment, hydrophilic polymer is a water-soluble polymer. Hydrophilicity of the polymer can be directly measured through determination of hydration energy, or determined through investigation between two liquid phases, or by chromatography on solid phases with known hydrophobicity, such as, for example, C4 or C18.

"Polymeric carrier" or "polymeric scaffold": The terms "polymeric carrier" or "polymeric scaffold", as used herein, refers to a polymer or a modified polymer, which is suitable for covalently attaching to or can be covalently attached to one or more drug molecules with a designated linker and/or one or more PBRMs with a designated linker. In some embodiments, the polymer or the modified polymer is covalently attached to one or more drug molecules and/or one or more PBRMs.

"Physiological conditions": The phrase "physiological conditions", as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Polysaccharide", "carbohydrate" or "oligosaccharide": The terms "polysaccharide", "carbohydrate", or "oligosaccharide" are known in the art and refer, generally, to substances having chemical formula $(CH_2O)_n$, where generally n>2, and their derivatives. Carbohydrates are polyhydroxy aldehydes or polyhydroxy ketones, or change to such substances on simple chemical transformations, such as hydrolysis, oxidation or reduction. Typically, carbohydrates are present in the form of cyclic acetals or ketals (such as, glucose or fructose). These cyclic units (monosaccharides) may be connected to each other to form molecules with few (oligosaccharides) or several (polysaccharides) monosaccharide units. Often, carbohydrates with well-defined number, types and positioning of monosaccharide units are called oligosaccharides, whereas carbohydrates consisting of mixtures of molecules of variable numbers and/or positioning of monosaccharide units are called polysaccharides. The terms "polysaccharide", "carbohydrate", and "oligosaccharide", are used herein interchangeably. A polysaccharide may include natural sugars (e.g., glucose, fructose, galactose, mannose, arabinose, ribose, and xylose) and/or derivatives of naturally occurring sugars (e.g., 2'-fluororibose, 2"-deoxyribose, and hexose).

"Drug": As used herein, the term "drug" refers to a compound which is biologically active and provides a desired physiological effect following administration to a subject in need thereof (e.g., an active pharmaceutical ingredient).

"Prodrug": As used herein the term "prodrug" refers to a precursor of an active drug, that is, a compound that can be transformed to an active drug. Typically such a prodrug is subject to processing in vivo, which converts the drug to a physiologically active form. In some instances, a prodrug may itself have a desired physiologic effect. A desired physiologic effect may be, e.g., therapeutic, cytotoxic, immunomodulatory, or the like.

"Cytotoxic": As used herein the term "cytotoxic" means toxic to cells or a selected cell population (e.g., cancer cells). The toxic effect may result in cell death and/or lysis. In certain instances, the toxic effect may be a sublethal destructive effect on the cell, e.g., slowing or arresting cell growth. In order to achieve a cytotoxic effect, the drug or prodrug may be selected from a group consisting of a DNA damaging agent, a microtubule disrupting agent, or a cytotoxic protein or polypeptide, amongst others.

"Cytostatic": As used herein the term "cytostatic" refers to a drug or other compound which inhibits or stops cell growth and/or multiplication.

"Small molecule": As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. In certain preferred embodiments, the small molecule is a drug and the small molecule is referred to as "drug molecule" or "drug" or "therapeutic agent". In certain embodiments, the drug molecule has MW less than or equal to about 5 kDa. In other embodiments, the drug molecule has MW less than or equal to about 1.5 kDa. In embodiments, the drug molecule is selected from vinca alkaloids, auristatins, duocarmycins, kinase inhibitors, MEK inhibitors, KSP inhibitors, PI3 kinase inhibitors, calicheamicins, SN38, camptothecin, topoisomerase inhibitors, non-natural camptothecins, protein synthesis inhibitor, RNA polymerase inhibitor, pyrrolobenzodiazepines, maytansinoids, DNA-binding drugs, DNA intercalation drugs and analogs thereof. Preferably, though not necessarily, the drug is one that has already been deemed safe and effective for use by an appropriate governmental agency or body, e.g., the FDA. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered suitable for use with the present hydrophilic polymers. Classes of drug molecules that can be used in the practice of the present invention include, but are not limited to, anti-cancer substances, radionuclides, vitamins, anti-AIDS substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents. Many large molecules are also drugs and such large molecules may be used in the conjugates and other constructs described herein. Examples of suitable large molecules include, e.g., amino acid based molecules. Amino acid based molecules may encompass, e.g., peptides, polypeptides, enzymes, antibodies, immunoglobulins, or functional fragments thereof, among others.

A more complete, although not exhaustive, listing of classes and specific drugs suitable for use in the present disclosure may be found in "Pharmaceutical Substances: Syntheses, Patents, Applications" by Axel Kleemann and Jurgen Engel, Thieme Medical Publishing, 1999 and the "Merck Index: An Encyclopedia of Chemicals, Drugs, and Biologicals", Edited by Susan Budavari et al., CRC Press, 1996, both of which are incorporated herein by reference. In preferred embodiments, the drug used in this disclosure is a therapeutic agent that has antiproliferative (cytostatic and/or cytotoxic) activity against a target cell or pathway. The drug may have a chemically reactive group such as, for example, —COOH, primary amine, secondary amine —NHR, —OH, —SH, —C(O)H, —C(O)R, —C(O)NHR$^{2b}$, C(S)OH, —S(O)$_2$OR$^{2b}$, —P(O)$_2$OR$^{2b}$, —CN, —NC or —ONO, in which R is an aliphatic, heteroaliphatic, carbocyclic or heterocycloalkyl moiety and R$^{2b}$ is a hydrogen, an aliphatic, heteroaliphatic, carbocyclic, or heterocyclic moiety.

"Drug derivative" or "modified drug" or the like as used herein, refers to a compound that comprises the drug molecule intended to be delivered by the conjugate of the disclosure and a functional group capable of attaching the drug molecule to the polymeric carrier.

"Active form" as used herein refers to a form of a compound that exhibits intended pharmaceutical efficacy in vivo or in vitro. In particular, when a drug molecule intended to be delivered by the conjugate of the disclosure is released from the conjugate, the active form can be the drug itself or its derivatives, which exhibit the intended therapeutic properties. The release of the drug from the conjugate can be achieved by cleavage of a biodegradable bond of the linker which attaches the drug to the polymeric carrier. The active drug derivatives accordingly can comprise a portion of the linker.

"Diagnostic label": As used herein, the term diagnostic label refers to an atom, group of atoms, moiety or functional group, a nanocrystal, or other discrete element of a composition of matter, that can be detected in vivo or ex vivo using analytical methods known in the art. When associated with a conjugate of the present disclosure, such diagnostic labels permit the monitoring of the conjugate in vivo. Alternatively or additionally, constructs and compositions that include diagnostic labels can be used to monitor biological functions or structures. Examples of diagnostic labels include, without limitation, labels that can be used in medical diagnostic procedures, such as, radioactive isotopes (radionuclides) for gamma scintigraphy and Positron Emission Tomography (PET), contrast agents for Magnetic Resonance Imaging (MM) (for example paramagnetic atoms and superparamagnetic nanocrystals), contrast agents for computed tomography and other X-ray-based imaging methods, agents for ultrasound-based diagnostic methods (sonography), agents for neutron activation (e.g., boron, gadolinium), fluorophores for various optical procedures, and, in general moieties which can emit, reflect, absorb, scatter or otherwise affect electromagnetic fields or waves (e.g., gamma-rays, X-rays, radiowaves, microwaves, light), particles (e.g., alpha particles, electrons, positrons, neutrons, protons) or other forms of radiation, e.g., ultrasound.

"Conjugate": The term "conjugate", as used herein, refers to a polymer or a modified polymer covalently attaching to, or being covalently attached to, one or more drug molecules with a designated linker and/or one or more PBRMs with a designated linker.

The following are more general terms used throughout the present application:

"Animal": The term animal, as used herein, refers to humans as well as non-human animals, at any stage of development, including, for example, mammals, birds, reptiles, amphibians, fish, worms and single cells. Cell cultures and live tissue samples are considered to be pluralities of animals. Preferably, the non-human animal is a mammal (e.g., a rodent, a mouse, a rat, a rabbit, a monkey, a dog, a cat, a primate, or a pig). An animal may be a transgenic animal or a human clone. The term "subject" encompasses animals.

"Efficient amount": In general, as it refers to an active agent or drug delivery device, the term "efficient amount" refers to the amount necessary to elicit the desired biological response. As will be appreciated by those of ordinary skill in this art, the efficient amount of an agent or device may vary depending on such factors as the desired biological endpoint, the agent to be delivered, the composition of the encapsulating matrix, the target tissue, etc. For example, the efficient amount of microparticles containing an antigen to be delivered to immunize an individual is the amount that results in an immune response sufficient to prevent infection with an organism having the administered antigen.

"PHF" refers to poly(1-hydroxymethylethylene hydroxymethyl-formal).

As used herein, the terms "polymer unit", "monomeric unit", "monomer", "monomer unit", "unit" all refer to a repeatable structural unit in a polymer.

As used herein, "molecular weight" or "MW" of a polymer or polymeric carrier/scaffold or polymer conjugates refers to the weight average molecular weight unless otherwise specified.

"Non-adsorptive chromatography" refers to chromatography using a non-adsorptive resin, including, but not limited to, Sephadex G-25, G-50, G-100, Sephacryl resin (e.g. S-200 and S-300), Superdex resin (e.g. Superdex 75 and Superdex 200), Bio-gel resins (e.g. P-6, P-10, P-30, P-60 and P-100) and others known to those skilled in the art.

The present disclosure is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present disclosure is intended to include all isomers of the compound, which refers to and includes, optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers.

Polymeric Carriers

In certain exemplary embodiments, the conjugates of the disclosure find use in biomedical applications, such as drug delivery and tissue engineering, and the carrier is biocompatible and biodegradable. In certain embodiments, the carrier is a soluble polymer, nanoparticle, gel, liposome, micelle, suture, implant, etc. In certain embodiments, the term "soluble polymer" encompasses biodegradable biocompatible polymer such as a polyal (e.g., hydrophilic polyacetal or polyketal). In certain other embodiments, the carrier is a fully synthetic, semi-synthetic or naturally-occurring polymer. In certain other embodiments, the carrier is hydrophilic.

In certain exemplary embodiments, the carriers used in the present disclosure are biodegradable biocompatible polyals comprising at least one hydrolysable bond in each monomer unit positioned within the main chain. This ensures that the degradation process (via hydrolysis/cleavage of the monomer units) will result in fragmentation of the polymer conjugate to the monomeric components (i.e., degradation), and confers to the polymer conjugates of the disclosure their biodegradable properties. The properties (e.g., solubility, bioadhesivity and hydrophilicity) of biodegradable biocompatible polymer conjugates can be modified by subsequent substitution of additional hydrophilic or hydrophobic groups. Examples of biodegradable biocompatible polymers suitable for practicing the invention can be found inter alia in U.S. Pat. Nos. 5,811,510; 5,863,990; 5,958,398; 7,838,619 and 7,790,150; each of the above listed patent documents is incorporated herein by reference in its entirety. Guidance on the significance, preparation, and applications of this type of polymers may be found in the above-cited documents. In certain embodiments, it is anticipated that the present invention will be particularly useful in combination with the above-referenced patent documents, as well as U.S. Pat. Nos. 5,582,172 and 6,822,086, each of the above listed patent documents is incorporated herein by reference in its entirety.

The conjugates of this disclosure are hydrophilic, hydrolysable and comprise drug molecules (e.g., vinca alkaloids or derivatives, topoisomerase inhibitors, such as, for example, SN38, camptothecin, topotecan, exatecan, non-natural camptothecin compounds or derivatives; auristatins, dolastatins, nemorubicine and its derivatives, PNU-159682, anthracycline, duocarmycins, kinase inhibitors (e.g., PI3 kinase inhibitors or MEK inhibitors), KSP inhibitors, calicheamicins, pyrrolobenzodiazepines, maytansinoids, elinafide, DNA-binding drugs, DNA intercalation drugs, and stereoisomers, isosteres, analogs and derivatives thereof) and antibodies (e.g., Trastuzumab, Cetuximab, Rituximab, Bevacizumab, Epratuzumab, Veltuzumab, Labetuzumab, B7-H4, B7-H3, CA125, CD33, CXCR2, EGFR, FGFR1, FGFR2, FGFR3, FGFR4, HER2, NaPi2b, c-Met, NOTCH1, NOTCH2, NOTCH3, NOTCH4, PD-L1, NaPi2b, c-Kit, MUC1, and anti-5T4) or peptides (LHRH receptor targeting peptides, EC-1 peptide) covalently attached to the polymer carrier via linkages that contain one or more biodegradable bonds. Thus, in certain exemplary embodiments, carriers suitable for practicing the present invention are polyals having at least one acetal/ketal oxygen atom in each monomer unit positioned within the main chain. As discussed above, this ensures that the degradation process (via hydrolysis/cleavage of the polymer acetal/ketal groups) will result in fragmentation of the polyal conjugate to low molecular weight components (i.e., degradation). In certain embodiments, biodegradable biocompatible polymer carriers, used for preparation of polymer conjugates of the disclosure, are naturally occurring polysaccharides, glycopolysaccharides, and synthetic polymers of polyglycoside, polyacetal, polyamide, polyether, and polyester origin and products of their oxidation, fictionalization, modification, cross-linking, and conjugation.

In certain other embodiments, the carrier is a hydrophilic biodegradable polymer selected from the group consisting of carbohydrates, glycopolysaccharides, glycolipids, glycoconjugates, polyacetals, polyketals, and derivatives thereof.

In certain exemplary embodiments, the carrier is a naturally occurring linear and/or branched biodegradable biocompatible homopolysaccharide selected from the group consisting of cellulose, amylose, dextran, levan, fucoidan, carraginan, inulin, pectin, amylopectin, glycogen and lixenan.

In certain other exemplary embodiments, the carrier is a naturally occurring linear and branched biodegradable biocompatible heteropolysaccharide selected from the group consisting of agarose, hyluronan, chondroitinsulfate, dermatansulfate, keratansulfate, alginic acid and heparin.

In yet other exemplary embodiments, the polymeric carrier comprises a copolymer of a polyacetal/polyketal and a hydrophilic polymer selected from the group consisting of polyacrylates, polyvinyl polymers, polyesters, polyorthoesters, polyamides, polypeptides, and derivatives thereof.

In yet another embodiment, the polymeric carrier is dextran that is produced by the hydrolysis of a starch obtained from various natural products such as, for example, wheat, rice, maize and tapioca. Depending on the structure of the starch starting material each dextran comprises a unique distribution of α-1,4 linkages and α-1,6 linkages. Since the rate of biodegradability of α-1,6 linkages is typically less than that for α-1,4 linkages, preferably the percentage of α-1,4 linkages is less than 10% and more preferably less than 5%. In one embodiment the molecular weight of the dextran is in the range of about 2 kDa to about 40 kDa, more preferably from about 2 kDa to about 20 kDa, or from about 3 kDa to about 15 kDa or from about 5 kDa to about 10 kDa or about 6.6 kDa.

In certain embodiments, the carrier comprises polysaccharides activated by selective oxidation of cyclic vicinal diols of 1,2-, 1,4-, 1,6-, and 2,6-pyranosides, and 1,2-, 1,5-, 1,6-furanosides, or by oxidation of lateral 6-hydroxy and 5,6-diol containing polysaccharides prior to conjugation with drug molecules or PBRMs.

In still other embodiments, the polymeric carrier comprises a biodegradable biocompatible polyacetal wherein at least a subset of the polyacetal repeat structural units have the following chemical structure:

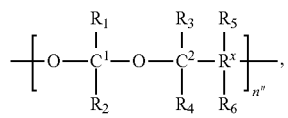

wherein for each occurrence of the n bracketed structure, one of $R_1$ and $R_2$ is hydrogen, and the other is a biocompatible group and includes a carbon atom covalently attached to $C^1$; $R^x$ is a carbon atom covalently attached to $C^2$; n" is an integer; each occurrence of $R_3$, $R_4$, $R_5$ and $R_6$ is a biocompatible group and is independently hydrogen or an organic moiety; and for each occurrence of the bracketed structure n, at least one of $R_1$, $R_2$, $R_3$, $R_4$, $R_5$ and $R_6$ comprises a functional group suitable for coupling. In certain embodiments, the functional group is a hydroxyl moiety.

In one embodiment, the polymeric carrier comprises activated hydrophilic biodegradable biocompatible polymers comprising from 0.1% to 100% polyacetal moieties whose backbone is represented by the following chemical structure:

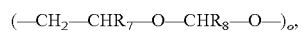

wherein:

$R_7$ and $R_8$ are independently hydrogen, hydroxyl, hydroxy alkyl (e.g., —CH$_2$OH, —CH(OH)—CH(OH), —CHO, —CH(OH)—CHO or -carbonyl; and o is an integer from 20 to 2000.

In yet other embodiments, the polymeric carrier comprises a biodegradable biocompatible polyketal wherein at least a subset of the polyketal repeatable structural units have the following chemical structure:

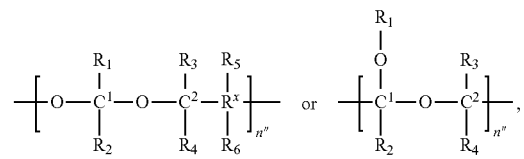

wherein each occurrence of $R_1$ and $R_2$ is a biocompatible group and $R^x$, $R_3$, $R_4$, $R_5$, $R_6$ and are as defined herein.

In certain embodiments, the ketal units are monomers of Formula (IIa) or (IIb):

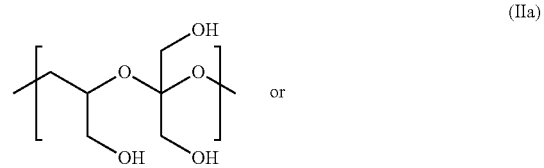

(IIa)

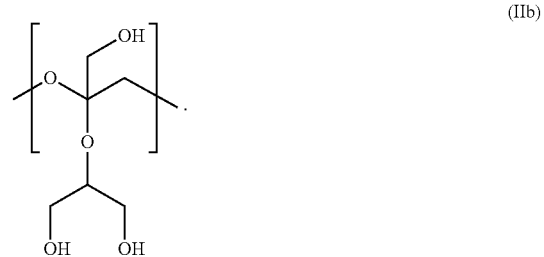

(IIb)

Biodegradable, biocompatible polyketal polymers and their methods of making have been described in U.S. Pat. Nos. 5,811,510, 7,790,150 and 7,838,619, which are hereby incorporated by reference in their entireties.

In one embodiment, the polymeric carrier can be obtained from partially oxidized dextran (☐1→6)-D-glucose) followed by reduction. In this embodiment, the polymer comprises a random mixture of the unmodified dextran (A), partially oxidized dextran acetal units (B) and exhaustively dextran acetal units (C) of the following structures:

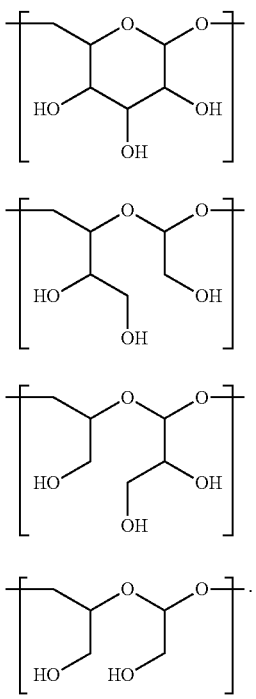

(A)

(B)

(B)

(C)

In another embodiment, the polymeric carrier comprises unmodified acetal units, i.e., polyacetal segments. In some embodiments, the polyacetals can be derived from exhaustively oxidized dextran followed by reduction. These polymers have been described in references, see, e.g., U.S. Pat. No. 5,811,510, which is hereby incorporated by reference for its description of polyacetals at column 2, line 65 to column 8, line 55 and their synthesis at column 10, line 45 to column 11, line 14. In one embodiment, the unmodified polyacetal polymer is a poly(hydroxymethylethylene hydroxymethyl formal) polymer (PHF).

In addition to poly(hydroxymethylethylene hydroxymethyl formal) polymers, the backbone of the polymeric carrier can also comprise co-polymers of poly(hydroxymethylethylene hydroxymethyl formal) blocks and other acetal or non-acetal monomers or polymers. For example, polyethylene glycol polymers are useful as a stealth agent in the polymer backbone because they can decrease interactions between polymer side chains of the appended functional groups. Such groups can also be useful in limiting interactions such as between serum factors and the modified polymer. Other stealth agent monomers for inclusion in the polymer backbone include, for example, ethyleneimine, methacrylic acid, acrylamide, glutamic acid, and combinations thereof.

The acetal or ketal units are present in the modified polymer in an amount effective to promote biocompatibility. The unmodified acetal or ketal unit can be described as a "stealth agent" that provides biocompatibility and solubility to the modified polymers. In addition, conjugation to a polyacetal or polyketal polymer can modify the susceptibility to metabolism and degradation of the moieties attached to it, and influence biodistribution, clearance and degradation.

The unmodified acetal units are monomers of Formula (III):

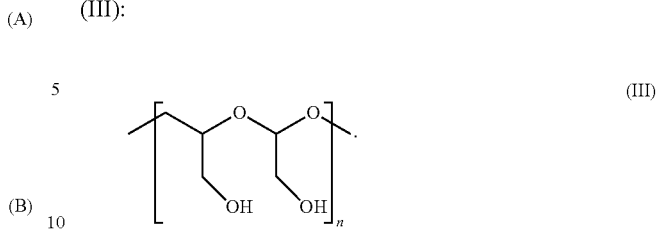

The molar fraction, n, of unmodified polyacetal units is the molar fraction available to promote biocompatibility, solubility and increase half-life, based on the total number of polymer units in the modified polymer. The molar fraction n may be the minimal fraction of unmodified monomer acetal units needed to provide biocompatibility, solubility, stability, or a particular half-life, or can be some larger fraction. The most desirable degree of cytotoxicity is substantially none, i.e., the modified polymer is substantially inert to the subject. However, as is understood by those of ordinary skill in the art, some degree of cytotoxicity can be tolerated depending on the severity of disease or symptom being treated, the efficacy of the treatment, the type and degree of immune response, and like considerations.

In one embodiment, the modified polymer backbone comprises units of Formula (IV):

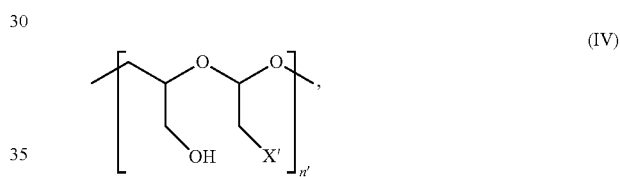

wherein X' indicates the substituent for the hydroxyl group of the polymer backbone. As shown in Formula (IV) and the other formulae described herein, each polyacetal unit has a single hydroxyl group attached to the glycerol moiety of the unit and an X' group (or another substituent such as -$L^D$-D attached to the glycolaldehyde moiety of the unit. This is for convenience only and it should be construed that the polymer having units of Formula (IV) and other formulae described herein can contain a random distribution of units having a X' group (or another substituent such as a linker comprising a maleimide terminus) attached to the glycolaldehyde moiety of the units and those having a single X' group (or another substituent such as a linker comprising a maleimide terminus) attached to the glycerol moiety of the units as well as units having two X' groups (or other substituents such as a linker comprising a maleimide terminus) with one attached to the glycolaldehyde moiety and the other attached to the glycerol moiety of the units.

In one embodiment, biodegradable biocompatible polyals suitable for practicing the present invention have a molecular weight of between about 0.5 and about 300 kDa. For example, the biodegradable biocompatible polyals have a molecular weight of between about 1 and about 300 kDa (e.g., between about 1 and about 200 kDa, between about 2 and about 300 kDa, between about 2 and about 200 kDa, between about 5 and about 100 kDa, between about 10 and about 70 kDa, between about 20 and about 50 kDa, between about 20 and about 300 kDa, between about 40 and about 150 kDa, between about 50 and about 100 kDa, between about 2 and about 40 kDa, between about 6 and about 20 kDa, or between about 8 and about 15 kDa). For example, the biodegradable biocompatible polyal used for the polymer scaffold or conjugate of the disclosure is PHF having a molecular weight of between about 2 and about 40 kDa (e.g., about 2-20 kDa, 3-15 kDa, 5-10 kDa, 6-8 kDa, or about 7-8 kDa).

In one embodiment, the biodegradable biocompatible polyals suitable for practicing the present invention are modified before conjugating with a drug or a PBRM. For example, the polyals contains —C(=O)—X—(CH$_2$)$_v$—C(=O)— with X being CH$_2$, O, or NH, and v being an integer from 1 to 6. Table A below provides some examples of the modified polyals suitable for conjugating with a drug or PBRM or derivatives thereof.

Therapeutic Agents

In certain embodiments, the therapeutic agent suitable for practicing the invention is a small molecule having a molecular weight preferably ≤about 5 kDa, more preferably ≤about 4 kDa, more preferably ≤about 3 kDa, most preferably ≤about 1.5 kDa or ≤about 1 kDa.

In certain embodiments, the therapeutic agent has an IC$_{50}$ of about less than 1 nM.

In another embodiment, the therapeutic agent has an IC$_{50}$ of about greater than 1 nM, for example, the therapeutic agent has an IC$_{50}$ of about 1 to 50 nM.

Some therapeutic agents having an IC$_{50}$ of greater than about 1 nM (e.g., "less potent drugs") are unsuitable for conjugation with a PBRM using art-recognized conjugation techniques. Without wishing to be bound by theory, such therapeutic agents have a potency that is insufficient for use in targeted PBRM-drug conjugates using conventional techniques as sufficient copies of the drug (i.e., more than 8) cannot be conjugated using art-recognized techniques without resulting in diminished pharmacokinetic and physiochemical properties of the conjugate. However sufficiently high loadings of these less potent drugs can be achieved using the conjugation strategies described herein thereby resulting in high loadings of the therapeutic agent while maintaining the desirable pharmacokinetic and physiochemical properties. Thus, the disclosure also relates to a PBRM-polymer-drug conjugate which includes a PBRM, PHF and at least eight therapeutic agent moieties, wherein the therapeutic agent has an IC$_{50}$ of greater than about 1 nM.

In certain embodiments, about 0.3 to about 15% monomers comprise a therapeutic agent, more preferably about 2 to about 12%, and even more preferably about 5 to about 10%.

The small molecule therapeutic agents used in this disclosure (e.g., antiproliferative (cytotoxic and cytostatic) agents capable of being linked to a polymer carrier) include cytotoxic compounds (e.g., broad spectrum), angiogenesis inhibitors, cell cycle progression inhibitors, PI3K/m-TOR/AKT pathway inhibitors, MAPK signaling pathway inhibitors, kinase inhibitors, protein chaperones inhibitors, HDAC inhibitors, PARP inhibitors, Wnt/Hedgehog signaling pathway inhibitors and RNA polymerase inhibitors.

Broad spectrum cytotoxins include, but are not limited to, DNA-binding, intercalating or alkylating drugs, microtubule stabilizing and destabilizing agents, platinum compounds, topoisomerase I inhibitors and protein synthesis inhibitors.

Exemplary DNA-binding, intercalation or alkylating drugs include, CC-1065 and its analogs, anthracyclines (doxorubicin, epirubicin, idarubicin, daunorubicin, nemorubicin and its derivatives, PNU-159682), bisnapthhalimide compounds such as elinafide (LU79553), and its analogs, alkylating agents, such as calicheamicins, dactinomycines, mitromycines, pyrrolobenzodiazepines, and the like. Exemplary CC-1065 analogs include duocarmycin SA, duocarmycin A, duocarmycin C1, duocarmycin C2, duocarmycin B1, duocarmycin B2, duocarmycin D, DU-86, KW-2189, adozelesin, bizelesin, carzelesin, seco-adozelesin, and related analogs and prodrug forms, examples of which are described in U.S. Pat. Nos. 5,475,092; 5,595,499; 5,846,545; 6,534,660; 6,586,618; 6,756,397 and 7,049,316. Doxorubicin and its analogs include those described in U.S. Pat. No. 6,630,579. Calicheamicins include, e.g., enediynes, e.g., esperamicin, and those described in U.S. Pat. Nos. 5,714,586 and 5,739,116. Duocarmycins include those described in U.S. Pat. Nos. 5,070,092; 5,101,038; 5,187,186; 6,548,530; 6,660,742; and 7,553,816 B2; and Li et al., *Tet Letts.*, 50:2932-2935 (2009).

Pyrrolobenzodiazepines (PBD) and analogs thereof include those described in Denny, *Exp. Opin. Ther. Patents.*, 10(4):459-474 (2000) and Antonow and Thurston, Chem Rev., 2815-2864 (2010).

Exemplary microtubule stabilizing and destabilizing agents include taxane compounds, such as paclitaxel, docetaxel, tesetaxel and carbazitaxel; maytansinoids, auristatins and analogs thereof, vinca alkaloid derivatives, epothilones and cryptophycins.

Exemplary maytansinoids or maytansinoid analogs include maytansinol and maytansinol analogs, maytansine or DM-1 and DM-4 are those described in U.S. Pat. Nos. 5,208,020; 5,416,064; 6,333.410; 6,441,163; 6,716,821; RE39,151 and 7,276,497. In certain embodiments, the cytotoxic agent is a maytansinoid, another group of anti-tubulin agents (ImmunoGen, Inc.; see also Chari et al., 1992, Cancer Res. 52:127-131), maytansinoids or maytansinoid analogs. Examples of suitable maytansinoids include maytansinol and maytansinol analogs. Suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Exemplary auristatins include auristatin E (also known as a derivative of dolastatin-10), auristatin EB (AEB), auristatin EFP (AEFP), monomethyl auristatin E (MMAE), monomethyl auristatin F (MMAF), auristatin F, auristatin F phenylenediamine (AFP), auristatin F HPA and dolastatin. Suitable auristatins are also described in U.S. Publication Nos. 2003/0083263, 2011/0020343, and 2011/0070248; PCT Application Publication Nos. WO 09/117531, WO 2005/081711, WO 04/010957; WO 02/088172 and WO01/24763, and U.S. Pat. Nos. 7,498,298; 6,884,869; 6,323,315; 6,239,104; 6,124,431; 6,034,065; 5,780,588; 5,767,237; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, the disclosures of which are incorporated herein by reference in their entirety.

Exemplary vinca alkaloids include vincristine, vinblastine, vindesine, and navelbine (vinorelbine). Suitable Vinca alkaloids that can be used in the present disclosure are also disclosed in U.S. Publication Nos. 2002/0103136 and 2010/0305149, and in U.S. Pat. No. 7,303,749 B1, the disclosures of which are incorporated herein by reference in their entirety.

Exemplary epothilone compounds include epothilone A, B, C, D, E and F, and derivatives thereof. Suitable epothilone compounds and derivatives thereof are described, for example, in U.S. Pat. Nos. 6,956,036; 6,989,450; 6,121,029; 6,117,659; 6,096,757; 6,043,372; 5,969,145; and 5,886,026; and WO 97/19086; WO 98/08849; WO 98/22461; WO 98/25929; WO 98/38192; WO 99/01124; WO 99/02514;

WO 99/03848; WO 99/07692; WO 99/27890; and WO 99/28324; the disclosures of which are incorporated herein by reference in their entirety.

Exemplary cryptophycin compounds are described in U.S. Pat. Nos. 6,680,311 and 6,747,021.

Exemplary platinum compounds include cisplatin (PLATINOL®), carboplatin (PARAPLATIN®), oxaliplatin (ELOXATINE®), iproplatin, ormaplatin, and tetraplatin.

Still other classes of compounds or compounds with these or other cytotoxic modes of action may be selected, including, e.g., mitomycin C, mitomycin A, daunorubicin, doxorubicin, morpholino-doxorubicin, cyanomorpholino-doxorubicin, aminopterin, bleomycin, 1-(chloromethyl)-2,3-dihydro-1H-benzo[e]indol-5-ol, pyrrolobenzodiazepine (PBD) polyamide and dimers thereof. Other suitable cytotoxic agents include, for example, puromycins, topotecan, rhizoxin, echinomycin, combretastatin, netropsin, estramustine, cryptophysins, cemadotin, discodermolide, eleutherobin, and mitoxantrone.

Exemplary topoisomerase I inhibitors include camptothecin, camptothecin derivatives, camptothecin analogs and non-natural camptothecins, such as, for example, CPT-11 (irinotecan), SN-38, GI-147211C, topotecan, 9-aminocamptothecin, 7-hydroxymethyl camptothecin, 7-aminomethyl camptothecin, 10-hydroxycamptothecin, (20S)-camptothecin, rubitecan, gimatecan, karenitecin, silatecan, lurtotecan, exatecan, diflomotecan, belotecan, lurtotecan and 539625. Other camptothecin compounds that can be used in the present disclosure include those described in, for example, J. Med. Chem., 29:2358-2363 (1986); J. Med. Chem., 23:554 (1980); J. Med. Chem., 30:1774 (1987).

Angiogenesis inhibitors include, but are not limited, MetAP2 inhibitors, VEGF inhibitors, PlGF inhibitors, VGFR inhibitors, PDGFR inhibitors, MetAP2 inhibitors. Exemplary VGFR and PDGFR inhibitors include sorafenib (Nexavar), sunitinib (Sutent) and vatalanib. Exemplary MetAP2 inhibitors include fumagillol analogs, meaning any compound that includes the fumagillin core structure, including fumagillamine, that inhibits the ability of MetAP-2 to remove $NH_2$-terminal methionines from proteins as described in Rodeschini et al., J. Org. Chem., 69, 357-373, 2004 and Liu, et al., Science 282, 1324-1327, 1998. Non limiting examples of "fumagillol analogs" are disclosed in J. Org. Chem., 69, 357, 2004; J. Org. Chem., 70, 6870, 2005; European Patent Application 0 354 787; J. Med. Chem., 49, 5645, 2006; Bioorg. Med. Chem., 11, 5051, 2003; Bioorg. Med. Chem., 14, 91, 2004; Tet. Lett. 40, 4797, 1999; WO99/61432; U.S. Pat. Nos. 6,603,812; 5,789,405; 5,767,293; 6,566,541; and 6,207,704.

Exemplary cell cycle progression inhibitors include CDK inhibitors such as, for example, BMS-387032 and PD0332991; Rho-kinase inhibitors such as, for example GSK429286; checkpoint kinase inhibitors such as, for example, AZD7762; aurora kinase inhibitors such as, for example, AZD1152, MLN8054 and MLN8237; PLK inhibitors such as, for example, BI 2536, B16727 (Volasertib), GSK461364, ON-01910 (Estybon); and KSP inhibitors such as, for example, SB 743921, SB 715992 (ispinesib), MK-0731, AZD8477, AZ3146 and ARRY-520.

Exemplary PI3K/m-TOR/AKT signaling pathway inhibitors include phosphoinositide 3-kinase (PI3K) inhibitors, GSK-3 inhibitors, ATM inhibitors, DNA-PK inhibitors and PDK-1 inhibitors.

Exemplary PI3 kinase inhibitors are disclosed in U.S. Pat. No. 6,608,053, and include BEZ235, BGT226, BKm120, CAL101, CAL263, demethoxyviridin, GDC-0941, GSK615, IC87114, LY294002, Palomid 529, perifosine, PI-103, PF-04691502, PX-866, SAR245408, SAR245409, SF1126, Wortmannin, XL147 and XL765.

Exemplary AKT inhibitors include, but are not limited to AT7867.

Exemplary MAPK signaling pathway inhibitors include MEK, Ras, JNK, B-Raf and p38 MAPK inhibitors.

Exemplary MEK inhibitors are disclosed in U.S. Pat. No. 7,517,994 and include GDC-0973, GSK1120212, MSC1936369B, AS703026, RO5126766 and RO4987655, PD0325901, AZD6244, AZD 8330 and GDC-0973.

Exemplary B-raf inhibitors include CDC-0879, PLX-4032, and SB590885.

Exemplary B p38 MAPK inhibitors include BIRB 796, LY2228820 and SB 202190.

Receptor tyrosine kinases (RTK) are cell surface receptors which are often associated with signaling pathways stimulating uncontrolled proliferation of cancer cells and neoangiogenesis. Many RTKs, which over express or have mutations leading to constitutive activation of the receptor, have been identified, including, but not limited to, VEGFR, EGFR, FGFR, PDGFR, EphR and RET receptor family receptors. Exemplary specific RTK targets include ErbB2, FLT-3, c-Kit, and c-Met.

Exemplary inhibitors of ErbB2 receptor (EGFR family) include but are not limited to AEE788 (NVP-AEE 788), BIBW2992, (Afatinib), Lapatinib, Erlotinib (Tarceva), and Gefitinib (Iressa).

Exemplary RTK inhibitors targeting more than one signaling pathway (multitargeted kinase inhibitors) include AP24534 (Ponatinib) that targets FGFR, FLT-3, VEGFR-PDGFR and Bcr-Abl receptors; ABT-869 (Linifanib) that targets FLT-3 and VEGFR-PDGFR receptors; AZD2171 that targets VEGFR-PDGFR, Flt-1 and VEGF receptors; CHR-258 (Dovitinib) that targets VEGFR-PDGFR, FGFR, Flt-3, and c-Kit receptors; Sunitinib (Sutent) that targets VEGFR, PDGFR, KIT, FLT-3 and CSF-IR; Sorafenib (Nexavar) and Vatalanib that target VEGFR, PDGFR as well as intracellular serine/threonine kinases in the Raf/Mek/Erk pathway.

Exemplary protein chaperon inhibitors include HSP90 inhibitors. Exemplary HSP90 inhibitors include 17AAG derivatives, BIIB021, BIIB028, SNX-5422, NVP-AUY-922 and KW-2478.

Exemplary HDAC inhibitors include Belinostat (PXD101), CUDC-101, Droxinostat, ITF2357 (Givinostat, Gavinostat), JNJ-26481585, LAQ824 (NVP-LAQ824, Dacinostat), LBH-589 (Panobinostat), MC1568, MGCD0103 (Mocetinostat), MS-275 (Entinostat), PCI-24781, Pyroxamide (NSC 696085), SB939, Trichostatin A and Vorinostat (SAHA).

Exemplary PARP inhibitors include iniparib (BSI 201), olaparib (AZD-2281), ABT-888 (Veliparib), AG014699, CEP 9722, MK 4827, KU-0059436 (AZD2281), LT-673, 3-aminobenzamide, A-966492, and AZD2461.

Exemplary Wnt/Hedgehog signaling pathway inhibitors include vismodegib (RG3616/GDC-0449), cyclopamine (11-deoxojervine) (Hedgehog pathway inhibitors) and XAV-939 (Wnt pathway inhibitor)

Exemplary RNA polymerase inhibitors include amatoxins. Exemplary amatoxins include α-amanitins, β-amanitins, γ-amanitins, ε-amanitins, amanullin, amanullic acid, amaninamide, amanin, and proamanullin.

Exemplary protein synthesis inhibitors include trichothecene compounds.

In one embodiment the drug of the disclosure is a topoisomerase inhibitor (such as, for example, a non-natural camptothecin compound), vinca alkaloid, kinase inhibitor (e.g., PI3 kinase inhibitor (GDC-0941 and PI-103)), MEK inhibitor, KSP inhibitor, RNA polymerase inhibitor, protein synthesis inhibitor, PARP inhibitor, docetaxel, paclitaxel, doxorubicin, duocarmycin, auristatin, dolastatin, calicheamicins, topotecan, SN38, camptothecin, exatecan, nemorubicin and its derivatives, PNU-159682, CC1065, elinafide, trichothecene, pyrrolobenzodiazepines, maytansinoids, DNA-binding drugs or a platinum compound, and analogs thereof. In specific embodiments, the drug is a derivative of SN-38, camptothecin, topotecan, exatecan, calicheamicin, exatecan, nemorubicin, PNU-159682, anthracycline, maytansinoid, taxane, trichothecene, CC1065, elinafide, vindesine, vinblastine, PI-103, AZD 8330, dolastatin, auristatin E, auristatin F, a duocarmycin compound, ispinesib, pyrrolobenzodiazepine, ARRY-520 and stereoisomers, isosteres and analogs thereof.

In another embodiment, the drug used in the disclosure is a combination of two or more drugs, such as, for example, PI3 kinase inhibitors and MEK inhibitors; broad spectrum cytotoxic compounds and platinum compounds; PARP inhibitors and platinum compounds; broad spectrum cytotoxic compounds and PARP inhibitors.

In yet another embodiment, the drug used in the disclosure is auristatin F-hydroxypropylamide-L-alanine.

In one embodiment, the Vinca alkaloid is a compound of Formula (V):

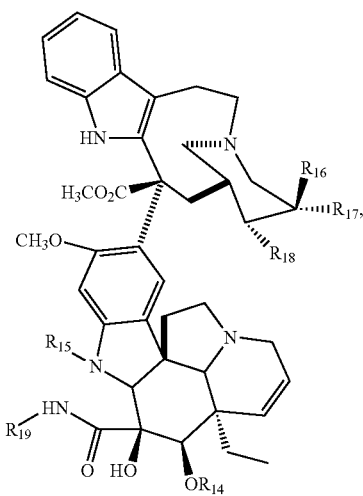

(V)

wherein:

$R_{14}$ is hydrogen, —C(O)—$C_{1-3}$ alkyl or —C(O)-chloro substituted $C_{1-3}$ alkyl;

$R_{15}$ is hydrogen, —CH$_3$ or —CHO;

when $R_{17}$ and $R_{18}$ are taken independently, $R_{18}$ is hydrogen, and either $R_{16}$ or $R_{17}$ is ethyl and the other is hydroxyl;

when $R_{17}$ and $R_{18}$ are taken together with the carbon to which they are attached to form an oxiran ring, $R_{16}$ is ethyl;

$R_{19}$ is hydrogen, OH, amino group, alkyl amino or —[C($R_{20}R_{21}$)]$_a$—$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —NH$_2$, —COOH, —$R_{82}$—C(O)(CH$_2$)$_c$—C(H)($R_{23}$)—N(H)($R_{23}$), —$R_{82}$—C(O)(CH$_2$)$_d$—(O CH$_2$—CH$_2$)$_f$—N(H)($R_{23}$) or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is hydrogen or $X^2$ and NR$_{77}$ form a nitrogen containing heterocyclic moiety;

$R_{82}$ is —NH, —N($C_{1-6}$ alkyl), or oxygen;

a is an integer from 1 to 6;

c is an integer from 0 to 3;

d is an integer from 1 to 3; and f is an integer from 1 to 12.

Further examples of Vinca alkaloids are described in U.S. Pat. No. 8,524,214B2 and US 2002/0103136.

In one embodiment the Vinca alkaloid of Formula (V) is a compound of Formula (VI):

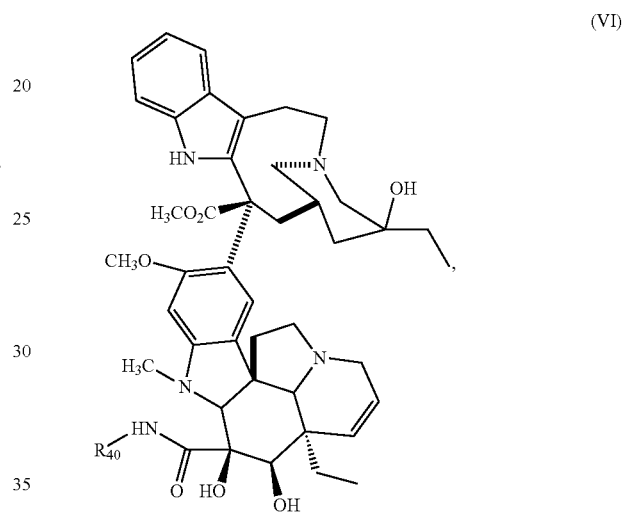

(VI)

wherein:

$R_{40}$ is hydrogen, —OH, —NH$_2$, or any of the following structures:

(1)

(2)

(3)

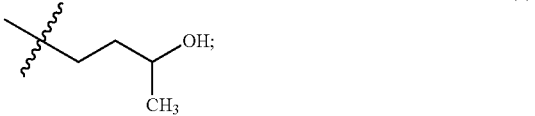

(4)

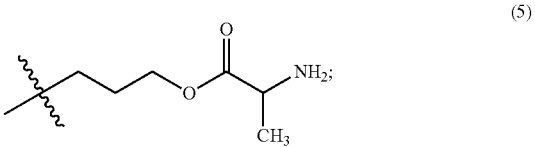

(5)

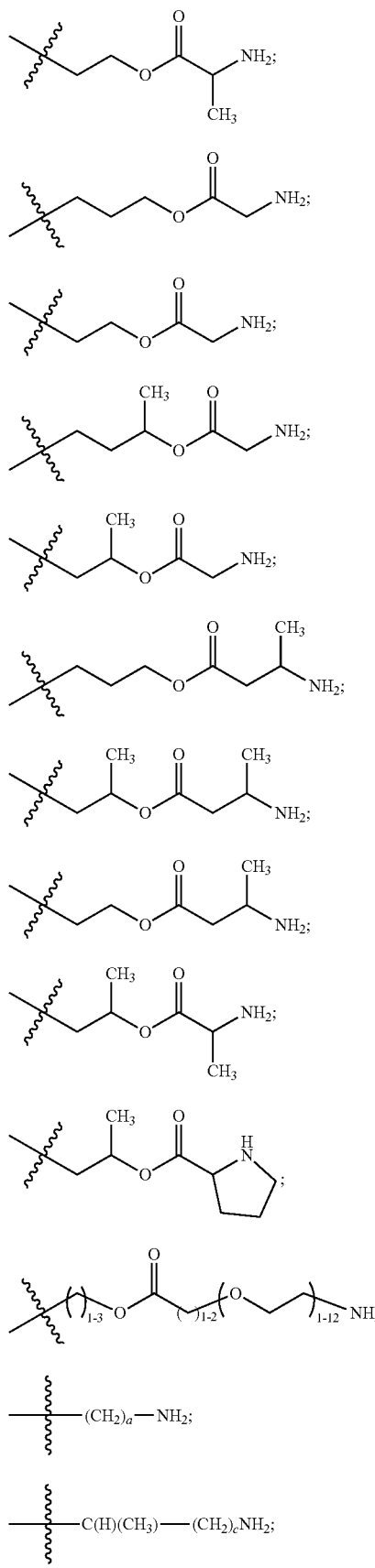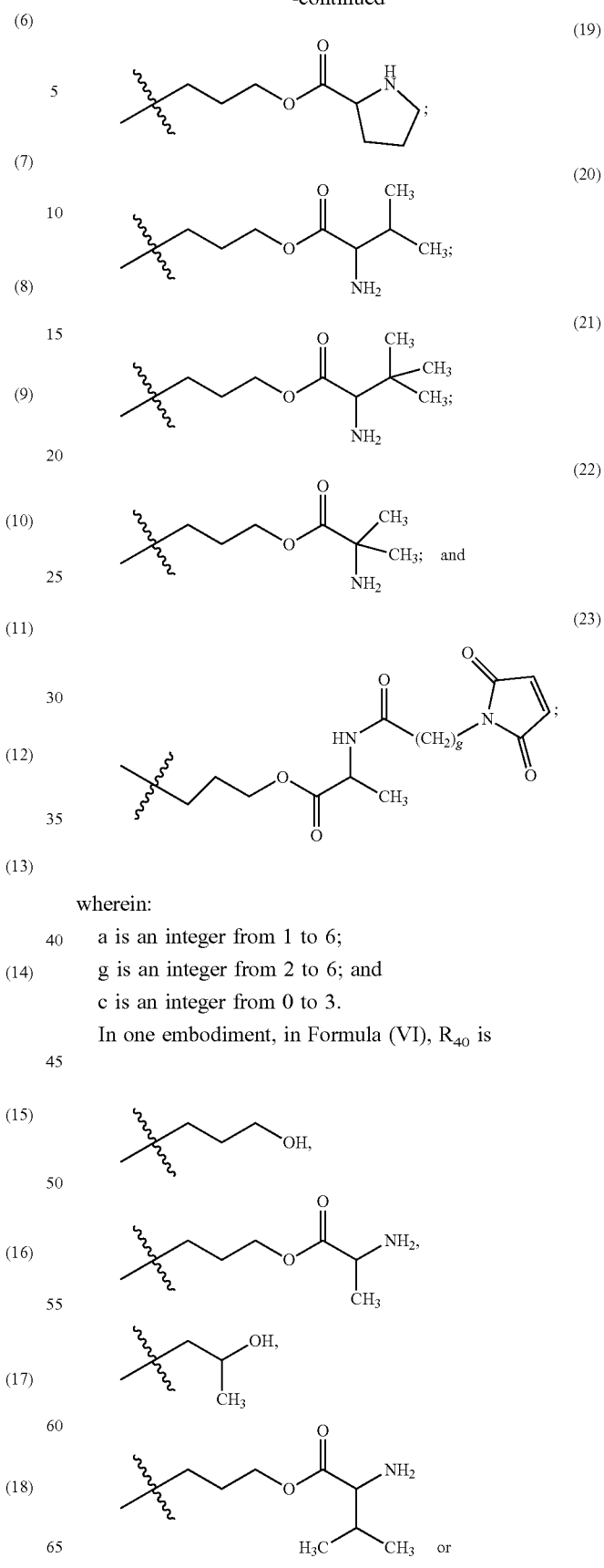
wherein:
a is an integer from 1 to 6;
g is an integer from 2 to 6; and
c is an integer from 0 to 3.
In one embodiment, in Formula (VI), R$_{40}$ is 35
-continued

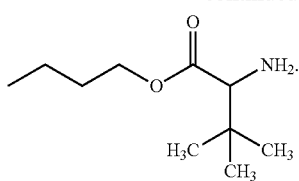

In another embodiment, $R_{40}$ is

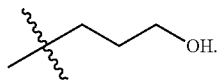 [SMILES: *CCCO]

In another embodiment, the compound of Formula (VI) is a compound of Formula (VIa), (VIb), (VIc) or (VId):

(VIa)

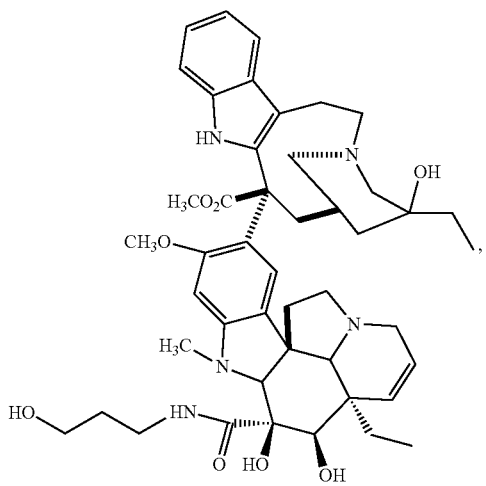

, (VIb)

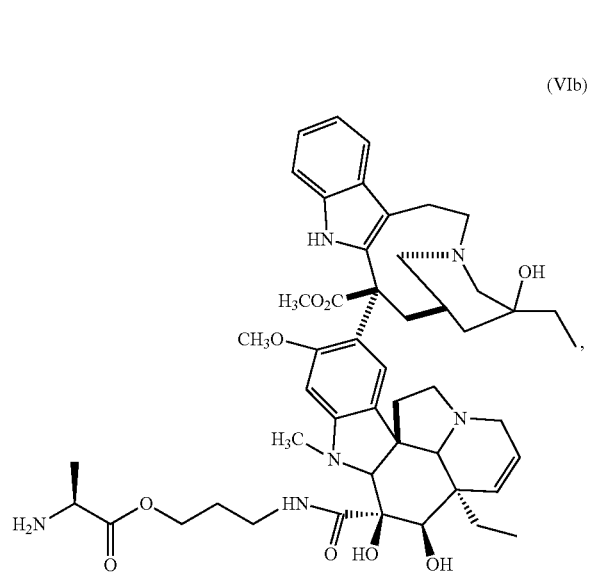

,

36
-continued (VIc)

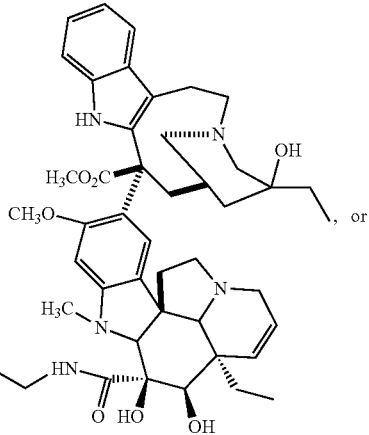

, or (VId)

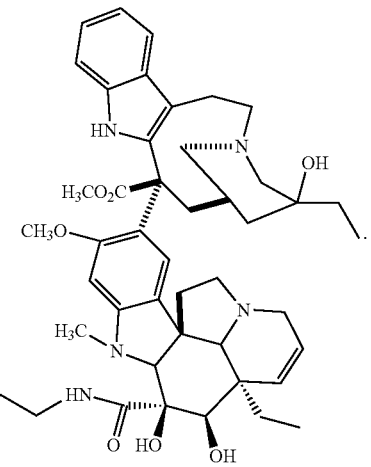

.

In another embodiment, the topoisomerase inhibitor is a camptothecin compound of Formula (VII):

(VII)

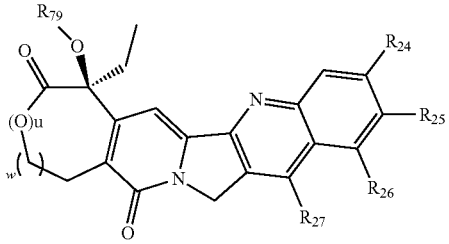

wherein:

$R_{24}$ is —H, —Cl, —F, —OH or alkyl; or $R_{24}$ and $R_{25}$, may be taken together to form an optionally substituted five- or six-membered ring;

$R_{25}$ is —H, —F, —OH, —CH$_3$, —CH=N—O-t-Butyl, —CH$_2$CH$_2$Si(CH$_3$)$_3$, —Si((CH$_3$)$_2$)-t-butyl, —O—C(O)—$R_{29}$;

$R_{29}$ is —NH$_2$, —$R_{28}$—$C_{1-6}$ alkyl-$R_{22}$, 5 to 12-membered heterocycloalkyl, $R_{28}$—$C_{5-12}$ heterocycloalkyl-$C_{1-6}$ alkyl-$R_{22}$ or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{26}$ is —H, —CH$_2$—N(CH$_3$)$_2$, NH$_2$, or NO$_2$;

$R_{27}$ is —H, ethyl, N-methyl piperidine, cycloalkyl, —CH$_2$OH, —CH$_2$CH$_2$NHCH(CH$_3$)$_2$, or —N-4-methylcyclohexylamine;

$R_{79}$ is —H or —C(O)—R$_{28}$—[C(R$_{20}$R$_{21}$)]$_a$—R$_{22}$;

each of $R_{20}$ and $R_{21}$ independently is hydrogen, C$_{1-6}$ alkyl, C$_{6-10}$ aryl, hydroxylated C$_{6-10}$ aryl, polyhydroxylated C$_{6-10}$ aryl, 5 to 12-membered heterocycle, C$_{3-8}$ cycloalkyl, hydroxylated C$_{3-8}$ cycloalkyl, polyhydroxylated C$_{3-8}$ cycloalkyl or a side chain of a natural or unnatural amino acid;

$R_{22}$ is —OH, —NH$_2$, —COOH, —R$_{82}$—C(O)(CH$_2$)$_c$—C(H)(R$_{23}$)—N(H)(R$_{23}$), —R$_{82}$—C(O)(CH$_2$)$_d$—(O CH$_2$—CH$_2$)$_f$—N(H)(R$_{23}$), or —R$_{82}$—(C(O)—CH(X$^2$)—NH)$_d$—R$_{77}$;

each $R_{23}$ independently is hydrogen, C$_{1-6}$ alkyl, C$_{6-10}$ aryl, C$_{3-8}$ cycloalkyl, —COOH, or —COO—C$_{1-6}$ alkyl;

X$^2$ is a side chain of a natural or unnatural amino acid;

$R_{77}$ is a hydrogen or X$^2$ and NR$_{77}$ form a nitrogen containing cyclic compound;

$R_{82}$ is —NH, —N(C$_{1-6}$ alkyl), or oxygen;

or $R_{26}$ and $R_{27}$ when taken together with the two carbon atoms to which they attach and the third carbon atom connecting the two carbon atoms form an optionally substituted six-membered ring;

$R_{28}$ is absent, —NH, —N(C$_{1-6}$ alkyl), or oxygen;

a is an integer from 1 to 6;

c is an integer from 0 to 3;

d is an integer from 1 to 3;

f is an integer from 1 to 12;

u is an integer 0 or 1;

w is an integer 0 or 1; and with the proviso that the compound of Formula (VII) must contain at least one of R$_{29}$ and R$_{79}$.

In one embodiment the camptothecin compound of Formula (VII) is a compound of Formula (VIII), (VIIIa), or (VIIIb), or Formula (XXV) or (XXVa):

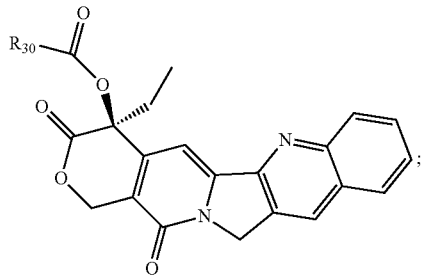
(VIII)

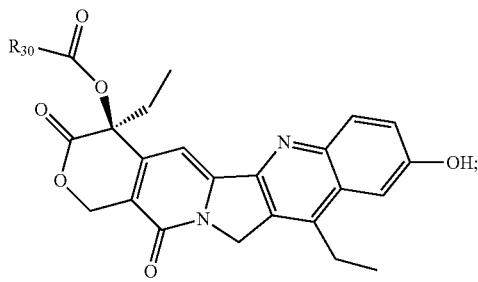
(VIIIa)

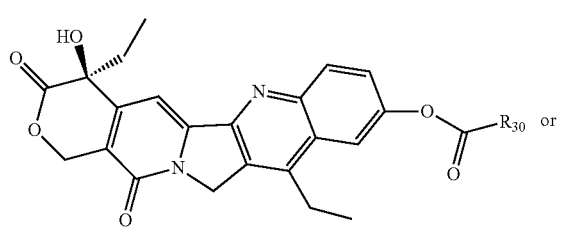
(VIIIb)

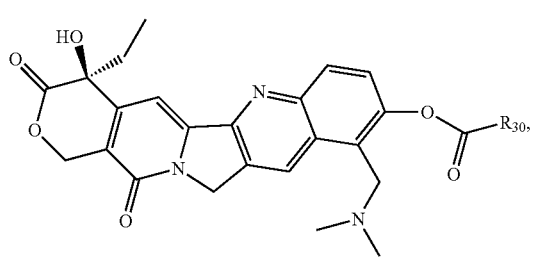
(XXV)

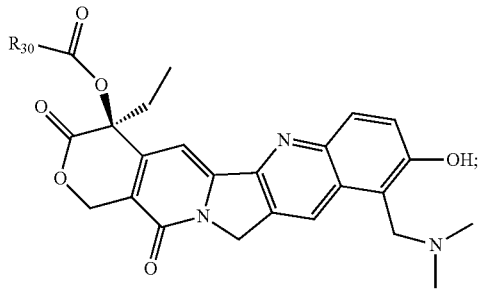
(XXVa)

wherein $R_{30}$ is —NH$_2$, —R$_{28}$—[C(R$_{20}$R$_{21}$)]$_a$—R$_{22}$, —R$_{28}$—C$_{1-6}$ alkyl-R$_{22}$, 5 to 12-membered heterocycloalkyl, R$_{28}$—C$_{5-12}$ heterocycloalkyl-C$_{1-6}$ alkyl-R$_{22}$ or —R$_{28}$—C$_{1-6}$ alkyl-C$_{6-12}$ aryl-C$_{1-6}$ alkyl-R$_{22}$;

$R_{28}$ is absent, —NH, —N(C$_{1-6}$ alkyl), or oxygen;

each of $R_{20}$ and $R_{21}$ independently is hydrogen, C$_{1-6}$ alkyl, C$_{6-10}$ aryl, hydroxylated C$_{6-10}$ aryl, polyhydroxylated C$_{6-10}$ aryl, 5 to 12-membered heterocycle, C$_{3-8}$ cycloalkyl, hydroxylated C$_{3-8}$ cycloalkyl, polyhydroxylated C$_{3-8}$ cycloalkyl or a side chain of a natural or unnatural amino acid;

$R_{22}$ is —OH, —NH$_2$, —COOH, —R$_{82}$—C(O)(CH$_2$)$_c$—C(H)(R$_{23}$)—N(H)(R$_{23}$), —R$_{82}$—C(O)(CH$_2$)$_d$—(O CH$_2$—CH$_2$)$_f$—N(H)(R$_{23}$) or —R$_{82}$—(C(O)—CH(X$^2$)—NH)$_d$—R$_{77}$;

each $R_{23}$ independently is hydrogen, C$_{1-6}$ alkyl, C$_{6-10}$ aryl, C$_{3-8}$ cycloalkyl, —COOH, or —COO—C$_{1-6}$ alkyl;

X$^2$ is a side chain of a natural or unnatural amino acid;

$R_{77}$ is a hydrogen or X$^2$ and NR$_{77}$ form a nitrogen containing cyclic compound;

$R_{82}$ is —NH, —N(C$_{1-6}$ alkyl), or oxygen;

a is an integer from 1 to 6;

c is an integer from 0 to 3;

d is an integer from 1 to 3; and f is an integer from 1 to 12.

In some embodiments $R_{30}$ is any one of the following structures:

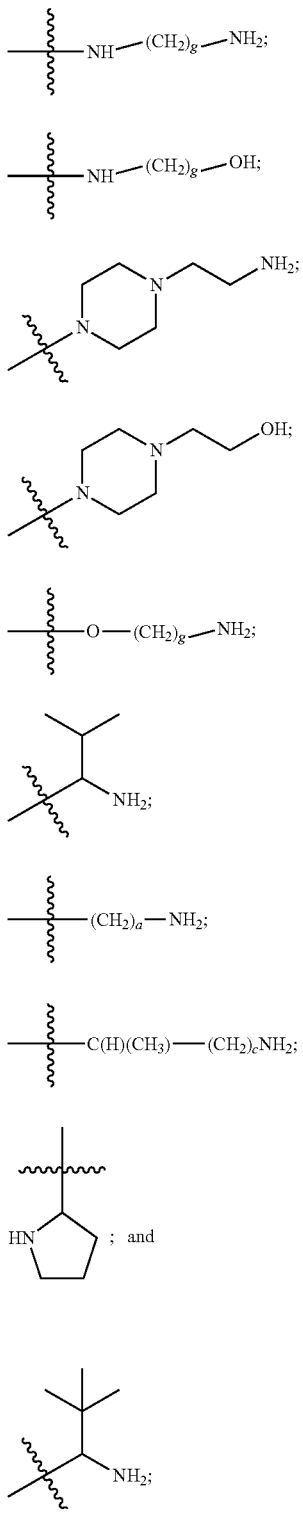
(1)
(2)
(3)
(4)
(5)
(6)
(7)
(8)
(9)
(10)
wherein:
a is an integer from 1 to 6;
c is an integer from 0 to 3; and
g is an integer from 2 to 6.
In one embodiment, in Formula (VII), $R_{30}$ is:
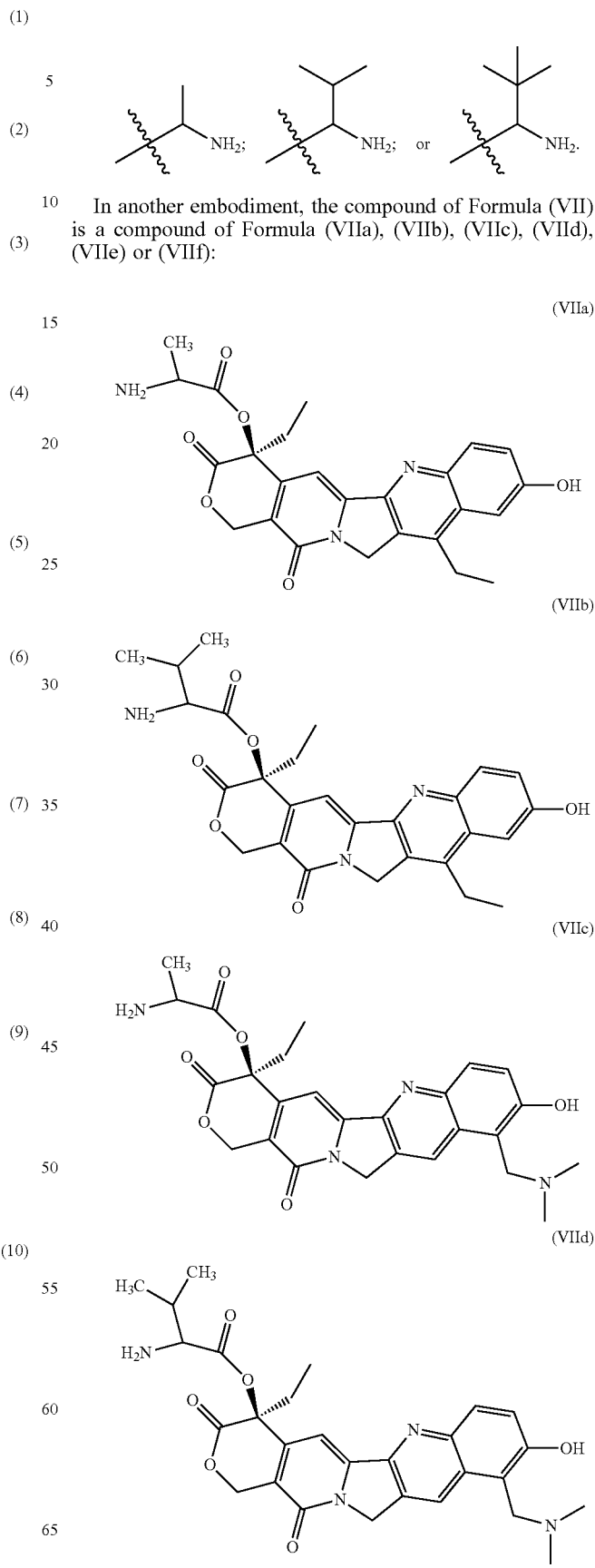
In another embodiment, the compound of Formula (VII) is a compound of Formula (VIIa), (VIIb), (VIIc), (VIId), (VIIe) or (VIIf):

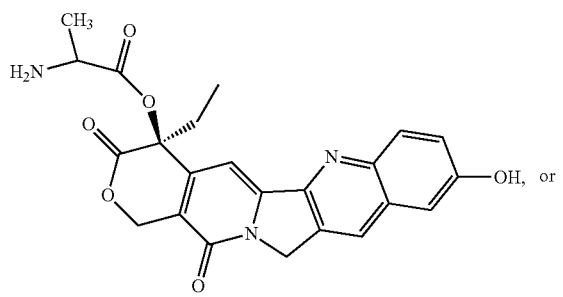

(VIIe)

(VIIf)

In another embodiment the PI3 kinase inhibitor is a compound of Formula (IX):

(IX)

wherein $R_{47}$ is an amino group, $-R_9-[C(R_{20}R_{21})]_a-R_{10}$, $-R_9-C_{5-12}$ heterocycloalkyl-$C_{1-6}$ alkyl-$R_{10}$, 5 to 12-membered heterocycloalkyl, or $-R_9-C_{6-10}$ aryl;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{10}$ is $-OH$, $-NHR_{83}$, $-N-(R_{83})R_{11}$, $-COOH$, $-R_{82}-C(O)(CH_2)_c-C(H)(R_{23})-N(H)(R_{23})$, $-R_{82}-C(O)(CH_2)_d-(OCH_2-CH_2)_f-N(H)(R_{23})$, $-R_{82}-(C(O)-CH(X^2)-NH)_d-R_{77}$ or $-R_{82}-C(O)-[C(R_{20}R_{21})]_a-R_{82}-R_{83}$;

each $R_{23}$ independently is hydrogen, $C_{1-6}$ alkyl, $C_{6-10}$ aryl, $C_{3-8}$ cycloalkyl, $-COOH$, or $-COO-C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is $-NH$, $-N(C_{1-6}$ alkyl), or oxygen;

$R_9$ is absent, $N-(R_{83})$ or oxygen;

$R_{83}$ is hydrogen or $CH_3$;

$R_{11}$ is:

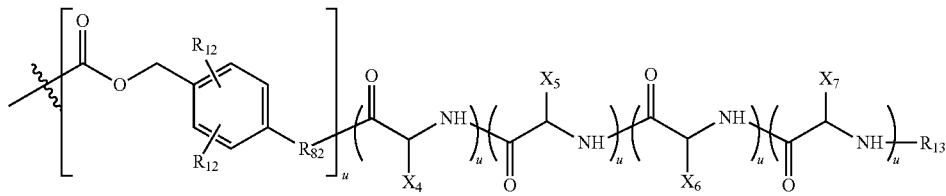

each $R_{12}$ independently is hydrogen, chloride, $-CH_3$ or $-OCH_3$;

$R_{13}$ is hydrogen or $-C(O)-(CH_2)_d-(O-CH_2-CH_2)_f-NH_2$;

$R_{82}$ is $-NH$, $-N(C_{1-6}$ alkyl), or oxygen $X_4$ is the side chain of lysine, arginine, citrulline, alanine or glycine;

$X_5$ is the side chain of phenylalanine, valine, leucine, isoleucine or tryptophan;

each of $X_6$ and $X_7$ is independently the side chain of glycine, alanine, serine, valine or proline;

a is an integer from 1 to 6;

c is an integer from 0 to 3;

d is an integer from 1 to 3;

f is an integer from 1 to 12; and each u independently is an integer 0 or 1;

or $R_{11}$ is —$Y_u$—$W_q$—$R_{88}$, wherein:
Y is any one of the following structures:

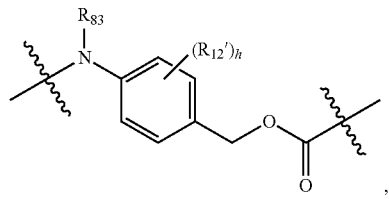

,

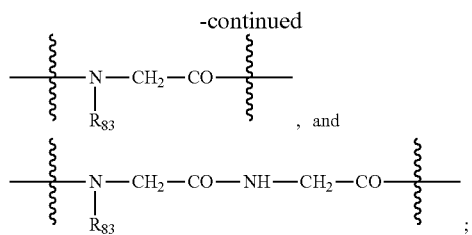

, and in each of which the terminal $NR_{83}$ group of Y is proximal to $R_{88}$;
$R_{83}$ is hydrogen or $CH_3$,
each W is an amino acid unit;
each $R_{12}'$ independently is halogen, —$C_{1-8}$ alkyl, —O—$C_{1-8}$ alkyl, nitro or cyano;
$R_{88}$ is hydrogen or —C(O)—$(CH_2)_{ff}$—(NH—C(O))$_{aa}$-$E_j$-$(CH_2)_{bb}$—$R_{85}$
$R_{85}$ is $NH_2$ or OH;
E is —$CH_2$— or —$CH_2CH_2O$—;
u is an integer 0 or 1;
q is an integer from 0 to 12;
aa is an integer 0 or 1;
bb is an integer 0 or 2;
ff is an integer from 0 to 10;
h is an integer from 0 to 4;
j is an integer from 0 to 12; and
when E is —$CH_2$—, bb is 0 and j is an integer from 0 to 10; and when E is —$CH_2CH_2$—O—, bb is 2 and j is an integer from 1 to 12;
or $R_{11}$ is

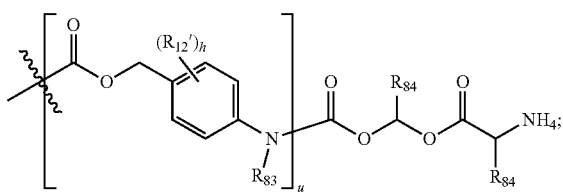

wherein:

$R_{83}$ is hydrogen or $CH_3$, $R_{84}$ is $C_{1-6}$ alkyl or $C_{6-10}$ aryl;

each $R_{12}'$ independently is halogen, —$C_{1-8}$ alkyl, —O—$C_{1-8}$ alkyl, nitro or cyano;

h is an integer from 0 to 4; and
u is an integer 0 or 1.
In some embodiments, $R_{11}$ is:

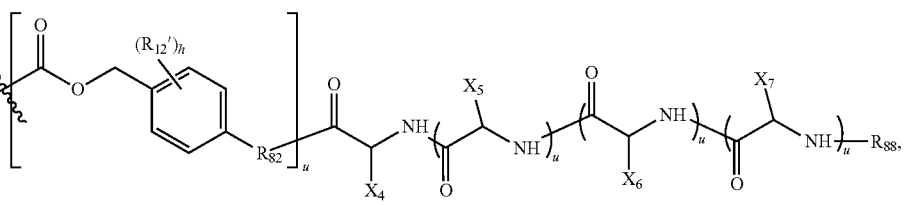

wherein:
each $R_{12}'$ independently is chloride, —$CH_3$ or —$OCH_3$;
$R_{88}$ is hydrogen or —C(O)—$(CH_2)_{ff}$—$(CH_2$—$CH_2O)_j$—$CH_2$—$CH_2$—$NH_2$;
$R_{82}$ is —NH, —N($C_{1-6}$ alkyl), or oxygen
$X_4$ is the side chain of lysine, arginine, citrulline, alanine or glycine;
$X_5$ is the side chain of phenylalanine, valine, leucine, isoleucine or tryptophan;
each of $X_6$ and $X_7$ is independently the side chain of glycine, alanine, serine, valine or proline;
ff is an integer from 1 to 3;
j is an integer from 1 to 12
h is an integer from 0 to 4; and
each u independently is an integer 0 or 1.
In some embodiments,

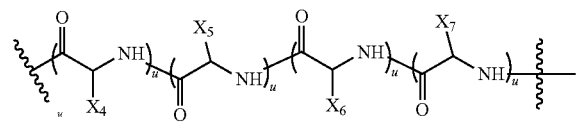

is citrulline-valine; lysine-phenylalanine; citrulline-phenylalanine; citrulline-leucine; citrulline-valine-glycine-glycine; glycine-phenylalanine-glycine-glycine; valine; proline; leucine or isoleucine.

In another embodiment, $R_{11}$ is any one of the following structures:
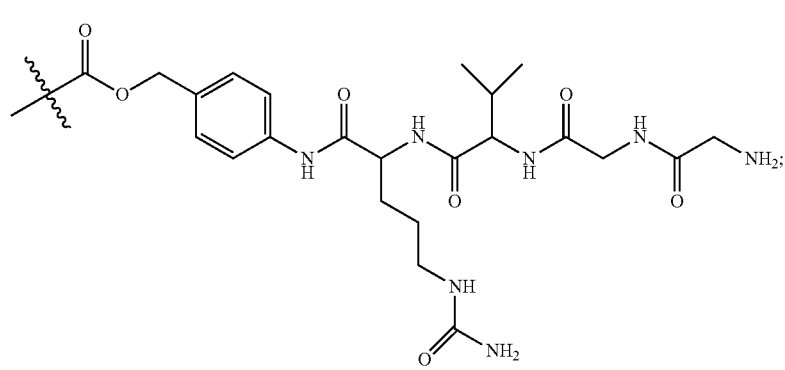
(1)
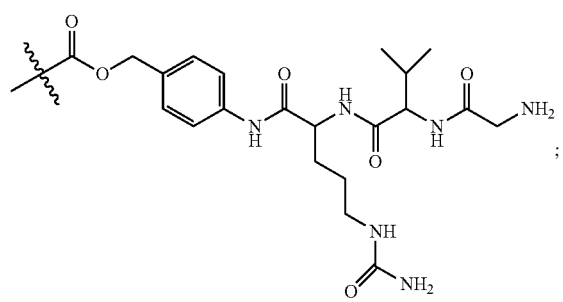
(2)
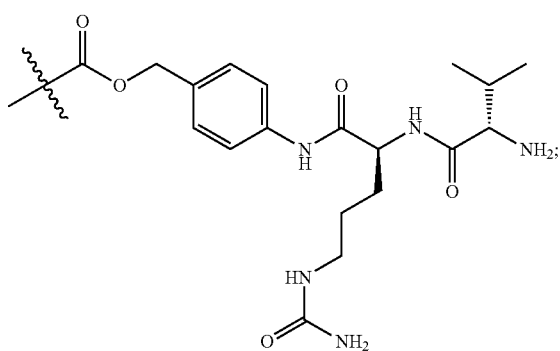
(3)
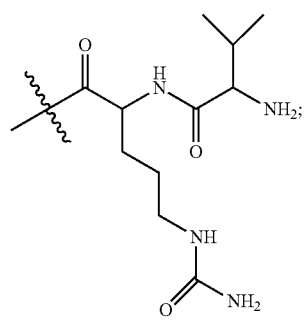
(4)
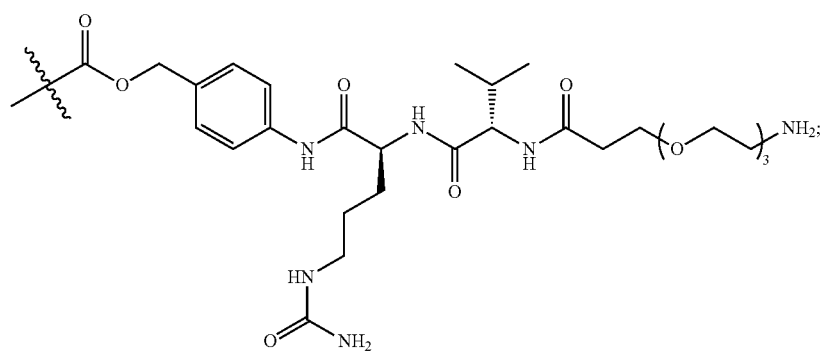
(5)

(6)
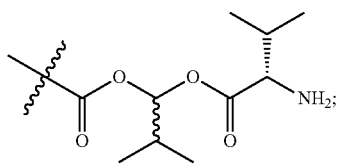
(7)
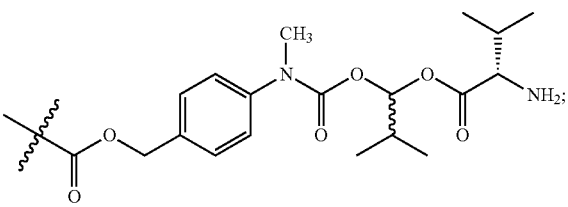
(8)
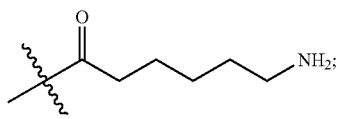
(9)
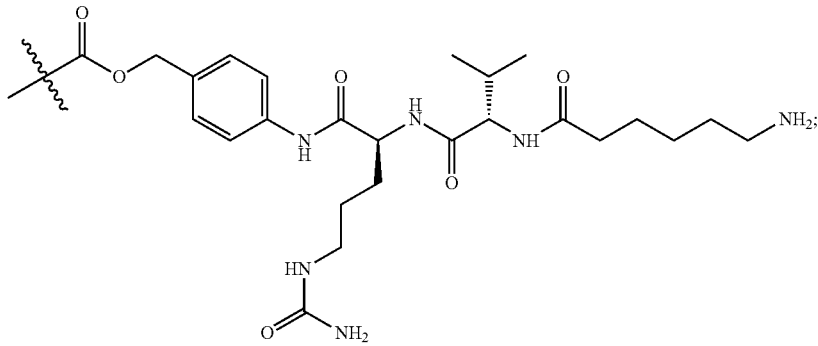
(10)
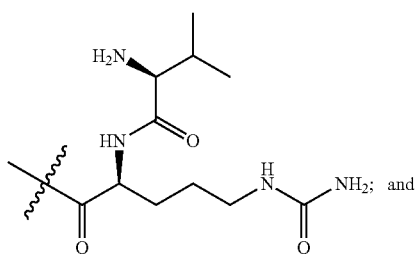
(11)
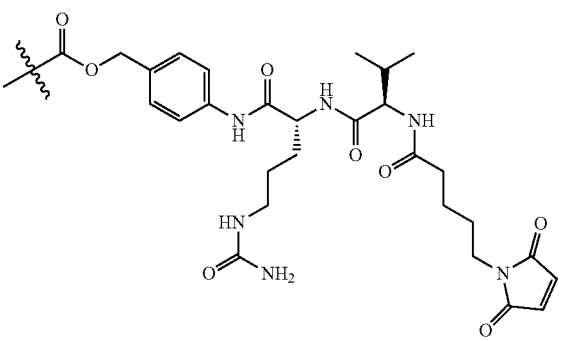
In some embodiments $R_{47}$ is any one of the following structures:
(1)
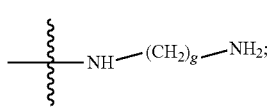
(2)
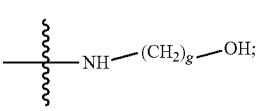
(3)
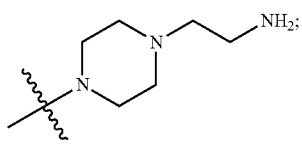
(4)
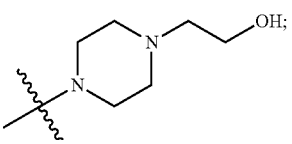
(5)
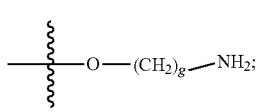
(6)
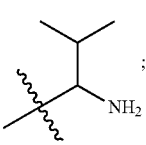

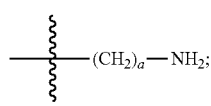 (7)
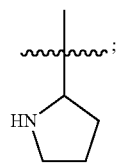 (9)
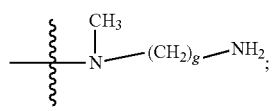 (11)
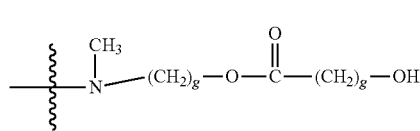 (13)
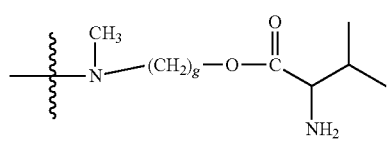 (15)
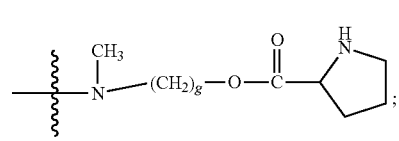 (8)
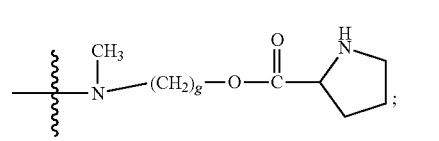 (10)
(12)
(14)
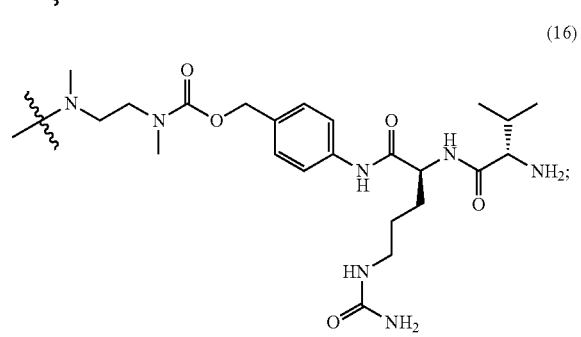 (16)
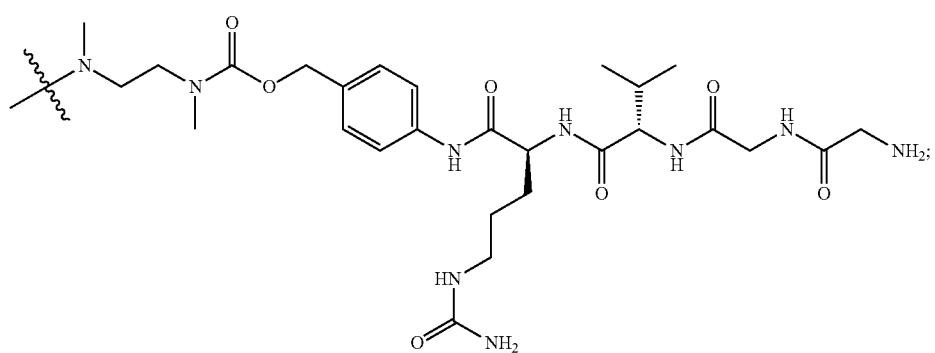 (17)
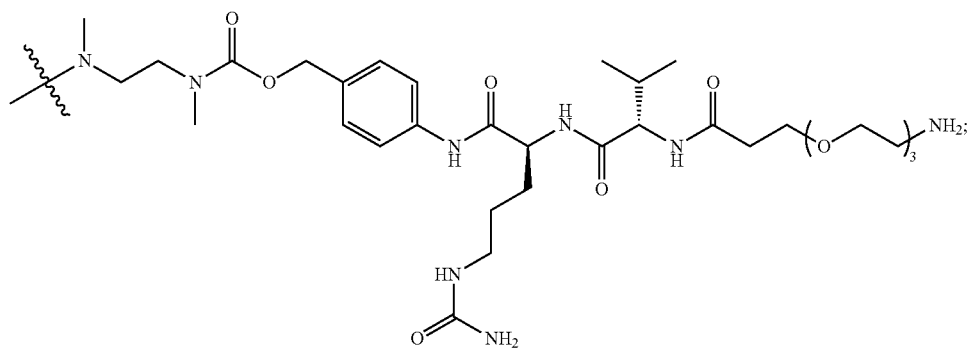 (18)

(19)

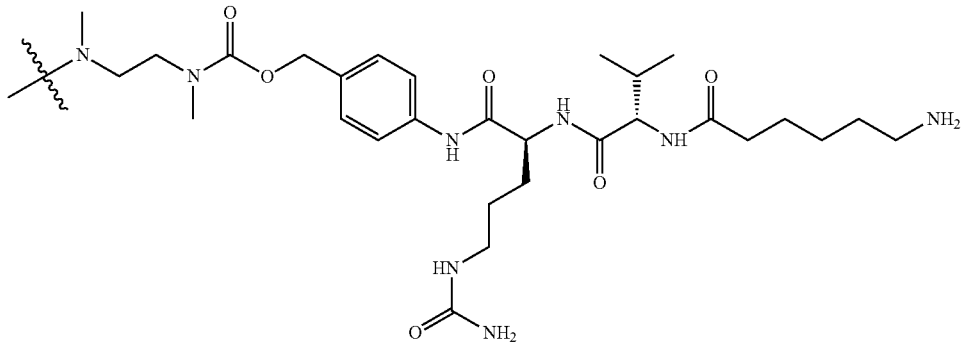

(20)

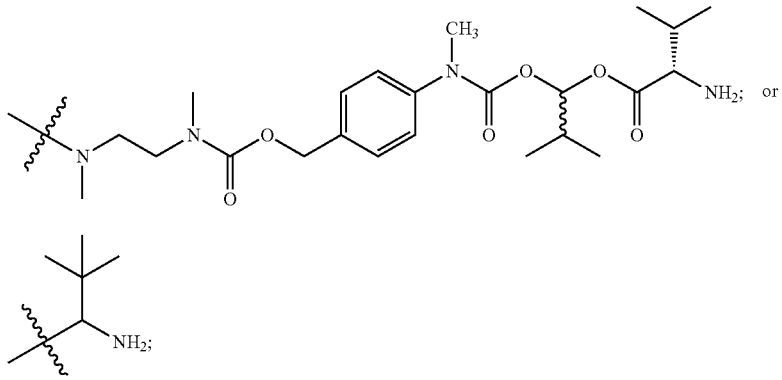

(21)

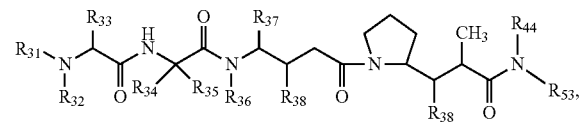

wherein:
a is an integer from 1 to 6;
c is an integer from 0 to 3; and
g is an integer from 2 to 6.

In another embodiment the auristatin is a compound of Formula (X):

(X)

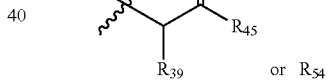

wherein:
each of $R_{31}$ and $R_{32}$ independently is hydrogen or $C_{1-8}$ alkyl and at most one of $R_{31}$ and $R_{32}$ is hydrogen;

$R_{33}$ is hydrogen, $C_{1-8}$ alkyl, $C_{3-8}$ carbocycle, $C_{6-10}$ aryl, $C_{1-8}$ alkyl-$C_{6-10}$ aryl, $X^1$—($C_{3-8}$ carbocycle), $C_{3-8}$ heterocycle or $X^1$—($C_{3-8}$ heterocycle);

$R_{34}$ is hydrogen, $C_{1-8}$ alkyl, $C_{3-8}$ carbocycle, $C_{6-10}$ aryl, $X^1$—$C_{6-10}$ aryl, $X^1$—($C_{3-8}$ carbocycle), $C_{3-8}$ heterocycle or $X^1$—($C_{3-8}$ heterocycle);

$R_{35}$ is hydrogen or methyl;

or $R_{34}$ and $R_{35}$, together with the carbon atom to which they attach form a carbocyclic ring having the formula —$(CR_{55}R_{41})_b$— wherein each of $R_{55}$ and $R_{41}$ independently is hydrogen or $C_{1-8}$ alkyl and b is an integer from 3 to 7;

$R_{36}$ is hydrogen or $C_{1-8}$ alkyl;

$R_{37}$ is hydrogen, $C_{1-8}$ alkyl, $C_{3-8}$ carbocycle, $C_{6-10}$ aryl, —$X^1$—$C_{6-10}$ aryl, —$X^1$—($C_{3-8}$ carbocycle), $C_{3-8}$ heterocycle or —$X^1$—($C_{3-8}$ heterocycle);

each $R_{38}$ independently is hydrogen, OH, $C_{1-8}$ alkyl, $C_{3-8}$ carbocycle or O—($C_{1-8}$ alkyl);

$R_{53}$ is:

$R_{39}$ is H, $C_{1-8}$ alkyl, $C_{6-10}$ aryl, —$X^1$—$C_{6-10}$ aryl, $C_{3-8}$ carbocycle, $C_{3-8}$ heterocycle, —$X^1$—$C_{3-8}$ heterocycle, —$C_{1-8}$ alkylene-$NH_2$, or $(CH_2)_2SCH_3$ each $X^1$ independently is $C_{1-10}$ alkylene or $C_{3-10}$ cycloalkylene;

$R_{44}$ is hydrogen or $C_{1-8}$ alkyl;

$R_{45}$ is $X^3$—$R_{42}$ or NH—$R_{19}$;

$X^3$ is O or S;

$R_{19}$ is hydrogen, OH, amino group, alkyl amino or —[C$(R_{20}R_{21})]_a$—$R_{22}$;

$R_{42}$ is an amino group, $C_{1-6}$ alkyl amino or —[C$(R_{20}R_{21})]_a$—$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NHR_{23}$, —COOH, —$R_{82}$—C(O)(CH$_2)_c$—C(H)($R_{23}$)—N(H)($R_{23}$), —$R_{82}$—C(O)(CH$_2)_d$—(OCH$_2$—CH$_2)_f$—N(H)($R_{23}$) or —$R_{82}$—(C(O)—CH($X^2$)—NH$)_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH, —N($C_{1-6}$ alkyl), or oxygen;

$R_{54}$ is —C($R_{56}$)$_2$—C($R_{56}$)$_2$—$C_{6-10}$ aryl, —C($R_{56}$)$_2$—C($R_{56}$)$_2$—$C_{3-8}$ heterocycle or —C($R_{56}$)$_2$—C($R_{56}$)$_2$—$C_{3-8}$ carbocycle;

$R_{56}$ is independently selected from H, OH, $C_{1-8}$ alkyl, $C_{3-8}$ carbocycle, —O—$C_{1-8}$ alkyl, —O—C(O)—$R_{29}$ and —O—$R_{23}$—O—$C_{1-6}$ alkyl-NH$_2$;

$R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —[C($R_{20}R_{21}$)]$_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, —NH, —N($C_{1-6}$ alkyl), or oxygen;

a is an integer from 1 to 6;

c is an integer from 0 to 3;

d is an integer from 1 to 3; and f is an integer from 1 to 12.

In some embodiments, in the auristatin compound of Formula (X):

$R_{39}$ is benzyl or

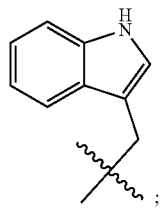 [SMILES: *Cc1c[nH]c2ccccc12]

and $R_{44}$ is hydrogen.

In another embodiment the auristatin is a compound of Formula (Xa):

(Xa)

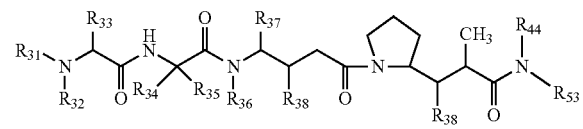

wherein:

$R_{33}$ through $R_{38}$, and $R_{44}$ are as defined herein, one of $R_{31}$ and $R_{32}$ is hydrogen or $C_{1-8}$ alkyl and the other is:

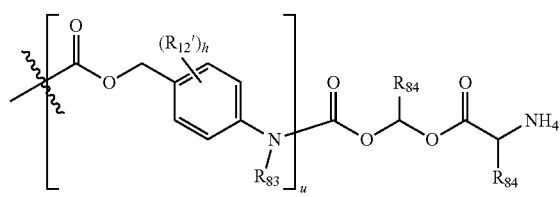

wherein:

$R_{83}$ is hydrogen or CH$_3$, $R_{84}$ is $C_{1-6}$ alkyl or $C_{6-10}$ aryl;

each $R_{12}'$ independently is halogen, —$C_{1-8}$ alkyl, —O—$C_{1-8}$ alkyl, nitro or cyano;

h is an integer from 0 to 4; and u is an integer 0 or 1;

$R_{53}$ is:

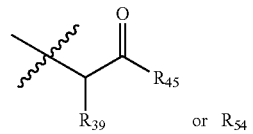

$R_{39}$ is H, $C_{1-8}$ alkyl, $C_{6-10}$ aryl, —$X^1$—$C_{6-10}$ aryl, $C_{3-8}$ carbocycle, $C_{3-8}$ heterocycle, —$X^1$—$C_{3-8}$ heterocycle, —$C_{1-8}$ alkylene-NH$_2$, or (CH$_2$)$_2$SCH$_3$, each $X^1$ independently is $C_{1-10}$ alkylene or $C_{3-10}$ cycloalkylene;

$R_{45}$ is $X^3$—$R_{42}$ or NH—$R_{19}$;

$X^3$ is O or S;

$R_{19}$ is hydrogen, OH, amino group, alkyl amino or —[C($R_{20}R_{21}$)]$_a$—$R_{22}$;

$R_{42}$ is H, an amino group, $C_{1-6}$ alkyl amino or —[C($R_{20}R_{21}$)]$_a$—$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —NHR$_{23}$, —COOH, —$R_{82}$—C(O)(CH$_2$)$_c$—C(H)($R_{23}$)—N(H)($R_{23}$), —$R_{82}$—C(O)(CH$_2$)$_d$—(OCH$_2$—CH$_2$)$_f$—N(H)($R_{23}$) or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH, —N($C_{1-6}$ alkyl), or oxygen;

$R_{54}$ is —C($R_{56}$)$_2$—C($R_{56}$)$_2$—$C_{6-10}$ aryl, —C($R_{56}$)$_2$—C($R_{56}$)$_2$—$C_{3-8}$ heterocycle or —C($R_{56}$)$_2$—C($R_{56}$)$_2$—$C_{3-8}$ carbocycle;

$R_{56}$ is independently selected from H, OH, $C_{1-8}$ alkyl, $C_{3-8}$ carbocycle, —O—$C_{1-8}$ alkyl, —O—C(O)—$R_{29}$ and —O—$R_{23}$—O—$C_{1-6}$ alkyl-NH$_2$;

$R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —[C($R_{20}R_{21}$)]$_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, —NH, —N($C_{1-6}$ alkyl), or oxygen;

a is an integer from 1 to 6;

c is an integer from 0 to 3;

d is an integer from 1 to 3; and f is an integer from 1 to 12.

In one embodiment, the auristatin compound of Formula (Xa) is a compound of Formula (XIa) or Formula (XIb):

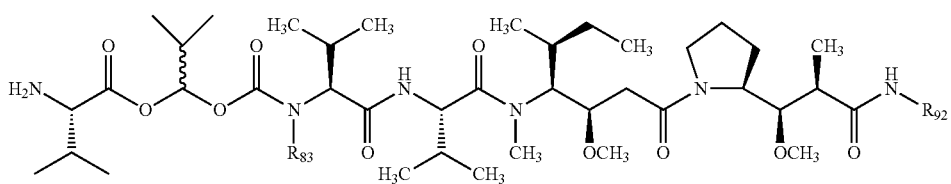
(XIa)
or
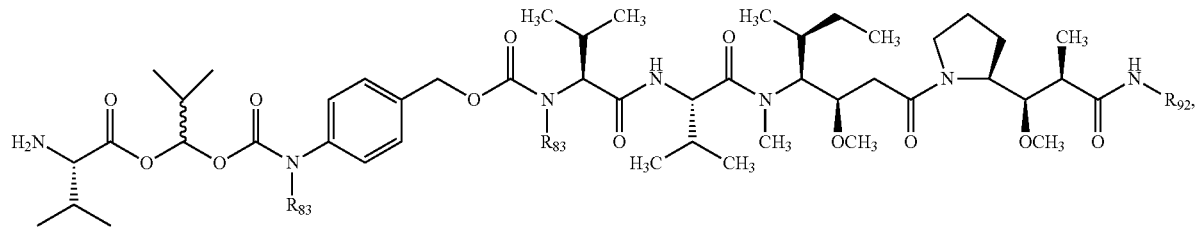
(XIb)
wherein:
R<sub>92</sub> is:
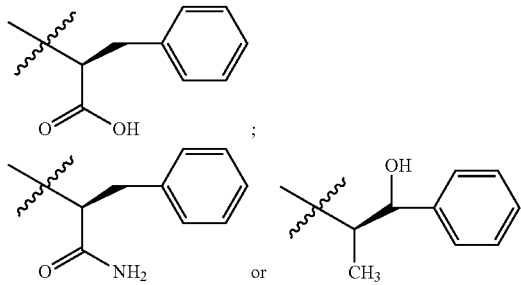
and
R<sub>83</sub> is hydrogen or CH<sub>3</sub>.
In one embodiment the auristatin of Formula (X) is a compound of Formula (XI), Formula (XII) or Formula (XIII):
wherein the compound of Formula (XI) is:
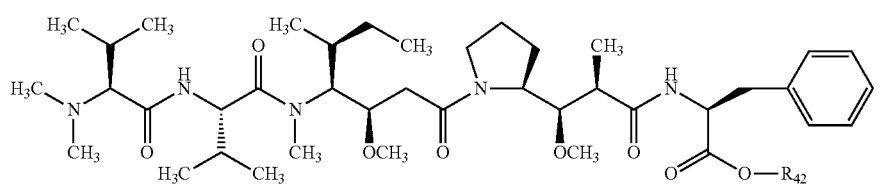
(XI)
wherein $R_{42}$ is —CH<sub>3</sub> or any one of the following structures:
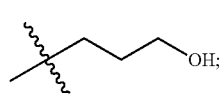
(1)
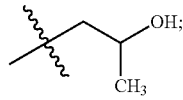
(2)
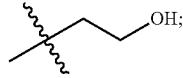
(3)
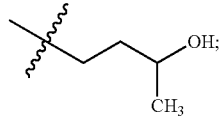
(4)
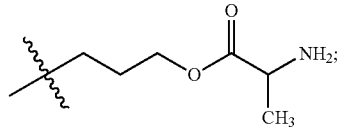
(5)
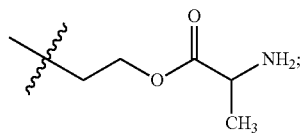
(6)

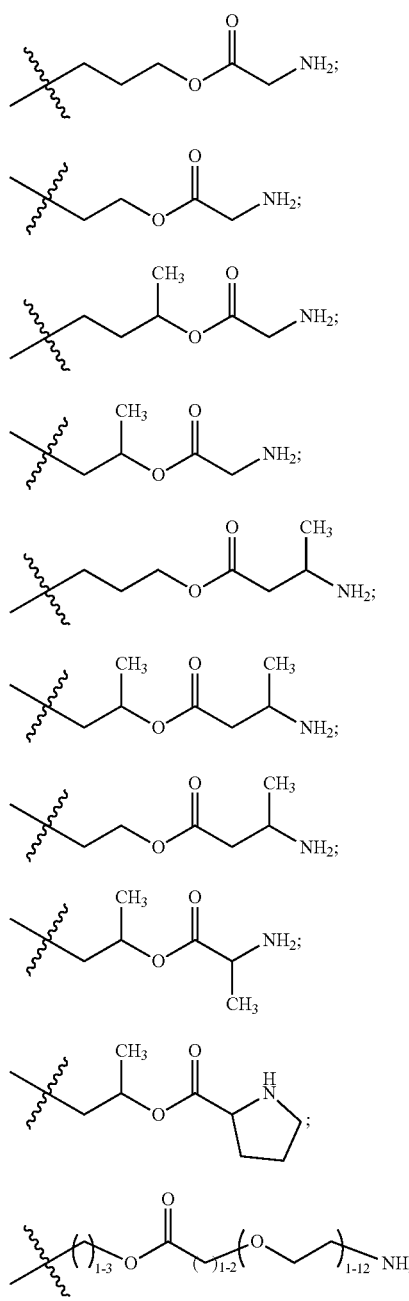
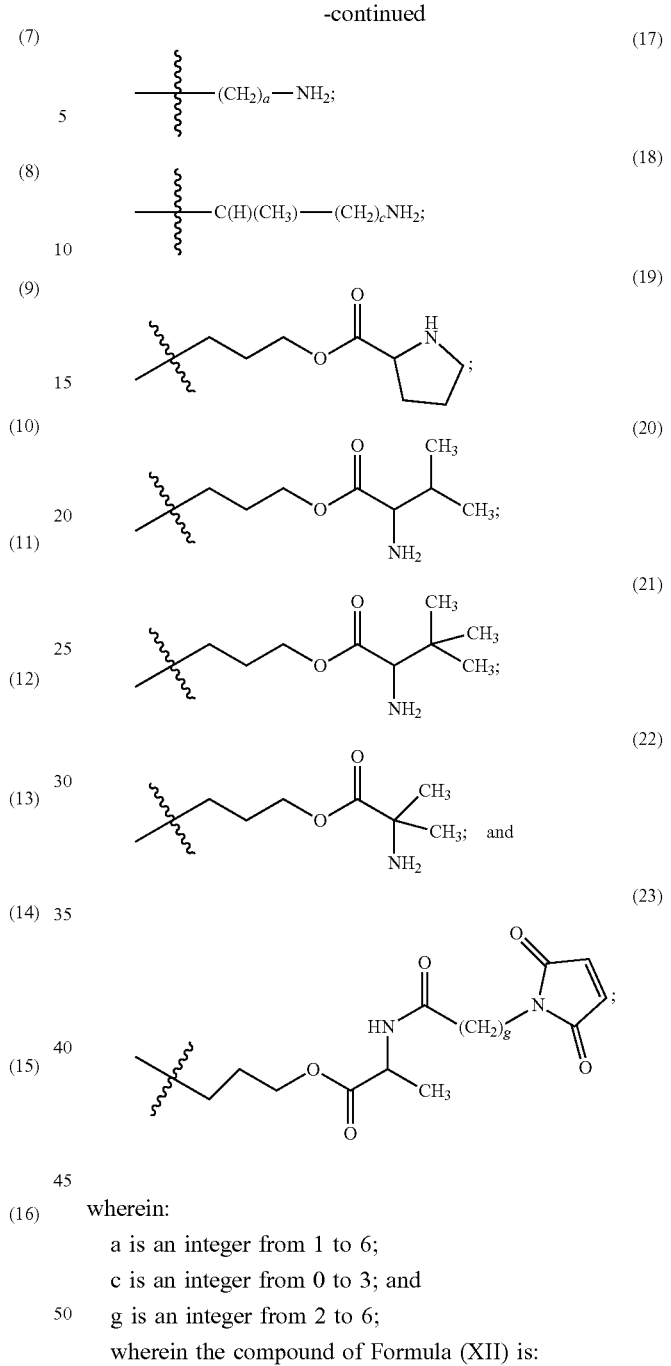
wherein:
a is an integer from 1 to 6;
c is an integer from 0 to 3; and
g is an integer from 2 to 6;
wherein the compound of Formula (XII) is:
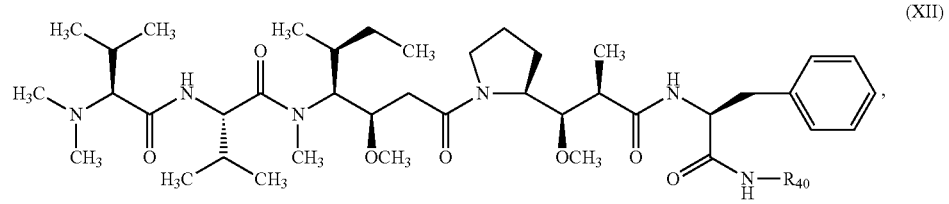

wherein $R_{40}$ is hydrogen, —OH, —NH$_2$, or any of the following structures:
(1) 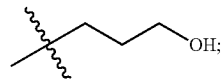
(2) 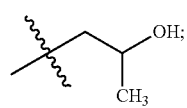
(3) 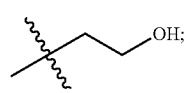
(4) 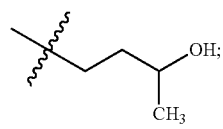
(5) 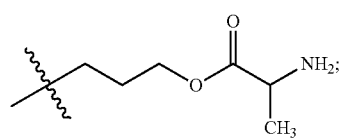
(6) 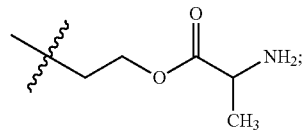
(7) 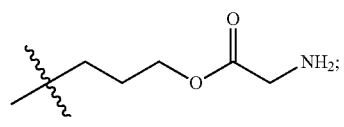
(8) 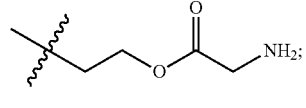
(9) 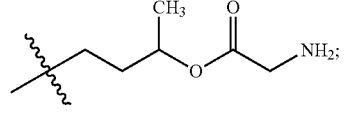
(10) 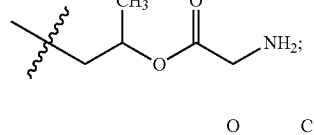
(11) 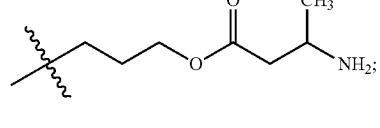
(12) 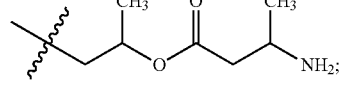
(13) 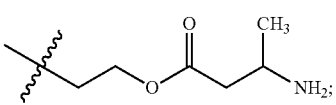
(14) 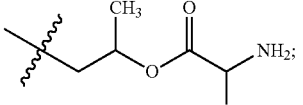
(15) 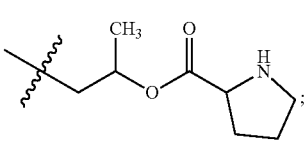
(16) 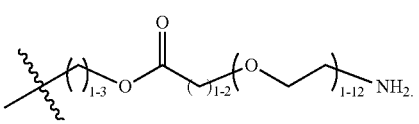
(17) 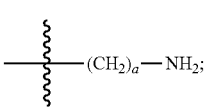
(18) 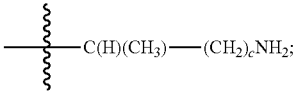
(19) 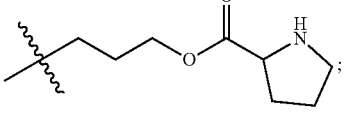
(20) 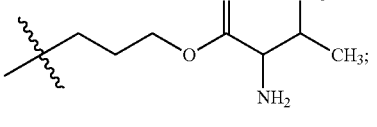
(21) 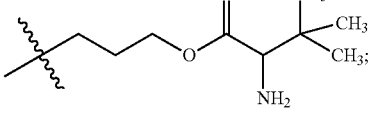
(22) 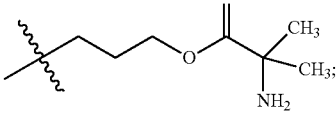
(23) 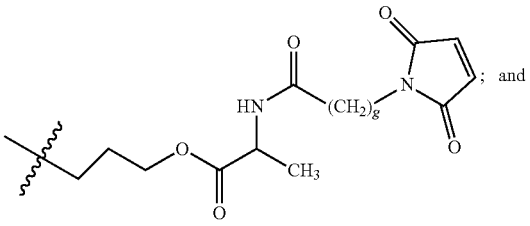
and -continued (24)

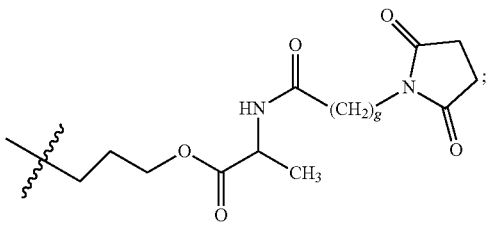

wherein:
a is an integer from 1 to 6;
g is an integer from 2 to 6; and
c is an integer from 0 to 3;
wherein the compound of Formula (XIII) is:

(XIII)

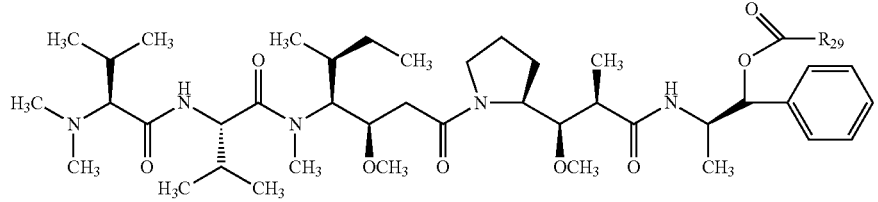

wherein $R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —$R_{28}$—[$C(R_{20}R_{21})]_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —NHR$_{23}$, —COOH, —$R_{82}$—C(O)(CH$_2$)$_c$—C(H)(R$_{23}$)—N(H)(R$_{23}$), —$R_{82}$—C(O)(CH$_2$)$_d$—(OCH$_2$—CH$_2$)$_f$—N(H)(R$_{23}$) or —$R_{82}$—(C(O)—CH(X$^2$)—NH)$_d$—R$_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and NR$_{77}$ form a nitrogen containing cyclic compound;

$R_{82}$ is —NH, —N(C$_{1-6}$ alkyl), or oxygen;

$R_{28}$ is absent, —NH, —N(C$_{1-6}$ alkyl), or oxygen;

a is an integer from 1 to 6;
c is an integer from 0 to 3;
d is an integer from 1 to 3; and
f is an integer from 1 to 12.

In one embodiment, in Formula (XII), $R_{40}$ is

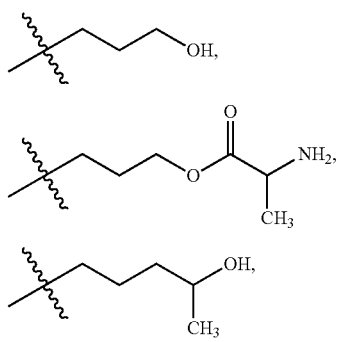

-continued

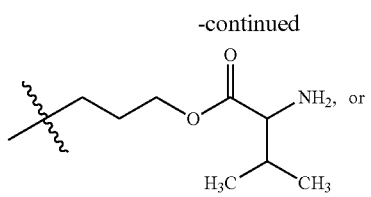

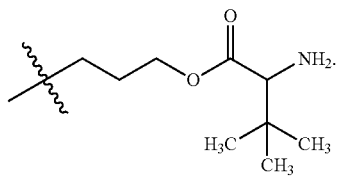

In another embodiment, the compound of Formula (XII) is a compound of Formula (XIIb) or (XIIc):

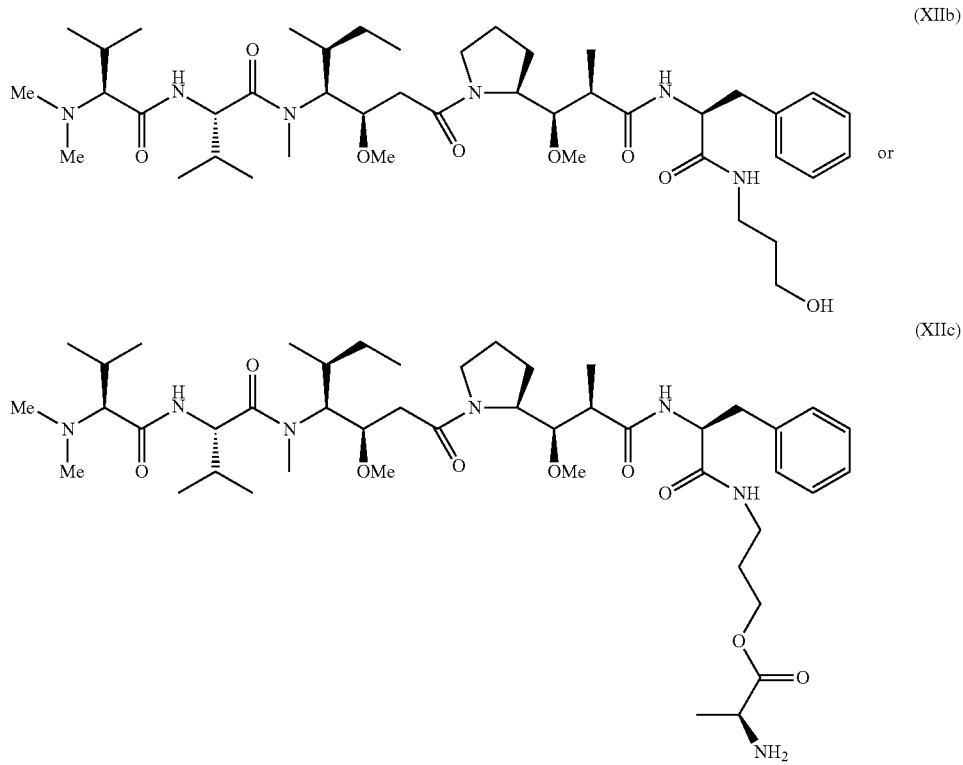

In one embodiment in the compound of Formula (XIII), $R_{29}$ is —$NH_2$, 5 membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$ or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, —NH, —N($C_{1-6}$ alkyl), or oxygen;

$R_{22}$ is —OH, —$NHR_{23}$, —COOH, —$R_{82}$—C(O)($CH_2$)$_c$—C(H)($R_{23}$)—N(H)($R_{23}$), —$R_{82}$—C(O)($CH_2$)$_d$—(O$CH_2$—$CH_2$)$_f$—N(H)($R_{23}$) or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH, —N($C_{1-6}$ alkyl), or oxygen;

c is an integer from 0 to 3;

d is an integer from 1 to 3; and f is an integer from 1 to 12.

In yet another embodiment, $R_{29}$ is any one of the following structures:

(1)
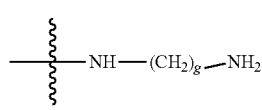

(2)
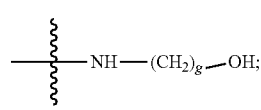

(3)
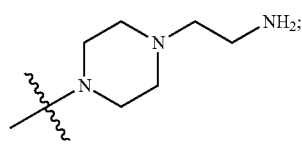

(4)
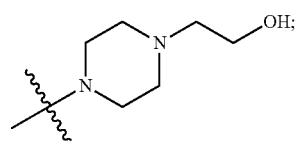

(5)
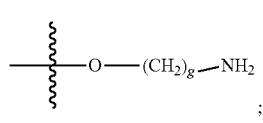

(6)
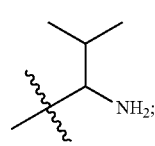

-continued
(7)
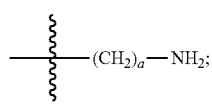
(8)
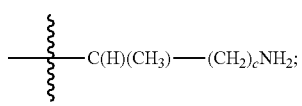
(9)
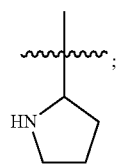
(10)
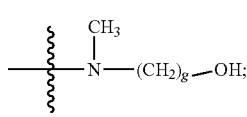
(11)
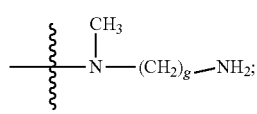
(12)
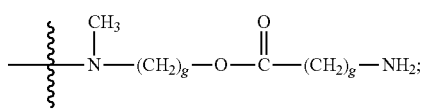
(13)
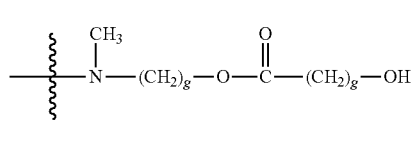
(14)
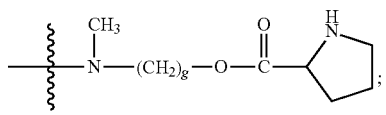
(15)
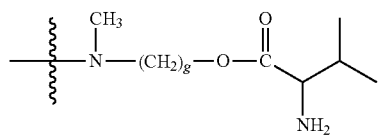
(16)
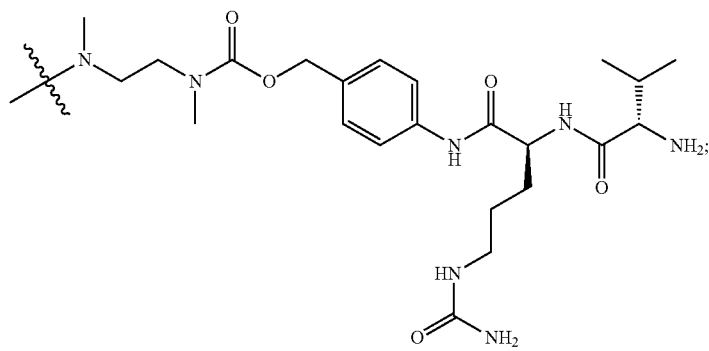
(17)
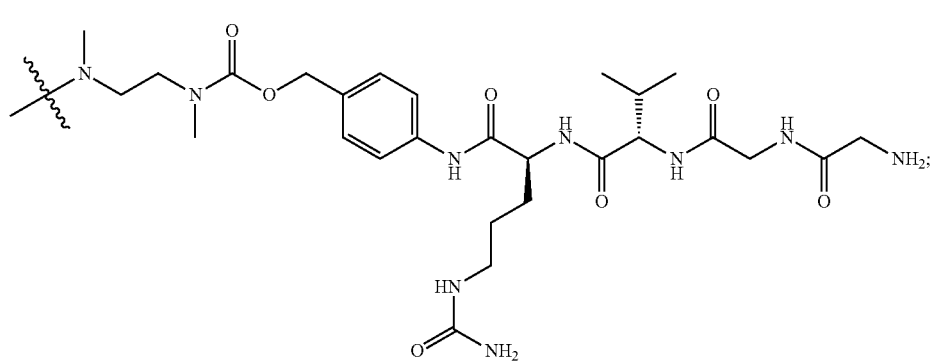

-continued

(18)
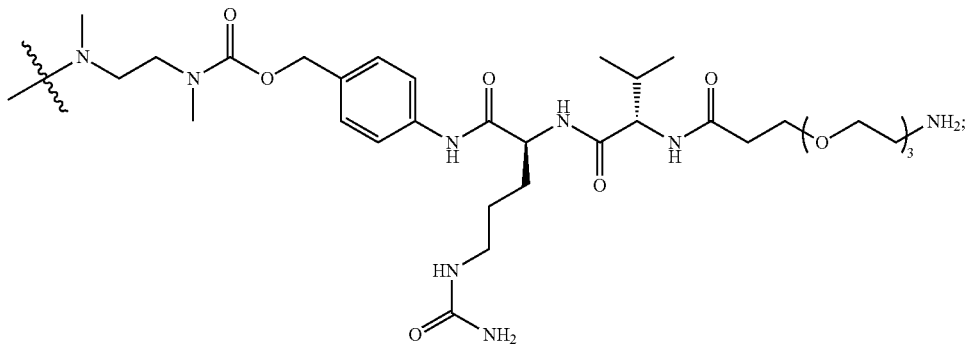

(19)
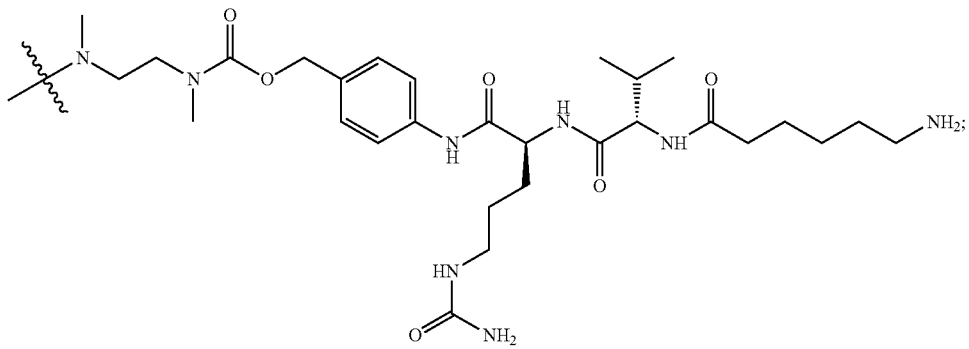

(20)
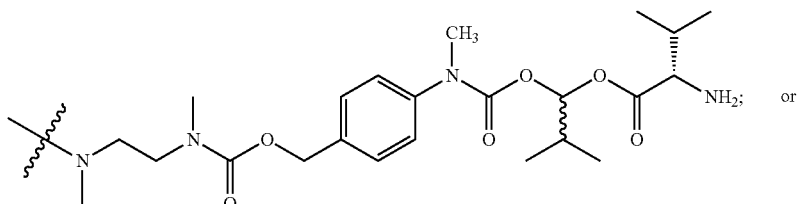

(21)
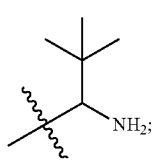

wherein:
a is an integer from 1 to 6;
c is an integer from 0 to 3; and
g is an integer from 2 to 6.

In one embodiment, the MEK inhibitor is a compound of Formula (XIV):

(XIV)
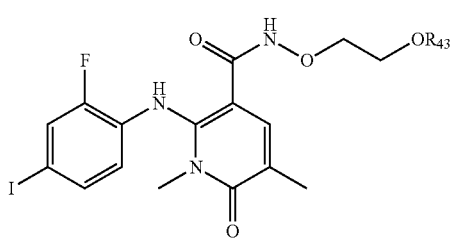

wherein $R_{43}$ is H or $—R_{46}—R_{47}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —NH$_2$, —COOH, —$R_{82}$—C(O)(CH$_2$)$_c$—C(H)(R$_{23}$)—N(H)(R$_{23}$), —$R_{82}$—C(O)(CH$_2$)$_d$—(O CH$_2$—CH$_2$)$_f$—N(H)(R$_{23}$) or —$R_{82}$—(C(O)—CH(X$^2$)—NH)$_d$—R$_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH, —N($C_{1-6}$ alkyl), or oxygen;

$R_{46}$ is —C(O)—; —C(O)—O—, —C(O)—NH—, or absent;

$R_{47}$ is as defined herein;

a is an integer from 1 to 6;

c is an integer from 0 to 3;

d is an integer from 1 to 3; and f is an integer from 1 to 12.

Further examples of the MEK inhibitor are disclosed in U.S. Pat. No. 7,517,994 B2.

In some embodiments $R_{43}$ is —C(O)—(CH$_2$)$_a$—NH$_2$, or —C(O)—C(H)(CH$_3$)—(CH$_2$)$_c$—NH$_2$; in which a is an integer from 1 to 6; and c is an integer from 0 to 3.

In another embodiment, the duocarmycin compound is a compound of Formula (XV):

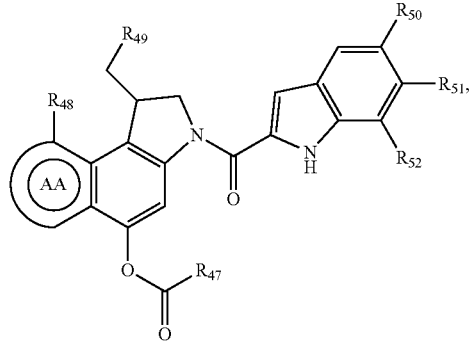

(XV)

wherein:

$R_{47}$ is as defined herein;

$R_{48}$ is hydrogen, —COOC$_{1-6}$ alkyl, —COOH, —NH$_2$ or —CH$_3$;

$R_{49}$ is C$_1$, Br or —OH;

$R_{50}$ is hydrogen, —OCH$_3$,

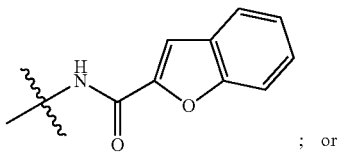

; or

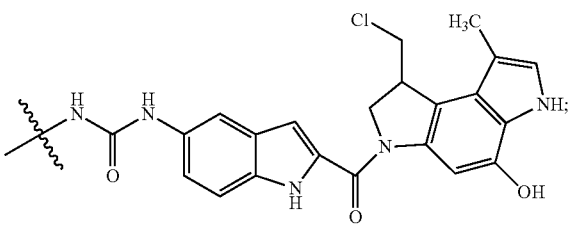

each of $R_{51}$ and $R_{52}$ independently is hydrogen or —OCH$_3$; and ring AA is either a phenyl or pyrrolyl ring.

Further examples of duocarmycin compounds are disclosed in U.S. Pat. No. 7,553,816.

In one embodiment the duocarmycin compound of Formula (XV) is a compound of Formula (XVI), (XVII), (XVIII) or (XIX):

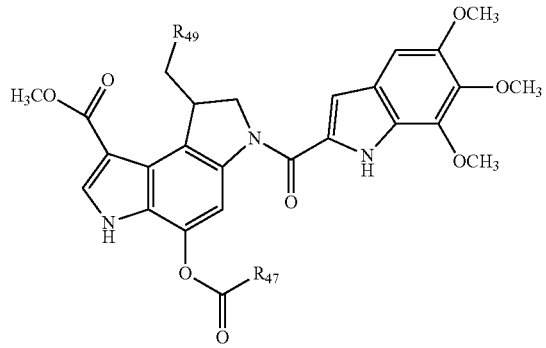

(XVI)

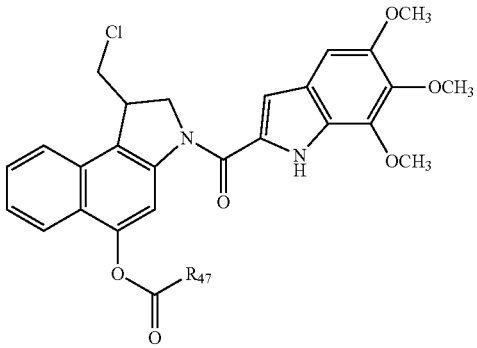

(XVII)

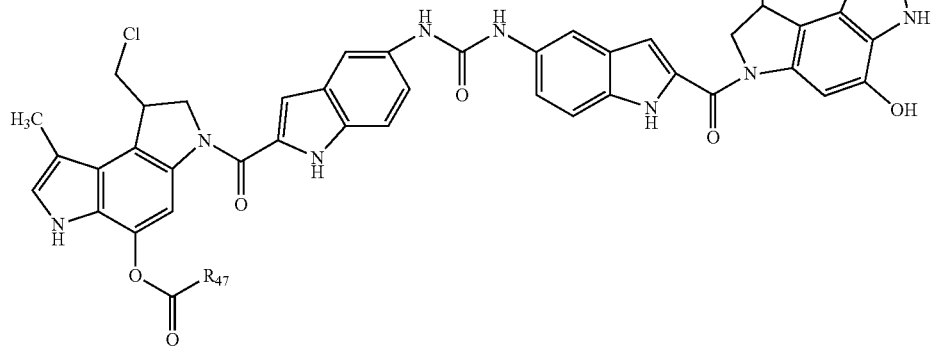

(XVIII)

-continued

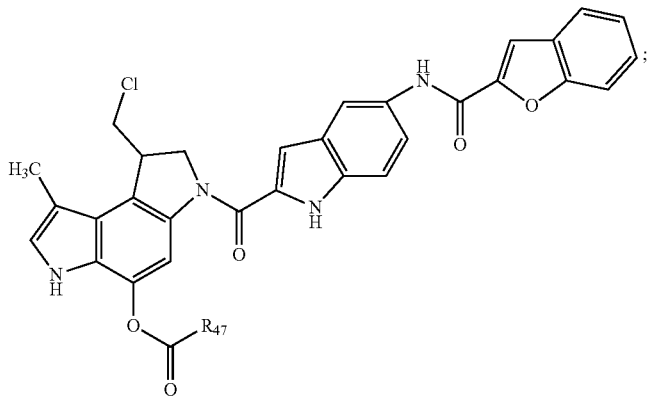
(XIX)

wherein:
$R_{49}$ is $C_1$, Br or —OH; and
$R_{47}$ is as defined herein.

In another embodiment, the duocarmycin compound is a duocarmycin SA compound of Formula (XX): U.S. Pat. No. 5,101,038; or (XXI):

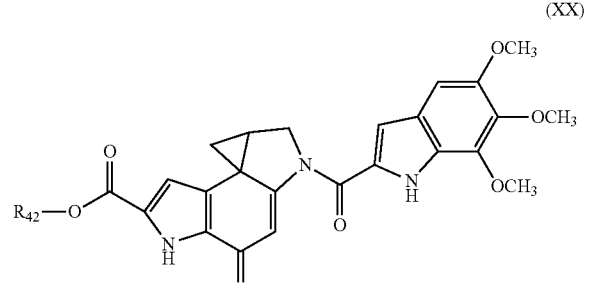
(XX)

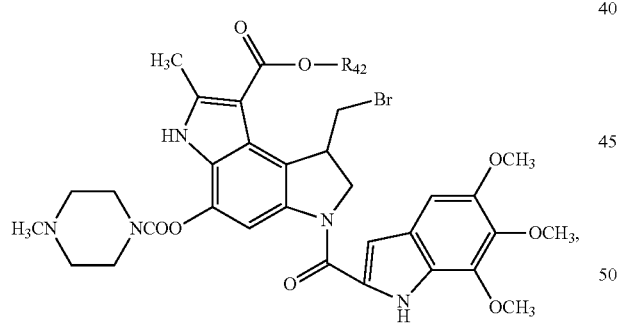
(XXI)

wherein:
$R_{42}$ is $C_{1-6}$ alkyl amino or —[C($R_{20}R_{21}$)]$_a$—$R_{22}$;
each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;
$R_{22}$ is —OH, —NH$_2$, —COOH, —$R_{82}$—C(O)(CH$_2$)$_c$—C(H)($R_{23}$)—N(H)($R_{23}$), —$R_{82}$—C(O)(CH$_2$)$_d$—(O CH$_2$—CH$_2$)$_f$—N(H)($R_{23}$), or —$R_{82}$—(C(O)—CH($X^2$)—NH)$_d$—$R_{77}$;
each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;
$X^2$ is a side chain of a natural or unnatural amino acid;
$R_{77}$ is a hydrogen or $X^2$ and $NR_{77}$ form a nitrogen containing cyclic compound;
$R_{82}$ is —NH, —N($C_{1-6}$ alkyl), or oxygen;
a is an integer from 1 to 6;
c is an integer from 0 to 3;
d is an integer from 1 to 3; and
f is an integer from 1 to 12.

In some embodiments, $R_{42}$ is any one of the following structures:

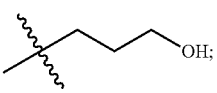
(1)

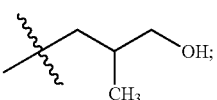
(2)

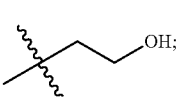
(3)

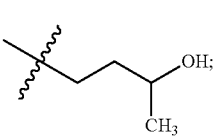
(4)

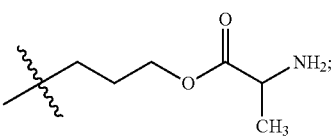
(5)

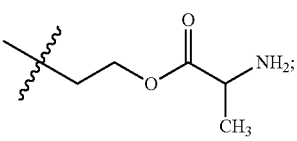
(6)

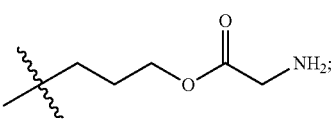
(7)

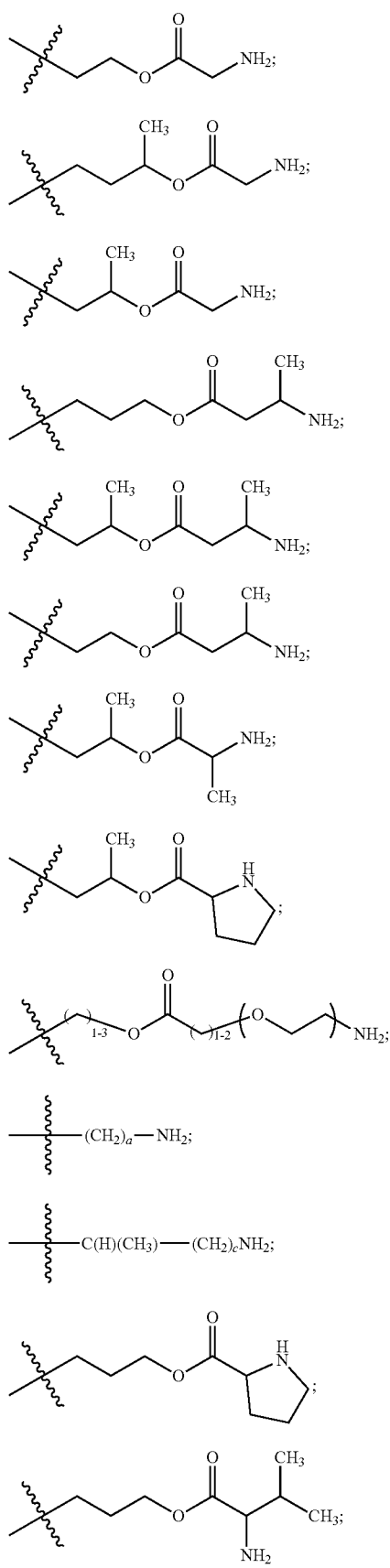
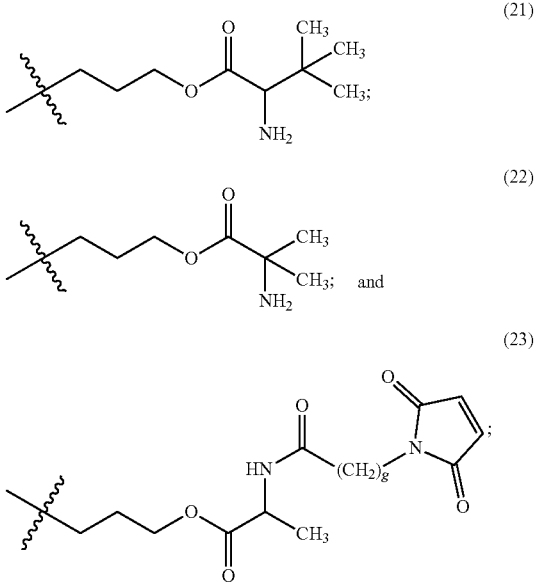
wherein:
a is an integer from 1 to 6;
g is an integer from 2 to 6; and
c is an integer from 0 to 3.
In another embodiment, the KSP inhibitor compound is a compound of Formula (XXVI):
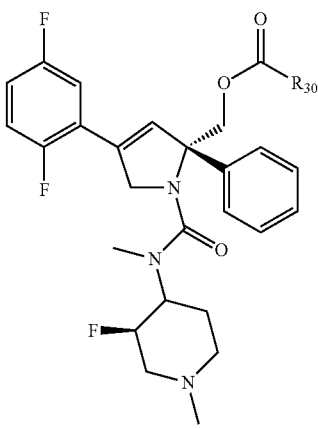
(XXVI)
wherein $R_{30}$ is as defined herein.
In some embodiments $R_{30}$ is:
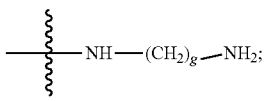
(1)
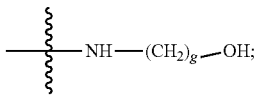
(2)

-continued (3)
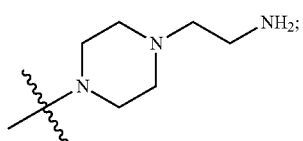

(4)
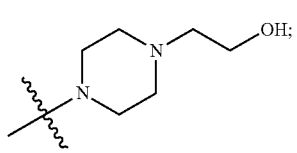

(5)
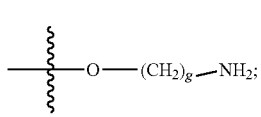

(6)
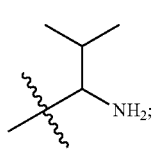

(7)
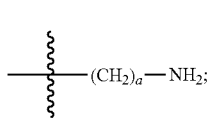

(8)
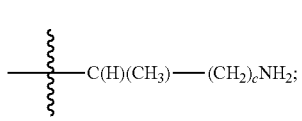

(9)
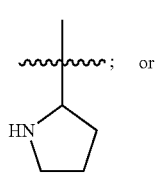

or

(10)
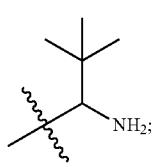

wherein:

a is an integer from 1 to 6;

c is an integer from 0 to 3; and g is an integer from 2 to 6.

In another embodiment, the duocarmycin compound is Duocarmycin A, Duocarmycin B1, Duocarmycin B2, Duocarmycin $C_1$, Duocarmycin $C_2$, Duocarmycin D, CC-1065, Adozelesin, Bizelesin or Carzelesin In another embodiment the KSP inhibitor compound is a compound of Formula (XXVII), (XXVIII) or (XXIX):

(XXVII)
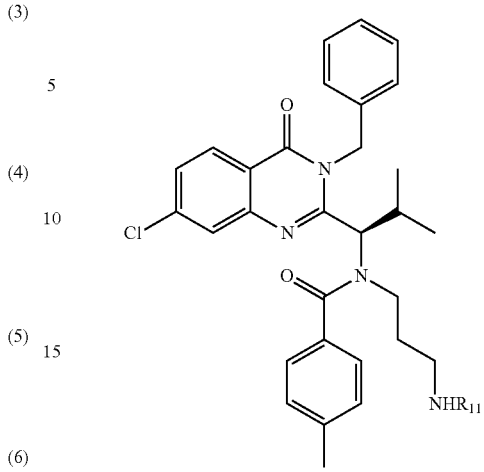

(XXVIII)
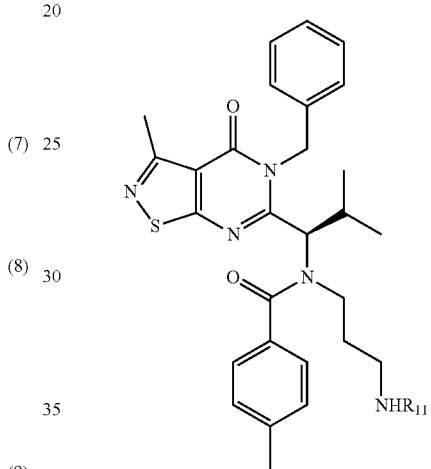

(XXIX)
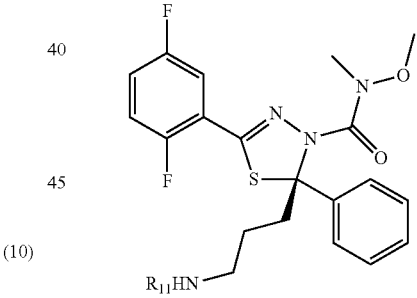

wherein:

$R_{11}$ is as defined herein.

One skilled in the art of therapeutic agents will readily understand that each of the therapeutic agents described herein can be modified in such a manner that the resulting compound still retains the specificity and/or activity of the original compound. The skilled artisan will also understand that many of these compounds can be used in place of the therapeutic agents described herein. Thus, the therapeutic agents of the present disclosure include analogs and derivatives of the compounds described herein.

Table A below provides more examples of the therapeutic agents and derivatives thereof suitable for conjugation to form the polymer-drug scaffolds or polymer-drug-protein conjugates of the disclosure. Spectral data of certain compounds are also provided (ND in the table means "not determined"). These examples may also be the active form of the drug when it is released from the conjugates in vitro or in vivo.

TABLE A
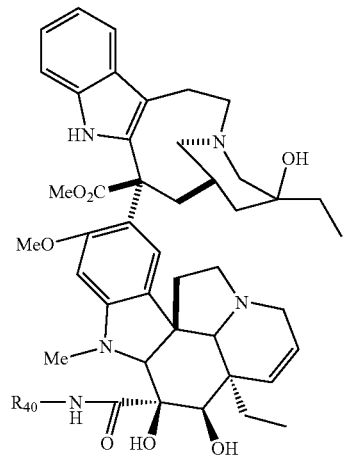
(VI)
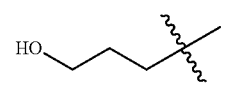 [SMILES: *CCCO]
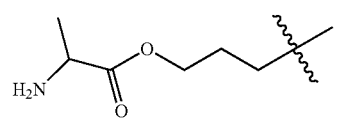 [SMILES: *CCCOC(=O)C(C)N]
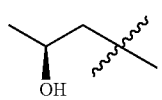
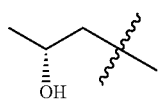 [SMILES: *C[C@@H](C)O]
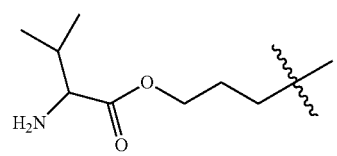 [SMILES: *CCCOC(=O)C(N)C(C)C]
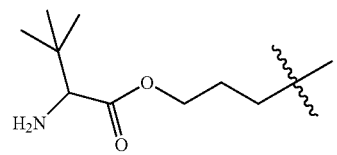 [SMILES: *CCCOC(=O)C(N)C(C)(C)C]
R40
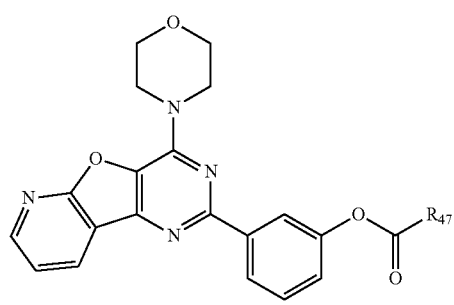
(IX)
R47    m/z TABLE A-continued

| Structure | Value |
|---|---|
| piperazine-ethylamine substituent | ND |
| NH-propyl-NH₂ substituent | ND |
| O-propyl-NH₂ substituent | ND |
| isopropyl-CH(NH₂) substituent | ND |

Formula (XI):

Peptide structure with R42 group: Me₂N-Val-Val-N(Me)-CH(OMe)-CH-C(Et)(iPr)-C(=O)-Pro-CH(Me)-CH(OMe)-C(=O)-NH-CH(CH₂Ph)-C(=O)-O-R42

| R42 | m/z |
|---|---|
| H | |
| —CH₃ | 760 |
| —C(CH₃)₂CH₂NH₂ | 802.6 |
| —CH(CH₃)CH₂CH₂NH₂ | 790 |
| —CH₂CH₂CH₂CH₂NH₂ | 804 |

Formula (XII):

Peptide structure with R40 group: Me₂N-Val-Val-N(Me)-CH(OMe)-CH-C(Et)(iPr)-C(=O)-Pro-CH(Me)-CH(OMe)-C(=O)-NH-CH(CH₂Ph)-C(=O)-NH-R40

| R40 | m/z |
|---|---|
| —H | |
| —C(CH₃)₂CH₂CH₂OH | 803.5 |
| —CH(CH₃)CH₂OH | 789.1 |

TABLE A-continued
| Structure | Value |
|---|---|
| 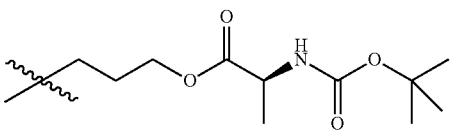 [SMILES: *CCCOC(=O)[C@H](C)NC(=O)OC(C)(C)C] | 974.2 |
| 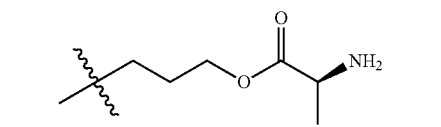 [SMILES: *CCCOC(=O)[C@H](C)N] | 874.5 |
| 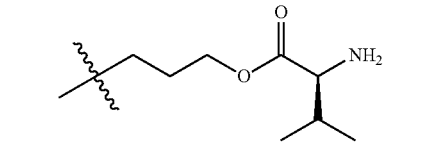 [SMILES: *CCCOC(=O)[C@@H](N)C(C)C] | 902.2 |
| 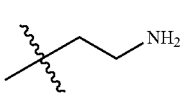 | ND |
| 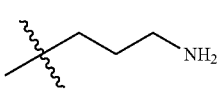 | ND |
| —OH | 788 |
| 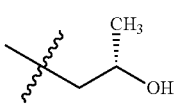 | 803.4 |
| 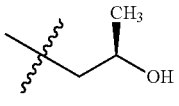 [SMILES: *C[C@@H](C)O] | 803.4 |
| 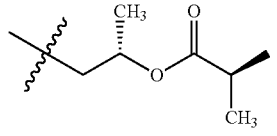 | 874.4 |
| 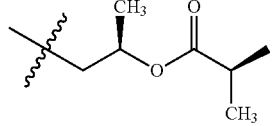 | 874.4 |
| 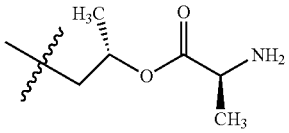 | 874.4 |
| 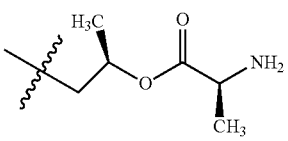 [SMILES: *C[C@@H](C)OC(=O)[C@H](C)N] | 874.4 |
| 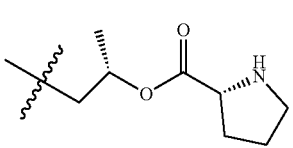 [SMILES: *C[C@H](C)OC(=O)[C@H]1CCCN1] | 900.2 |

TABLE A-continued
| | |
|---|---|
| 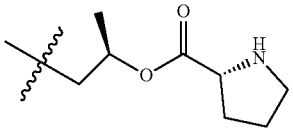 [SMILES: *C[C@@H](C)OC(=O)[C@H]1CCCN1] | 900.2 |
| 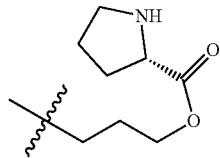 [SMILES: *CCCOC(=O)[C@@H]1CCCN1] | 900.5 |
| 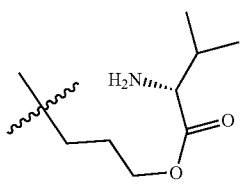 [SMILES: *CCCOC(=O)[C@H](N)C(C)C] | 900.5 |
| 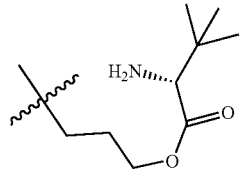 [SMILES: *CCCOC(=O)[C@H](N)C(C)(C)C] | 1016.6 |
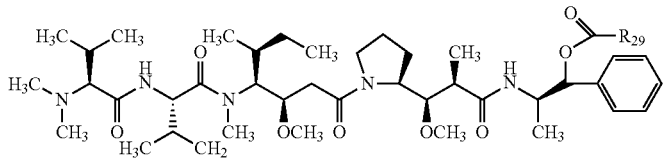 (XIII)
| —C(O)—R$_{29}$ | m/z |
|---|---|
| 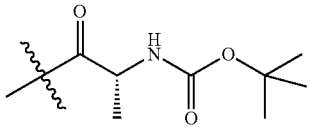 [SMILES: *C(=O)[C@@H](C)NC(=O)OC(C)(C)C] | 903.2 |
| 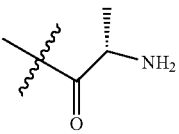 [SMILES: *C(=O)[C@H](C)N] | 803.1 |
| 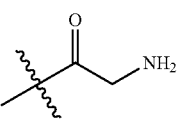 [SMILES: *C(=O)CN] | 790 |
| 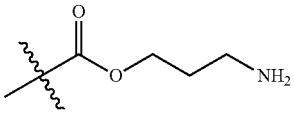 [SMILES: *C(=O)OCCCN] | 832.6 |
| 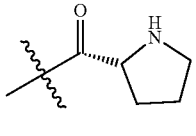 | 829.1 |

TABLE A-continued
| | |
|---|---|
| 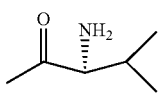 | 802 |
| 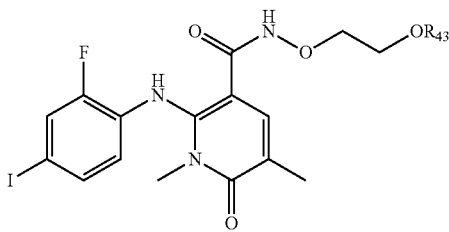 | (XIV) |
| R$_{43}$ | m/z |
| 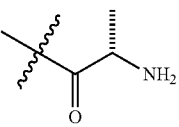 [SMILES: *C(=O)[C@H](C)N] | ND |
| 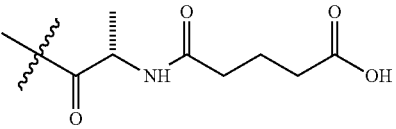 [SMILES: *C(=O)[C@H](C)NC(=O)CCCC(=O)O] | 644.9 |
| 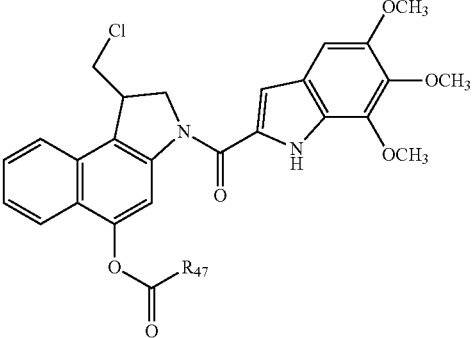 | (XVII) |
| R$_{47}$ | m/z |
| 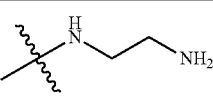 | 553.1 |
| 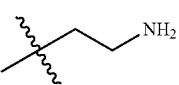 | 538.1 |
| 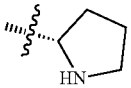 | 564.1 |
| 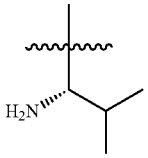 [SMILES: *[C@@H](N)C(C)C] | 566.1 |

TABLE A-continued

| Structure | Value |
|---|---|
| N-methyl-N-(2-hydroxyethyl)amine substituent | 568.1 |
| N-methyl-N-(2-(β-alanyloxy)ethyl)amine substituent | ND |
| N-methyl-N-(2-(prolyloxy)ethyl)amine substituent | ND |
| N-methyl-N-(2-(valyloxy)ethyl)amine substituent | 667.2 |
| 4-(2-aminoethyl)piperazin-1-yl substituent | 622.2 |
| 4-nitrophenoxy substituent | 632.02 |
| Val-Cit-PABC-N-methyl-N-(2-(dimethylamino)ethyl) substituent | 986.2 |

TABLE A-continued
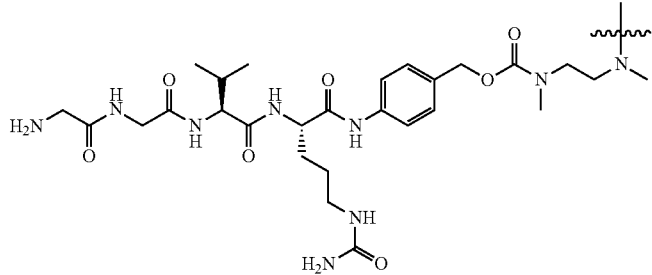 [SMILES: *N(C)CCN(C)C(=O)OCc1ccc(NC(=O)[C@H](CCCNC(N)=O)NC(=O)[C@@H](NC(=O)CNC(=O)CN)C(C)C)cc1]
ND
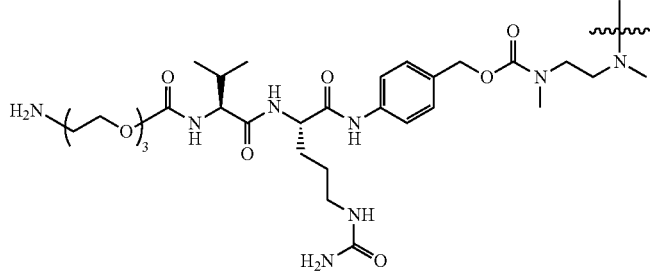
ND
| (XXVII) | (XXVIII) | (XXIX) |
|---|---|---|
| 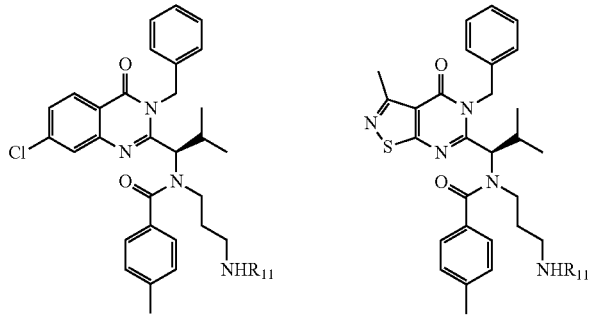 | 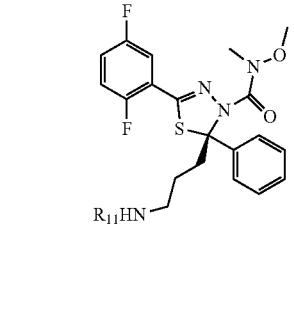 | 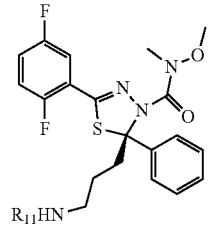 |
| $R_{11}$ | m/z (XXVII) |
|---|---|
| 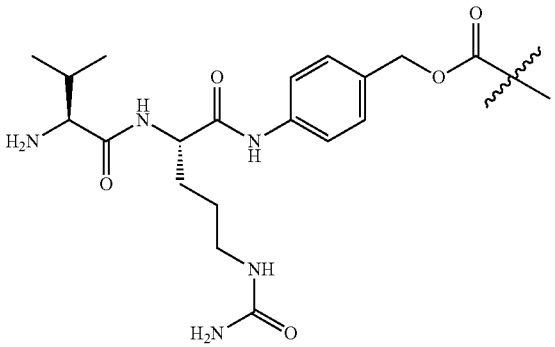 [SMILES: *C(=O)OCc1ccc(NC(=O)[C@H](CCCNC(N)=O)NC(=O)[C@@H](N)C(C)C)cc1] | 922.3 |
| 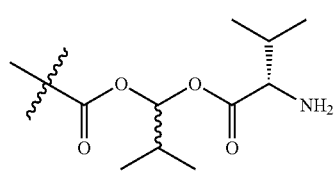 [SMILES: *C(=O)OC(OC(=O)[C@@H](N)C(C)C)C(C)C] | 732.2 |

TABLE A-continued

| | | |
|---|---|---|
| 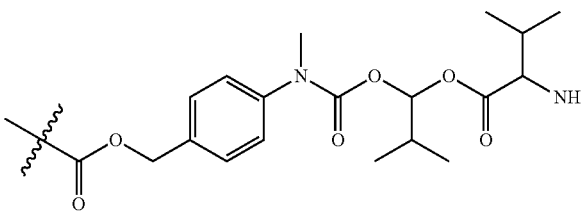 [SMILES: *C(=O)OCc1ccc(N(C)C(=O)OC(OC(=O)C(N)C(C)C)C(C)C)cc1] | | ND |
| $R_{11}$ | | m/z (XXVII) |
| 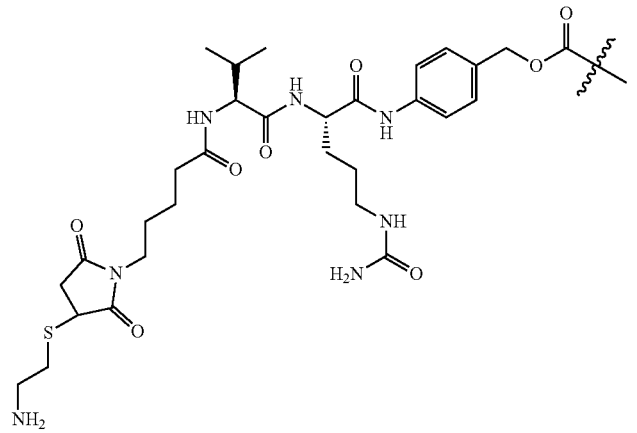 [SMILES: *C(=O)OCc1ccc(NC(=O)[C@H](CCCNC(N)=O)NC(=O)[C@@H](NC(=O)CCCCN2C(=O)CC(SCCN)C2=O)C(C)C)cc1] | | ND |
| 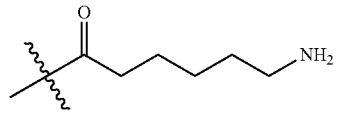 [SMILES: *C(=O)CCCCCN] | | ND |
| 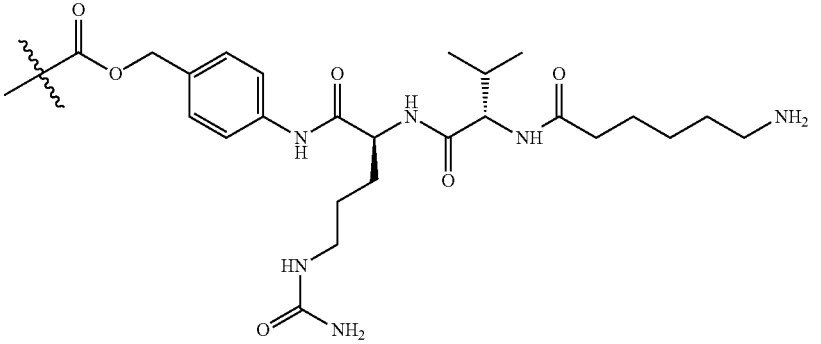 [SMILES: *C(=O)OCc1ccc(NC(=O)[C@H](CCCNC(N)=O)NC(=O)[C@@H](NC(=O)CCCCCN)C(C)C)cc1] | | ND |

Protein-Based Recognition Molecules (PBRMs)

The protein-based recognition molecule directs the drug-polymer carrier conjugates to specific tissues, cells, or locations in a cell. The protein-based recognition molecule can direct the modified polymer in culture or in a whole organism, or both. In each case, the protein-based recognition molecule has a ligand that is present on the cell surface of the targeted cell(s) to which it binds with an effective specificity, affinity and avidity. In some embodiments, the protein-based recognition molecule targets the modified polymer to tissues other than the liver. In other embodiments the protein-based recognition molecule targets the modified polymer to a specific tissue such as the liver, kidney, lung or pancreas. The protein-based recognition molecule can target the modified polymer to a target cell such as a cancer cell, such as a receptor expressed on a cell such as a cancer cell, a matrix tissue, or a protein associated with cancer such as tumor antigen. Alternatively, cells comprising the tumor vasculature may be targeted. Protein-based recognition molecules can direct the polymer to specific types of cells such as specific targeting to hepatocytes in the liver as opposed to Kupffer cells. In other cases, protein-based recognition molecules can direct the polymer to cells of the reticular endothelial or lymphatic system, or to professional phagocytic cells such as macrophages or eosinophils. (In such cases the polymer itself might also be an effective delivery system, without the need for specific targeting).

In still other embodiments, the protein based recognition molecule can target the modified polymer to a location within the cell, such as the nucleus, the cytoplasm, or the endosome, for example. In specific embodiments, the protein based recognition molecule can enhance cellular binding to receptors, or cytoplasmic transport to the nucleus and nuclear entry or release from endosomes or other intracellular vesicles.

In specific embodiments, the protein based recognition molecules include antibodies, proteins and peptides or peptide mimics.

In a preferred embodiment, the protein based recognition molecule comprises a sulfhydryl group and the protein based recognition molecule is conjugated to the polymer-drug conjugate by forming a covalent bond via the sulfhydryl group and a functional group of the polymer.

Exemplary antibodies or antibodies derived from Fab, Fab2, scFv or camel antibody heavy-chain fragments specific to the cell surface markers, include, but are not limited to, 5T4, AOC3, ALK, AXL, $C_{242}$, CA-125, CCL11, CCR 5, CD2, CD3, CD4, CD5, CD15, CA15-3, CD18, CD19, CA19-9, CD20, CD22, CD23, CD25, CD28, CD30, CD31, CD33, CD37, CD38, CD40, CD41, CD44, CD44 v6, CD51, CD52, CD54, CD56, CD62E, CD62P, CD62L, CD70, CD74, CD79-B, CD80, CD125, CD138, CD141, CD147, CD152, CD 154, CD326, CEA, clumping factor, CTLA-4, CXCR2, EGFR (HER1), ErbB2, ErbB3, EpCAM, EPHA2, EPHB2, EPHB4, FGFR (i.e. FGFR1, FGFR2, FGFR3, FGFR4), FLT3, folate receptor, FAP, GD2, GD3, GPNMB, HGF, HER2, HER3, HMI.24, ICAM, ICOS-L, IGF-1 receptor, VEGFR1, EphA2, TRPV1, CFTR, gpNMB, CA9, Cripto, c-KIT, c-MET, ACE, APP, adrenergic receptor-beta2, Claudine 3, Mesothelin, MUC1, NaPi2b, NOTCH1, NOTCH2, NOTCH3, NOTCH4, RON, ROR1, PD-L1, PD-L2, B7-H3, B7-B4, IL-2 receptor, IL-4 receptor, IL-13 receptor, integrins (including $\alpha_4$, $\alpha_v\beta_3$, $\alpha_v\beta_5$, $\alpha_v\beta_6$, $\alpha_1\beta_4$, $\alpha_4\beta_1$, $\alpha_4\beta_7$, $\alpha_5\beta_1$, $\alpha_6\beta_4$, $a_{IIb}\beta_3$ interigins), IFN-$\alpha$, IFN-$\gamma$, IgE, IgE, IGF-1 receptor, IL-1, IL-12, IL-23, IL-13, IL-22, IL-4, IL-5, IL-6, interferon receptor, ITGB2 (CD18), LFA-1 (CD11a), L-selectin (CD62L), mucin, MUC1, myostatin, NCA-90, NGF, PDGFRa, phosphatidylserine, prostatic carcinoma cell, *Pseudomonas aeruginosa*, rabies, RANKL, respiratory syncytial virus, Rhesus factor, SLAMF7, sphingosine-1-phosphate, TAG-72, T-cell receptor, tenascin C, TGF-1, TGF-☐2, TGF-$\beta$, TNF-$\alpha$, TRAIL-R1, TRAIL-R2, tumor antigen CTAA16.88, VEGF-A, VEGFR2, vimentin, and the like.

In one embodiment the antibodies or antibody derived from Fab, Fab2, scFv or camel antibody heavy-chain fragments specific to the cell surface markers include CA-125, C242, CD3, CD19, CD22, CD25, CD30, CD31, CD33, CD37, CD40, CD44, CD51, CD54, CD56, CD62E, CD62P, CD62L, CD70, CD138, CD141, CD326, CEA, CTLA-4, EGFR (HER1), ErbB2, ErbB3, FAP, folate receptor, IGF-1 receptor, GD3, GPNMB, HGF, HER2, VEGF-A, VEGFR2, VEGFR1, EphA2, EpCAM, 5T4, TAG-72, tenascin C, TRPV1, CFTR, gpNMB, CA9, Cripto, ACE, APP, PDGFR $\alpha$, phosphatidylserine, prostatic carcinoma cells, adrenergic receptor-beta2, Claudine 3, mucin, MUC1, Mesothelin, IL-2 receptor, IL-4 receptor, IL-13 receptor and integrins (including $\alpha_v\beta_3$, $\alpha_v\beta_5$, $\alpha_v\beta_6$, $\alpha_1\beta_4$, $\alpha_4\beta_1$, $\alpha_5\beta_1$, $\alpha_6\beta_4$ interigins), tenascin C, TRAIL-R2 and vimentin.

Exemplary antibodies include 3F8, abagovomab, abciximab (REOPRO), adalimumab (HUMIRA), adecatumumab, afelimomab, afutuzumab, alacizumab, ALD518, alemtuzumab (CAMPATH), altumomab, amatuximab, anatumomab, anrukinzumab, apolizumab, arcitumomab (CEA-SCAN), aselizumab, atlizumab (tocilizumab, Actemra, RoActemra), atorolimumab, bapineuzumab, basiliximab (Simulect), bavituximab, bectumomab (LYMPHOSCAN), belimumab (BENLYSTA), benralizumab, bertilimumab, besilesomab (SCINITIMUN), bevacizumab (AVASTIN), biciromab (FIBRISCINT), bivatuzumab, blinatumomab, brentuximab, briakinumab, canakinumab (ILARIS), cantuzumab, capromab, catumaxomab (REMOVAB), CC49, cedelizumab, certolizumab, cetuximab (ERBITUX), citatuzumab, cixutumumab, clenoliximab, clivatuzumab, conatumumab, CR6261, dacetuzumab, daclizumab (ZENAPAX), daratumumab, denosumab (PROLIA), detumomab, dorlimomab, dorlixizumab, ecromeximab, eculizumab (SOLIRIS), edobacomab, edrecolomab (PANOREX), efalizumab (RAPTIVA), efungumab (MYCOGRAB), elotuzumab, elsilimomab, enlimomab, epitumomab, epratuzumab, erlizumab, ertumaxomab (REXOMUN), etaracizumab (ABEGRIN), exbivirumab, fanolesomab (NEUTROSPEC), faralimomab, farletuzumab, felvizumab, fezakinumab, figitumumab, fontolizumab (HuZAF), foravirumab, fresolimumab, galiximab, gantenerumab, gavilimomab, gemtuzumab, girentuximab, glembatumumab, golimumab (SIMPONI), gomiliximab, ibalizumab, ibritumomab, igovomab (INDIMACIS-125), imciromab (MYOSCINT), infliximab (REMICADE), intetumumab, inolimomab, inotuzumab, ipilimumab, iratumumab, keliximab, labetuzumab (CEA-CIDE), lebrikizumab, lemalesomab, lerdelimumab, lexatumumab, libivirumab, lintuzumab, lucatumumab, lumiliximab, mapatumumab, maslimomab, matuzumab, mepolizumab (BOSATRIA), metelimumab, milatuzumab, minretumomab, mitumomab, morolimumab, motavizumab (NUMAX), muromonab-CD3 (ORTHOCLONE OKT3), nacolomab, naptumomab, natalizumab (TYSABRI), nebacumab, necitumumab, nerelimomab, nimotuzumab (THERACIM), nofetumomab, ocrelizumab, odulimomab, ofatumumab (ARZERRA), olaratumab, omalizumab (XOLAIR), ontecizumab, oportuzumab, oregovomab (OVAREX), otelixizumab, pagibaximab, palivizumab (SYNAGIS), panitumumab (VECTIBIX), panobacumab, pascolizumab, pemtumomab (THERAGYN), pertuzumab (OMNITARG), pexelizumab, pintumomab, priliximab, pritumumab, PRO 140, rafivirumab, ramucirumab, ranibizumab (LUCENTIS), raxibacumab, regavirumab, reslizumab, rilotumumab, rituximab (RITUXAN), robatumumab, rontalizumab, rovelizumab (LEUKARREST), ruplizumab (ANTOVA), satumomab pendetide, sevirumab, sibrotuzumab, sifalimumab, siltuximab, siplizumab, solanezumab, sonepcizumab, sontuzumab, stamulumab, sulesomab (LEUKOSCAN), tacatuzumab (AFP-CIDE), tetraxetan, tadocizumab, talizumab, tanezumab, taplitumomab paptox, tefibazumab (AUREXIS), telimomab, tenatumomab, teneliximab, teplizumab, TGN1412, ticilimumab (tremelimumab), tigatuzumab, TNX-650, tocilizumab (atlizumab, ACTEMRA), toralizumab, tositumomab (BEXXAR), trastuzumab (HERCEPTIN), tremelimumab, tucotuzumab, tuvirumab, urtoxazumab, ustekinumab (STELERA), vapaliximab, vedolizumab, veltuzumab, vepalimomab, visilizumab (NUVION), volociximab (HUMASPECT), votumumab, zalutumumab (HuMEX-EGFr), zanolimumab (HuMAX-CD4), ziralimumab and zolimomab.

In some embodiments, the antibodies are directed to cell surface markers for 5T4, CA-125, CEA, CD3, CD19, CD20, CD22, CD30, CD33, CD40, CD44, CD51, CTLA-4, EpCAM, HER2, EGFR (HER1), FAP, folate receptor, HGF, integrin integrin $\alpha_v\beta_3$, $\alpha_5\beta_1$, IGF-1 receptor, GD3, GPNMB, mucin, MUC1, phosphatidylserine, prostatic carcinoma cells, PDGFR α, TAG-72, tenascin C, TRAIL-R2, VEGF-A and VEGFR2. In this embodiment the antibodies are abagovomab, adecatumumab, alacizumab, altumomab, anatumomab, arcitumomab, bavituximab, bevacizumab (AVASTIN), bivatuzumab, blinatumomab, brentuximab, cantuzumab, catumaxomab, capromab, cetuximab, citatuzumab, clivatuzumab, conatumumab, dacetuzumab, edrecolomab, epratuzumab, ertumaxomab, etaracizumab, farletuzumab, figitumumab, gemtuzumab, glembatumumab, ibritumomab, igovomab, intetumumab, inotuzumab, labetuzumab, lexatumumab, lintuzumab, lucatumumab, matuzumab, mitumomab, naptumomab estafenatox, necitumumab, oportuzumab, oregovomab, panitumumab, pemtumomab, pertuzumab, pritumumab, rituximab (RITUXAN), rilotumumab, robatumumab, satumomab, sibrotuzumab, taplitumomab, tenatumomab, tenatumomab, ticilimumab (tremelimumab), tigatuzumab, trastuzumab (HERCEPTIN), tositumomab, tremelimumab, tucotuzumab celmoleukin, volociximab and zalutumumab.

In specific embodiments, the antibodies directed to cell surface markers for HER2 are pertuzumab or trastuzumab and for EGFR (HER1) the antibody is cetuximab or panitumumab; and for CD20 the antibody is rituximab and for VEGF-A is bevacizumab and for CD-22 the antibody is epratuzumab or veltuzumab and for CEA the antibody is labetuzumab.

Exemplary peptides or peptide mimics include integrin targeting peptides (RGD peptides), LHRH receptor targeting peptides, ErbB2 (HER2) receptor targeting peptides, prostate specific membrane bound antigen (PSMA) targeting peptides, lipoprotein receptor LRP1 targeting, ApoE protein derived peptides, ApoA protein peptides, somatostatin receptor targeting peptides, chlorotoxin derived peptides, and bombesin.

In specific embodiments, the peptides or peptide mimics are LHRH receptor targeting peptides and ErbB2 (HER2) receptor targeting peptides Exemplary proteins comprise insulin, transferrin, fibrinogen-gamma fragment, thrombospondin, claudin, apolipoprotein E, Affibody molecules such as, for example, ABY-025, Ankyrin repeat proteins, ankyrin-like repeats proteins and synthetic peptides.

In some embodiments, the protein-polymer-drug conjugates (e.g., PBRM-polymer-drug conjugates) comprise broad spectrum cytotoxins in combination with cell surface markers for HER2 such as pertuzumab or trastuzumab; for EGFR such as cetuximab and panitumumab; for CEA such as labetuzumab; for CD20 such as rituximab; for VEGF-A such as bevacizumab; or for CD-22 such as epratuzumab or veltuzumab.

In other embodiments, the protein-drug-polymer conjugates or protein-polymer conjugates (e.g., PBRM-polymer-drug conjugates) used in the disclosure comprise combinations of two or more protein based recognition molecules, such as, for example, combination of bispecific antibodies directed to the EGF receptor (EGFR) on tumor cells and to CD3 and CD28 on T cells; combination of antibodies or antibody derived from Fab, Fab2, scFv or camel antibody heavy-chain fragments and peptides or peptide mimetics; combination of antibodies or antibody derived from Fab, Fab2, scFv or camel antibody heavy-chain fragments and proteins; combination of two bispecific antibodies such as CD3×CD19 plus CD28×CD22 bispecific antibodies.

In other embodiments, the protein-drug-polymer conjugates or protein-polymer conjugates (e.g., PBRM-polymer-drug conjugates) used in the disclosure comprise protein based recognition molecules are antibodies against antigens, such as, for example, Trastuzumab, Cetuximab, Rituximab, Bevacizumab, Epratuzumab, Veltuzumab, Labetuzumab, B7-H4, B7-H3, CA125, CD33, CXCR2, EGFR, FGFR1, FGFR2, FGFR3, FGFR4, HER2, NaPi2b, c-Met, NOTCH1, NOTCH2, NOTCH3, NOTCH4, PD-L1, c-Kit, MUC1 and 5T4.

These targeting ligands, the linkers and the drug or prodrug fragments described herein can be assembled into the therapeutic drug and targeting conjugate of the disclosure, for example according to the disclosed techniques and methods. Therapeutic and targeting conjugates of the disclosure, and methods for producing them, are described below by way of non-limiting example.

Conjugates or Polymeric Scaffolds

Conjugates of the disclosure comprise one or more occurrences of D, where D is a therapeutic agent, e.g., a drug, wherein the one or more occurrences of D may be the same or different.

In certain other embodiments, one or more occurrences of PBRM is attached to the polymeric carrier, wherein the one or more occurrences of PBRM may be the same or different. In certain other embodiments, one or more polymer carriers that contains one or more occurrences of D are connected to a PBRM (e.g., an antibody).

As discussed more generally above, in certain embodiments, each polymeric carrier independently, has about 0.1% to about 25% monomers comprising a D, more preferably about 0.5% to about 20%, more preferably about 1% to about 15%, and even more preferably about 2% to about 10%. In some embodiments, the polymeric carrier is PHF having a molecular weight of about 2 kDa to about 40 kDa and has about 0.3% to about 15% monomers comprising auristatin F, more preferably about 2%-12%, more preferably about 5%-10%.

In certain embodiments, when D is drug that has an $IC_{50<10}$ pM for antiproliferative activity in a broad range of cell lines, the polymeric carrier is PHF having a molecular weight of about 2 kDa to about 40 kDa and has about 0.1% to about 25% monomers comprising D, more preferably about 2%-10%, more preferably about 2%-5%.

In certain embodiments, the scaffold that can be synthesized using the methods of this disclosure is of Formula (Id):

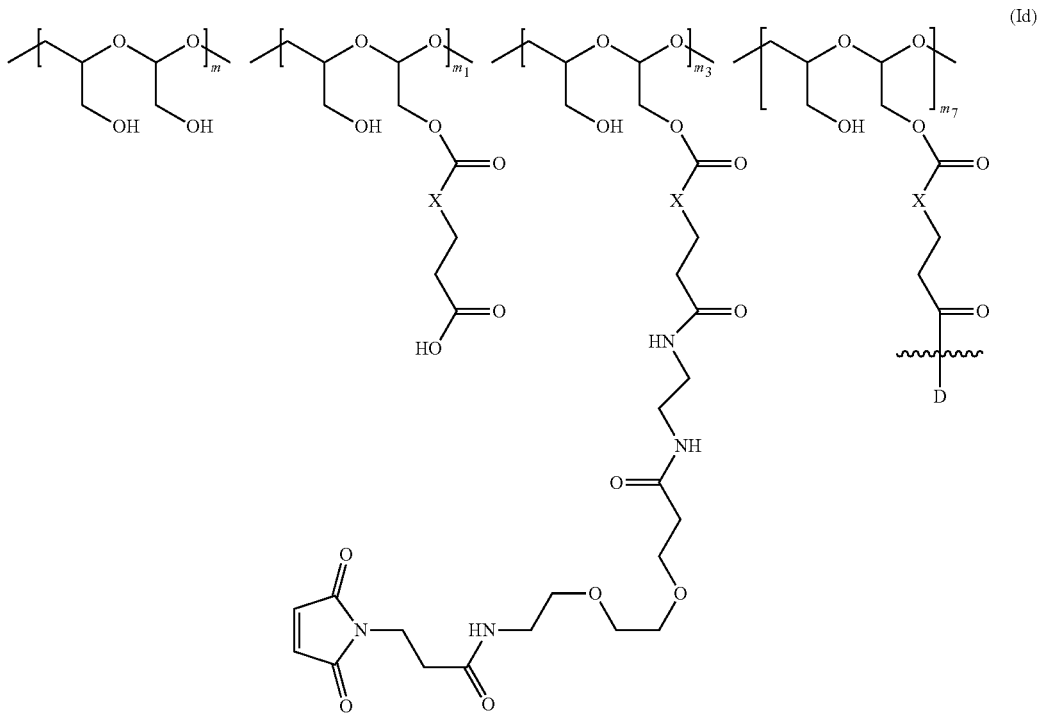

wherein:

each occurrence of D independently is a therapeutic agent having a molecular weight of ≤5 kDa, and the ⁓ between D and the carbonyl group denotes direct or indirect attachment of D to the carbonyl group, $m_1$ is an integer from 1 to about 140, and $m_7$ is an integer from 1 to about 40, wherein the sum of $m_1$ and $m_7$ is $m_6$ (i.e., 2 to about 180).

In one embodiment, D is a) an auristatin compound; (b) a calicheamicin compound; (c) a duocarmycin compound; (d) a topoisomerase inhibitor, (e) a pyrrolobenzodiazepine compound; (f) a vinca compound; (g) a protein synthesis inhibitor; (h) a RNA polymerase inhibitor; (i) a tubulin binding compound; or an analog thereof.

In certain embodiment, D is (a) an auristatin compound; (b) a calicheamicin compound; (c) a duocarmycin compound; (d) a camptothecin compound, (e) a pyrrolobenzodiazepine compound; (f) a vinca compound; or an analog thereof.

In some embodiments, the auristatin compound is auristatin, dolastatin, monomethylauristatin E (MMAE), monomethylauristatin F (MMAF), auristatin F, AF HPA, phenylenediamine (AFP).

In some embodiments, the duocarmycin or an analog thereof is duocarmycin A, duocarmycin B1, duocarmycin B2, duocarmycin $C_1$, duocarmycin $C_2$, duocarmycin D, duocarmycin SA, CC-1065, adozelesin, bizelesin, or carzelesin.

In some embodiments, the camptothecin compound is camptothecin, CPT-11 (irinotecan), SN-38, or topotecan.

In some embodiments, the pyrrolobenzodiazepine compound is a pyrrolobenzodiazepine monomer, a symmetrical pyrrolobenzodiazepine dimer or an unsymmetrical pyrrolobenzodiazepine dimer.

The polymer-drug scaffold of Formula (Id) is useful for conjugation with a PBRM that has a molecular weight of about 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa).

In some embodiments, for conjugating a PBRM having a molecular weight of 40 kDa or greater (e.g., 60 kDa or greater, 80 kDa or greater, 100 kDa or greater, 120 kDa or greater, 140 kDa or greater, 160 kDa or greater or 180 kDa or greater), the polymeric carrier of the scaffold of the disclosure is a polyacetal, e.g., a PHF having a molecular weight (i.e., MW of the unmodified PHF) ranging from about 2 kDa to about 40 kDa (e.g., about 2-20 kDa, about 3-15 kDa, about 5-10 kDa, about 6-8 kDa, or about 7-8 kDa).

In some embodiments, for conjugating a PBRM having a molecular weight of 40 kDa to 200 kDa, the polymeric carrier of the scaffold of the disclosure is a polyacetal, e.g., a PHF having a molecular weight (i.e., MW of the unmodified PHF) ranging from about 2 kDa to about 40 kDa (e.g., about 2-20 kDa, about 3-15 kDa, about 5-10 kDa, about 6-8 kDa, or about 7-8 kDa).

In some embodiments, for conjugating a PBRM having a molecular weight of 40 kDa to 80 kDa, the polymeric carrier of the scaffold of the disclosure is a polyacetal, e.g., a PHF having a molecular weight (i.e., MW of the unmodified PHF) ranging from about 2 kDa to about 40 kDa (e.g., about 2-20 kDa, about 3-15 kDa, about 5-10 kDa, about 6-8 kDa, or about 7-8 kDa). For example the PHF has a molecular weight of about 5 kDa, 10 kDa or 15 kDa.

PBRMs in this molecular weight range include, but are not limited to, for example, antibody fragments, such as, for example, Fabs.

In some embodiments, for conjugating a PBRM having a molecular weight of 60 kDa to 120 kDa, the polymeric carrier of the scaffold of the disclosure is a polyacetal, e.g., a PHF having a molecular weight (i.e., MW of the unmodified PHF) ranging from about 2 kDa to about 40 kDa (e.g., about 2-20 kDa, about 3-15 kDa, about 5-10 kDa, about 6-8 kDa, or about 7-8 kDa). For example the PHF has a molecular weight of about 5 kDa, 10 kDa or 15 kDa.

PBRMs in this molecular weight range include, but are not limited to, for example, camelids, Fab2, scFvFc, and the like.

In some embodiments, for conjugating a PBRM having a molecular weight of 140 kDa to 180 kDa, the polymeric carrier of the scaffold of the disclosure is a polyacetal, e.g., a PHF having a molecular weight (i.e., MW of the unmodified PHF) ranging from about 2 kDa to about 40 kDa (e.g., about 2-20 kDa, about 3-15 kDa, about 5-10 kDa, about 6-8 kDa, or about 7-8 kDa). For example the PHF has a molecular weight of about 5 kDa, 10 kDa or 15 kDa. PBRMs in this molecular weight range include, but are not limited to, for example, full length antibodies, such as, IgG, IgM.

In some embodiments, when the PHF has a molecular weight ranging from 2 kDa to 40 kDa, (e.g., about 2-20 kDa, about 3-15 kDa, about 5-10 kDa, about 6-8 kDa, about 7-8 kDa), the number of drugs per PHF (e.g., $m_2$) is an integer from 1 to about 40, (e.g., about 1:20 or about 2-15 or about 3:10). This scaffold can be used, for example, for conjugating a PBRM having a molecular weight of 140 kDa to 180 kDa. In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4 or between about 1:2 and about 1:3. PBRMs in this molecular weight range include, but are not limited to, for example, full length antibodies, such as, IgG, IgM.

In some embodiments, when the PHF has a molecular weight ranging from 2 kDa to 40 kDa, (e.g., about 2-20 kDa, about 3-15 kDa, about 5-10 kDa, about 6-8 kDa, or about 7-8 kDa), the number of drugs per PHF (e.g., $m_2$) is an integer from 1 to about 40, (e.g., about 1:20 or about 2:15 or about 3:10). This scaffold can be used, for example, for conjugating a PBRM having a molecular weight of 60 kDa to 120 kDa. In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4 or between about 1:2 and about 1:3. PBRMs in this molecular weight range include, but are not limited to, for example, antibody fragments such as, for example Fab2, scFcFv and camelids.

In some embodiments, when the PHF has a molecular weight ranging from 2 kDa to 40 kDa, (e.g., about 2-20 kDa, about 3-15 kDa, about 5-10 kDa, about 6-8 kDa, or about 7-8 kDa), the number of drugs per PHF (e.g., $m_2$) is an integer from 1 to about 40, (e.g., about 1:20 or about 2-15 or about 3:10). This scaffold can be used, for example, for conjugating a PBRM having a molecular weight of 40 kDa to 80 kDa. In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4 or between about 1:2 and about 1:3. PBRMs in this molecular weight range include, but are not limited to, for example, antibody fragments, such as, Fabs.

In some embodiments, the scaffold that can be synthesized using the methods of this disclosure is of Formula (A):

(A)

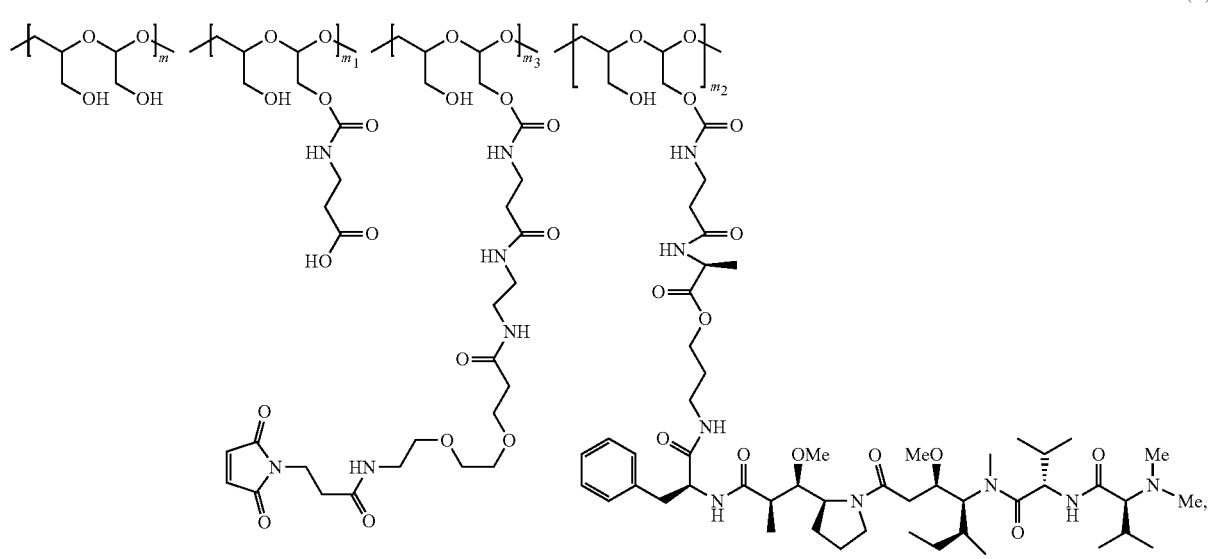

or a salt thereof,
wherein:
the scaffold of Formula (A) comprises poly(1-hydroxymethylethylene hydroxymethyl-formal) (PHF) having a molecular weight ranging from about 5 kDa to about 10 kDa;

m is an integer from about 20 to about 75, $m_1$ is an integer from about 5 to about 35, $m_2$ is an integer from about 3 to about 10, $m_3$ is an integer from about 1 to about 5, and the sum of m, $m_1$, $m_2$ and $m_3$ ranges from about 40 to about 75.

In certain embodiments, the PBRM-polymer-drug conjugate that can be synthesized using the methods of this disclosure is of Formula (Ie):

(Ie)
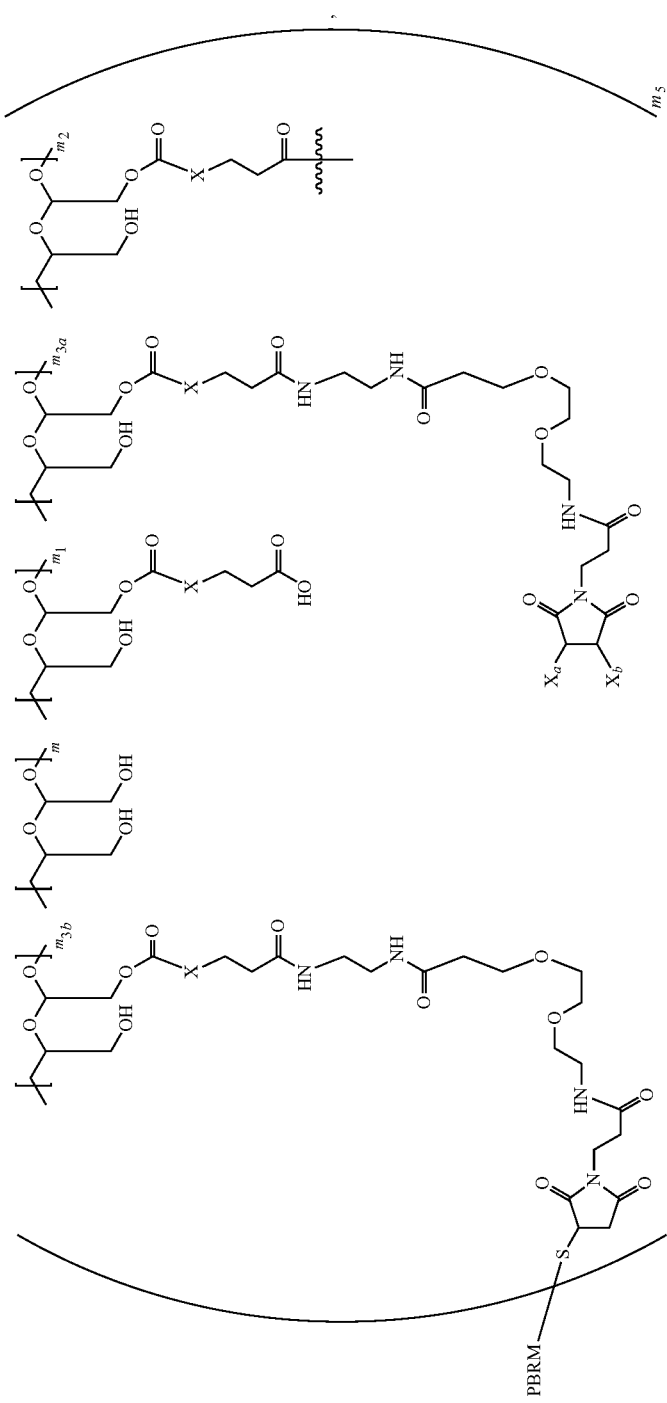

wherein:

each occurrence of D independently is a therapeutic agent having a molecular weight of ≤5 kDa, and the ⁓ between D and the carbonyl group denotes direct or indirect attachment of D to the carbonyl group, one of $X_a$ and $X_b$ is H and the other is a maleimido blocking moiety, or $X_a$ and $X_b$, together with the carbon atoms to which they are attached form a carbon-carbon double bond;

$m_{3a}$ is an integer from 0 to about 17, $m_{3b}$ is an integer from 1 to about 8, wherein the sum of $m_{3a}$ and $m_{3b}$ is $m_3$, the sum of m, $m_1$, $m_7$, $m_{3a}$, and $m_{3b}$ ranges from about 15 to about 300, and $m_5$ is an integer from 1 to about 10.

In some embodiments, the PBRM has a molecular weight of about 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa).

In some embodiments, the PBRM has a molecular weight of about 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa) and has a sulfhydryl (i.e., —SH or thiol) group.

In some embodiments, the total number of sulfide bonds formed between the PHF and the PBRM (or total number of attachment points) is about 10 or less.

In some embodiments, the ratio between $m_7$ and $m_{3b}$ is greater than about 1:1 and less than or equal to about 10:1.

In some embodiments, the ratio between $m_7$ and $m_{3b}$ is about 9:1, 8:1, 7:1, 6:1, 5:1, 4:1, 3:1, or 2:1.

In some embodiments, the ratio between $m_7$ and $m_{3b}$ is between about 2:1 and about 8:1.

In some embodiments, the ratio between $m_7$ and $m_{3b}$ is about 8:1, 7:1, 6:1, 5:1, 4:1, 3:1, or 2:1.

In some embodiments, the ratio between $m_7$ and $m_{3b}$ is between about 2:1 and about 5:1.

In some embodiments, the ratio between $m_7$ and $m_{3b}$ is about 5:1, 4:1, 3:1, or 2:1.

In some embodiments, the ratio between $m_7$ and $m_{3b}$ ranges from about 2:1 to about 4:1.

In some embodiments, the ratio between $m_7$ and $m_{3b}$ is about 4:1, 3:1, or 2:1.

In some embodiments, the ratio between $m_7$ and $m_{3b}$ is about 4:1 or 3:1.

In some embodiments, the ratio between $m_7$ and $m_{3b}$ is about 4:1.

In some embodiments, the ratio between $m_7$ and $m_{3b}$ is about 3:1.

In some embodiments, the ratio between D and PBRM can range from about 2:1 to about 40:1, from about 4:1 to about 30:1, from about 6:1 to about 20:1, from about 8:1 to about 18:1, or from 10:1 to about 15:1.

In some embodiments, when the PHF in Formula (Ie) has a molecular weight ranging from about 2 kDa to about 20 kDa, the sum of m, $m_1$, $m_7$, $m_{3a}$ and $m_{3b}$ ranges from about 15 to about 150, $m_1$ is an integer from 1 to about 70, $m_7$ is an integer from 1 to about 20, $m_{3a}$ is an integer from 0 to about 9, $m_{3b}$ is an integer from 1 to about 8 and $m_5$ is an integer from 2 to about 8.

In some embodiments, when the PHF in Formula (Ie) has a molecular weight ranging from about 3 kDa to about 15 kDa, the sum of m, $m_1$, $m_7$, $m_{3a}$ and $m_{3b}$ ranges from about 20 to about 110, $m_1$ is an integer from 2 to about 50, $m_7$ is an integer from 2 to about 15, $m_{3a}$ is an integer from 0 to about 7, $m_{3b}$ is an integer from 1 to about 8 and $m_5$ is an integer from 2 to about 4.

In some embodiments, when the PHF in Formula (Ie) has a molecular weight ranging from about 5 kDa to about 10 kDa, the sum of m, $m_1$, $m_7$, $m_{3a}$ and $m_{3b}$ ranges from about 40 to about 75, $m_1$ is an integer from about 5 to about 35, $m_7$ is an integer from about 3 to about 10, $m_{3a}$ is an integer from 0 to about 4, $m_{3b}$ is an integer from 1 to about 5 and $m_5$ is an integer from 2 to about 4.

In some embodiments, the PBRM-polymer-drug conjugate that can be synthesized using the methods of this disclosure is of Formula (B):

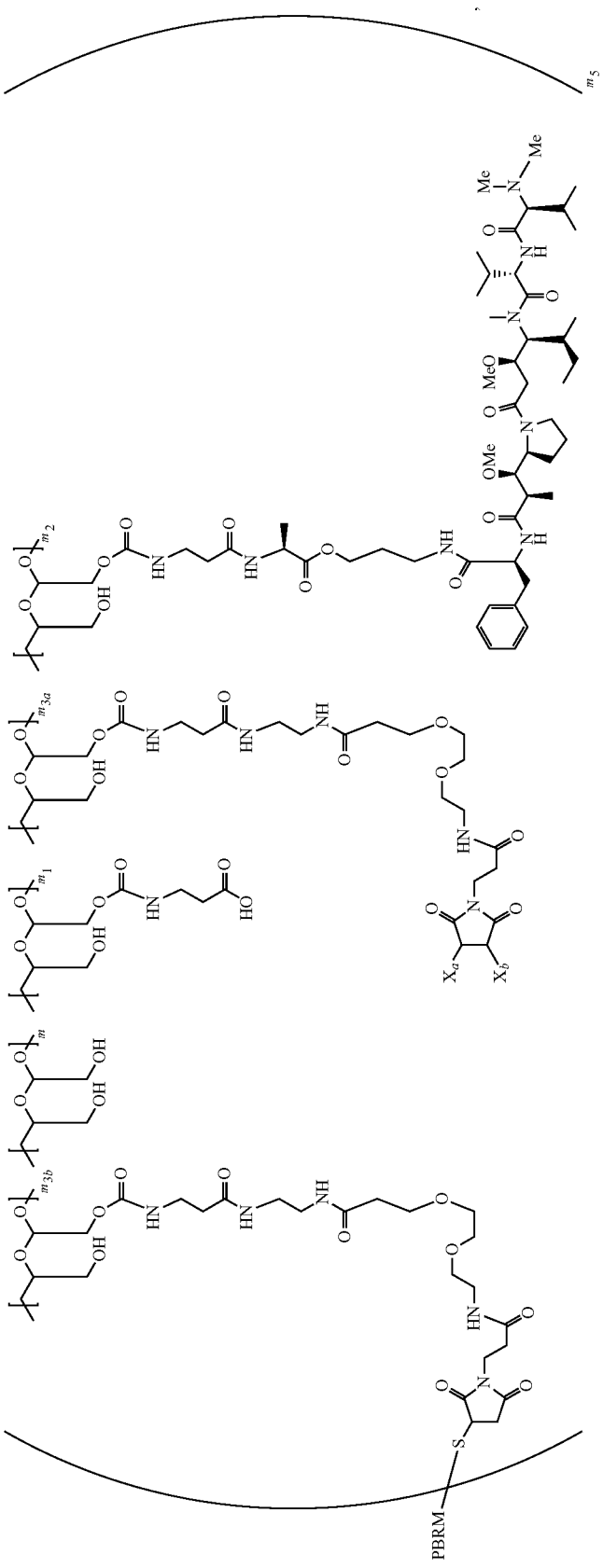

wherein:

one of $X_a$ and $X_b$ is H and the other is a water-soluble maleimido blocking moiety, or $X_a$ and $X_b$, together with the carbon atoms to which they are attached form a carbon-carbon double bond;

the PHF has a molecular weight ranging from about 5 kDa to about 10 kDa;

m is an integer from 20 to 75, $m_1$ is an integer from about 5 to about 35, $m_2$ is an integer from about 3 to about 10, $m_{3a}$ is an integer from about 0 to about 4, $m_{3b}$ is an integer from about 1 to about 5, the sum of m, $m_1$, $m_2$, $m_{3a}$, and $m_{3b}$ ranges from about 40 to about 75, and $m_5$ is an integer from 2 to about 5.

In some embodiments, the ratio between AF HPA and PBRM can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and PBRM can be about 20:1, 19:1, 18:1, 17:1, 16:1, 15:1, 14:1, 13:1, 12:1, 11:1, 10:1 or 9:1.

In some embodiments, the ratio between AF HPA and PBRM can be about 18:1, 17:1, 16:1, 15:1, 14:1, 13:1 or 12:1.

In some embodiments, the ratio between AF HPA and PBRM can be about 15:1, 14:1, 13:1, 12:1, 11:1, 10:1 or 9:1.

In some embodiments, the ratio between AF HPA and PBRM can be about 15:1, 14:1, 13:1, 12:1, 11:1 or 10:1.

In some embodiments, the ratio between AF HPA and PBRM can be about 15:1, 14:1, 13:1 or 12:1.

In some embodiments, the ratio between AF HPA and PBRM can be about 14:1, 13:1, 12:1, 11:1, 10:1 or 9:1.

In some embodiments, the ratio between AF HPA and PBRM can be about 13:1, 12:1, 11:1, 10:1 or 9:1.

In some embodiments, the ratio between AF HPA and PBRM can be about 12:1, 11:1, 10:1 or 9:1.

In some embodiments, the ratio between AF HPA and PBRM can be about 11:1, 10:1 or 9:1.

In some embodiments, the ratio between PHF and PBRM can be about 10:1, 9:1, 8:1, 7:1, 6:1, 5:1, 4:1, 3:1, or 2:1.

In some embodiments, the ratio between PHF and PBRM can range from about 10:1 to about 1:1, from about 7:1 to about 2:1, or from about 5:1 to about 3:1

In some embodiments, the ratio between PHF and PBRM can be about 6:1, 5:1, 4:1, 3:1, or 2:1.

In some embodiments, the ratio between PHF and PBRM can be about 5:1, 4:1, 3:1, or 2:1.

In some embodiments, the ratio between PHF and PBRM can be about 5:1, 4:1 or 3:1.

In some embodiments, the ratio between PHF and PBRM can be about 4:1 or 3:1.

In some embodiments, the PBRM has a molecular weight of about 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa).

In some embodiments, the total number of sulfide bonds formed between the PHF and the PBRM (or total number of attachment points) is 10 or less.

In some embodiments, the total number of sulfide bonds formed between the PHF and the PBRM ranges from about 3 to about 10.

In some embodiments, the total number of sulfide bonds formed between the PHF and the PBRM is about 3, 4, 5, 6, 7, 8, 9, or 10.

In some embodiments, the total number of sulfide bonds formed between the PHF and the PBRM is about 3, 4, 5, 6, 7 or 8.

In some embodiments, the total number of sulfide bonds formed between the PHF and the PBRM is about 3, 4 or 5.

In some embodiments, m is an integer from about 20 to about 60, from about 25 to about 45, from about 30 to about 40, or from about 33 to about 37. In some embodiments, m is about 33, 34, 35, 36, or 37.

In some embodiments, $m_1$ is an integer from about 5 to about 20, from about 6 to about 15, from about 7 to about 10, or from about 8 to about 10.

In some embodiments, $m_2$ is an integer from about 3 to about 8, from about 3 to about 6, or from about 3 or about 5. In some embodiments, $m_2$ is about 3, 4, or 5.

In some embodiments, $m_{3a}$ is an integer from about 0 to about 3, from about 0 to about 2, or from about 0 to about 1.

In some embodiments, $m_{3b}$ is an integer from about 1 to about 4, from about 1 to about 3, or from about 1 to about 2.

In some embodiments, $m_5$ is an integer from about 2 to about 8, from about 2 to about 6, or from about 3 to about 5.

In some embodiments, the ratio between $m_2$ and $m_{3b}$ ranges from about 1:1 to about 10:1.

In some embodiments, the ratio between $m_2$ and $m_{3b}$ is about 9:1, 8:1, 7:1, 6:1, 5:1, 4:1, 3:1, or 2:1.

In some embodiments, the ratio between $m_2$ and $m_{3b}$ is between about 2:1 and about 8:1.

In some embodiments, the ratio between $m_2$ and $m_{3b}$ is about 8:1, 7:1, 6:1, 5:1, 4:1, 3:1, or 2:1.

In some embodiments, the ratio between $m_2$ and $m_{3b}$ is between about 2:1 and about 4:1.

In some embodiments, the ratio between $m_2$ and $m_{3b}$ is about 4:1, 3:1, or 2:1.

In some embodiments, the ratio between $m_2$ and $m_{3b}$ is about 4:1 or 3:1.

In some embodiments, when the PHF in Formula (B) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 5 to about 35, $m_2$ is an integer from about 3 to about 10, $m_{3a}$ is an integer from 0 to about 4, $m_{3b}$ is an integer from 1 to about 5 and $m_5$ is an integer from 2 to about 4.

When the PHF in Formula B has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of $m_{3a}$ and $m_{3b}$ ranges from 1 and about 5; and the ratio between the PHF and the antibody is an integer from 2 to about 8 (e.g., from about 2 to about 6 or from about 2 to about 4).

In some embodiments, the ratio between auristatin F hydroxylpropylamide ("AF HPA") and the PBRM can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and the PBRM can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and the PBRM can be about 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and PBRM can be about 16:1, 15:1, 14:1, 13:1, 12:1, 11:1 or 10:1.

In some embodiments, the ratio between AF HPA and PBRM can be about 15:1, 14:1, 13:1, 12:1, 11:1 or 10:1.

In some embodiments, the ratio between AF HPA and PBRM can be about 15:1, 14:1, 13:1 or 12:1.

In some embodiments, the ratio between AF HPA and PBRM can be about 12:1, 11:1, 10:1 or 9:1.

In some embodiments, the ratio between PHF and PBRM can be about 10:1, 9:1, 8:1, 7:1, 6:1, 5:1, 4:1, 3:1, 2:1 or 1:1.

In some embodiments, the ratio between PHF and PBRM can be about 8:1, 7:1, 6:1, 5:1, 4:1, 3:1 or 2:1.

In some embodiments, the ratio between PHF and PBRM can be about 6:1, 5:1, 4:1, 3:1, 2:1 or 1:1.

In some embodiments, the ratio between PHF and PBRM can be about 6:1, 5:1, 4:1, 3:1 or 2:1.

In some embodiments, the ratio between PHF and PBRM can be about 6:1, 5:1, 4:1 or 3:1.

In some embodiments, the ratio between PHF and PBRM can be about 5:1, 4:1 or 3:1.

In some embodiments, the ratio between PHF and PBRM can be about 4:1, 3:1 or 2:1.

In some embodiments, the ratio between PHF and PBRM can be about 4:1 or 3:1.

In some embodiments, the maleimido blocking moieties are moieties that can be covalently attached to one of the two olefin carbon atoms upon reaction of the maleimido group with a thiol-containing compound of Formula (II):

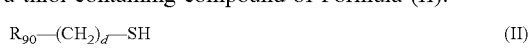

$$R_{90}\text{—}(CH_2)_d\text{—}SH \quad (II)$$

wherein:

$R_{90}$ is $NHR_{91}$, OH, $COOR_{93}$, $CH(NHR_{91})COOR_{93}$ or a substituted phenyl group;

$R_{93}$ is hydrogen or $C_{1-4}$ alkyl;

$R_{91}$ is hydrogen, $CH_3$ or $CH_3CO$ and d is an integer from 1 to 3.

In some embodiments, the maleimido blocking compound of Formula (II) can be cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol. The one or more hydrophilic substituents on phenyl comprise OH, SH, methoxy, ethoxy, COOH, CHO, $COC_{1-4}$ alkyl, $NH_2$, F, cyano, $SO_3H$, POSH, and the like.

In some embodiments, the maleimido blocking group is —S—$(CH_2)_d$—$R_{90}$, in which, $R_{90}$ is OH, COOH, or $CH(NHR_{91})COOR_{93}$;

$R_{93}$ is hydrogen or $CH_3$;

$R_{91}$ is hydrogen or $CH_3CO$; and d is 1 or 2.

In some embodiments, the maleimido blocking group is —S—$CH_2$—$CH(NH_2)COOH$.

In certain embodiments, the conjugates or scaffolds are formed in several steps. These steps include (1) modifying a polymer so that it contains a functional group that can react with a functional group of the drug or its derivative; (2) reacting the modified polymer with the drug or its derivative so that the drug is linked to the polymer; (3) modifying the polymer-drug conjugate so that the polymer contains a functional group that can react with a functional group of the PBRM or its derivative; and (4) reacting the modified polymer-drug conjugate with the PBRM or its derivative to form the conjugate of this disclosure. Step (3) may be omitted if the modified polymer produced by step (1) contains a functional group that can react with a functional group of the PBRM or its derivative. The sequence of step (3) and steps (1) to (2) can be reversed i.e. step (3) may also be performed prior to steps (1) and (2).

In another embodiment the conjugates or scaffolds are formed in several steps: (1) modifying a polymer so that it contains a functional group that can react with a functional group of a first drug or its derivative; (2) reacting the modified polymer with the first drug or its derivative so that the first drug is linked to the polymer; (3) modifying the polymer-drug conjugate so that it contains a different functional group that can react with a functional group of a second drug or its derivative (4) reacting the modified polymer-drug conjugate with the second drug or its derivative so that the second drug is linked to the polymer-drug conjugate; (5) modifying the polymer-drug conjugate containing 2 different drugs so that the polymer contains a functional group that can react with a functional group of the PBRM or its derivative; and (6) reacting the modified polymer-drug conjugate of step (5) with the PBRM or its derivative to form the conjugate of this disclosure. Steps (5) and (6) may be repeated if 2 different PBRM or its derivatives are to be conjugated to form a polymer-drug conjugate comprising two different drugs and two different PBRMs. The sequence of step (5) and steps (1) to (4) can be reversed i.e. step (5) may also be performed prior to steps (1) to (4).

In yet another embodiment, the conjugates or scaffolds are formed in several steps. These steps include (1) modifying a polymer so that it contains a functional group that can react with a functional group of the drug or its derivative; (2) further modifying the polymer so that it also contains a functional group that can react with a functional group of the PBRM or its derivative; (3) reacting the modified polymer with the drug or its derivative so that the drug is linked to the polymer; and (4) reacting the modified polymer-drug conjugate with the PBRM or its derivative to form the conjugate of this disclosure. The sequence of steps (1) and (2) or that of steps (3) and (4) can be reversed. Further either step (1) or (2) may be omitted if the modified polymer contains a functional group that can react with both a functional group of the drug or its derivatives and a functional group of the PBRM or its derivative. The sequence of step (2) and step (1) can be reversed i.e. step (2) may also be performed prior to step (1).

In another embodiment the conjugates or scaffolds are formed in several steps: (1) modifying a polymer so that it contains a functional group that can react with a functional group of a first drug or its derivative; (2) further modifying a polymer so that it contains a functional group that can react with a functional group of the PBRM or its derivative; (3) reacting the modified polymer with the first drug or its derivative so that the first drug is linked to the polymer; (4) modifying the polymer-drug conjugate so that it contains a different functional group that can react with a functional group of a second drug or its derivative (5) reacting the modified polymer-drug conjugate with the second drug or its derivative so that the second drug is linked to the polymer-drug conjugate; (6) reacting the modified polymer-drug conjugate containing 2 different drugs so that the polymer with the PBRM or its derivative to form the conjugate of this disclosure. Step (6) may be repeated if 2 different PBRM or its derivatives are to be conjugated to form a polymer-drug conjugate comprising two different drugs and two different PBRMs. Step (4) may be carried out after step (1) so that the modified polymer contains two different functional groups that can react with two different drugs or their derivatives. In this embodiment, the modified polymer containing two different functional group that can react with two different drugs or their derivatives can be further modified so that it contains a functional group that can react with a functional group of the PBRM or its derivative; prior to the reaction of the modified polymer with either the two different drugs (step (3) and step (5) or PBRM (step (6). The sequence of step (2) and step (1) can be reversed i.e. step (2) may also be performed prior to step (1).

The biodegradable biocompatible conjugates or scaffolds of the disclosure can be prepared to meet desired requirements of biodegradability and hydrophilicity. For example, under physiological conditions, a balance between biodegradability and stability can be reached. For instance, it is known that molecules with molecular weights beyond a certain threshold (generally, above 40-100 kDa, depending on the physical shape of the molecule) are not excreted through kidneys, as small molecules are, and can be cleared from the body only through uptake by cells and degradation in intracellular compartments, most notably lysosomes. This observation exemplifies how functionally stable yet biodegradable materials may be designed by modulating their stability under general physiological conditions (pH=7.5±0.5) and at lysosomal pH (pH near 5). For example, hydrolysis of acetal and ketal groups is known to be catalyzed by acids, therefore polyals will be in general less stable in acidic lysosomal environment than, for example, in blood plasma. One can design a test to compare polymer degradation profile at, for example, pH=5 and pH=7.5 at 37° C. in aqueous media, and thus to determine the expected balance of polymer stability in normal physiological environment and in the "digestive" lysosomal compartment after uptake by cells. Polymer integrity in such tests can be measured, for example, by size exclusion HPLC. One skilled on the art can select other suitable methods for studying various fragments of the degraded conjugates of this disclosure.

In many cases, it will be preferable that at pH=7.5 the effective size of the polymer will not detectably change over 1 to 7 days, and remain within 50% from the original for at least several weeks. At pH=5, on the other hand, the polymer should preferably detectably degrade over 1 to 5 days, and be completely transformed into low molecular weight fragments within a two-week to several-month time frame. Although faster degradation may be in some cases preferable, in general it may be more desirable that the polymer degrades in cells with the rate that does not exceed the rate of metabolization or excretion of polymer fragments by the cells. Accordingly, in certain embodiments, the conjugates of the present disclosure are expected to be biodegradable, in particular upon uptake by cells, and relatively "inert" in relation to biological systems. The products of carrier degradation are preferably uncharged and do not significantly shift the pH of the environment. It is proposed that the abundance of alcohol groups may provide low rate of polymer recognition by cell receptors, particularly of phagocytes. The polymer backbones of the present disclosure generally contain few, if any, antigenic determinants (characteristic, for example, for some polysaccharides and polypeptides) and generally do not comprise rigid structures capable of engaging in "key-and-lock" type interactions in vivo unless the latter are desirable. Thus, the soluble, crosslinked and solid conjugates of this disclosure are predicted to have low toxicity and bioadhesivity, which makes them suitable for several biomedical applications.

In certain embodiments, the biodegradable biocompatible conjugates or scaffolds can form linear or branched structures. In some embodiments, the biodegradable biocompatible polyal conjugates or scaffolds of the present disclosure can be chiral (optically active). Optionally, the biodegradable biocompatible polyal conjugates or scaffolds of the present disclosure can be scalemic.

In certain embodiments, the conjugates or scaffolds of the disclosure are water-soluble. In certain embodiments, the conjugates or scaffolds of the disclosure are water-insoluble. In certain embodiments, the conjugate or scaffold is in a solid form. In certain embodiments, the conjugates or scaffolds of the disclosure are colloids. In certain embodiments, the conjugates or scaffolds of the disclosure are in particle form. In certain embodiments, the conjugates or scaffolds of the disclosure are in gel form.

This disclosure also features a polymeric scaffold useful for conjugating with a PBRM to form a polymer-drug-PBRM conjugate described herein as well as methods of synthesizing the scaffold. The scaffold comprises a polymeric carrier of Formula (Ia) useful to conjugate with a PBRM, e.g., PBRM with a molecular weight of about 40 kDa or greater:

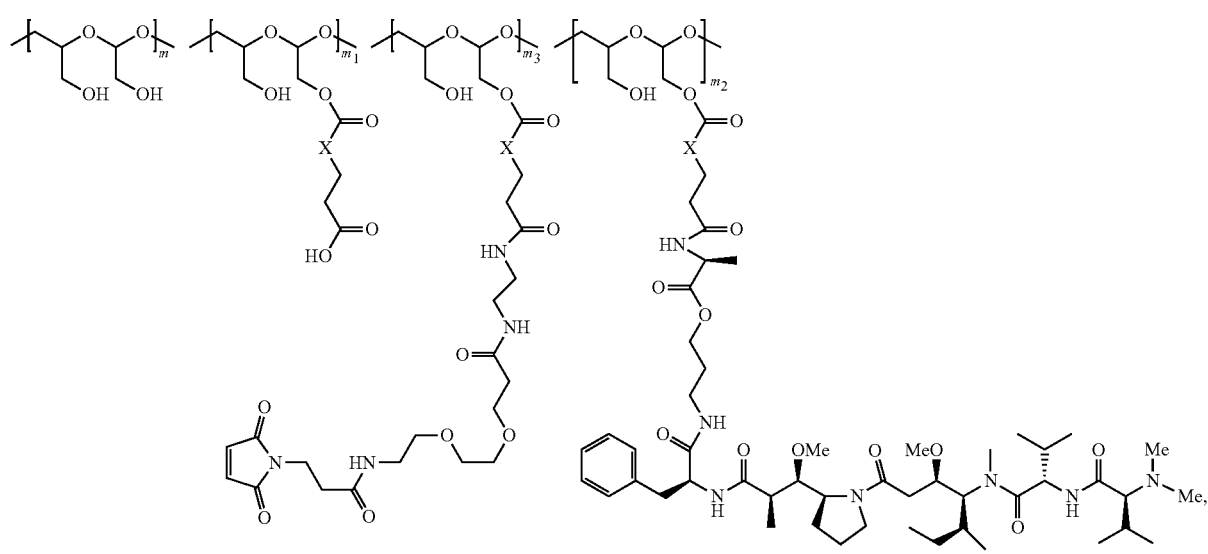

(Ia)

the scaffold comprises poly(1-hydroxymethylethylene hydroxymethyl-formal) (PHF) having a molecular weight ranging from about 2 kDa to about 40 kDa;

X is $CH_2$, O, or NH;

m is an integer from 1 to about 300, $m_1$ is an integer from 1 to about 140, $m_2$ is an integer from 1 to about 40, $m_3$ is an integer from 1 to about 18, and the sum of m, $m_1$, $m_2$ and $m_3$ ranges from about 15 to about 300.

In some embodiments, each occurrence of the maleimido moiety in the "$m_3$" unit of Formula (Ia) is yet to form a covalent bond with a functional group of the PBRM.

In some embodiments, for conjugating a PBRM having a molecular weight of 40 kDa or greater (e.g., 60 kDa or greater, 80 kDa or greater, 100 kDa or greater, 120 kDa or greater, 140 kDa or greater, 160 kDa or greater or 180 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa), the polymeric carrier of the scaffold of the disclosure is a polyacetal, e.g., a PHF having a molecular weight (i.e., MW of the unmodified PHF) ranging from about 2 kDa to about 40 kDa (e.g., about 2-20 kDa, about 3-15 kDa, about 5-10 kDa, about 6-8 kDa, or about 7-8 kDa).

In some embodiments, for conjugating a PBRM having a molecular weight of 40 kDa to 200 kDa, the polymeric carrier of the scaffold of the disclosure is a polyacetal, e.g., a PHF having a molecular weight (i.e., MW of the unmodified PHF) ranging from about 2 kDa to about 40 kDa (e.g., about 2-20 kDa, about 3-15 kDa, about 5-10 kDa, about 6-8 kDa, or about 7-8 kDa).

In some embodiments, for conjugating a PBRM having a molecular weight of 40 kDa to 80 kDa, the polymeric carrier of the scaffold of the disclosure is a polyacetal, e.g., a PHF having a molecular weight (i.e., MW of the unmodified PHF) (i.e., MW of the unmodified PHF) ranging from about 2 kDa to about 40 kDa (e.g., about 2-20 kDa, about 3-15 kDa, about 5-10 kDa, about 6-8 kDa, or about 7-8 kDa). For example the PHF has a molecular weight of about 5 kDa, 6 kDa, 7 kDa, 8 kDa, 10 kDa, 13 KDa or 15 kDa.

PBRMs in this molecular weight range include, but are not limited to, for example, antibody fragments, such as, for example, Fabs.

In some embodiments, for conjugating a PBRM having a molecular weight of 60 kDa to 120 kDa, the polymeric carrier of the scaffold of the disclosure is a polyacetal, e.g., a PHF having a molecular weight (i.e., MW of the unmodified PHF) ranging from about 5 kDa to about 40 kDa (e.g., about 5-30 kDa, about 5-20 kDa, about 5-15 kDa, about 5-10 kDa, about 6-8 kDa, or about 7-8 kDa). For example, the PHF has a molecular weight of about 10 kDa, 20 kDa, 30 kDa or 40 kDa.

PBRMs in this molecular weight range include, but are not limited to, for example, camelids, Fab2, scFcFv, and the like.

In some embodiments, for conjugating a PBRM having a molecular weight of 140 kDa to 180 kDa, the polymeric carrier of the scaffold of the disclosure is a polyacetal, e.g., a PHF having a molecular weight (i.e., MW of the unmodified PHF) ranging from about 2 kDa to about 40 kDa (e.g., about 2-20 kDa, about 3-15 kDa, about 5-10 kDa, about 6-8 kDa, or about 7-8 kDa). For example the PHF has a molecular weight of about 5 kDa, 8 kDa, 10 kDa, 13 kDa or 15 kDa.

PBRMs in this molecular weight range include, but are not limited to, for example, full length antibodies, such as, IgG, IgM.

In some embodiments, when the PHF in Formula (Ia) has a molecular weight ranging from about 2 kDa to about 40 kDa (i.e., the sum of m, $m_1$, $m_2$, and $m_3$ ranging from about 1 to about 300), $m_2$ is an integer from 1 to about 40, $m_3$ is an integer from 1 to about 18, and/or $m_1$ is an integer from 1 to about 140 (e.g., $m_1$ being about 1-90).

In some embodiments, when the PHF in Formula (Ia) has a molecular weight ranging from about 2 kDa to about 20 kDa (i.e., the sum of m, $m_1$, $m_2$, and $m_3$ ranging from about 1 to about 150), $m_2$ is an integer from 1 to about 20, $m_3$ is an integer from 1 to about 10, and/or $m_1$ is an integer from 1 to about 70 (e.g., $m_1$ being about 4-45).

In some embodiments, when the PHF in Formula (Ia) has a molecular weight ranging from about 3 kDa to about 15 kDa (i.e., the sum of m, $m_1$, $m_2$, and $m_3$ ranging from about 1 to about 110), $m_2$ is an integer from 2 to about 15, $m_3$ is an integer from 1 to about 8, and/or $m_1$ is an integer from 2 to about 50 (e.g., $m_1$ being about 4-30).

In some embodiments, when the PHF in Formula (Ia) has a molecular weight ranging from about 5 kDa to about 10 kDa (i.e., the sum of m, $m_1$, $m_2$, and $m_3$ ranging from about 1 to about 75), $m_2$ is an integer from 3 to about 10, $m_3$ is an integer from 1 to about 5, and/or $m_1$ is an integer from 5 to about 35 (e.g., $m_1$ being about 10-25).

In some embodiments, one or more drug-carrying polymeric carriers are connected to one PBRM. In some embodiments, the scaffold (e.g., a PBRM-polymer-drug conjugate) comprises a PBRM with a molecular weight of about 40 kDa or greater and one or more D-carrying polymeric carriers connected to the PBRM.

In some embodiments, the scaffold further comprises a PBRM connected to the polymeric carrier via the maleimido group.

In some embodiments, the method of synthesizing the scaffold of Formula (Ia) includes reacting

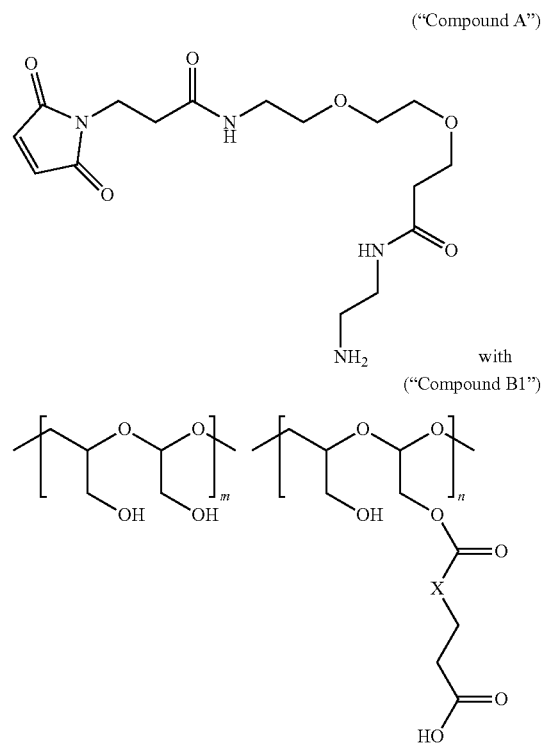

to form a first mixture; and
(2) adding

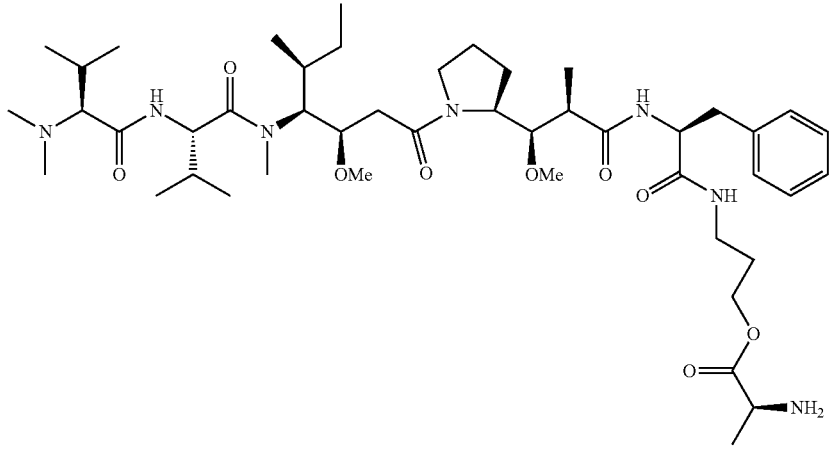

("Compound C")

or a salt thereof to react with the first mixture to produce the scaffold of Formula (Ia) or salt thereof; wherein n is the sum of $m_1$, $m_2$ and $m_3$. In some embodiments, n is an integer from about 7 to about 40. In some embodiments, the ratio between m and n is about 2:1 to about 3:1.

In some embodiments, X is NH.

In some embodiments, the scaffold of Formula (Ia) is of Formula (A):

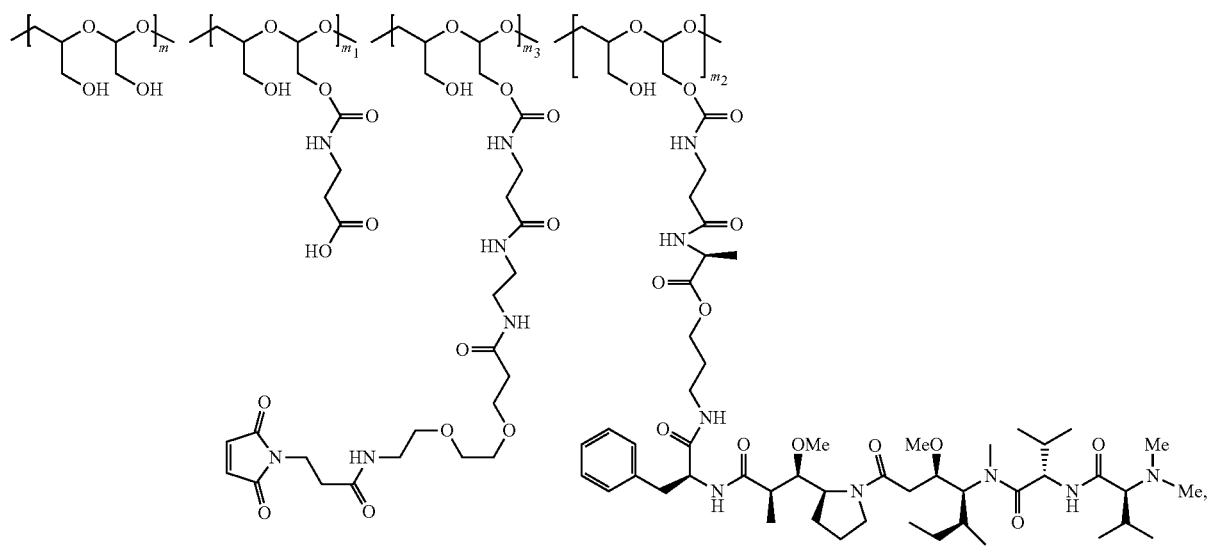

(A)

or a salt thereof, wherein
m is an integer from 20 to about 75,
$m_1$ is an integer from about 5 to about 35,
$m_2$ is an integer from about 3 to about 10,
$m_3$ is an integer from 1 to about 5, and
the sum of m, $m_1$, $m_2$ and $m_3$ ranges from 40 to about 75.

In some embodiments, the first mixture from reacting Compounds A and B1 includes polymeric scaffolds of Formula (Ic) of molecular weight ranging from about 2 kDa to about 40 kDa;

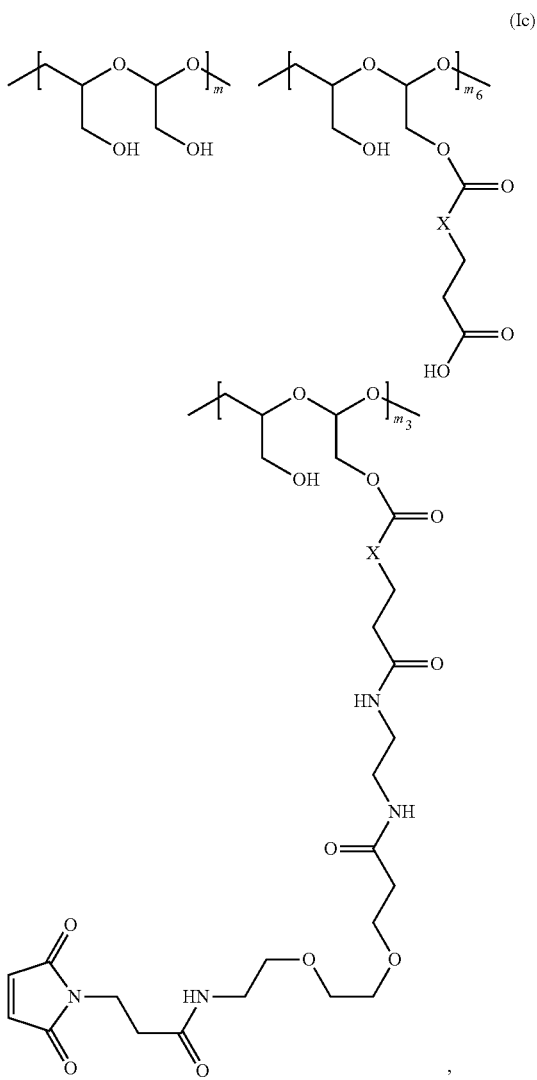

(Ic)

wherein:
X is $CH_2$, O, or NH;
m is an integer from 1 to about 300,
$m_6$ is an integer from 2 to about 180,
$m_3$ is an integer from 1 to about 18, and
the sum of m, $m_6$, and $m_3$ ranges from about 15 to about 300.

In some embodiments, each occurrence of the maleimido moiety in the "$m_3$" unit of Formula (Ic) is yet to form a covalent bond with a functional group of the PBRM.

In some embodiments, when the PHF in Formula (Ic) has a molecular weight ranging from about 2 kDa to about 20 kDa (i.e., the sum of m, $m_6$, and $m_3$ ranging from about 15 to about 150), $m_3$ is an integer from 1 to about 9, and/or $m_6$ is an integer from 2 to about 90 (e.g., $m_6$ being about 6-60).

In some embodiments, when the PHF in Formula (Ic) has a molecular weight ranging from about 3 kDa to about 15 kDa (i.e., the sum of m, $m_6$, and $m_3$ ranging from about 20 to about 110), $m_3$ is an integer from 1 to about 8, and/or $m_6$ is an integer from 4 to about 65 (e.g., $m_6$ being about 6-45).

In some embodiments, when the PHF in Formula (Ic) has a molecular weight ranging from about 5 kDa to about 10 kDa, the sum of m, $m_6$ and $m_3$ ranges from about 40 to about 75, $m_6$ is an integer from about 8 to about 45, and $m_3$ is an integer from 1 to about 5.

In some embodiments, the polymeric scaffold (e.g., a polyacetal polymer such as PHF) is conjugated with PBRMs by utilizing cysteine-based bioconjugation strategy. See, e.g., WO2010100430 and U.S. Pat. No. 7,595,292, the contents of which are hereby incorporated by reference in their entireties. In one embodiment, the polymeric scaffold (e.g., a polyacetal polymer such as PHF) conjugates with a PBRM (e.g., an antibody) via cysteines in the antibody hinge region. Without wishing to be bound by the theory, the resulting conjugate is stabilized through the formation of inter-chain bridge structures.

Accordingly, the disclosure also relates to a polymeric scaffold (e.g., a polyal polymer) comprising at least two moieties connected to the polymeric scaffold, in which each moiety is capable of conjugation to a thiol group from an amino acid (e.g., cysteine) in a PBRM so as to form a protein-polymer conjugate (e.g., a PBRM-polymer-drug conjugate). In one embodiment, at least two moieties connected to the polymeric scaffold are maleimide groups.

Synthetic Methods

According to the present disclosure, any available techniques can be used to make the conjugates, polymeric scaffolds, or compositions including them, and intermediates and components (e.g., carriers and modifiers) useful for making them. In some embodiments, semi-synthetic and fully synthetic methods may be used.

Carriers

Methods for preparing polymer carriers (e.g., biocompatible, biodegradable polymer carriers) suitable for conjugation to modifiers are known in the art. For example, synthetic guidance can be found in U.S. Pat. Nos. 5,811,510; 5,863,990; 5,958,398; 7,838,619; 7,790,150; 8,685,383; and 8,815,226, the contents of each of which are hereby incorporated by reference in their entireties. The skilled practitioner will know how to adapt these methods to make polymer carriers for use in the practice of the invention.

In one embodiment, a method for forming the biodegradable biocompatible polyal conjugates of the present disclosure comprises a process by which a suitable polysaccharide is combined with an efficient amount of a glycol-specific oxidizing agent to form an aldehyde intermediate. The aldehyde intermediate, which is a polyal itself, may then be reduced to the corresponding polyol, succinulated, and coupled with one or more suitable modifiers to form a biodegradable biocompatible polyal conjugate comprising succinamide-containing linkages.

In another preferred embodiment, fully synthetic biodegradable biocompatible polyals for used in the present disclosure can be prepared by reacting a suitable initiator with a suitable precursor compound.

In some embodiments, fully synthetic polyals may be prepared by condensation of vinyl ethers with protected substituted diols. Other methods, such as cycle opening polymerization, may be used, in which the method efficacy may depend on the degree of substitution and bulkiness of the protective groups.

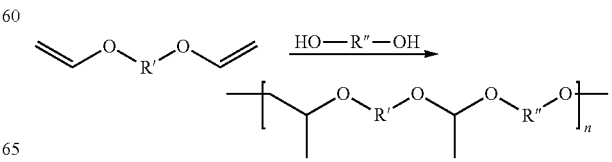

One of ordinary skill in the art will appreciate that solvent systems, catalysts and other factors may be optimized to obtain high molecular weight products.

In some embodiments, the carrier is PHF.

3 shows a method for modifying a non-natural camptothecin derivative. Scheme 4 shows a method for modifying auristatin F. More modification methods are described in US 2010/0305149, which is hereby incorporated by reference.

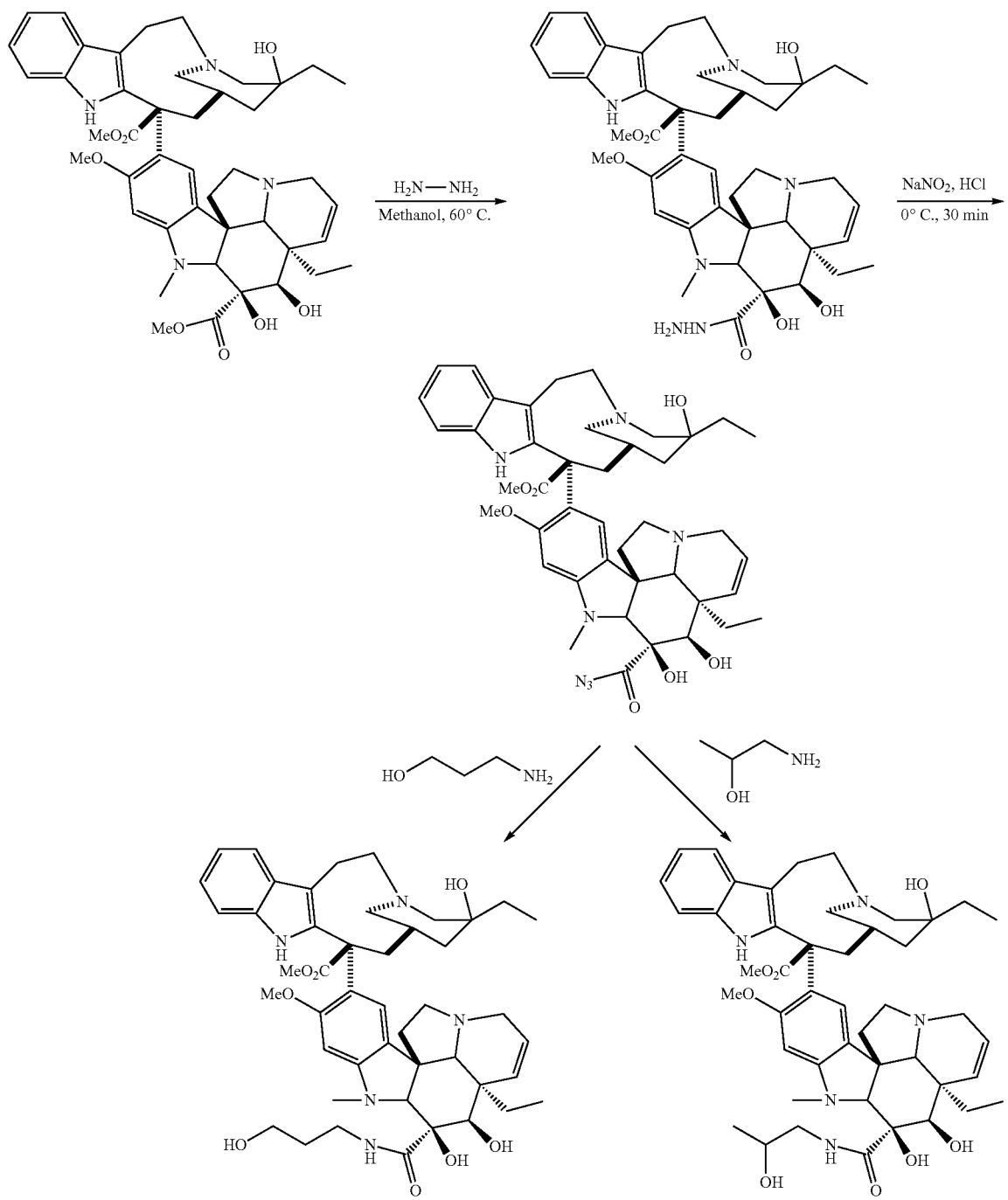

Scheme 1

In embodiments, the polymer carrier is PHF having a polydispersity index (PDI) of less than 1.5, e.g., <1.2.

Drugs and Drug Derivatives

In certain embodiments, the drug may be modified before conjugation to the polymeric carrier. Schemes 1 and 2 are illustrative methods for modifying a Vinca alkaloid. Scheme Reaction of the $C_{23}$ ester of a Vinca alkaloid with hydrazine followed by treatment with $NaNO_2$ results in an active azido ester. Reaction of the azido ester with an amino compound such as propanolamine or 1-aminopropan-2-ol results in a Vinca alkaloid derivative with a functionalized hydroxyl which can be further derivatized with amino containing compounds, such as, for example, alanine or methyl alanine derivatives, for conjugation with polymers (see Scheme 1).

Scheme 2

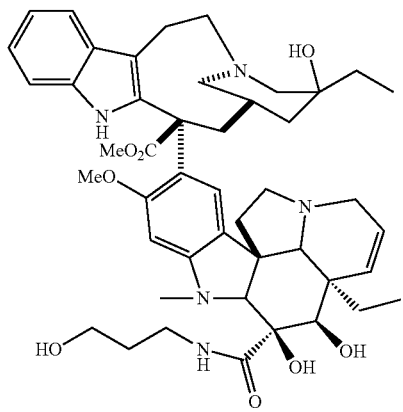

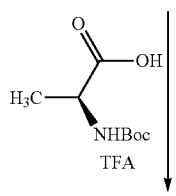

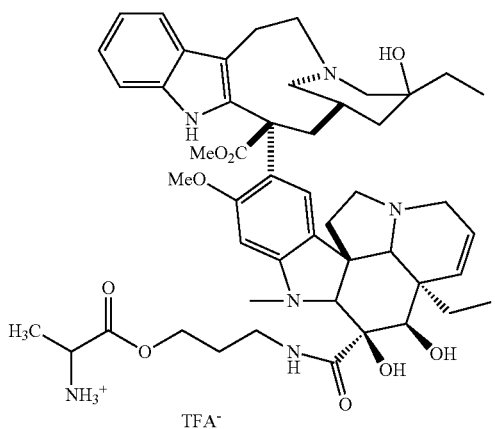

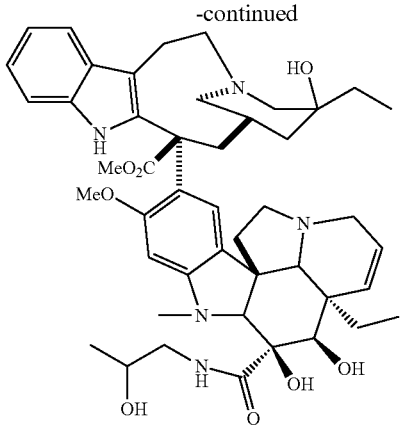

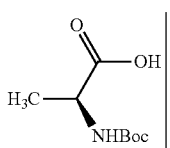

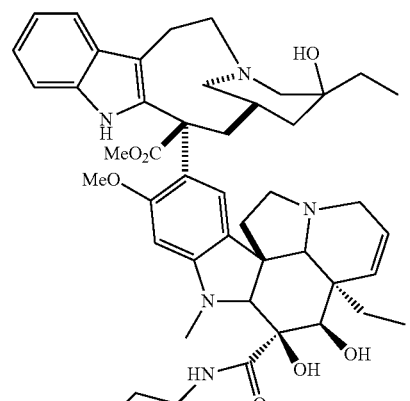

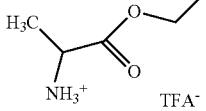

Treatment of the hydroxyl derivative of the Vinca alkaloid with a protected amino containing tether such as t-butoxy esterified amino acid followed by TFA hydrolysis of the ester gives the TFA salt of the vinca alkaloid. (Scheme 2) Conjugation of the vinca alkaloid to functionalized polymers results in drug-polymer conjugates that can be further conjugated with a PBRM or its derivative to result in protein-polymer-drug conjugates (e.g., PBRM-polymer-drug conjugates).

Scheme 3

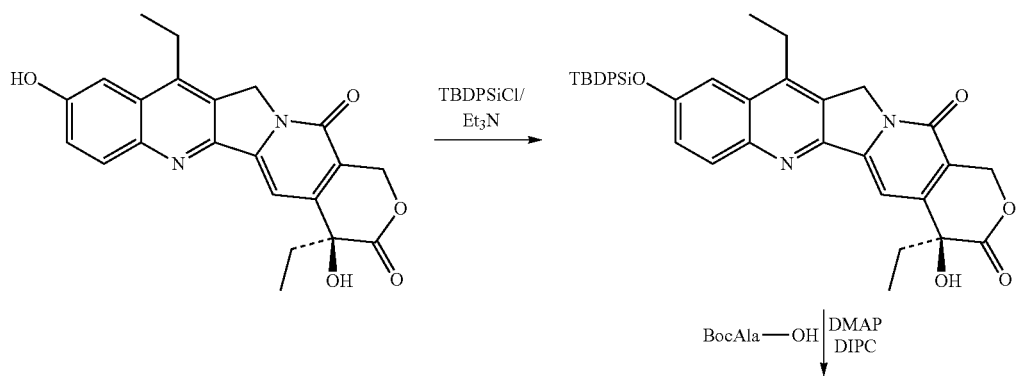

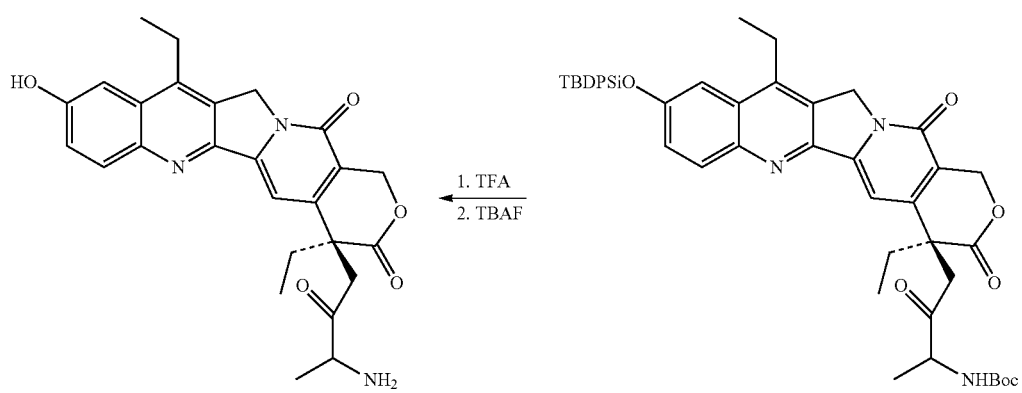

The 10-hydroxy group of non-natural camptothecin derivative, for example, SN38, is selectively protected by reacting the derivative with tert-butyldiphenylsilyl chloride (TBDPSiCl) in the presence of triethylamine. The 20-hydroxy group can be by reacted with t-butylcarbonyl-alanine to form the alanine derivative using the procedure described in Sapra, P. et al., Clin. Cancer Res., 14: 1888-1896 (2008).

Alternatively, other amino acids can be employed, e.g., glycine. The primary amine is unmasked by removing the Boc protecting group by treatment with trifluoroacetic acid, followed by removing the TBDPS protecting group with tetrabutylammonium fluoride (see Scheme 3). The resulting amino derivatized SN38 compound can be conjugated with a functionalized polymer to form a drug-polymer conjugate.

Scheme 4

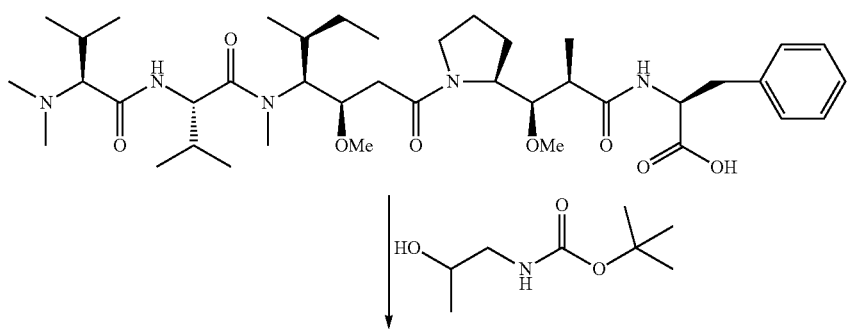

-continued

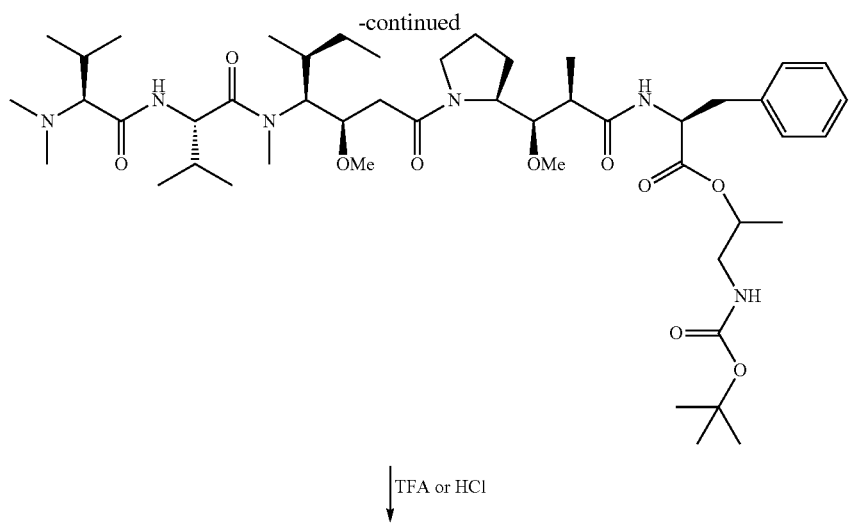

↓ TFA or HCl

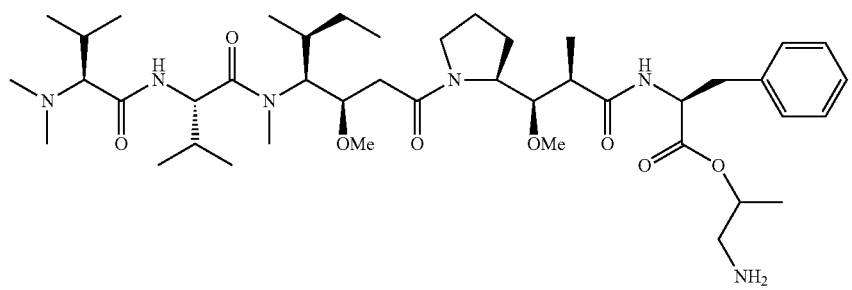

Treatment of auristatin F with a protected amino containing tether such as t-butoxy esterified 2-hydroxypropyl amine followed by hydrolysis (e.g., TFA hydrolysis or HCl hydrolysis) of the ester gives the 2-hydroxylpropyl amino derivative of auristatin F (see Scheme 4). Conjugation of the auristatin F derivative to functionalized polymers results in drug-polymer conjugates that can be further conjugated with a PBRM or its derivative to result in protein-polymer-drug conjugates.

Conjugates or Polymeric Scaffolds

Schemes 5A and 5B below shows alternative synthetic routes of making the polymeric drug scaffolds of the disclosure. In one embodiment, the conjugates are formed in several steps: (1) the polymer, PHF is modified to contain a COOH moiety (e.g., —C(O)—X—(CH$_2$)$_2$—COOH); (2) the polymer is then further modified so that it contains a maleimido moiety (e.g., EG2-MI) that can react with a functional group of a PBRM; (3) the modified polymer, containing two different functional groups, is reacted with a functional group of a drug or its derivative (e.g., AF-HPA-Ala) to form a polymer-drug conjugate; (4) the disulfide bonds of a PBRM are reduced; (5) the reduced PBRM is then reacted with the polymer-drug conjugate to form the protein-polymer-drug conjugate (e.g., PBRM-polymer-drug conjugate); and (6) the remaining maleimido moieties are optionally reacted with a maleimido blocking compound (e.g., cysteine).

In another embodiment, the order of steps (2) and (3) can be reversed as depicted in the right side route in Scheme 5A or 5B below.

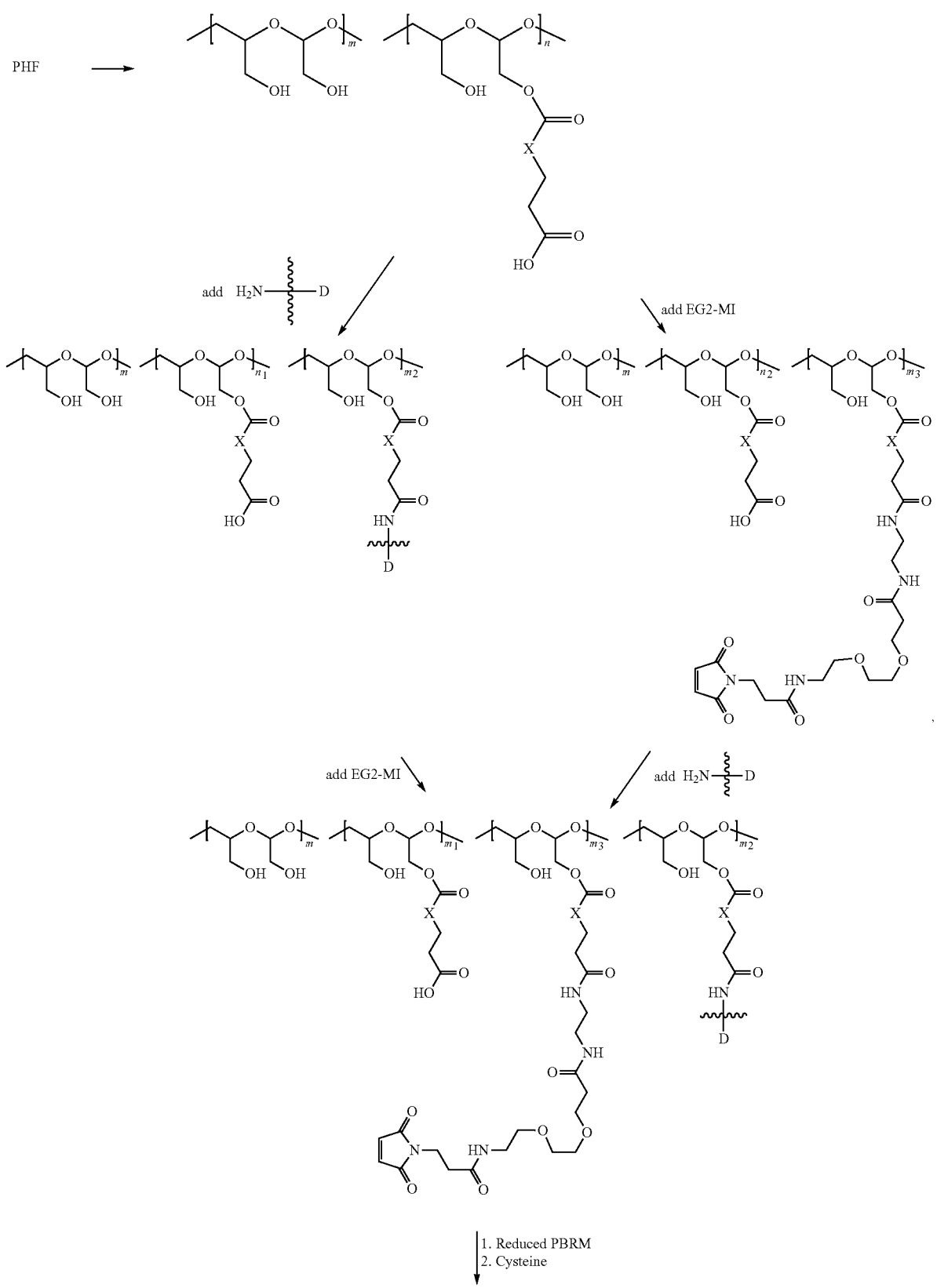
Scheme 5A 131 132
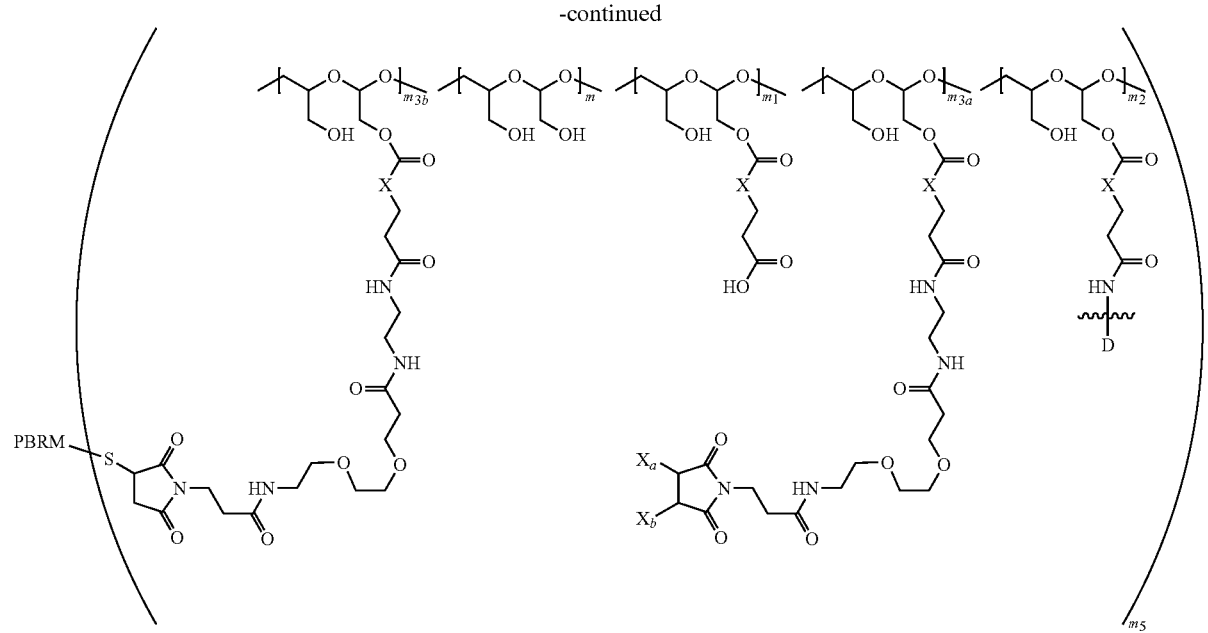
-continued

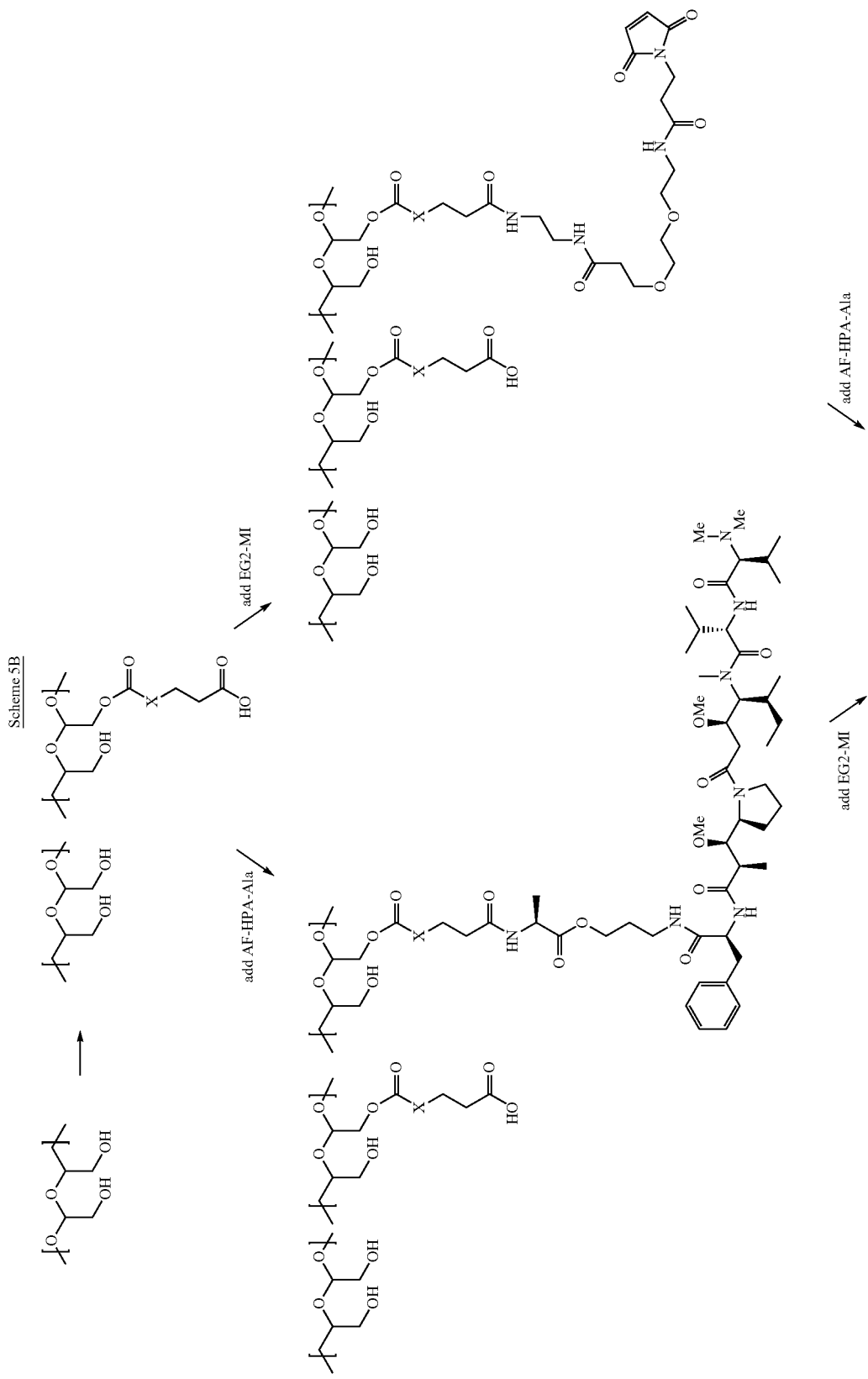

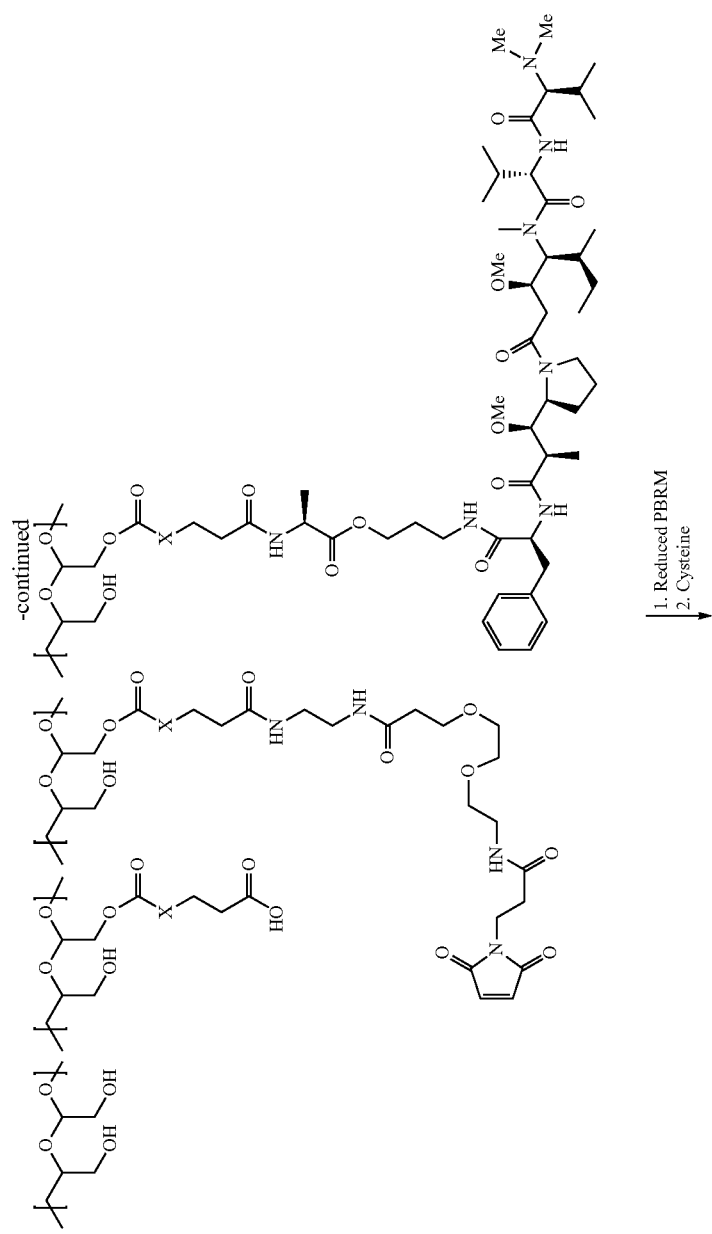

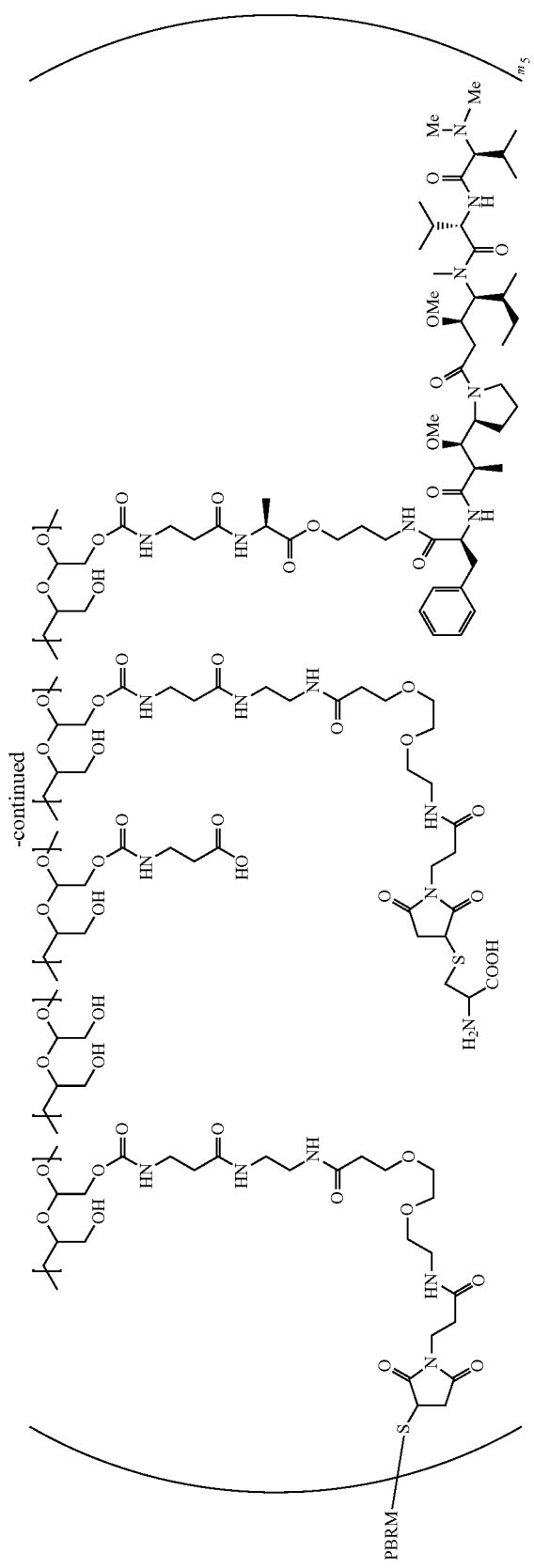

In yet another embodiment, steps (2) and (3) above are carried out simultaneously as depicted in Scheme 6A or 6B below.
Scheme 6A
PHF →
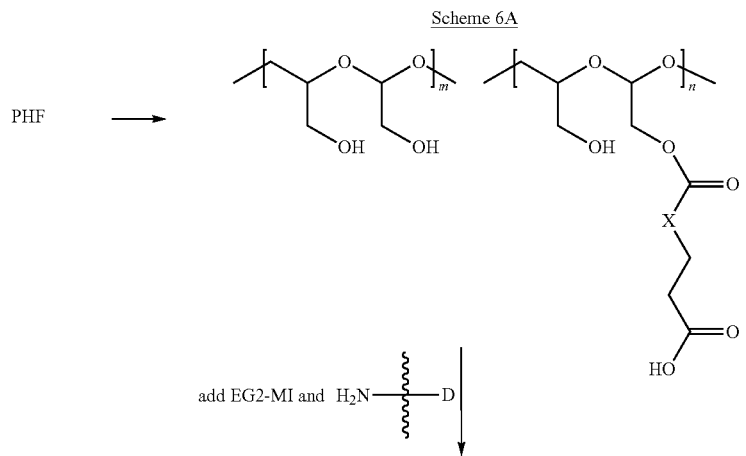
add EG2-MI and H₂N—D
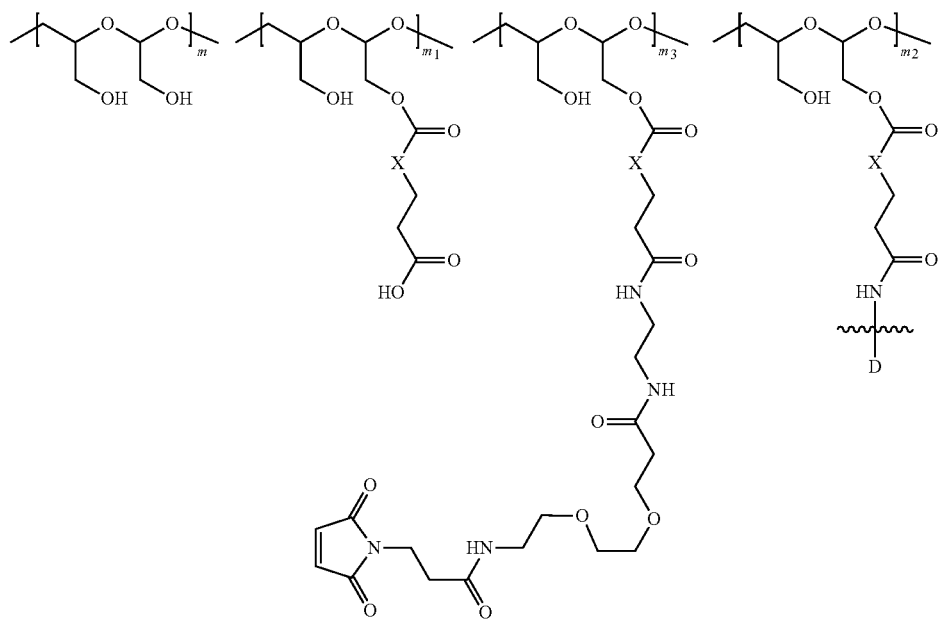
1. Reduced PBRM
2. Cysteine 141 142
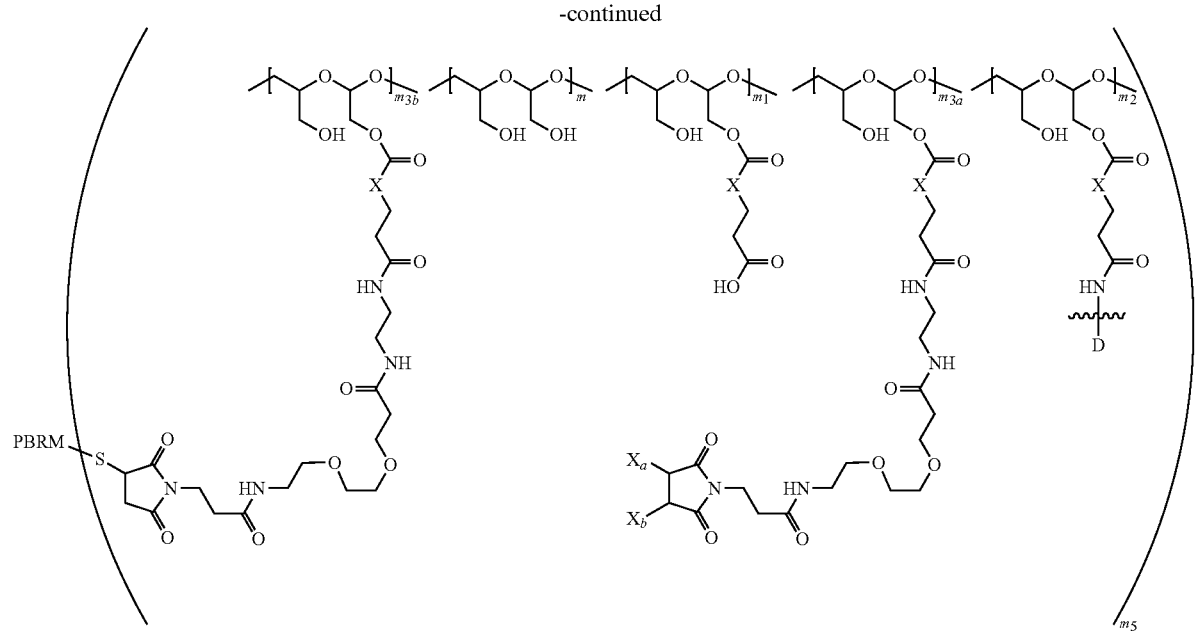

Scheme 6B
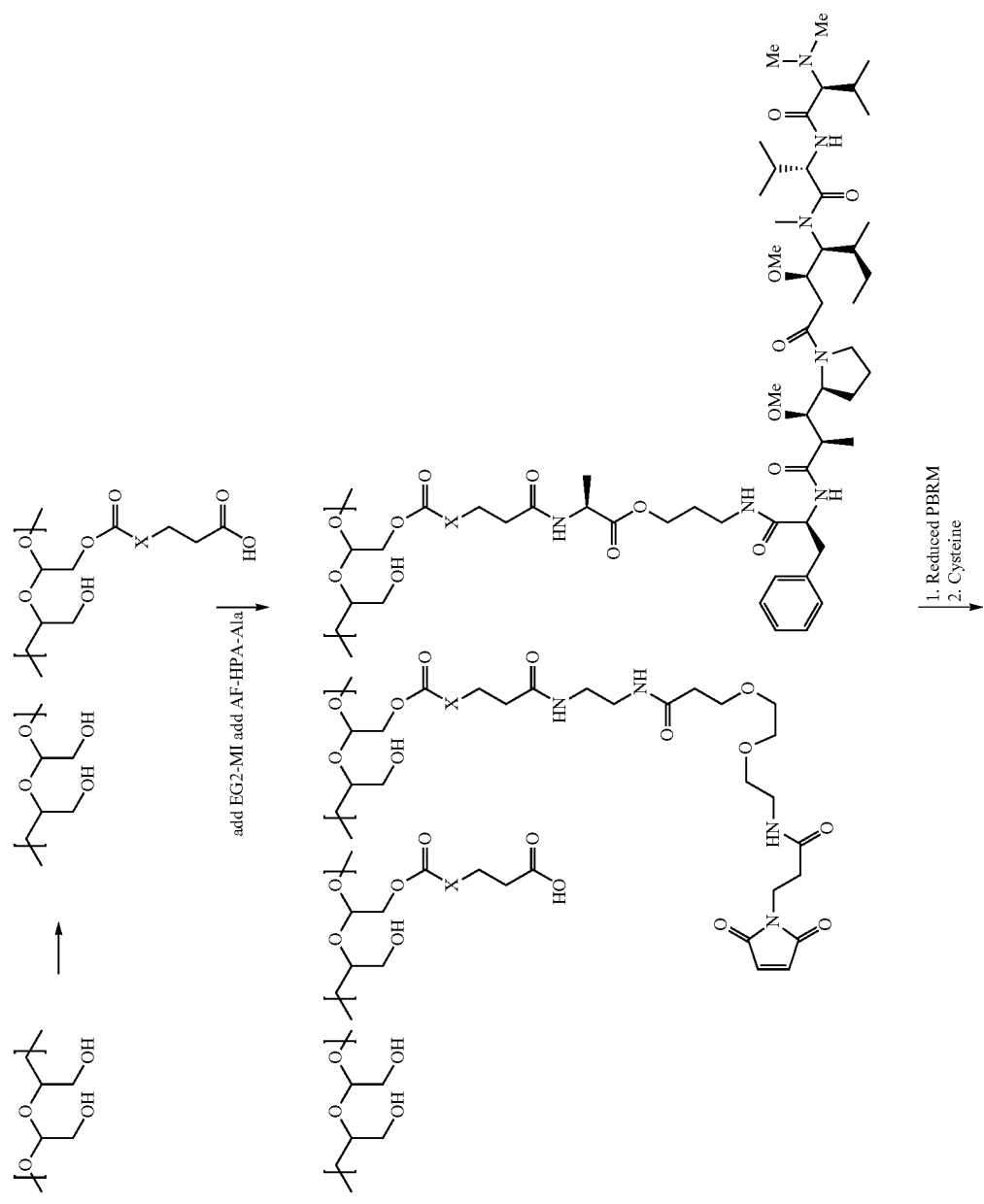

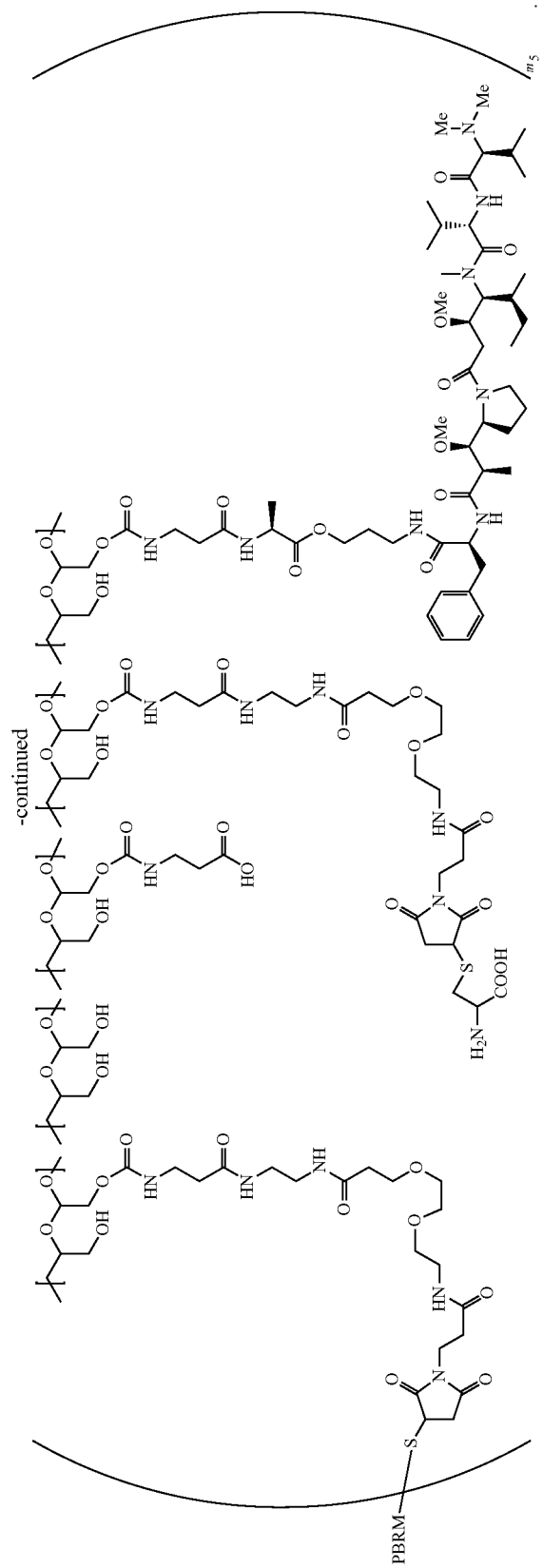
-continued

In one aspect, the disclosure relates to a method of making a polymeric scaffold of Formula (A):

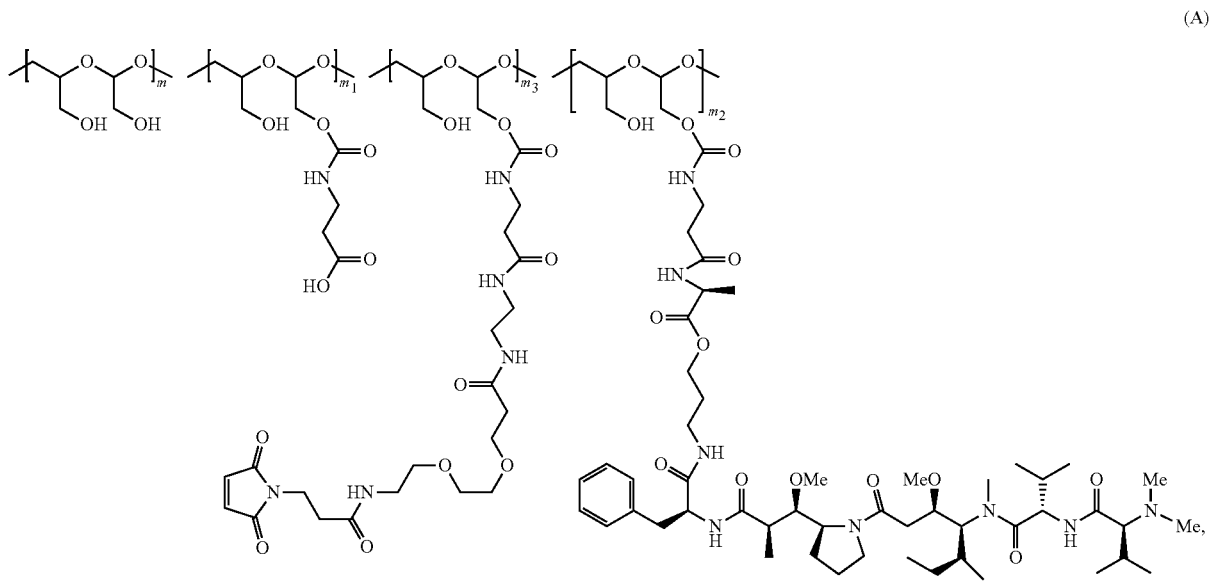

(A)

or a salt thereof. The method comprising one or more steps selected from:

(1) reacting

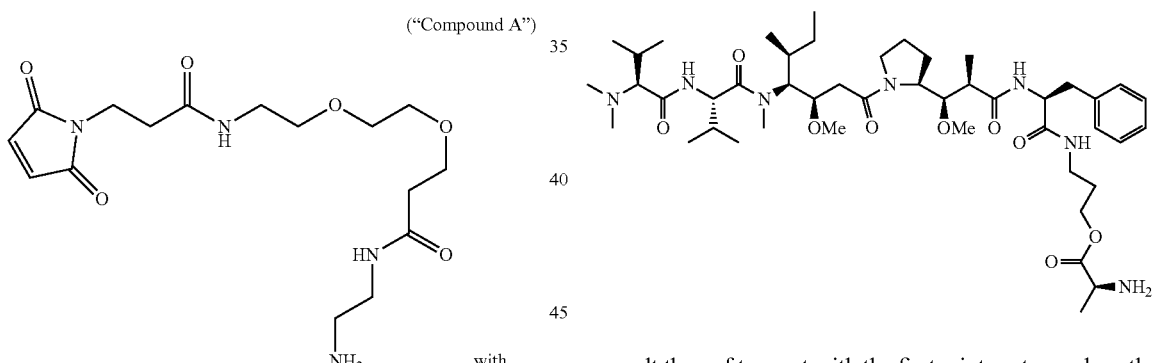

("Compound A")

("Compound B")

with or a salt thereof to react with the first mixture to produce the scaffold of Formula (A) or salt thereof; wherein:

Compound B or the scaffold of Formula (A) comprises poly(1-hydroxymethylethylene hydroxymethyl-formal) (PHF) having a molecular weight ranging from about 5 kDa to about 10 kDa (e.g., from about 6 kDa to about 8 kDa or from about 6 kDa to about 7 kDa);

m is an integer from 20 to about 75, n is an integer from about 7 to about 40, and the ratio between m and n is about 2:1 to about 3:1, $m_1$ is an integer from about 5 to about 35, $m_2$ is an integer from about 3 to about 10, $m_3$ is an integer from 1 to about 5, and the sum of m, $m_1$, $m_2$ and $m_3$ ranges from 40 to about 75.

Further, the disclosure also relates to a method of purifying a polymeric scaffold, such as Compound B or a scaffold of Formula (A) disclosed herein.

The disclosure also provides to a method of preparing a conjugate that comprises a polymeric scaffold of Formula (A) and a PBRM. The method comprises reacting a scaffold of Formula (A) with a PBRM or a derivative thereof.

to form a first mixture; and (2) adding ("Compound C")

In embodiments, the methods of the disclosure may have one or more of the following features when applicable.

In some embodiments, Compound B used for the method of the disclosure has a molecular weight ranging from about 6 kDa to about 13 kDa, e.g., from about 7 kDa to about 12 kDa, or from about 10 kDa to about 12 kDa. In some embodiments, in Compound B, n is about 26-34% (e.g., about 29-33%) of the sum of m and n.

In some embodiments, at least 70% (e.g., at least 75%, 80%, 85%, 90%, or 95%) of Compound A is consumed (e.g., as monitored by RP-HPLC) before Compound C or a salt thereof is added to react with the first mixture.

In some embodiments, wherein the first mixture is not worked up before Compound C or a salt thereof is added.

In some embodiments, the reaction between Compound A and Compound B is performed in the presence of an activating reagent for a carboxylic acid and a coupling agent under a first temperature. In some embodiments, the activating reagent is N-hydroxysuccinimide (NHS). In some embodiments, the coupling reagent is ethyl(dimethylaminopropyl) carbodiimide hydrochloride (EDC.HCl). In some embodiments, the reaction between Compound A and Compound B is performed at a pH of between about 4 and about 6 (e.g., about 4.2-5.4 or about 4.2-6).

In some embodiments, the reaction between the first mixture and Compound C or a salt thereof is performed in the presence of an activating reagent for a carboxylic acid and a coupling agent under a second temperature. In some embodiments, the activating reagent is N-hydroxysuccinimide (NHS). In some embodiments, the coupling reagent is ethyl(dimethylaminopropyl) carbodiimide hydrochloride (EDC.HCl). In some embodiments, the reaction between the first mixture and Compound C or a salt thereof is performed at a pH of between about 4 and about 6 (e.g., 5.0±0.3, about 4.2-5.4 or about 4.2-6).

In some embodiments, the first temperature is between about 0° C. and 15° C.

In some embodiments, the second temperature is between about 5° C. and 15° C.

In some embodiments, the method further comprises providing Compound A by deprotecting a protected form of Compound A, e.g.,

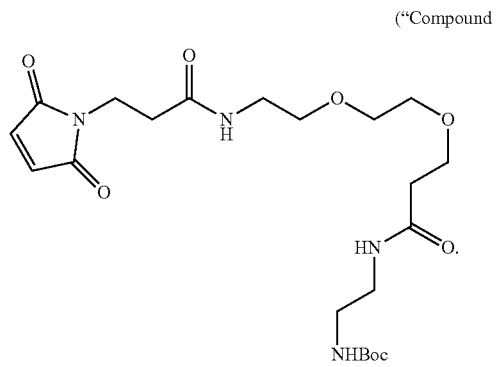

("Compound AA")

In some embodiments, the method further comprises providing Compound AA by reacting 2,5-dioxopyrrolidin-1-yl 3-(2-(2-(3-(2,5-dioxo-2,5-dihydro-1H-pyrrol-1-yl)propanamido)ethoxy)ethoxy)propanoate with tert-butyl (2-aminoethyl)carbamate at, e.g., a temperature between about 0° C. and 25° C.

In some embodiments, the method further comprises providing Compound B by reacting PHF (e.g., PHF having a molecular weight ranging from about 5 kDa to about 10 kDa, from about 6 kDa to about 8 kDa, from about 6 kDa to about 7 kDa, with methyl 3-isocyanatopropanoate to form a methyl ester of Compound B and converting the methyl ester to Compound B.

In some embodiments, the method further comprises purification of Compound B such that Compound B thus purified has a molecular weight ranging from about 6 kDa to about 13 kDa, and n is about 26-34% of the sum of m and n. In some embodiments, Compound B thus purified has a molecular weight ranging from about 7 kDa to about 12 kDa, and n is about 28-32% (e.g., 29-34%, or on average about 31%) of the sum of m and n. In some embodiments, Compound B has a molecular weight ranging from about 10 kDa to about 12 kDa. In some embodiments, Compound B has an average molecular weight of 11.3 kDa.

In some embodiments, Compound B has a polydispersity index (PDI) of less than 2.0, less than 1.9, less than 1.8, less than 1.7, or less than 1.6. In some embodiments, Compound B has a polydispersity index (PDI) of less than 1.5.

In some embodiments, the purification of Compound B comprises weak anion exchange (WAX) chromatography purification. In some embodiments, the mobile phase for the weak anion exchange chromatography purification comprises a sodium phosphate buffer. In some embodiments, the purification further comprises one or more filtrations, such as one or more gel filtrations, one or more tangential flow filtrations, one or more diafiltration, one or more ultrafiltration, one or more nanofiltrations, or combinations thereof.

In some embodiments, a crude product of Compound B is first purified by non-adsorptive chromatography such as gel filtration (e.g., using Sephadex G-25 column chromatography) to remove inorganic salts followed by a tangential flow filtration (TFF) diafiltration (e.g., with a 1 kDa MWCO membrane) while maintaining the pH at, e.g., about 6-8, about 6.5-7.5, or 7.0±0.1. In some embodiments, a crude product of Compound B is first purified by non-adsorptive chromatography such as gel filtration (e.g., using Sephadex G-25 column chromatography) to remove inorganic salts followed by a nanofiltration (e.g., with a 3.5 kDa MWCO membrane) while maintaining the pH at, e.g., about 6-8, about 6.5-7.5, or 7.0±0.1. In some embodiments, the product is purified by WAX using, e.g., a gradient of 20 mM sodium phosphate, pH 7.0 to 20 mM sodium phosphate and 1M NaCl, pH 7.0. In some embodiments, selected fractions containing Compound B having about n being 29-34% of the sum of m and n (as determined by e.g., SEC analysis) are combined and concentrated by e.g., TFF diafiltration (e.g., with a 1 kDa MWCO membrane) before reaction with Compound A.

In some embodiments, the method further comprises providing Compound C or a salt thereof by deprotecting a protected form of Compound C, e.g.,

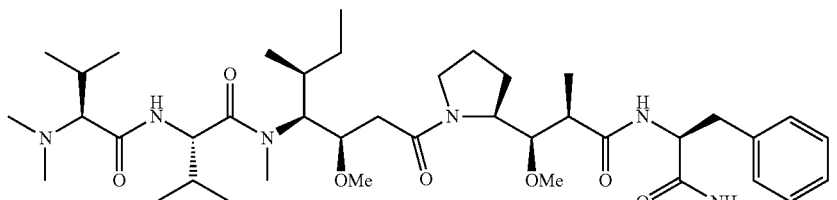
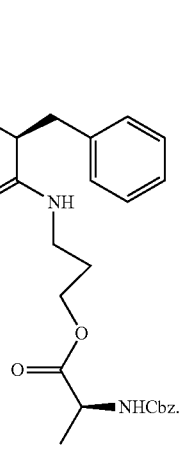

("Compound CC")

In some embodiments, the salt of Compound C is a trifluoroacetate.

In some embodiments, the method further comprises purification of the scaffold of Formula (A), e.g., via a reverse phase HPLC chromatographic separation. In some embodiments, sodium acetate buffer and acetonitrile are used as the mobile phase. In some embodiments, the purification further comprises one or more filtrations, such as one or more gel filtrations, one or more tangential flow filtrations, one or more diafiltration, one or more ultrafiltration, one or more nanofiltrations, or combinations thereof. In some embodiments, prior to HPLC purification, the product from the reaction between the first mixture and Compound C or a salt thereof is concentrated while maintaining pH 5.0±0.3. In some embodiments, the resulting concentrate is then subjected to non-adsorptive chromatography such as gel filtration (e.g., using Sephadex G-25 chromatography) to, e.g., remove the salts and unreacted reagents followed by, e.g., a tangential flow filtration (TFF) diafiltration (e.g., 1 kDa MWCO membrane) at e.g., about 5-15° C. while maintaining the pH at 4 to 5. In some embodiments, the product is further purified by preparative HPLC (e.g., butyl HG, 200 Å, 10 µm, 250×50 mm, 1,000 psi column) using sodium acetate and acetonitrile as the eluant (with e.g., a pH value of about 5-6, e.g., pH of 5.8). In some embodiments, selected fractions (based on, e.g., $^1$H-NMR and SEC analysis) containing polymeric scaffolds of Formula (A) with 7-13 kDa MW in which $m_2$ is about 6-10% of the sum of m, $m_1$, $m_2$ and $m_3$ are pooled, and concentrated (e.g., by rotary evaporation, followed TFF 1 kDa MWCO membrane) to remove solvents, buffers and salts. In some embodiments, the resulting aqueous solution is subjected to a filtration, e.g., ultrafiltration with a TFF device (with a 50 or 100 kDa MWCO membrane) and the permeate is collected, e.g., followed by a 0.1-micron sterile filtration. In some embodiments, the purification of the scaffold of Formula (A) does not comprise gel filtration and/or rotary evaporation.

In some embodiments, the yield of the scaffold of Formula (A) produced by the methods of the disclosure is at least 60%, 65%, 67%, 70%, 75%, 80%, or at least 85%.

In some embodiments, upon purification, the scaffold of Formula (A) has a molecular weight ranging from about 4 kDa to about 18 kDa, from about 5 kDa to about 17 kDa, from about 6 kDa to about 16 kDa, or from about 7 kDa to about 14.5 kDa (e.g., about 8 kDa to about 14.5 kDa, or about 7 kDa to about 13 kDa).

In some embodiments, upon purification, the scaffold of Formula (A) has a molecular weight ranging from 7 kDa to about 13 kDa).

In some embodiments, in the scaffold of Formula (A), $m_2$ is about 5% to about 13%, about 6% to about 12%, about 7% to about 11%, or about 7.5% to about 10.5% of the sum of m, $m_1$, $m_2$ and $m_3$.

In some embodiments, in the scaffold of Formula (A), $m_2$ is about 8% to about 10% of the sum of m, $m_1$, $m_2$ and $m_3$.

In some embodiments, in the scaffold of Formula (A), $m_3$ is about 2% to about 4% of the sum of m, $m_1$, $m_2$ and $m_3$.

In some embodiments, the scaffold of Formula (A) or salt thereof thus produced has a purity of at least 75%, 80%, 85%, 90%, or at least 95%.

In some embodiments, the scaffold of Formula (A) or salt thereof is produced at a large scale. In some embodiments, at least 100 g of the scaffold of Formula (A) or salt thereof is produced in a single batch.

In some embodiments, at least 200 g, 500 g, 1 kg, at least 2 kg, or at least 2.5 kg of the scaffold of Formula (A) or salt thereof is produced in a single batch.

In some embodiments, the scaffold of Formula (A) has a PDI of less than 3.0, less than 2.8, less than 2.6, less than 2.4, or less than 2.2. In some embodiments, the scaffold of Formula (A) has a PDI of less than 2.0.

In some embodiments, for any method of disclosure, at least one non-adsorptive chromatography is performed.

In some embodiments, for any method of disclosure, at least one of the non-adsorptive chromatographies is performed with Sephadex column chromatography.

In some embodiments, for any method of disclosure, at least one of the tangential flow filtrations is performed with a membrane having a molecular weight cutoff between about 650 Da and 1000 Da. In some embodiments, for any method of disclosure, the membrane has a molecular weight cutoff at about 650 Da. In some embodiments, for any method of disclosure, at least one of the tangential flow filtrations is performed with a membrane having a molecular weight cutoff between about 50 kDa and 100 kDa to obtain a permeate that contains the scaffold of Formula (A) or salt thereof.

In some embodiments, for any method of disclosure, at least one of the nanofiltrations is performed with a membrane of molecular weight cut off between 1000 Da to 4000 Da.

In some embodiments, for any method of disclosure, at least one of the tangential flow filtrations is performed with a membrane having a molecular weight cutoff between about 1500 kDa and 3500 kDa to obtain a permeate that contains the scaffold of Formula (A) or salt thereof.

In another aspect, the disclosure relates to a method of a PBRM-polymer-drug conjugate of Formula (B):

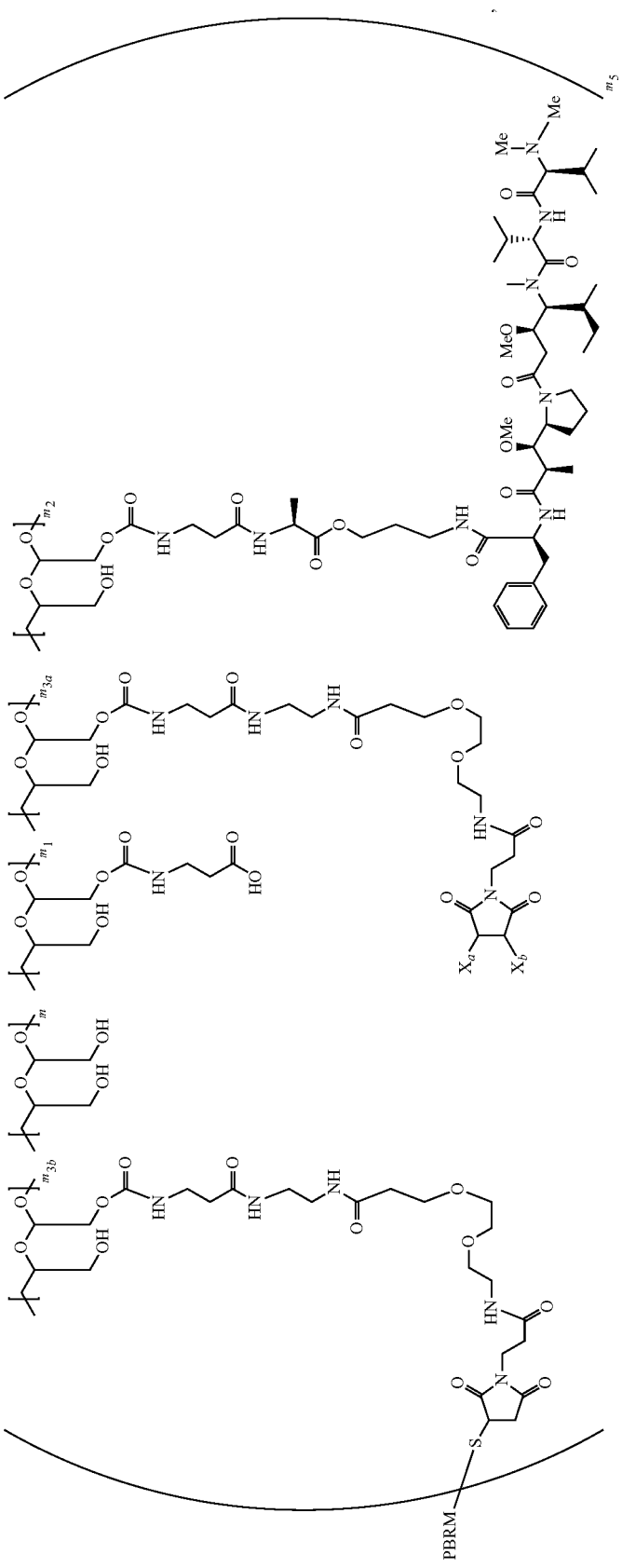

wherein:
one of $X_a$ and $X_b$ is H and the other is a water-soluble maleimido blocking moiety, or $X_a$ and $X_b$, together with the carbon atoms to which they are attached form a carbon-carbon double bond;

the PHF has a molecular weight ranging from about 5 kDa to about 10 kDa;

m is an integer from 20 to 75,
$m_1$ is an integer from about 5 to about 35,
$m_2$ is an integer from about 3 to about 10,
$m_{3a}$ is an integer from 0 to about 4,
$m_{3b}$ is an integer from 1 to about 5,
the sum of m, $m_1$, $m_2$, $m_{3a}$, and $m_{3b}$ ranges from about 40 to about 75, and
$m_5$ is an integer from 2 to about 4.

The method comprises one or more steps selected from:
(1) providing a polymeric scaffold of Formula (A) or a salt thereof and a reduced PBRM;
(2) adding the reduced PBRM to the polymeric scaffold of Formula (A) or the salt thereof to form a third reaction mixture comprising a PBRM-polymer-drug conjugate of Formula (B).

In some embodiments, the polymeric scaffold of Formula (A) or the salt thereof is prepared by performing a method of the disclosure.

In some embodiments, the reduced PBM is prepared by reacting a PBRM with a reducing agent, wherein one or more disulfide bonds of the PBRM are reduced by the reducing agent to one or more thiol groups.

In some embodiments, the partial selective reduction of the inter-chain disulfide groups or unpaired disulfide in the relevant PBRM prior to conjugation with the polymer-drug conjugate is achieved by using a reducing agent, such as, for example, TCEP, DTT or β-mercaptoethanol. The reaction is typically conducted at about 25±2° C. for about 1.5 hours In some embodiments, the degree of conversion of the PBRM disulfide groups into reactive sulfhydryl groups depends on the stoichiometry of PBRM, reducing agent, pH, temperature and/or duration of the reaction. When some but not all of the disulfide groups in the PBRM are reduced, the reduced PBRM is a partially reduced PBRM.

In some embodiments, disulfide bonds on the PBRM are partially reduced with TCEP.HCl using about 2 to about 4 molar equivalents to PBRM to form thiol groups (SH).

In some embodiments, disulfide bonds on the PBRM are partially reduced with TCEP.HCl using about 2.4 molar equivalents to PBRM to form thiol groups.

In some embodiments, disulfide bonds on the PBRM are partially reduced with TCEP.HCl using about 2.5 molar equivalents to PBRM to form thiol groups.

In some embodiments, disulfide bonds on the PBRM are partially reduced with TCEP.HCl using about 2.7 molar equivalents to PBRM to form thiol groups.

In some embodiments, disulfide bonds on the PBRM are partially reduced with TCEP.HCl using about 3.0 molar equivalents to PBRM to form thiol groups.

In some embodiments, disulfide bonds on the PBRM are partially reduced with TCEP.HCl using about 3.25 molar equivalents to PBRM to form thiol groups.

In some embodiments, disulfide bonds on the PBRM are partially reduced with TCEP.HCl using about 3.4 molar equivalents to PBRM to form thiol groups.

The conjugation of the partially reduced PBRM to the polymeric scaffold of Formula (A) or the salt thereof is conducted under neutral or slightly basic conditions (pH 5.5-8.5) at a ratio of polymer-drug conjugate to PBRM concentrations of 0.5 to 2.0 (w/w) for about 60 minutes to about 120 minutes at about 25±2° C.

In some embodiments, conjugation of the partially reduced PBRM to the polymeric scaffold of Formula (A) or the salt thereof is conducted at a ratio of the polymeric scaffold of Formula (A) or the salt thereof to the PBRM at 0.7 (w/w), 0.8 (w/w), 0.9 (w/w), 1.0 (w/w), 1.2 (w/w) or 1.5 (w/w).

In some embodiments, conjugation of the partially reduced PBRM to the polymeric scaffold of Formula (A) or the salt thereof is conducted at a ratio of the polymeric scaffold of Formula (A) or the salt thereof to the PBRM at 1.0 (w/w). In some embodiments, conjugation of the partially reduced PBRM to the polymeric scaffold of Formula (A) or the salt thereof is conducted at a ratio of the polymeric scaffold of Formula (A) or the salt thereof to the PBRM at 0.9 (w/w). In some embodiments, conjugation of the partially reduced PBRM to the polymeric scaffold of Formula (A) or the salt thereof is conducted at a ratio of the polymeric scaffold of Formula (A) or the salt thereof to the PBRM at 0.8 (w/w). In some embodiments, conjugation of the partially reduced PBRM to the polymeric scaffold of Formula (A) or the salt thereof is conducted at a ratio of the polymeric scaffold of Formula (A) or the salt thereof to the PBRM at 0.75 (w/w). In some embodiments, conjugation of the partially reduced PBRM to the polymeric scaffold of Formula (A) or the salt thereof is conducted at a ratio of the polymeric scaffold of Formula (A) or the salt thereof to the PBRM at 0.7 (w/w). After the PBRM is conjugated to the maleimido group of the polymer-drug conjugate, the conjugation is terminated by the addition of a water-soluble maleimido blocking compound, such as, for example, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol, and the like.

In some embodiments, the maleimido blocking compound can be cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol. The one or more hydrophilic substituents on phenyl comprise OH, SH, methoxy, ethoxy, COOH, CHO, $COC_{1-4}$ alkyl, $NH_2$, F, cyano, $SO_3H$, POSH, and the like.

In some embodiments, the maleimido blocking group is —S—$(CH_2)_d$—$R_{90}$, in which,
$R_{90}$ is OH, COOH, or $CH(NHR_{91})COOR_{93}$;
$R_{93}$ is hydrogen or $CH_3$;
$R_{91}$ is hydrogen or $CH_3CO$; and
d is 1 or 2.

In some embodiments, the maleimido blocking group is —S—$CH_2$—$CH(NH_2)COOH$.

The resulting PBRM-polymer-drug conjugate of Formula (B) is typically purified by diafiltration to remove any unconjugated polymer-drug conjugate, unconjugated drug and small molecule impurities. Alternatively or additionally, appropriate chromatographic separation procedures such as, for example, size-exclusion chromatography, hydrophobic interaction chromatography, ion chromatography such as, for example, WCX chromatography, SCX chromatography, reverse phase chromatography, hydroxyl apatite chromatography, ceramic hydroxyl apatite chromatography, affinity chromatography or combinations thereof may be used to purify the PBRM-polymer-drug conjugate.

In some embodiments, the PBRM-polymer-drug conjugate of Formula (B) is isolated from the third reaction mixture with a chromatography separation, e.g., an ion exchange chromatography separation.

In some embodiments, the PBRM-polymer-drug conjugate of Formula (B) is isolated with a strong cation exchange (SCX) chromatography separation. In some embodiments, the SCX chromatography separation is performed with a mobile phase comprising sodium acetate, sodium chloride, or a combination thereof. In some embodiments, the mobile phase has a pH value ranging from about 5 to about 7, from about 5.5 to about 6.5, or from about 5.8 to about 5.9.

In some embodiments, the SCX chromatography separation removes one or more acidic fractions (as determined by analytical HPLC WCX chromatography) with high AF HPA to PBRM ratio from the third reaction mixture. In some embodiments the one or more acidic fractions have compromised activity due to weak antigen binding. In some embodiments, the SCX chromatography separation removes one or more basic fractions (as determined by analytical HPLC WCX chromatography) with low AF HPA to PBRM ratio from the third reaction mixture. In some embodiments, the SCX chromatography separation removes one or more aggregated species as well as any unreacted PBRM from the third reaction mixture.

In some embodiments, wherein one or more main fractions with the desired AF HPA to PBRM ratio are collected during the strong cation exchange chromatography separation, thereby providing the PBRM-polymer-drug conjugate of Formula (B) thus purified.

The resulting purified PBRM-polymer-drug conjugate of Formula (B) is typically formulated in one or more buffers, at pH 5.0-6.5 and optionally one or more stabilizing agents, one or more surfactants and/or one or more inorganic salts.

In some embodiments, the one or more stabilizing agent is trehalose, sorbitol, mannitol, sucrose, lactose, glucose, xylitol, maltose, hydroxypropyl-β-cyclodextrin, lactitol, dextrose, glycerin, or maltitol.

In some embodiments, the stabilizing agent is trehalose, sorbitol or mannitol.

In some embodiments, the stabilizing agent is trehalose.

In some embodiments, the one or more buffers is sodium citrate, ascorbate, succinate, lactate, citric acid, boric acid, borax, hydrochloric acid, disodium hydrogen phosphate, acetic acid, formic acid, glycine, bicarbonate, tartaric acid, Tris-glycine, Tris-NaCl, Tris-ethylenediamine tetraacetic acid ("EDTA"), Tris-borate-EDTA, Tris-acteate-EDTA ("TAE") buffer and Tris-buffered saline, 4-(2-hydroxyethyl)-1-piperazineethanesulfonic acid ("HEPES"), 3-(N-morpholino)propanesulfonic acid ("MOPS"), Piperazine-1,4-bis(2-ethanesulfonic acid) ("PIPES"), 2-(N-morpholino) ethanesulfonic acid ("MES"), histidine, phosphate buffered saline ("PBS"), saline-sodium citrate ("SSC"), saline-tris-EDTA ("STE"), or tris-magnesium.

For example the buffer is sodium citrate.

In some embodiments, the one or more surfactants is Polysorbate 80, Polysorbate 20, Poloxamer 407, Solutol HS 15, Poloxamer 188, sodium lauryl sulphate, ether sulphates, sulphated oils, cetrimide BP, benzalkonium chloride, lecithin, cetromacrogel 1000 BPC, or alkali metal soaps of the formula RCOOX where R is $C_{10}$-$C_{20}$ alkyl group.

Conjugates of the present disclosure and the drug compounds included therein can be conveniently prepared by a variety of methods familiar to those skilled in the art. The conjugates or compounds of this disclosure with each of the formulae described herein may be prepared according to the following procedures from commercially available starting materials or starting materials which can be prepared using literature procedures. These procedures show the preparation of representative conjugates of this disclosure.

Conjugates designed, selected and/or optimized by methods described above, once produced, can be characterized using a variety of assays known to those skilled in the art to determine whether the conjugates have biological activity. In some embodiments, the conjugates can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the conjugate molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following working examples are illustrative and are not intended to be limiting and it will be readily understood by one of skill in the art that other reagents or methods may be utilized.

Conjugates described herein can be prepared by the schemes generally outlined above and by methods described in the Examples below. The term "content" as used in certain examples below, unless otherwise specified, means the molar fraction or molar percentage of the polymer structural units that are substituted with the intended moiety, such as the linker or the drug molecule. Accordingly, the reported percentages for the various polymer units in the drug-carrying polymer scaffolds as used in the Examples below are molar percentages, unless otherwise specified.

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples.

ACN Acetonitrile
AF-HPA Auristatin F-hydroxypropylamide
Ala Alanine
BA β-Alanine
BOC tert-Butyloxycarbonyl
DAR Drug to antibody/PBRM ratio
DCM Dichloromethane
DMAc N,N-Dimethylacetamide EDC.HCl 1-Ethyl-3-[3-dimethylaminopropyl]carbodiimide hydrochloride HPLC High pressure liquid chromatography icIEF Imaged capillary isoelectric focusing MWCO Molecular Weight Cut-Off nd Not determined NF Nanofiltration NHS 1-Hydroxypyrrolidine-2,5-dione (i.e., N-hydroxysuccinimide)

MI Maleimide or maleimido

HPA-Ala Hydroxypropylamide-L-alanine

PDI Polydispersity index

PHF poly(l-hydroxymethylethylene hydroxylmethylformal), or FLEXIMER®

RP-HPLC Reverse-phase high performance liquid chromatography

SEC Size exclusion chromatography

SCX Strong cation exchange chromatography

TCEP HCl Tris (2-carboxyethyl)-phosphine hydrochloride

TFF Tangential Flow Filtration

TFA Trifluoroacetic acid

WAX Weak anion exchange chromatography

General Information

The polymer-drug conjugates described herein, once produced, can be characterized with a variety of analytical techniques known to those skilled in the art. In some embodiments, the polymer-drug conjugates can be characterized by conventional analytical techniques, including but not limited to those techniques described below.

RP-HPLC analysis was performed on a Phenomenex Gemini 5 μm 110 Å, 250×10 mm, 5 micron, semi-preparation column.

Prep-HPLC purification was performed on a Butyl HG, 200 Å, 10 μm, 250×50 mm, 250×75 mm, and 250×150 mm (height×diameter)≥1,000 psi column.

SEC-HPLC analysis was performed on a Tosoh Biosciences TSK gel G5000 column (7.8 mm×30 cm, 10 um) or Superose 12 column.

SEC purification was performed on a Sephadex G-25 (27 cm diameter, 74 cm heightglass column) with a RI detector.

WAX was performed on CAPTO DEAE (GE Healthcare and/or Bo Ge Long) column (8/45 cm diameter, 33/35 cm height) with a UV detection at 205 nm.

HPLC purification was performed on a Phenomenex Gemini 5 μm 110 Å, 250×10 mm, 5 micron, semi-preparation column To determine the concentration of the free drug in a polymer conjugate, an acidified sample was treated with acetonitrile. The free drug was extracted and the acetonitrile supernatant was analyzed. To determine the concentration of conjugated AF-HPA, the sample was subjected to exhaustive basic hydrolysis. The acetonitrile supernatant containing the released AF-HPA and AF was analyzed.

Analysis of AF and AF-HPA was conducted by RP-HPLC using a C-18 column, an acetonitrile gradient and UV detection. Peak areas are integrated and compared to AF and AF-HPA standards. The method AF-HPA is quantitive for AF-HPA from 0.05% to 5% and for AF up to 0.2% n plasma and tumor and tissue homogenates were linear over the concentration ranges of 0.3 to 3,000 ng/mL and 10 to 20,000 ng/mL, respectively.

The maleimido and hydrolyzed maleimdo content of the polymeric scaffolds was determined by $^1$H-NMR.

Endotoxin was determined by the Limulus Amebocyte Lysate (LAL) gel clot assay or Limulus Amebocyte Lysate (LAL) kinetic chromogenic assay.

The molecular weights of the polymer conjugates (reported as the apparent weight average molecular weights or peak molecular weights) were determined by SEC with either polysaccharide or protein molecular weight standards. More specifically, for the polymer or polymer-drug conjugates, polysaccharide molecular weights standard were used, and for protein-drug-polymer conjugates, protein standards are used. Unless specifically indicated the reported polymer carrier molecular weight is the weight average molecular weight of PHF; and the polymer-drug conjugate molecular weight and the protein-polymer-drug conjugates is the peak molecular weight. The polymer conjugates synthesized/measured typically have a polydispersity ≤1.5.

MALDI-TOF mass spectrometry was used to determine the intact molecular weight of the PBRM-polymer-drug conjugates. The PBRM-polymer-drug conjugate was treated with a bifunctional reagent to cross link the lysine residues thereby stabilizing the PBRM-polymer-drug conjugate under the MALDI-TOF mass spectrometry analysis conditions. In general analysis of the cross-linked PBRM-polymer-drug conjugate showed a peak with a broad mass range consistent with an intact antibody linked to 1 to 3 polymer-drug conjugates The protein content of the PBRM-polymer-drug conjugates was determined spectrophotometrically at 280 nm or by ELISA.

In general, the PBRM-polymer-drug conjugates typically contained <5% (w/w, e.g., <2% w/w) aggregated fraction as determined by SEC; <0.5% (w/w, e.g., <0.1% w/w) free (unconjugated) drug as determined by RP-HPLC or LC-MS/MS; <1% (w/w) of free polymer-drug conjugate as determined by SEC and/or RP-HPLC and <2% (w/w, e.g., <1% w/w) unconjugated PBRM as determined by HIC-HPLC and/or WCX HPLC. Reduced or partially reduced antibodies were prepared using procedures described in the literature, see, for example, Francisco et al., Blood 102 (4): 1458-1465 (2003). The total drug (conjugated and unconjugated) concentration was determined by LC-MS/MS or RP-HPLC.

LC-MS or Western blots were used to characterize the specificity and distribution of the cysteine bioconjugation sites in the PBRM-polymer-drug conjugates. The Western blot results gave the positional distribution of the drug-polymer conjugates on the heavy (H) and light (L) chains of the PBRM. LC-MS of a tryptic digest showed that conjugation to the PBRM occurred at the heavy chain and light chain interchain cysteine hinge regions.

For the Western blot analysis the DTT reduced PBRM-polymer-drug conjugate was first separated based on size using denaturing gel electrophoresis and then the separated PBRM fragments were transferred to a polyvinylidene difluoride (PVDF) membrane, referred to as a "blot". The crosslinking was detected on the blot using monoclonal antibodies that have specificity for the drug, human IgG FC (heavy chain) and human IgG Kappa (light chain). The presence of high molecular species, greater than 50 kDa, detected by all three antibodies suggested that inter-chain crosslinking of the heavy and light chain of the PBRM by the polymer-drug conjugate had occurred.

For LC-MS analysis of a tryptic digest of the PBRM-polymer-drug conjugate, the cysteine-containing tryptic peptides attached to the maleimide-containing fragment of the polymer-drug conjugate was characterized by the mass of the peptide plus 601 Da for the molecular weight of the maleimide residue. The results showed that the hinge region cysteines of the PBRM were linked to the polymer-drug conjugate.

The icIEF separates PBRM-polymer-drug conjugates protein species based on their charge differences in a pH gradient. icIEF couples the resolving power of conventional isoelectric focusing with the automation and quantitation of capillary electrophoresis. The sample is focused in a capillary column under high voltage with real-time monitoring during the focusing process using a whole column imaging detection system. The resolved charge species appear as electrophoretic peaks which are detected using UV absorbance at 280 nm. All major peaks within the pI markers are integrated and split into three species: acidic, main, and basic. The percent of each species is determined as an AUC percentage by comparing the individual species areas to the combined area of all three species. The pI value of the largest peak in each species is also reported.

Multi-signal sedimentation velocity (MSSV) technique was used to determine the PBRM to polymer-drug conjugate ratio. The sedimentation velocity data of the PBRM-polymer-drug conjugate was acquired by the simultaneous acquisition of absorbance and refractive index to obtain the data necessary for the determination of the stoichiometry of the PBRM to polymer-drug conjugate ratio.

Example 1. Synthesis of PHF-13-Alanine (Compound B)

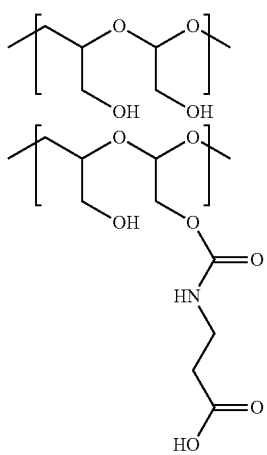

("Compound B")

PHF (7.5 kDa, 1.12 kg, 8.35 moles, 1.0 eq) was dissolved in DMAc (99%, 12.7 kg, 12 volumes) under nitrogen, then stirred at 60-65° C. and the residual water was removed by azeotropic distillation of DMAc under vacuum. The solution was cooled to ~38° C. followed by the successive addition of pyridine (1.3 kg, 16.43 moles, 1.97 eq), methyl 3-isocyanatopropanoate (402.3 g, 3.12 moles, 0.37 eq) and DMAc (107 g). The resulting mixture was heated to 60±5° C. and the distillation resumed. The resulting thick yellow oil was cooled to about 30° C., then 0.5 N NaOH (850 g NaOH in 41.6 kg water, 21.25 moles, 2.5 eq) was added in two equal portions, the temperature adjusted to about 25° C. and the resulting solution was stirred for at least 12 hours. The pH was adjusted to pH 6.1 using 2N HCl and then the solution was cooled to 2-8° C. to give the crude product.

The crude product was first purified by Sephadex G-25 column chromatography to remove the inorganic salts followed by TFF diafiltration (1 kDa MWCO membrane) while maintaining the pH at 7.0±0.1. The product was purified by WAX using a multi-step gradient system of 20 mM sodium phosphate, pH 7.0, to 20 mM sodium phosphate and 1M NaCl, pH 7.0. Appropriate fractions containing PHF-β-Alanine (Compound B) having about 29-34% β-alanine loading as determined by SEC analysis as indicated in Table 1 were combined and concentrated and desalted by TFF diafiltration (1 kDa MWCO membrane) to give the title compound (461 g, ~39% yield) having an average molecular weight of 11.9 kDa, 32.7% 0-Alanine, PDI<1.5.

$^1$H-NMR (400 MHz, D$_2$O): δ 4.8-5.1 (1H, m, O—C$\underline{H}$—O, acetal proton, polymer), 4.2-4.3 (4H, m, —O—CH$_2$, polymer back bone and linker protons), 4.0 ppm (1H, m, O—CH—CH$_2$, polymer backbone), 3.9 (2H, m, CH$_2$, polymer back bone), 3.8 (4H, m, CH$_2$, polymer back bone, —CH$_2$OH) 3.7 (2H, m, CH$_2$—NH—, beta-alanine and linker protons), 2.4 (2H, m, CH$_2$—COOH—, beta-alanine and linker protons).

TABLE 1

| Fraction No. | MWt (KDa) | β-Alanine (%) |
|---|---|---|
| 1 | 4.7 | |
| 3 | 5.3 | |
| 5 | 7.9 | 20.8 |
| 6 | 9.8 | 25.4 |
| 7 | 11.6 | 29.9 |
| 8 | 12.4 | 31.6 |
| 9 | 12.9 | 32.5 |
| 10 | 13.4 | 33.6 |
| 11 | 13.9 | 33.9 |
| 12 | 14.3 | 35.5 |
| 13 | 14.6 | 36.1 |
| 14 | 14.9 | 36.7 |
| 16 | 15.3 | |
| 18 | 16.5 | |
| 20 | 17.7 | |

Five batches of Compound B were synthesized according to the procedures described above. Table 2 shows the analytical characteristics of the Compound B produced.

TABLE 2

| Batch # | PHF (kg) | Yield (%) | MWt (KDa) | PDI | β-Alanine (%) |
|---|---|---|---|---|---|
| 1 | 0.51 | 33 | 10.2 | 1.19 | 31 |
| 2 | 0.79 | 28 | 11.0 | 1.29 | 29 |
| 3 | 1.6 | 40 | 10.6 | 1.23 | 30 |
| 4 | 1.0 | 32 | 10.9 | 1.24 | 30 |
| 5 | 0.9 | 29 | 11.8 | 1.25 | 31 |

Example 1A. Synthesis of PHF-β-Alanine (Compound B)

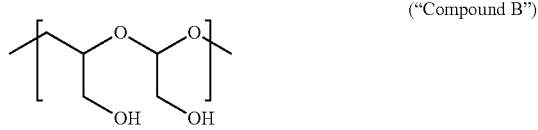

("Compound B")

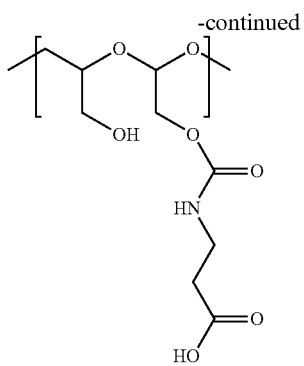

PHF (5.5 k Da, 1.003 kg, 7.48 moles, 1.0 eq) was dissolved in DMAc (99%, 10 kg, 10 volumes) under nitrogen, then stirred at 55-60° C. and the residual water was removed by azeotropic distillation of DMAc under vacuum. The solution was cooled to 20~30° C. followed by the successive addition of pyridine (1.18 kg, 14.95 moles, 2.0 eq), methyl 3-isocyanatopropanoate (0.175 Kg, 1.36 moles, 0.182 eq). The resulting mixture was heated to 55~60° C. and stirred overnight at the same temperature. The reaction system was monitored by $^1$HNMR for the β-alanine loading. The second portion of methyl 3-isocyanatopropanoate (0.135 Kg, 1.05 moles, 0.140 eq.) was added and the reaction was stirred overnight. The homogeneous solution was concentrated to a thick syrup by vacuum distillation at 55-60° C. The resulting thick yellow oil was cooled to about 20~30° C., then 0.5 N NaOH (200 g NaOH in 10 kg water, 5 moles, 0.67 eq) was added in one portions, the temperature adjusted to about 20~30° C. and the resulting solution was stirred for at least 15 hours. The pH was adjusted to pH 6.2 using 2N HCl and then the solution was cooled to 2-8° C. to give the crude product. The resulting solution was filtered by 0.22 um filter.

The crude product was purified in four cycles by nanofiltration (3.5 kDa MWCO membrane) to both desalinate and concentrate the batch. Following this, the product was purified by WAX using a multi-step gradient system of 20 mM sodium phosphate, pH 7.0, to 20 mM sodium phosphate and 1M NaCl, pH 7.0. Appropriate fractions containing PHF-β-Alanine (Compound B) having about 27-35% BA loading as determined by $^1$H-NMR analysis and 7-14 kDa MW as detected by SEC as indicated in Table 1A were combined and then again concentrated and desalted by nanofiltration (3.5 kDa MWCO membrane). The resulting aqueous solution was subjected to TFF (50 kDa MWCO membrane and the permeate collected as product), followed by a 0.2-micron filtration to give the title compound (461 g, ~39% yield) having an average molecular weight of 11.9 kDa, 32.7% β-Alanine, PDI<1.5.

$^1$H-NMR (400 MHz, D$_2$O): δ 4.8-5.1 (1H, m, O—CH—O, acetal proton, polymer), 4.2-4.3 (4H, m, —O—CH$_2$, polymer back bone and linker protons), 4.0 ppm (1H, m, O—CH—CH$_2$, polymer backbone), 3.9 (2H, m, CH$_2$, polymer back bone), 3.8 (4H, m, CH$_2$, polymer back bone, —CH$_2$OH) 3.7 (2H, m, CH$_2$—NH—, beta-alanine and linker protons), 2.4 (2H, m, CH$_2$—COOH—, beta-alanine and linker protons).

TABLE 1A

| Column # | Fraction No. | MWt (KDa) | β-Alanine (%) |
|---|---|---|---|
| 1 | 1 | ND | ND |
| 1 | 2 | ND | ND |

TABLE 1A-continued

| Column # | Fraction No. | MWt (KDa) | β-Alanine (%) |
|---|---|---|---|
| 1 | 3 | 8.6 | 28.8 |
| 1 | 4 | 10.6 | 31.5 |
| 1 | 5 | 11.3 | 36.8 |
| 1 | 6 | 11.8 | 38.5 |
| 1 | 7 | 11.8 | 37.8 |
| 1 | 8 | 11.7 | 38.0 |
| 2 | 1 | ND | ND |
| 2 | 2 | ND | ND |
| 2 | 3 | 7.5 | 27.8 |
| 2 | 4 | 9.5 | 29.3 |
| 2 | 5 | 10.2 | 33.8 |
| 2 | 6 | 10.9 | 36.0 |
| 2 | 7 | 11.4 | 36.0 |
| 2 | 8 | 11.3 | 37.3 |

ND = not determined

Six batches of Compound B were synthesized according to the procedures described above. Table 2A shows the analytical characteristics of the Compound B produced.

TABLE 2A

| Batch # | PHF (kg) | Yield (%) | MWt (KDa) | PDI | β-Alanine (%) |
|---|---|---|---|---|---|
| 1 | 0.51 | 33 | 10.2 | 1.19 | 31 |
| 2 | 0.79 | 28 | 11.0 | 1.29 | 29 |
| 3 | 1.6 | 40 | 10.6 | 1.23 | 30 |
| 4 | 1.0 | 32 | 10.9 | 1.24 | 30 |
| 5 | 0.9 | 29 | 11.8 | 1.25 | 31 |
| 6 | 1.0 | 39 | 9.7 | 1.22 | 30 |

Example 2: Synthesis of tert-butyl(16-(2,5-dioxo-2,5-dihydro-1H-pyrrol-1-yl)-4,14-dioxo-7,10-dioxa-3,13-diazahexadecyl) carbamate (Compound AA)

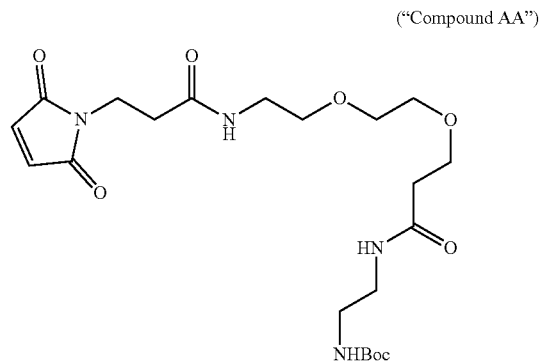 [SMILES: CC(C)(C)OC(=O)NCCNC(=O)CCOCCOCCNC(=O)CCN1C(=O)C=CC1=O]

("Compound AA")

To a cooled solution of 2,5-dioxopyrrolidin-1-yl 3-(2-(2-(3-(2,5-dioxo-2,5-dihydro-1H-pyrrol-1-yl)propanamido)ethoxy)ethoxy)propanoate ("maleimide-PEG2-succinimidyl ester", 656 g, 1.54 moles, 1.0 eq) in anhydrous DCM (6.4 kg) is slowly added a solution of tert-butyl (2-aminoethyl) carbamate ("N—BOC-ethylenediamine", 272 g, 1.70 moles, 1.1 eq) in anhydrous DCM (13.5 kg, 2.0 w/w) while maintaining the temperature below 10° C. The reaction mixture was stirred at ambient temperature until RP-HPLC analysis indicated ~98% conversion to the desired product. The organic phase was washed with water, 10% NaCl solution and concentrated on a rotary evaporator under reduced pressure at 32° C. to approximately 6 volumes. Finally, the title compound was precipitated in EtOAc:heptane (2:1), filtered, washed twice with heptane and subjected to vacuum drying at 25° C. to give 575 g (1.22 moles, 80% yield). ESI-MS: $C_{21}H_{34}N_4O_8$ (M+1) 471.3.

$^1$H-NMR (400 MHz, DMSO $d_6$): δ 8.0 (1H, m), 7.8 (1H, m), 7.0 (2H, s), 6.8 (1H, m), 3.6 (4H, m), 3.5 (4H, m), 3.4 (2H, m), 3.3 (2H, m), 3.1 (2H, m), 3.0 (2H, m), 2.3 (4H, m), 1.4 (9H, s).

$^{13}$C-NMR (400 MHz, DMSO $d_6$): δ 135, 70, 69, 66, 40, 39, 38, 36, 34, 28

Example 2: Synthesis of tert-butyl(16-(2,5-dioxo-2,5-dihydro-1H-pyrrol-1-yl)-4,14-dioxo-7,10-dioxa-3,13-diazahexadecyl) carbamate (Compound AA)

Example 2A: Synthesis of tert-butyl(16-(2,5-dioxo-2,5-dihydro-1H-pyrrol-1-yl)-4,14-dioxo-7,10-dioxa-3,13-diazahexadecyl) carbamate (Compound AA)

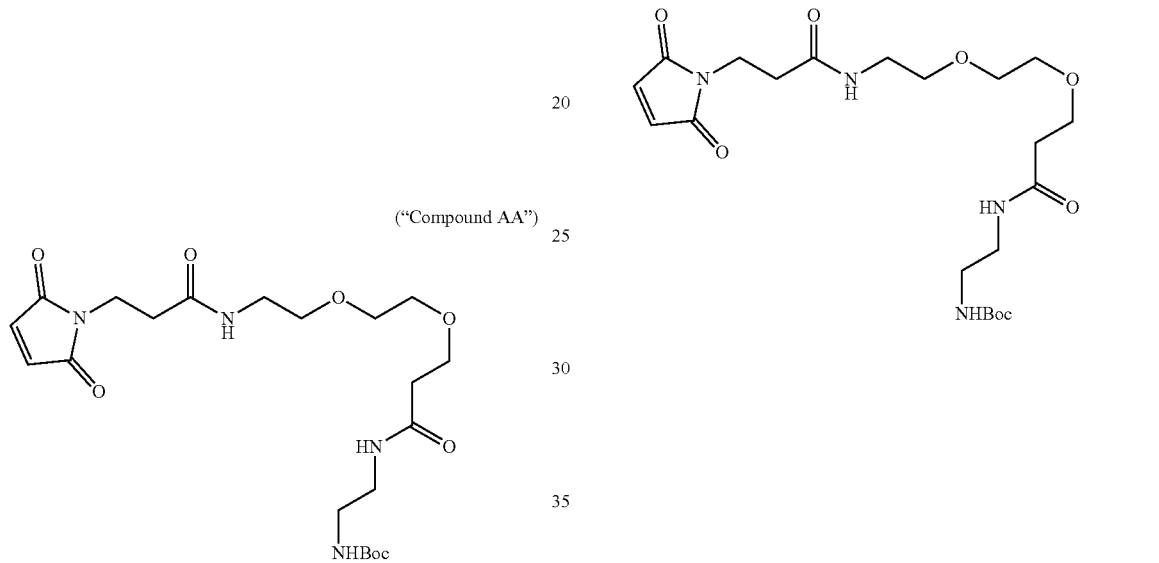

("Compound AA")

To a cooled solution of 2,5-dioxopyrrolidin-1-yl 3-(2-(2-(3-(2,5-dioxo-2,5-dihydro-1H-pyrrol-1-yl)propanamido)ethoxy)ethoxy)propanoate ("maleimide-PEG2-succinimidyl ester", 140 g, 0.33 moles, 1.0 eq) in anhydrous DCM (1.2 kg) is slowly added a solution of tert-butyl (2-aminoethyl) carbamate ("N—BOC-ethylenediamine", 58 g, 0.36 moles, 1.1 eq) in anhydrous DCM (0.19 kg, 2.0 w/w) while maintaining the temperature below 10° C. The reaction mixture was stirred at ambient temperature until RP-HPLC analysis indicated ~98% conversion to the desired product. The organic phase was washed with water, 10% NaCl solution and concentrated on a rotary evaporator under reduced pressure at 32° C. to approximately 6 volumes. Finally, the title compound was precipitated in EtOAc:heptane (2:1), filtered, washed twice with heptane and subjected to vacuum drying at 25° C. to give 113 g (0.24 moles, 67% yield). ESI-MS: $C_{21}H_{34}N_4O_8$ (M+1) 471.3.

$^1$H-NMR (400 MHz, DMSO $d_6$): δ 8.0 (1H, m), 7.8 (1H, m), 7.0 (2H, s), 6.8 (1H, m), 3.6 (4H, m), 3.5 (4H, m), 3.4 (2H, m), 3.3 (2H, m), 3.1 (2H, m), 3.0 (2H, m), 2.3 (4H, m), 1.4 (9H, s).

$^{13}$C-NMR (400 MHz, DMSO $d_6$): δ 135, 70, 69, 66, 40, 39, 38, 36, 34, 28

To a cooled solution of 2,5-dioxopyrrolidin-1-yl 3-(2-(2-(3-(2,5-dioxo-2,5-dihydro-1H-pyrrol-1-yl)propanamido)ethoxy)ethoxy)propanoate ("maleimide-PEG2-succinimidyl ester", 140 g, 0.33 moles, 1.0 eq) in anhydrous DCM (1.2 kg) is slowly added a solution of tert-butyl (2-aminoethyl) carbamate ("N—BOC-ethylenediamine", 58 g, 0.36 moles, 1.1 eq) in anhydrous DCM (0.19 kg, 2.0 w/w) while maintaining the temperature below 10° C. The reaction mixture was stirred at ambient temperature until RP-HPLC analysis indicated ~98% conversion to the desired product. The organic phase was washed with water, 10% NaCl solution and concentrated on a rotary evaporator under reduced pressure at 32° C. to approximately 6 volumes. Finally, the title compound was precipitated in EtOAc:heptane (2:1), filtered, washed twice with heptane and subjected to vacuum drying at 25° C. to give 113 g (0.24 moles, 67% yield). ESI-MS: $C_{21}H_{34}N_4O_8$ (M+1) 471.3.

$^1$H-NMR (400 MHz, DMSO $d_6$): δ 8.0 (1H, m), 7.8 (1H, m), 7.0 (2H, s), 6.8 (1H, m), 3.6 (4H, m), 3.5 (4H, m), 3.4 (2H, m), 3.3 (2H, m), 3.1 (2H, m), 3.0 (2H, m), 2.3 (4H, m), 1.4 (9H, s).

$^{13}$C-NMR (400 MHz, DMSO $d_6$): δ 135, 70, 69, 66, 40, 39, 38, 36, 34, 28

Example 3: Synthesis of Auristatin F Hydroxypropyl Alanine (AF-HPA-ala) (Compound C)

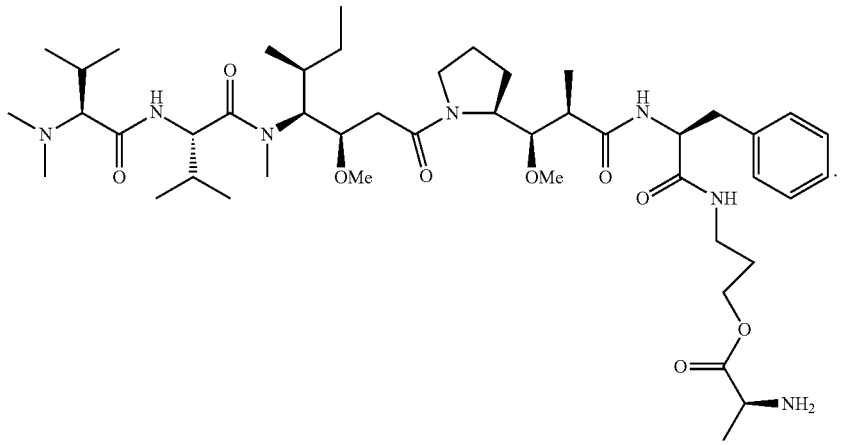

("Compound C")

To CBz protected AF-HPA-ala (i.e., Compound CC, 250 g, 0.248 moles, 1.0 eq) in a Parr pressure reactor was added 10% palladium on carbon, 50% wet (37.5 g, 0.15 w/w), 2-propanol (6.6. kg, 26 w/w), and TFA (28 g, 0.248 moles, 1.0 eq). The reactor was then subjected to 50 PSI hydrogen until analysis of an aliquot showed 98% conversion to the title compound. The contents of the reactor were first filtered with the help of additional 2-propanol (786 g) to remove the spent catalyst and then TFA (42 g, 0.368 moles, 1.5 eq) in 2-propanol (193 g) was added. The reaction mixture was stirred for 1 hr at 20° C., then tert-butyl methyl ester (1.87 kg) was added and the stirring continued for an additional two hours at ~20° C. and then overnight at ~10° C. The title compound was isolated by filtration and dried under vacuum to give 250 g (80% yield). ESI-MS: $C_{46}H_{79}N_7O_9$ (M+1) 873.5.

Example 3A: Synthesis of Auristatin F Hydroxypropyl Alanine (AF-HPA-ala) (Compound C)

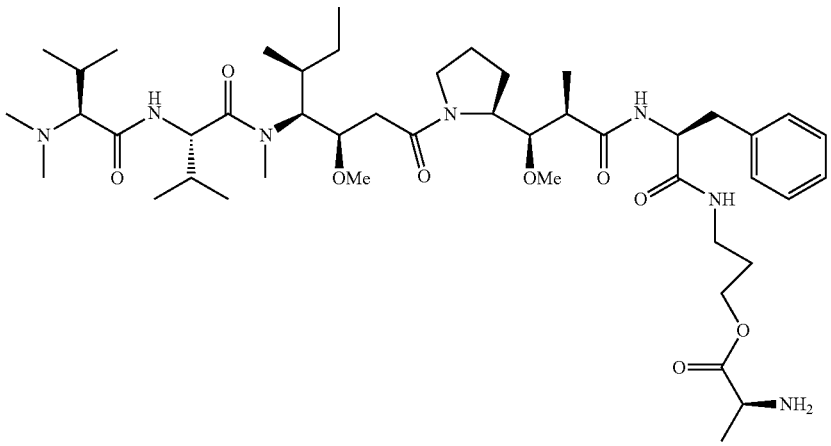

("Compound C")

To CBz protected AF-HPA-ala (i.e., Compound CC, 350 g, 0.347 moles, 1.0 eq) in a 20 L glass reactor was added 2-propanol (4.2 kg, 12 w/w), and TFA (39 g, 0.347 moles, 1.0 eq) followed by 10% palladium on carbon, 50% wet (53 g, 0.15 w/w). The reactor was then subjected to hydrogen at atmospheric pressure until analysis of an aliquot showed 98% conversion to the title compound. The contents of the reactor were first filtered with the help of additional 2-propanol (5.5 kg) to remove the spent catalyst and then concentrated to ~3 vol. TFA (60 g, 0.515 moles, 1.5 eq) in 2-propanol (274 g) was added. The reaction mixture was stirred for 1 hr at 20° C., then tert-butyl methyl ester (2.6 kg) was added and the stirring continued for an additional two hours at ~20° C. and then overnight at ~10° C. The title compound was isolated by filtration and dried under vacuum to give 334 g (85% yield). ESI-MS: $C_{46}H_{79}N_7O_9$ (M+1) 873.5.

Example 4: Synthesis of Polymeric Scaffold of Formula A

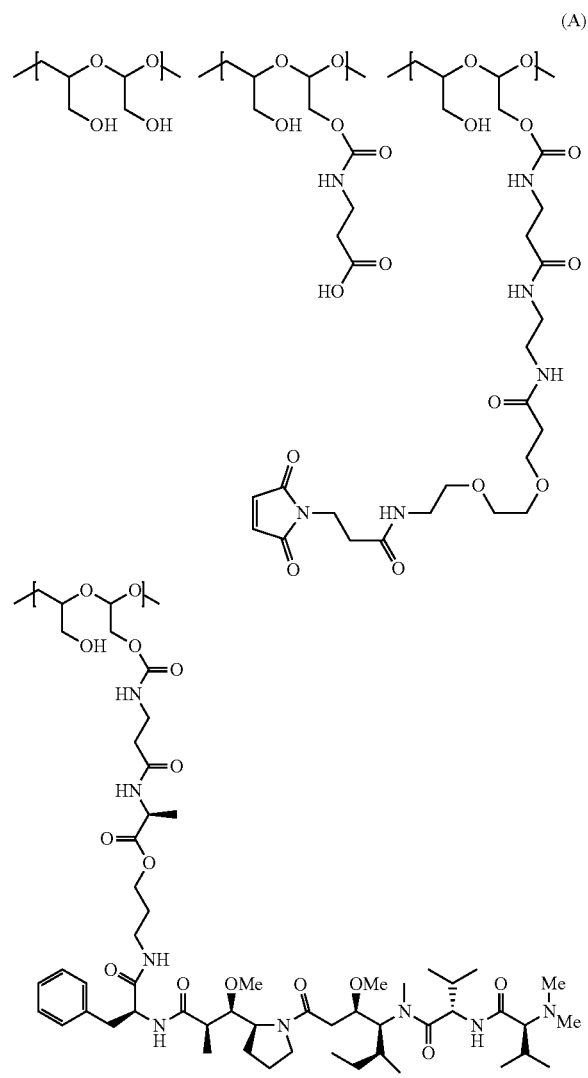

To the product of Example 2 (28.3 g, 0.06 moles, 0.04 eq) in DCM (375 g) under nitrogen at <5° C. was added TFA (163 g, 1.43 moles, 0.95 eq) over 20 minutes while maintaining the temperature below 5° C. The resulting mixture was stirred at ambient temperature for two hours. Analysis of an aliquot by HPLC indicated that the deprotection reaction was complete. The reaction mixture was concentrated by rotary evaporator at 30° C. to give the desired product, O—[N-(3-maleimidopropionyl)aminoethyl]-O'-[3-(N-(2-aminoethyl)amino)-3-oxopropyl]ethylene glycol ("Compound A"), as an oil.

Separately to PHF-β-Alanine (6296 g aqueous solution containing 257 g on dry basis, 1.5 moles, 1.0 eq, pH 6.5) at ~8° C. was added NHS (47 g, 0.07 moles, 0.046 eq) in ACN/water (55 g) followed by Compound A, as prepared above, in ACN (594 g). The pH of the resulting mixture was adjusted from pH 4.2 to pH 5.4 using 0.1N $NaHCO_3$ followed by the addition of EDC.HCl (36 g, 0.188 moles, 0.125 eq) in ACN/water (148 g) in 3 portions, final pH 6. After the addition of EDC.HCl was complete stirring was continued for 1.5 hr. After the consumption of ~80% of Compound A, as monitored by RP-HPLC, NHS (16 g, 0.139 moles, 0.092 eq) in ACN/water (64 g) followed by the product of Example 3, AF-HPA-ala or Compound C (132 g, 0.124 moles, 0.083 eq) in water (1316 g) was added, followed by the batch wise addition of EDC.HCl (71 g, 0.370 moles, 0.247 eq) in ACN/water (272 g) over 1.5 hr. The resulting mixture was stirred at ambient temperature overnight. Analysis of an aliquot by RP-HPLC indicated that <1% AF-HPA-ala remained. NaCl (252 g) was added and the stirring continued 1 hour then the mixture was concentrated to ~2 L while maintaining pH 5.0±0.3. The entire concentrate was subjected to Sephadex G-25 chromatography to remove the salts and unreacted reagents followed by TFF diafiltration (1 kDa MWCO membrane) at 5–15° C. while maintaining the pH at 4 to 5.

The retentate was further purified by preparative HPLC (butyl HG, 200 Å, 10 µm, 250×50 mm, 1,000 psi column) using a 25 mM sodium acetate and acetonitrile, pH 5.8 as the eluant). Selected fractions, based on $^1$H-NMR and SEC analysis, containing polymeric scaffolds with 6-10% AF-HPA loading and 7-13 kDa MW were pooled, subjected to rotary evaporation, followed TFF 1 kDa MWCO membrane) concentration to remove solvents, buffers and salts. The resulting aqueous solution was subjected to TFF (100 kDa MWCO membrane and collected permeate as product), followed by a 0.1-micron sterile filtration. The title polymeric scaffold was obtained is a colorless to pale amber aqueous solution (233 g, ~67% yield, 11.4 kDa, 3.8% MI, 9.0% AF-HPA).

Seven batches of the scaffold of Formula (A) were synthesized according to the procedures described above. Table 3 shows the analytical characteristics of the polymeric scaffolds produced.

TABLE 3

| Analytical Characteristics | Batch # (Formula A) | | | | | | |
|---|---|---|---|---|---|---|---|
| | 1 | 2 | 3 | 4 | 5 | 6 | 7 |
| MWt (KDa) | 8.3 | 12.5 | 10.8 | 11.2 | 11.4 | 9.3 | 11.3 |
| PDI | 1.3 | 1.6 | 1.5 | 1.4 | 1.4 | 1.3 | 1.4 |
| AF-HPA (%) | 9.4 | 9.5 | 9.0 | 9.1 | 9.0 | 9.1 | 9.0 |
| Free AF-HPA (%) | 0.4 | 0.7 | 0.1 | 0.2 | 0.2 | 0.4 | 0.1 |
| Maleimide Linker (%) | 2.4 | 3.5 | 3.6 | 3.5 | 3.8 | 3.5 | 3.5 |
| Hydrolyzed Maleimide Linker (%) | nd | 35 | nd | 10 | 4.4 | 5.9 | 3.1 |
| Endotoxin EU/mg | nd | nd | 0.24 | 1.4 | 0.05 | 0.03 | 0.01 |

Example 4A: Synthesis of Polymeric Scaffold of Formula A

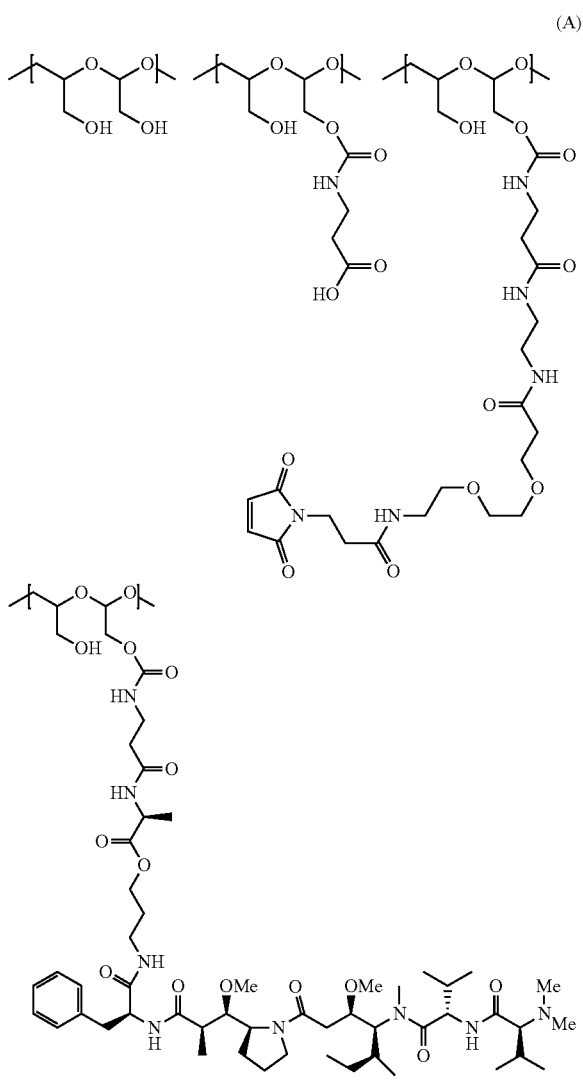

To the product of Example 2A (34.0 g, 0.072 moles, 0.04 eq) in DCM (459 g) under nitrogen at <5° C. was added TFA (195 g, 1.71 moles, 0.95 eq) over 20 minutes while maintaining the temperature below 5° C. The resulting mixture was stirred at ambient temperature for two hours. Analysis of an aliquot by HPLC indicated that the deprotection reaction was complete. The reaction mixture was concentrated by rotary evaporator at 30° C. to give the desired product, O—[N-(3-maleimidopropionyl)aminoethyl]-O'-[3-(N-(2-aminoethyl)amino)-3-oxopropyl]ethylene glycol ("Compound A"), as an oil.

Separately to PHF-β-Alanine (1.01 kg aqueous solution containing 310 g on dry basis, 1.80 moles, 1.0 eq, pH 6.5) at ~8° C. was added NHS (8.4 g, 0.072 moles, 0.04 eq) in ACN/water (37 g) followed by Compound A, as prepared above, in ACN (704 g). The pH of the resulting mixture was adjusted from pH 4.2 to pH 5.4 using 0.1N NaHCO₃ followed by the addition of EDC.HCl (45 g, 0.235 moles, 0.125 eq) in ACN/water (162 g) in 3 portions, final pH 6. After the addition of EDC.HCl was complete stirring was continued for 1.5 hr. After the consumption of ~80% of Compound A, as monitored by RP-HPLC, NHS (20 g, 0.170 moles, 0.092 eq) in ACN/water (82 g) followed by the product of Example 3A, AF-HPA-ala or Compound C (172 g, 0.197 moles, 0.083 eq) in water (1605 g) was added, followed by the batch wise addition of EDC.HCl (85 g, 0.441 moles, 0.247 eq) in ACN/water (321 g) over 3.5 hr. The resulting mixture was stirred at ambient temperature overnight. Analysis of an aliquot by RP-HPLC indicated that <1% AF-HPA-ala remained. NaCl (126 g) was added and the stirring continued 1 hour then the mixture was diluted with ~32 L of water while maintaining pH 5.0±0.3. The entire product solution was subjected to TFF diafiltration (1 kDa MWCO membrane) at 5-15° C. while maintaining the pH at 4 to 5.

The retentate was further purified by preparative HPLC (butyl HG, 200 Å, 10 μm, 250×75 mm, >1,000 psi column) using a 25 mM sodium acetate and acetonitrile, pH 5.8 as the eluant). Selected fractions, based on ¹H-NMR and SEC analysis, containing polymeric scaffolds with 6-10% AF-HPA loading and 7-13 kDa MW were pooled, diluted with a total of ~200 L of water, followed TFF (1 kDa MWCO membrane) concentration to remove solvents, buffers and salts. The resulting aqueous solution was subjected to TFF (100 kDa MWCO membrane, and the permeate was collected as the product), followed by a 0.1-micron sterile filtration. The title polymeric scaffold was obtained is a colorless to pale amber aqueous solution (233 g, 50% yield, 9.5 kDa, 3.2% MI, 8.9% AF-HPA).

Four batches of the scaffold of Formula (A) were synthesized according to the procedures described above. Table 3A shows the analytical characteristics of the polymeric scaffolds produced.

TABLE 3A

| Analytical | Batch # | | | |
| --- | --- | --- | --- | --- |
| Characteristics | 1 | 2 | 3 | 4 |
| MWt (KDa) | 9.2 | 11.0 | 8.9 | 9.5 |
| PDI | 1.7 | 1.7 | 1.4 | 1.4 |
| AF-HPA (%) | 8.9 | 9.2 | 8.7 | 8.9 |
| Free AF-HPA (%) | 0.19 | 0.1 | nd | nd |
| Maleimide Linker (%) | 2.5 | 2.8 | 3.5 | 3.2 |
| Hydrolyzed Maleimide Linker (%) | nd | 3.4 | 0.5 | 2.0 |
| Endotoxin EU/mg | <2.5 | <2.5 | <2.5 | <2.5 |

Example 5: Synthesis of Reduced PBRM

The pH of a PBRM solution (5.0 mg/mL) in 50 mM TEAA or 50 mM sodium acetate, 1 mM EDTA, pH 7.0 was adjusted to pH 7.0±0.5 using 0.5 M sodium bicarbonate (pH 8.5). The disulfide bonds in the PBRM were partially reduced by slowly adding 2.0 to 4.0 molar equivalents of tris(2-carboxyethyl)phosphine hydrochloride (TCEP.HCl) to the PBRM solution over a period of 10 min. After the addition of the TCEP.HCl was complete, the resulting solution was stirred for 1.5 hours at 25±2° C. The pH of the resulting solution was then adjusted to between 5.5 and 7.0 using 1.0 M acetic acid.

Multiple batches of the reduced PBRM were synthesized according to the above procedures using, e.g., 2.4, 2.5, 2.75, 3.0, 3.25 or 3.4 molar equivalents of TCEP.HCl. A linear correlation between the molar equivalents of TCEP.HCl to the PBRM used in the reduction and the DAR of the further produced PBRM-polymer-drug conjugate was observed. The required molar equivalents of TCEP.HCl for reducing the antibody depends on factors including the nature of the antibody and the desired DAR of the further produced PBRM-polymer-drug conjugate. It is to be understood that one skilled in the art would be able to determine the required molar equivalents of TCEP.HCl with routine experimentation.

Example 6: Synthesis of PBRM-Polymer-Drug Conjugate of Formula B

Conjugation of Polymeric Scaffold of Formula a and Reduced PBRM

The reduced PBRM of Example 5 was added to a solution of polymeric scaffold of Formula A in pH 7.0 buffer over a period of 20 minutes to form a solution of Formula A and the PBRM at a ratio of 0.9 (w/w) or 0.75 (w/w). The resulted solution was mixed for about 45 to 60 minutes at 25° C.

Alternatively a solution of polymeric scaffold of Formula A in pH 7.0 buffer is added to the reduced PBRM of Example 5 to form a solution of Formula A such that the PBRM is at a ratio of 0.9 (w/w) or 0.75 (w/w).

Multiple batches of the conjugation were carried out using polymeric scaffold of Formula A and PBRM at ratios varying from 0.5:1 to 1.2:1. The ratio between polymeric scaffold of Formula A to antibody used in the conjugation reaction depends on factors including the nature of the antibody and the desired DAR of the produced PBRM-polymer-drug conjugate. It is to be understood that one skilled in the art would be able to determine the ratio with routine experimentation.

Quenching the Reaction

The reaction is quenched by adding 25 molar equivalents of L-Cysteine (relative to the antibody), and the resulted solution of the PBRM-polymer-drug conjugate was mixed for 30 minutes at 25° C.

Purification of PBM-Polymer-Drug Conjugate of Formula B

The resulted mixture containing conjugate of Formula B was purified to remove the unreacted polymeric scaffold of Formula A, undesired conjugate of Formula B with low and high DAR, any aggregated species and unreacted PBRM thereby providing the purified conjugate of Formula B with the desired DAR. The pH of the quenched solution containing the PBRM-polymer-drug conjugate was adjusted to 5.8 with 1.0 M acetic acid, and the resulted mixture was filtered through a 0.2 μm filter. The crude mixture containing the PBRM-polymer-drug conjugate was purified by SCX chromatography (POROS HS50) using a multi-step gradient from 50 mM sodium acetate (NaOAc; in pH 5.8) to 50 mM sodium acetate and 1.0 M NaCl (pH 5.8) as shown in Table 4 below. The elution profile was monitored by UV absorbance. The SCX chromatography is designed to remove both the early eluting acidic fractions (high molecular weight and high DAR) and late eluting basic fractions (low DAR ratios, <10, as determined by WCX analytical method) as well as any aggregated species and unreacted PBRM. The main fractions containing the conjugate of Formula B with the desired DAR were collected.

TABLE 4

| Gradient Step # | Batch #1 | Batch #2 |
|---|---|---|
| 1 | 50 mM NaOAc (pH 5.8) | 50 mM NaOAc (pH 5.8) |
| 2 | 50 mM NaOAc + 35 mM NaCl (pH 5.8) | 50 mM NaOAc + 40 mM NaCl (pH 5.8) |
| 3 | 50 mM NaOAc + 90 mM NaCl (pH 5.8) | 50 mM NaOAc + 95 mM NaCl (pH 5.8) |
| 4 | 50 mM NaOAc + 1.0M NaCl (pH 5.8) | 50 mM NaOAc + 1.0M NaCl (pH 5.8) |

The column fractions were analyzed by analytical HPLC WCX chromatography to categorize the conjugate of Formula B as acidic (early eluting) fractions, basic (late eluting) fractions, or main fractions eluting between acidic and basic fractions.

Table 5 shows the analytic characteristics of the purification of three batches of conjugate of Formula B by analytical HPLC WCX chromatography.

TABLE 5

| Batch # | Acidic Fraction (%) | Main Fraction (%) | Basic Fraction (%) |
|---|---|---|---|
| 1 | 14.0 | 71.0 | 15.0 |
| 2 | 10.0 | 86.4 | 3.6 |
| 3 | 13.5 | 84.4 | 2.1 |

Buffer Exchange of PBM-Polymer-Drug Conjugate of Formula B

The collected fractions containing the conjugate of Formula B with desired DAR were combined, and the resulted solution was then buffer exchanged against a solution of 25 mM sodium citrate and 75 mM sodium chloride (pH 5.5 buffer) using 30 kDa MWCO membrane. After the exchange is complete, the retentate was filtered through a 0.2 μm filter to provide a solution of the purified PBRM-polymer-drug conjugate of Formula B.

Formulation of PBRM-Polymer-Drug Conjugate of Formula B

The solution of purified PBRM-polymer-drug conjugate of Formula B was diluted to a concentration of 15 mg/mL by adding a solution of 25 mM sodium citrate and 75 mM sodium chloride (pH 5.5). The resulted solution was then formulated to a concentration of 10 mg/mL by adding a solution of 25 mM sodium citrate, 75 mM sodium chloride, and 150 g/L trehalose (pH 5.5). The resulted formulation of the PBRM-polymer-drug conjugate of Formula B was filtered through a 0.22 μm filter and stored at ≤−60° C.).

Three batches of the PBRM-polymer-drug conjugate of Formula B were synthesized according to the procedures described above. Table 6 shows the analytical characteristics of the PBRM-polymer-drug conjugates produced.

TABLE 6

| Analytical Characteristic | Batch #1 | Batch #2 | Batch #3 |
|---|---|---|---|
| AF-HPA:PBRM | 12 | 12 | 12 |
| AF-HPA:PHF | 3.8 | 3.8 | 4 |
| PHF:PBRM | 3.2 | 3.2 | 2.8 |
| Main Fraction (%) (WCX) | 86.4 | 84.4 | 90.3 |
| Free AF-HPA (%) | 0.01 | nd | nd |
| Free PBRM (%) | 1.9 | 1.0 | 1.1 |

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:
1. A method of making a polymeric scaffold of Formula (A):
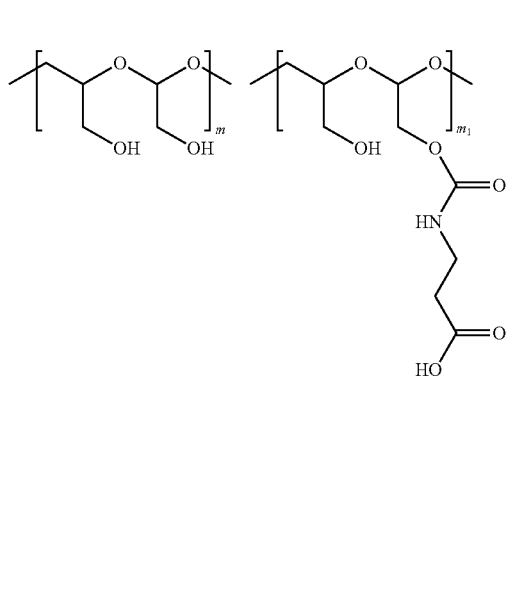
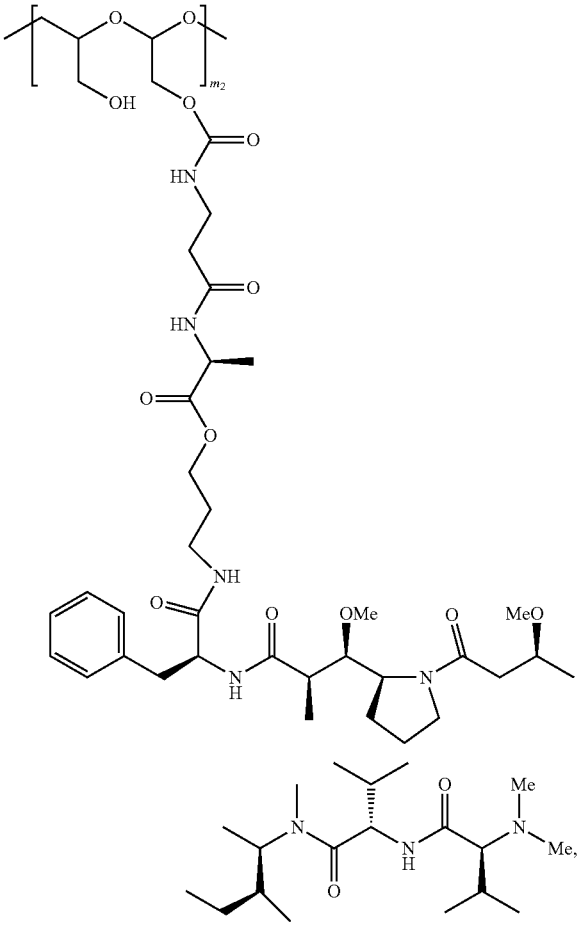
or a salt thereof, the method comprising one or more steps selected from:
(1) reacting
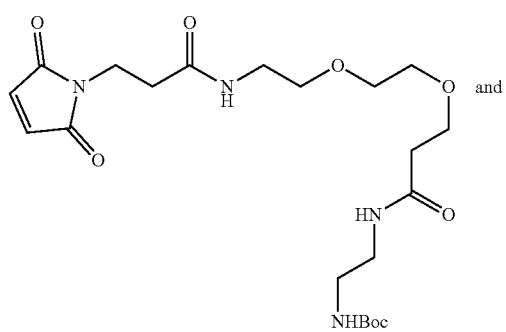
("Compound A")
and
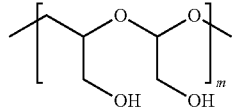
("Compound B")

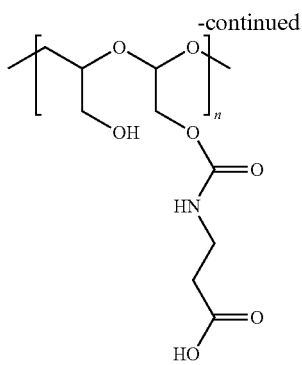

under conditions to form a first reaction mixture; and
(2) adding

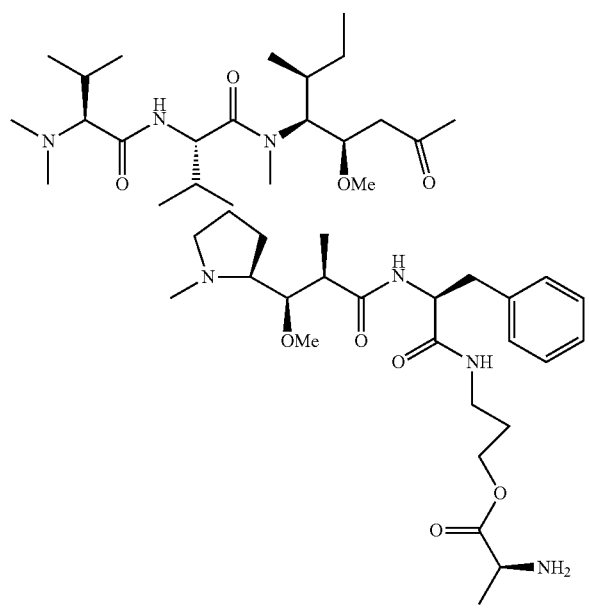

("Compound C")

or a salt thereof to the first reaction mixture to form a second reaction mixture comprising the scaffold of Formula (A) or the salt thereof;

wherein:

Compound B or the scaffold of Formula (A) comprises poly(1-hydroxymethylethylene hydroxymethyl-formal) (PHF) having a molecular weight ranging from about 5 kDa to about 10 kDa;

n is an integer from about 7 to about 40, and the ratio between m and n is about 2:1 to about 3:1, $m_1$ is an integer from about 5 to about 35, $m_2$ is an integer from about 3 to about 10, $m_3$ is an integer from about 1 to about 5, and the sum of m, $m_1$, $m_2$, and $m_3$ ranges from about 40 to about 75, wherein the scaffold of Formula (A) or the salt thereof is isolated with a reverse phase HPLC separation using a mobile phase comprising sodium acetate buffer and acetonitrile.

2. The method of claim 1, wherein the PHF has a molecular weight ranging from about 6 kDa to about 8 kDa.

3. The method of claim 1, wherein Compound B has a molecular weight ranging from about 6 kDa to about 13 kDa, and n is about 26-34% of the sum of m and n.

4. The method of claim 1, wherein prior to the reverse phase HPLC separation, the second reaction mixture is subject to one or more filtrations, one or more tangential flow filtrations, one or more diafiltration, one or more ultrafiltration, one or more nanofiltrations, one or more non-adsorptive chromatography separations, or combinations thereof.

5. The method of claim 1, wherein after the reverse phase HPLC separation, the second reaction mixture is subject to one or more filtrations, one or more tangential flow filtrations, one or more diafiltration, one or more ultrafiltration, one or more nanofiltrations, or one or more non-adsorptive chromatography separations or combinations thereof.

6. The method claim 1, wherein the scaffold of Formula (A) has a molecular weight ranging from about 4 kDa to about 18 kDa.

7. The method of claim 1, wherein $m_2$ is from about 5% to about 13% of the sum of m, $m_1$, $m_2$ and $m_3$.

8. The method of claim 1, wherein $m_3$ is about 2% to about 4% of the sum of m, $m_1$, $m_2$ and $m_3$.

9. The method of claim 1, wherein at least 80% of Compound A is consumed before Compound C or a salt thereof is added to the first reaction mixture, and the first reaction mixture is not isolated before Compound C or a salt thereof is added.

10. The method of claim 1, wherein the reaction of Compound A and Compound B is performed in the presence of an activating reagent for a carboxylic acid and a coupling agent under a first temperature between about 0° C. and about 15° C.

11. The method of claim 1, wherein the reaction of the first reaction mixture and Compound C or a salt thereof is performed in the presence of an activating reagent for a carboxylic acid and a coupling agent under a second temperature between about 5° C. and about 15° C.

12. The method of claim 10, wherein the activating reagent is N-hydroxysuccinimide (NHS), and the coupling reagent is ethyl(dimethylaminopropyl) carbodiimide hydrochloride (EDC.HCl).

13. The method of claim 1, further comprising providing Compound A by deprotecting a protected form of Compound A, wherein the protected form of Compound A is ("Compound AA")

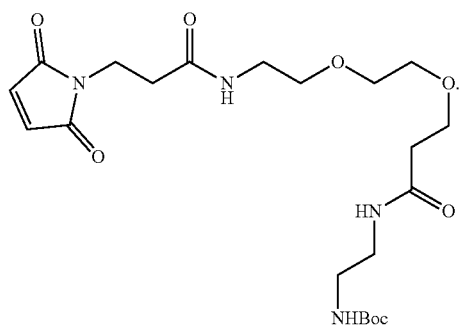

14. The method of claim 13, further comprising providing Compound AA by reacting 2,5-dioxopyrrolidin-1-yl 3-(2-(2-(3-(2,5-dioxo-2,5-dihydro-1H-pyrrol-1-yl)propanamido)

ethoxy)ethoxy)propanoate with tert-butyl (2-aminoethyl) carbamate at a temperature between about 0° C. and about 25° C.

15. The method of claim 1, further comprising providing Compound B by reacting PHF with methyl 3-isocyanatopropanoate to form a methyl ester of Compound B and converting the methyl ester to Compound B, wherein the PHF has a molecular weight ranging from about 5 kDa to about 10 kDa.

16. The method of claim 15, further comprising purifying Compound B such that:

Compound B thus purified has a molecular weight ranging from about 6 kDa to about 13 kDa, and n is about 26-34% of the sum of m and n.

17. The method of claim 16, wherein Compound B is purified with a weak anion exchange chromatography separation using a mobile phase comprising a sodium phosphate buffer.

18. The method of claim 17, wherein prior to the weak anion exchange chromatography separation, compound B is purified with one or more filtrations, one or more tangential flow filtrations, one or more diafiltration, one or more ultrafiltration, one or more nanofiltrations, one or more non-adsorptive chromatography separations, or combinations thereof.

19. The method of claim 1, further comprising providing Compound C or a salt thereof by deprotecting a protected form of Compound C, wherein the protected form of Compound C is a trifluoroacetate salt of

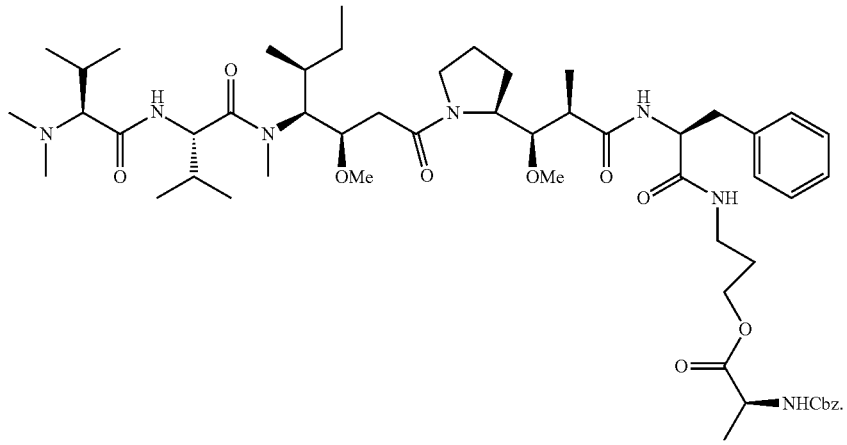

("Compound CC")

20. The method of claim 18, wherein at least one of the non-adsorptive chromatography separations is performed with a column comprising cross-linked dextran.

21. The method of claim 18, wherein at least one of the tangential flow filtrations is performed with a membrane having a molecular weight cutoff between about 650 Da and 1000 Da.

22. The method of claim 18, wherein at least one of the nanofiltrations is performed with a membrane having a molecular weight cutoff between about 1000 Da and 4000 Da.

23. The method of claim 18, wherein at least one of the filtrations is performed with a membrane having a molecular weight cutoff between about 50 kDa and 100 kDa to obtain a permeate that contains the scaffold of Formula (A) or the salt thereof.

24. The method of claim 1, wherein the scaffold of Formula (A) or the salt thereof thus produced has a purity of at least 75%; and/or
wherein at least 100 g of the scaffold of Formula (A) or salt thereof is produced in a single batch.

25. A method of making a PBRM-polymer-drug conjugate, the method comprising:
(1) providing a polymeric scaffold of Formula (A):
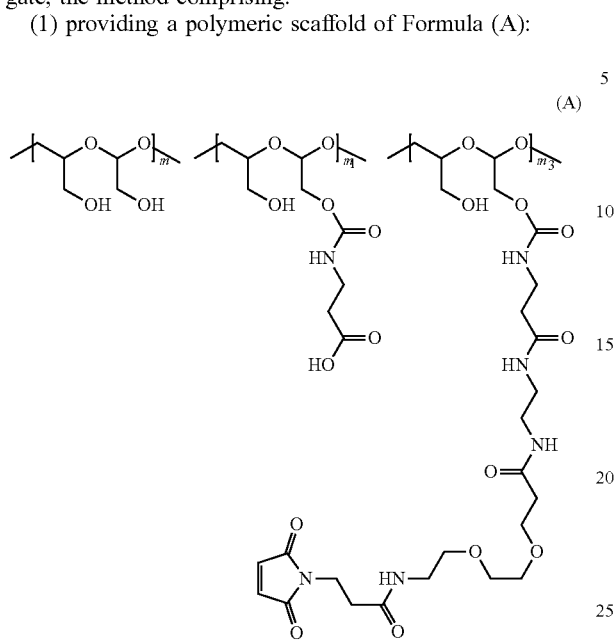
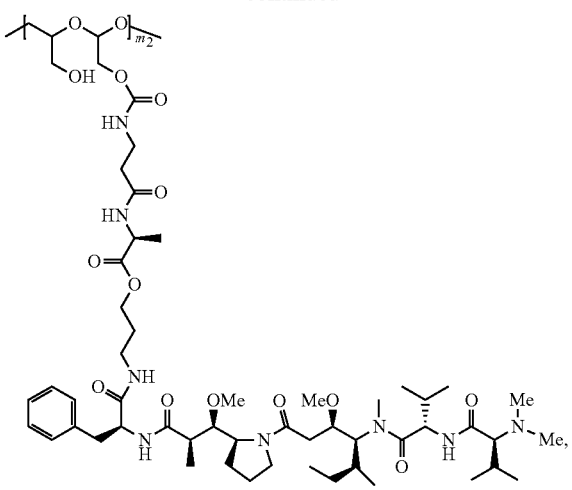
or a salt thereof and a reduced PBRM;
(2) adding the reduced PBRM to the polymeric scaffold of Formula (A) or the salt thereof to form a third reaction mixture comprising a PBRM-polymer-drug conjugate of Formula (B):

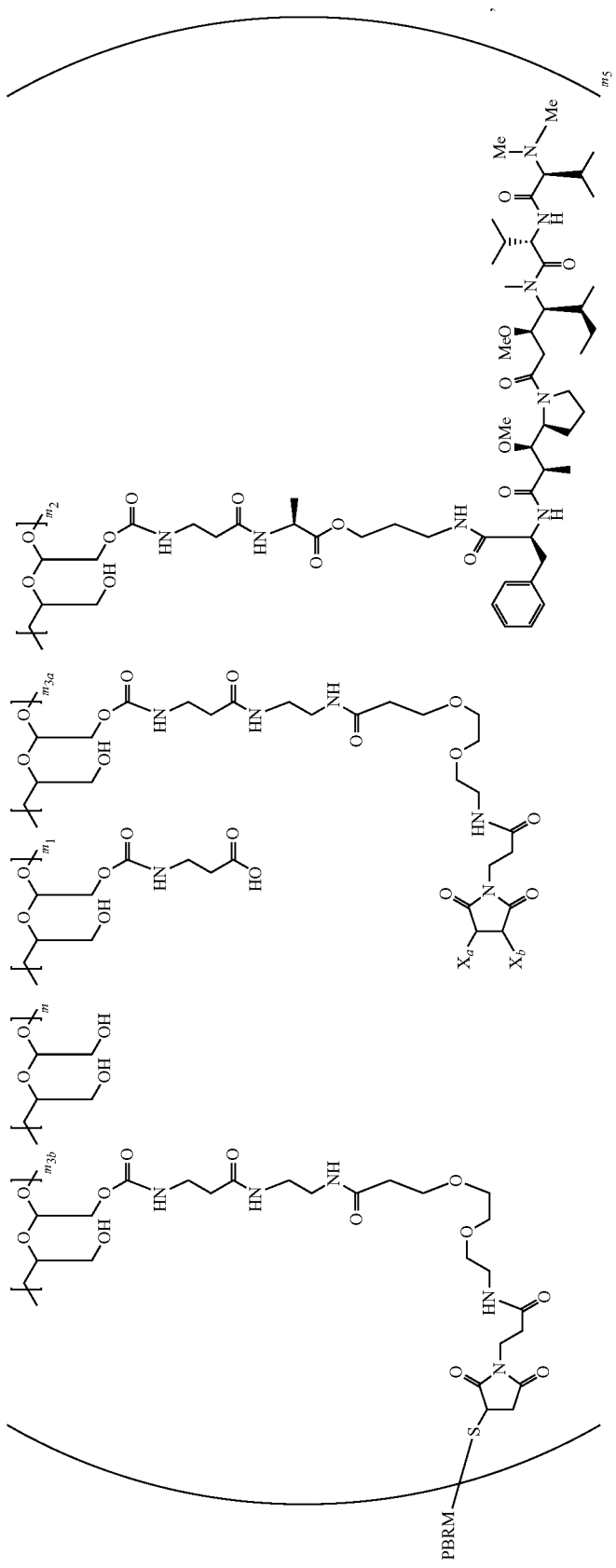

wherein:
one of $X_a$ and $X_b$ is H and the other is a water-soluble maleimido blocking moiety, or $X_a$ and $X_b$, together with the carbon atoms to which they are attached form a carbon-carbon double bond;

the PHF has a molecular weight ranging from about 5 kDa to about 10 kDa;

$m_1$ is an integer from about 5 to about 35, $m_2$ is an integer from about 3 to about 10, $m_{3a}$ is an integer from 0 to about 4, $m_{3b}$ is an integer from 1 to about 5, the sum of m, $m_1$, $m_2$, $m_{3a}$, and $m_{3b}$ ranges from about 40 to about 75, and $m_5$ is an integer from 2 to about 10, and further comprising isolating the PBRM-polymer-drug conjugate of Formula (B) from the third reaction mixture with a chromatography separation, wherein the chromatography separation is an ion exchange chromatography separation or a strong cation exchange (SCX) chromatography separation, wherein the strong cation exchange chromatography separation removes one or more acidic fractions, as determined by analytical HPLC WCX chromatography, and/or wherein the strong cation exchange chromatography separation removes one or more basic fractions, as determined by analytical HPLC WCX chromatography, from the third reaction mixture and removes one or more aggregated species and any unreacted PBRM from the third reaction mixture.

26. The method of claim 25, wherein the reduced PBRM is prepared by reacting a PBRM with a reducing agent at a molar ratio ranging from about 1:2 to about 1:4.

27. The method of claim 25, wherein one or more disulfide bonds of the PBRM are reduced by the reducing agent to one or more thiol groups, and wherein the reducing agent is tris(2-carboxyethyl)phosphine (TCEP) or a salt thereof or tris(2-carboxyethyl)phosphine (TECP) hydrochloride.

28. The method of claim 25, wherein the polymeric scaffold of Formula (A) or the salt thereof is reacted with the reduced PBRM at a weight ratio ranging from about 0.5:1 to about 1.2:1.

29. The method of claim 25, wherein the reaction of the polymeric scaffold of Formula (A) or the salt thereof with the reduced PBRM is terminated by adding a maleimido blocking compound, wherein the maleimido blocking compound is selected from the group consisting of cysteine, N-acetyl cysteine, cysteine methyl ester, N-methyl cysteine, 2-mercaptoethanol, 3-mercaptopropanoic acid, 2-mercaptoacetic acid, mercaptomethanol, benzyl thiol, and salts thereof.

30. The method of claim 29, wherein the maleimido blocking compound is cysteine.

31. The method of claim 25, wherein the chromatography separation is performed with a mobile phase comprising sodium acetate, sodium chloride, or a combination thereof, wherein the mobile phase has a pH value ranging from about 5 to about 7.

32. The method of claim 25, wherein one or more main fractions eluting between the acidic and basic fractions, as determined by analytical HPLC WCX chromatography, with the desired AF HPA to PBRM ratio are collected during the strong cation exchange chromatography separation, thereby providing the PBRM-polymer-drug conjugate of Formula (B) thus purified has a AF HPA to PBRM ratio ranging from about 20:1 to about 6:1.

33. The method of claim 32, wherein the PBRM-polymer-drug conjugate of Formula (B) has the ratio between AF HPA and PBRM ranging from about 10:1 to about 15:1.

34. The method of claim 32, wherein the ratio between AF HPA and PHF ranges from about 4:1 to about 3:1.

35. The method of claim 25, wherein the PBRM-polymer-drug conjugate of Formula (B) thus produced comprises PHF and PBRM at a ratio ranging from about 6:1 to about 2:1.

36. The method of claim 35, wherein the ratio between PHF and PBRM ranges from about 4:1 to about 3:1.

37. The method of claim 25, wherein the PBRM-polymer-drug conjugate of Formula (B) thus produced has a purity of at least about 75%; and/or
wherein at least 100 g of the PBRM-polymer-drug conjugate of Formula (B) is produced in a single batch.

38. A method of making a pharmaceutical composition comprising PBRM-polymer-drug conjugate, the method comprising:
(a) providing a PBRM-polymer-drug conjugate being prepared by the method of claim 25; and
(b) adding one or more pharmaceutically acceptable excipients to the PBRM-polymer-drug conjugate to form the pharmaceutical composition.

39. The method of claim 32, wherein the PBRM-polymer-drug conjugate of Formula (B) has the ratio between AF HPA and PBRM ranging from about 10:1 to about 12:1.

40. The method of claim 35, wherein the ratio between PHF and PBRM is about 3:1.

41. The method of claim 35, wherein the ratio between PHF and PBRM is about 4:1.

* * * * *

UNITED STATES PATENT AND TRADEMARK OFFICE
CERTIFICATE OF CORRECTION

PATENT NO. : 10,772,971 B2  Page 1 of 1
APPLICATION NO. : 16/015623
DATED : September 15, 2020
INVENTOR(S) : Venu Gurijala et al.

It is certified that error appears in the above-identified patent and that said Letters Patent is hereby corrected as shown below:

On the Title Page

Item (73):
"(73) Assignee: Mersana Therpeutics, Inc., Cambridge, MA (US)"
Should read:
-- (73) Assignee: Mersana Therapeutics, Inc., Cambridge, MA (US) --

In the Claims

At Column 178, Claim number 1, Line number 46-65:
        and
"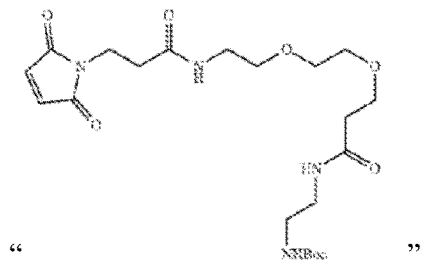"

Should read:
        and
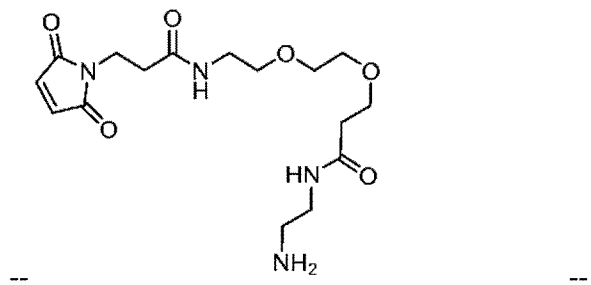
--                              --

Signed and Sealed this
Fifth Day of January, 2021

Andrei Iancu
*Director of the United States Patent and Trademark Office*